US010214546B2

(12) United States Patent
Liu et al.

(10) Patent No.: US 10,214,546 B2
(45) Date of Patent: Feb. 26, 2019

(54) BTK INHIBITORS

(71) Applicant: MERCK SHARP & DOHME CORP., Rahway, NJ (US)

(72) Inventors: Jian Liu, Edison, NJ (US); Joseph A. Kozlowski, Princeton, NJ (US); Sobhana Babu Boga, Scotch Plains, NJ (US); Xiaolei Gao, Bridgewater, NJ (US); Deodial Guy Guiadeen, Chesterfield, NJ (US); Jiaqiang Cai, Shanghai (CN); Shilan Liu, Shanghai (CN); Dahai Wang, Shanghai (CN); Hao Wu, Shanghai (CN); Chundao Yang, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/538,971

(22) PCT Filed: Dec. 17, 2015

(86) PCT No.: PCT/US2015/066219
§ 371 (c)(1),
(2) Date: Jun. 22, 2017

(87) PCT Pub. No.: WO2016/109216
PCT Pub. Date: Jul. 7, 2016

(65) Prior Publication Data
US 2018/0118766 A1    May 3, 2018

(30) Foreign Application Priority Data
Dec. 31, 2014  (WO) ................ PCT/CN2014/095769

(51) Int. Cl.
C07D 519/00   (2006.01)
A61K 45/06    (2006.01)
A61K 31/4985  (2006.01)
A61P 19/02    (2006.01)

(52) U.S. Cl.
CPC ........ *C07D 519/00* (2013.01); *A61K 31/4985* (2013.01); *A61K 45/06* (2013.01); *A61P 19/02* (2018.01); *A61K 2300/00* (2013.01)

(58) Field of Classification Search
CPC .................................................. C07D 519/00
See application file for complete search history.

(56) References Cited

U.S. PATENT DOCUMENTS

| 8,673,925 B1 | 3/2014 | Goldstein |
| 8,697,711 B2 | 4/2014 | Honigberg et al. |
| 2008/0076921 A1 | 3/2008 | Honigberg et al. |
| 2009/0286768 A1 | 11/2009 | Crew et al. |
| 2014/0206681 A1 | 7/2014 | Kim et al. |

FOREIGN PATENT DOCUMENTS

| WO | WO02080926 | 10/2002 |
| WO | WO2005014599 | 2/2005 |
| WO | WO2007064993 A2 | 6/2007 |
| WO | WO2013010380 A1 | 1/2013 |
| WO | WO2014113932 | 7/2014 |
| WO | WO2014114185 | 7/2014 |
| WO | WO2015132799 A2 | 9/2015 |
| WO | WO2016106628 A1 | 7/2016 |
| WO | WO2016109222 A1 | 7/2016 |

*Primary Examiner* — Brian E McDowell
(74) *Attorney, Agent, or Firm* — Matthew A. Leff; Laura M. Ginkel

(57) ABSTRACT

The present invention provides Bruton's Tyrosine Kinase (Btk) inhibitor compounds according to Formula (I), or pharmaceutically acceptable salts thereof, or to pharmaceutical compositions comprising these compounds and to their use in therapy. In particular, the present invention relates to the use of Btk inhibitor compounds of Formula (I) in the treatment of Btk mediated disorders.

(I)

7 Claims, No Drawings
Specification includes a Sequence Listing.

BTK INHIBITORS

FIELD OF THE INVENTION

The present invention relates to Btk inhibitor compounds, to pharmaceutical compositions comprising these compounds and to their use in therapy. In particular, the present invention relates to the use of Btk inhibitor compounds in the treatment of Bruton's Tyrosine Kinase (Btk) mediated disorders.

BACKGROUND OF THE INVENTION

B lymphocyte activation is key in the generation of adaptive immune responses. Derailed B lymphocyte activation is a hallmark of many autoimmune diseases and modulation of this immune response is therefore of therapeutic interest. Recently the success of B cell therapies in autoimmune diseases has been established. Treatment of rheumatoid arthritis (RA) patients with Rituximab (anti-CD20 therapy) is an accepted clinical therapy by now. More recent clinical trial studies show that treatment with Rituximab also ameliorates disease symptoms in relapsing remitting multiple sclerosis (RRMS) and systemic lupus erythematosus (SLE) patients. This success supports the potential for future therapies in autoimmune diseases targeting B cell immunity.

Bruton tyrosine kinase (Btk) is a Tec family non-receptor protein kinase, expressed in B cells and myeloid cells. The function of Btk in signaling pathways activated by the engagement of the B cell receptor (BCR) and FcεR1 on mast cells is well established. In addition, a function for Btk as a downstream target in Toll-like receptor signaling was suggested. Functional mutations in Btk in human results in the primary immunodeficiency disease called XLA which is characterized by a defect in B cell development with a block between pro- and pre-B cell stage. This results in an almost complete absence of B lymphocytes in human causing a pronounced reduction of serum immunoglobulin of all classes. These finding support the key role for Btk in the regulation of the production of auto-antibodies in autoimmune diseases. In addition, regulation of Btk may affect BCR-induced production of pro-inflammatory cytokines and chemokines by B cells, indicating a broad potential for Btk in the treatment of autoimmune diseases.

With the regulatory role reported for Btk in FcR-mediated mast cell activation, Btk inhibitors may also show potential in the treatment of allergic responses [Gilfillan et al, Immunological Reviews 288 (2009) pp 149-169].

Furthermore, Btk is also reported to be implicated in RANKL-induced osteoclast differentiation [Shinohara et al, Cell 132 (2008) pp 794-806] and therefore may also be of interest for the treatment of bone resorption disorders.

Other diseases with an important role for dysfunctional B cells are B cell malignancies. Indeed anti-CD20 therapy is used effectively in the clinic for the treatment of follicular lymphoma, diffuse large B-cell lymphoma and chronic lymphocytic leukemia [Lim et al, Haematologica, 95 (2010) pp 135-143]. The reported role for Btk in the regulation of proliferation and apoptosis of B cells indicates there is potential for Btk inhibitors in the treatment of B cell lymphomas as well. Inhibition of Btk seems to be relevant in particular for B cell lymphomas due to chronic active BCR signaling [Davis et al, Nature, 463 (2010) pp 88-94].

Some classes of Btk inhibitor compounds have been described as kinase inhibitors, e.g. Imidazo[1,5-f][1,2,4] triazine compounds have been described in WO2005097800 and WO2007064993. Imidazo[1,5-a]pyrazine compounds have been described in WO2005037836 and WO2001019828 as IGF-1R enzyme inhibitors.

Some of the Btk inhibitors reported are not selective over Src-family kinases. With dramatic adverse effects reported for knockouts of Src-family kinases, especially for double and triple knockouts, this is seen as prohibitive for the development of Btk inhibitors that are not selective over the Src-family kinases.

Both Lyn-deficient and Fyn-deficient mice exhibit autoimmunity mimicking the phenotype of human lupus nephritis. In addition, Fyn-deficient mice also show pronounced neurological defects. Lyn knockout mice also show an allergic-like phenotype, indicating Lyn as a broad negative regulator of the IgE-mediated allergic response by controlling mast cell responsiveness and allergy-associated traits [Odom et al, J. Exp. Med., 199 (2004) pp 1491-1502]. Furthermore, aged Lyn knock-out mice develop severe splenomegaly (myeloid expansion) and disseminated monocyte/macrophage tumors [Harder et al, Immunity, 15 (2001) pp 603-615]. These observations are in line with hyperresponsive B cells, mast cells and myeloid cells, and increased Ig levels observed in Lyn-deficient mice. Female Src knockout mice are infertile due to reduced follicle development and ovulation [Roby et al, Endocrine, 26 (2005) pp 169-176]. The double knockouts $Src^{-/-}Fyn^{-/-}$ and $Src^{-/-}Yes^{-/-}$ show a severe phenotype with effects on movement and breathing. The triple knockouts $Src^{-/-}Fyn^{-/-}Yes^{-/-}$ die at day 9.5 [Klinghoffer et al, EMBO J., 18 (1999) pp 2459-2471]. For the double knockout $Src^{-/-}Hck^{-/-}$, two thirds of the mice die at birth, with surviving mice developing osteopetrosis, extramedullary hematopoieseis, anemia, leukopenia [Lowell et al, Blood, 87 (1996) pp 1780-1792].

Hence, an inhibitor that inhibits multiple or all kinases of the Src-family kinases simultaneously may cause serious adverse effects.

SUMMARY OF THE INVENTION

The present invention provides compounds which inhibit Btk activity, their use for treatment of Btk mediated diseases and disorders, in particular autoimmune diseases and inflammatory diseases, as well as pharmaceutical compositions comprising such compounds and pharmaceutical carriers.

DETAILED DESCRIPTION

Definitions

The terms used herein have their ordinary meaning and the meaning of such terms is independent at each occurrence thereof. That notwithstanding, and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "alkoxy", etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond having the specified number of carbon atoms. In different embodiments, an alkyl group contains, for example, from 1 to 6 carbon atoms (1-6C)alkyl or from 1 to 4 carbon atoms (1-4C)alkyl or from 1 to 3 carbon atoms (1-3C)alkyl. In one embodiment, an alkyl group is linear. In another embodiment, an alkyl group is branched. Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl.

"Alkoxy" refers to an alkyl-O— group represented by a linear or branched alkyl group of indicated number of carbon atoms attached through an oxygen bridge; for example "(1-6C)Alkoxy" includes —OCH$_3$, —OCH$_2$CH$_3$, —OCH(CH$_3$)$_2$, —O(CH$_2$)$_5$CH$_3$, and the like.

Unless otherwise specifically noted as only "unsubstituted" or only "substituted", alkyl groups are unsubstituted or substituted with 1 to 3 substituents on each carbon atom.

The term "amount effective" or "effective amount" as used herein, refers to an amount of the compound of Formula I and/or an additional therapeutic agent, or a composition thereof, that is effective in producing the desired therapeutic, ameliorative, inhibitory or preventative effect when administered to a subject suffering from a BTK-mediated disease or disorder. In the combination therapies of the present invention, an effective amount can refer to each individual agent or to the combination as a whole, wherein the amounts of all agents administered are together effective, but wherein the component agent of the combination may not be present individually in an effective amount.

The term "aryl" as used herein, shall mean an aromatic hydrocarbon group having 6-10 carbon atoms, such as phenyl, naphthyl, tetrahydronaphthyl or indenyl. The preferred aryl group is phenyl.

The term "cycloalkyl," as used herein, refers to a saturated mono- or multicyclic ring system containing up to 10 ring carbon atoms, and no heteroatom. In a like manner the term "(C$_{3-6}$) cycloalkyl" or (3-6C)cycloalkyl" refers to a saturated ring having from 3 to 6 ring carbon atoms. Non-limiting examples of monocyclic cycloalkyls include cyclopropyl, cyclobutyl, cyclopentyl, and cyclohexyl. In one embodiment, the cycloalkyl is cyclopropyl.

The term "heterocycloalkyl", as used herein, refers to a monocyclic ring having a 5- or 6-membered saturated ring system having 1 or 2 heteroatoms selected from N and/or O such that the heterocycloalkyl may be linked through a carbon or nitrogen atom. Non-limiting examples of heterocycloalkyls include tetrahydrofuran, tetrahydropyran and piperidine. Additionally, heterocycloalkyl may refer to a multicyclic ring having up to 10 carbon atoms with one or two heteroatoms selected from N or O.

The multiring system of the cycloalkyl and heteocycloalkyl groups may be composed of two or more rings that may be joined together to form: a fused or a spiro-ring system. A fused ring system is one in which two or more rings are fused across two adjacent ring carbon atoms. A nonlimiting example of a fused ring system is

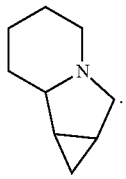

A spiro ring system is a bicyclic ring wherein the two rings are joined through a common ring carbon atom. Nonlimiting examples of spiro ring systems include spiro[2.4]heptane, spiro[cyclopropane-1,1'-indolizin]-3'(2'H)-one, spiro[cyclopropane-1,3'-pyrido[1,2-a]pyrazin]-4'-one, and the like.

"Cycloalkoxy" refers to a cycloalkyl-O— group represented by a cycloalkyl group of indicated number of carbon atoms attached through an oxygen bridge to the compound of the invention; for example "(3-6C)cycloalkoxy" includes —O-cyclopropyl, —O-cyclobutyl, —O— cyclopentyl, or —O-cyclohexyl.

The term "halogen", as used herein, refers to fluorine, chlorine, bromine or iodine. Fluorine, chlorine or bromine being preferred halogens; fluorine being more preferred.

The term "haloalkyl", as used herein, refers to an alkyl group as defined above having one or more hydrogen atoms substituted with a halogen atom. Nonlimiting examples include difluoromethyl, trifluoromethyl, and the like.

The term "purified" as used herein, refers to the physical state of a compound after the compound has been isolated through a synthetic process (e.g., from a reaction mixture), from a natural source, or a combination thereof. The term "purified" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

The term "substituted", as used herein, means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means that a compound may or may not be substituted with the specified groups, radicals or moieties.

A "subject" is a human or non-human mammal. In one embodiment, a subject is a human. In another embodiment, the subject is a chimpanzee.

The term "C$_0$" as employed in expressions such as "(C$_{0-6}$)alkylene" means a direct covalent bond; or when employed in expressions such as "(C$_{0-6}$)alkyl" means hydrogen. Similarly, when an integer defining the presence of a certain number of atoms in a group is equal to zero, it means that the atoms adjacent thereto are connected directly by a bond; for example, in the structure

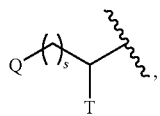

wherein s is an integer equal to zero, 1 or 2, the structure is

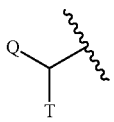

when s is zero; or it means that the indicated atom is absent; for example —S(O)$_0$— means —S—.

Unless expressly stated to the contrary, all ranges cited herein are inclusive. For example, a heterocycloalkyl described as containing from "1 to 4 heteroatoms" means the heterocycloalkyl can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds. For variable definitions containing terms having repeated terms, e.g., (CRiRj)$_r$, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)$_2$ can be

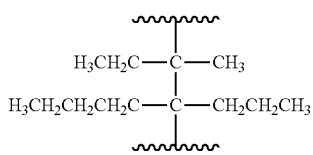

As used herein, the term "X$_a$-X$_b$", shall have the same meaning as the term "X$_{a-b}$" or "(a–bX)", wherein X is any atom and a and b are any integers. For example, "C$_1$-C$_4$" shall have the same meaning as "C$_{1-4}$" or "(1-4C)". Additionally, when referring to a functional group generically, "A$^x$" shall have the same meaning, and be interchangeable with, "AX", wherein "A" is any atom and "x" or "X" are any integer. For example, "R$^1$" shall have the same meaning, and be interchangeable with, "R1".

In the above definitions with multifunctional groups, the attachment point is at the last group. For example, the term (C$_{1-3}$)alkoxycarbonyl refers to, e.g.

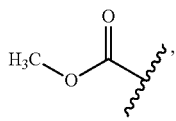 [SMILES: *C(=O)OC]

and the term (C$_{1-4}$)alkylcarbonyloxy refers to, e.g.

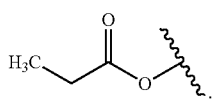

In the above definitions with multifunctional groups, the attachment point is at the last group, unless otherwise specified on the substituent group by a dash. A dash on the substituent group would then represent the point of attachment.

It should be noted that any carbon as well as heteroatom with unsatisfied valences in the text, schemes, examples and tables herein is assumed to have the sufficient number of hydrogen atom(s) to satisfy the valences.

Compounds of the Invention

The present invention provides Btk inhibitor compounds according to Formula I or a pharmaceutically acceptable salt thereof Formula I

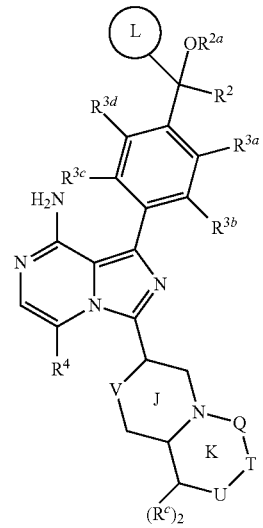

wherein:

L is selected from the group consisting of:

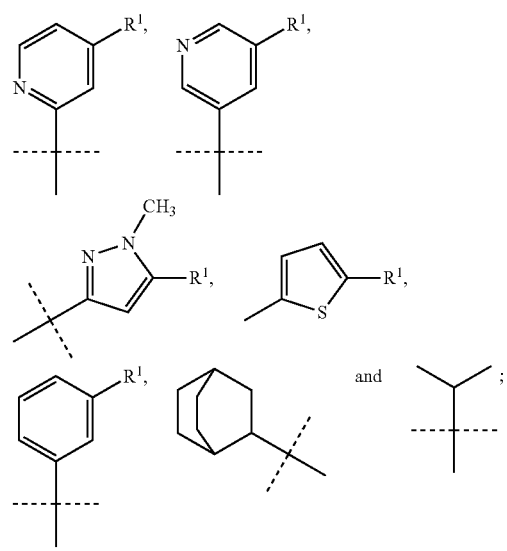

R$^1$ is H, cyano, halogen, (1-4C)alkyl, (3-6C)cycloalkyl, (1-3C)alkoxy, (3-6C)cycloalkoxy, morpholino, aryl or imidazolyl,
  wherein (1-4C)alkyl or (1-3C)alkoxy may optionally be substituted with one, two or three halogens;
R$^2$ is selected from H, (1-3C)alkyl, (1-3C)alkoxy, cyclopropyl, aminocarbonyl, wherein the (1-3C)alkyl or (1-3C)alkoxy may optionally be substituted with hydroxyl or one, two or three halogen;

$R^{2a}$ is hydrogen or methyl;

$R^{3a}$, $R^{3b}$, $R^{3c}$ and $R^{3d}$ are each independently selected from H, halogen, (1-3C)alkyl, (1-6C)alkoxy, and (3-6C)cycloalkyl, wherein (1-3C)alkyl may be substituted with hydroxyl or one, two or three halogen;

$R^4$ is independently selected from the group consisting of:
 a) H,
 b) halogen, and
 c) haloalkyl;

wherein in ring system J-K:

Q is C=O or CH$_2$;

T is C($R^e$)$_2$, O, N$R^c$, or a bond;

U is C($R^d$)$_2$, O, or N$R^d$;

V is CH$_2$ or O;

$R^c$ is independently selected from H, fluoro, methyl or trifluoromethyl,
 or two $R^c$ groups can join to form a spirofused cyclopropyl group with the carbon atom to which they are attached;

$R^d$ is independently selected from H, (1-3C)alkyl or trifluoromethyl;

$R^e$ is independently selected from H or (1-6C)alkyl,
 or two $R^e$ groups can join to form a spirofused cyclopropyl group with the carbon atom to which they are attached;

when T is a bond, Q is C=O and U is C($R^d$)2,
 $R^c$ and $R^d$ can join to form a 3-6 membered ring with the carbons to which they are attached; and with the proviso that:

when Q is CH$_2$, then T is C($R^e$)$_2$.

In one aspect the invention relates to a compound according to Formula I wherein the ring system J-K is selected from the group consisting of

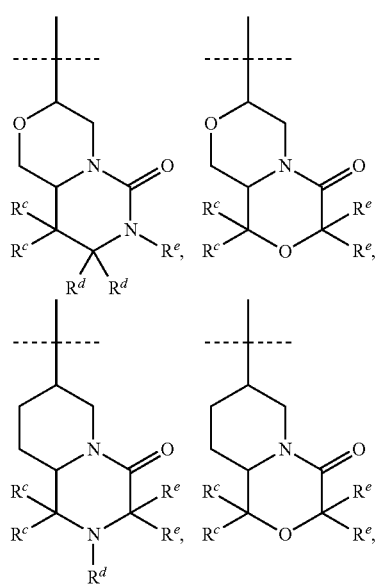

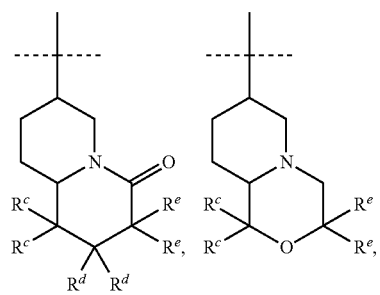

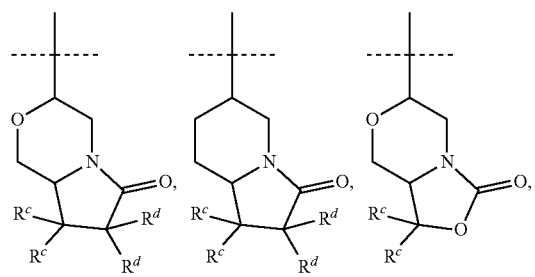

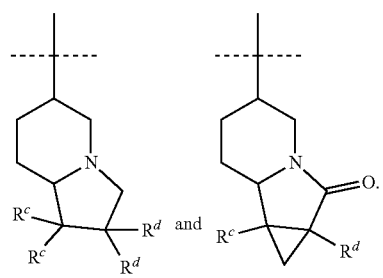

In another aspect the invention relates to a compound according to Formula I wherein L is

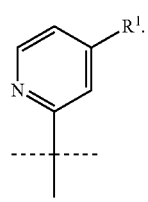

In a further aspect the invention relates to a compound according to Formula I wherein $R^1$ is trifluoromethyl.

In a final aspect the invention relates to a compound having Formula Ia

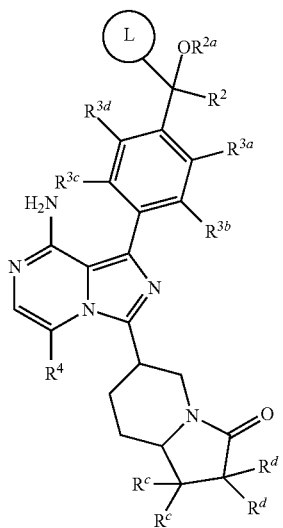

Formula Ia or a pharmaceutically acceptable salt thereof.

The invention also relates to those compounds wherein all specific definitions for $R^1$, $R^2$, $R^{2a}$, $R^{3a}$, $R^{3b}$, $R^{3c}$, $R^{3d}$, $R^4$, Q, T, U, V, $R^c$, $R^d$, $R^e$, and all substituent groups in the various aspects of the inventions defined here above occur in any combination within the definition of the Btk inhibitor compounds of Formula I or pharmaceutically acceptable salts thereof.

Non-limiting examples of the compounds of the present invention include:

(6R,8aS)-6-(8-amino-1-{4-[(1S)-1-hydroxy-1-phenylethyl]phenyl}imidazo[1,5-a]pyrazin-3-yl)hexahydroindolizin-3(2H)-one;

(6R,8aS)-6-(8-amino-1-{4-[(1R)-1-hydroxy-1-phenylethyl]phenyl}imidazo[1,5-a]pyrazin-3-yl)hexahydroindolizin-3(2H)-one;

(6R,8aS)-6-[8-amino-1-(4-{(1R)-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-5-chloro-1-(4-{(1S)-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-5-chloro-1-(4-{(1R)-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[3-(trifluoromethyl)phenyl]ethyl}phenyl)imidazo[1,5-a]pyrazin-3-yl]-2,2-dimethylhexahydroindolizin-3(2H)-one;

(1S,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-methyltetrahydro-1H-[1,3]oxazolo[4,3-c][1,4]oxazin-3-one;

(1R,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-methyltetrahydro-1H-[1,3]oxazolo[4,3-c][1,4]oxazin-3-one;

(6R,8aS)-6-[8-amino-1-(2-methoxy-4-{2,2,2-trifluoro-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(2-methoxy-4-{2,2,2-trifluoro-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-{8-amino-1-[4-(2,2,2-trifluoro-1-hydroxy-1-phenylethyl)phenyl]imidazo[1,5-a]pyrazin-3-yl}hexahydroindolizin-3(2H)-one;

(6R,8aS)-6-(8-amino-1-(4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-{8-amino-1-[4-(1-hydroxy-1,2-dimethylpropyl)phenyl]imidazo[1,5-a]pyrazin-3-yl}hexahydroindolizin-3(2H)-one;

(6R,8aS)-6-(8-amino-1-(4-{1-hydroxy-1-[4-(trifluoromethyl)phenyl]ethyl}phenyl)imidazo[1,5-a]pyrazin-3-yl]hexahydroindolizin-3(2H)-one;

(6R,8aS)-6-{8-amino-1-{4-[1-(3-fluorophenyl)-1-hydroxyethyl]phenyl}imidazo[1,5-a]pyrazin-3-yl)hexahydroindolizin-3(2H)-one;

(6R,8aS)-6-{8-amino-1-[4-(1-hydroxy-1-pyridin-2-ylethyl)phenyl]imidazo[1,5-a]pyrazin-3-yl}hexahydroindolizin-3(2H)-one;

(6R,8aS)-6-{8-amino-1-[4-(1-hydroxy-1-pyridin-3-ylethyl)phenyl]imidazo[1,5-a]pyrazin-3-yl}hexahydroindolizin-3(2H)-one;

(6R,8aS)-6-(8-amino-1-{4-[1-(4-fluorophenyl)-1-hydroxyethyl]phenyl}imidazo[1,5-a]pyrazin-3-yl)hexahydroindolizin-3(2H)-one;

(6R,8aS)-6-{8-amino-1-[2-(hydroxymethyl)-4-{(1S)-1-hydroxy-1-[3-(trifluoromethyl)phenyl]ethyl}phenyl]imidazo[1,5-a]pyrazin-3-yl}hexahydroindolizin-3(2H)-one;

(6R,8aS)-6-{8-amino-1-[2-(hydroxymethyl)-4-{(1R)-1-hydroxy-1-[3-(trifluoromethyl)phenyl]ethyl}phenyl]imidazo[1,5-a]pyrazin-3-yl}hexahydroindolizin-3(2H)-one;

(6R,8aS)-6-[8-amino-1-(2-ethoxy-6-fluoro-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-{8-amino-1-[4-(1-hydroxy-1-phenylethyl)phenyl]imidazo[1,5-a]pyrazin-3-yl}hexahydroindolizin-3(2H)-one;

(6R,8aS)-6-{8-amino-1-[2-fluoro-4-(1-hydroxy-1-phenylethyl)phenyl]imidazo[1,5-a]pyrazin-3-yl}hexahydroindolizin-3(2H)-one;

(6R,8aS)-6-(8-amino-1-{4-[(1R)-2,2,2-trifluoro-1-hydroxy-1-phenylethyl]phenyl}imidazo[1,5-a]pyrazin-3-yl)hexahydroindolizin-3(2H)-one;

(6R,8aS)-6-(8-amino-1-{4-[(1S)-2,2,2-trifluoro-1-hydroxy-1-phenylethyl]phenyl}imidazo[1,5-a]pyrazin-3-yl)hexahydroindolizin-3(2H)-one;

(6R,8aS)-6-[8-amino-1-(4-{2,2,2-trifluoro-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{2,2,2-trifluoro-1-hydroxy-1-[4-(trifluoromethyl)phenyl]ethyl}phenyl)imidazo[1,5-a]pyrazin-3-yl]hexahydroindolizin-3(2H)-one;

(6R,8aS)-6-(8-amino-1-{4-[2,2,2-trifluoro-1-(3-fluorophenyl)-1-hydroxyethyl]phenyl}imidazo[1,5-a]pyrazin-3-yl)hexahydroindolizin-3(2H)-one;

(6R,8aS)-6-{8-amino-1-[2-fluoro-4-(2,2,2-trifluoro-1-hydroxy-1-phenylethyl)phenyl]imidazo[1,5-a]pyrazin-3-yl}hexahydroindolizin-3(2H)-one;

(6R,8aS)-6-(8-amino-1-(4-{1-hydroxy-1-[2-(trifluoromethyl)phenyl]ethyl}phenyl)imidazo[1,5-a]pyrazin-3-yl]hexahydroindolizin-3(2H)-one;

(6R,8aS)-6-(8-amino-1-{4-[2,2,2-trifluoro-1-(4-fluorophenyl)-1-hydroxyethyl]phenyl}imidazo[1,5-a]pyrazin-3-yl)hexahydroindolizin-3(2H)-one;

(6R,8aS)-6-(8-amino-1-{2-methoxy-4-[(1S)-2,2,2-trifluoro-1-hydroxy-1-phenylethyl]phenyl}imidazo[1,5-a]pyrazin-3-yl)hexahydroindolizin-3(2H)-one;

(6R,8aS)-6-(8-amino-1-{2-methoxy-4-[(1S)-2,2,2-trifluoro-1-hydroxy-1-phenylethyl]phenyl}imidazo[1,5-a]pyrazin-3-yl)hexahydroindolizin-3(2H)-one;

(6R,8aS)-6-[8-amino-1-(4-{1-hydroxy-1-[1-methyl-5-(trifluoromethyl)-1H-pyrazol-3-yl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[4-(trifluoromethyl)pyridin-2-yl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[4-(trifluoromethyl)pyridin-2-yl]ethyl}phenyl)imidazo[1,5-a]pyrazin-3-yl]hexahydroindolizin-3(2H)-one;

(6R,8aS)-6-(8-amino-1-{4-[(1R)-1-(3-cyclopropylphenyl)-1-hydroxyethyl]phenyl}imidazo[1,5-a]pyrazin-3-yl)hexahydroindolizin-3(2H)-one;

(6R,8aS)-6-(8-amino-1-{4-[(1S)-1-(3-tert-butylphenyl)-1-hydroxyethyl]phenyl}imidazo[1,5-a]pyrazin-3-yl)hexahydroindolizin-3(2H)-one;

(6R,8aS)-6-(8-amino-1-{4-[(1R)-1-(3-tert-butylphenyl)-1-hydroxyethyl]phenyl}imidazo[1,5-a]pyrazin-3-yl)hexahydroindolizin-3(2H)-one;

(6R,8aS)-6-(8-amino-1-{4-[(1S)-1-(3-chlorophenyl)-1-hydroxyethyl]phenyl}imidazo[1,5-a]pyrazin-3-yl)hexahydroindolizin-3(2H)-one;

(6R,8aS)-6-(8-amino-1-(4-{1-hydroxy-1-[3-(trifluoromethyl)phenyl]ethyl}-3-methylphenyl)imidazo[1,5-a]pyrazin-3-yl)hexahydroindolizin-3(2H)-one;

(6R,8aS)-6-(8-amino-1-(4-{1-hydroxy-1-[3-(trifluoromethyl)phenyl]ethyl}-3-methylphenyl)imidazo[1,5-a]pyrazin-3-yl)hexahydroindolizin-3(2H)-one;

(6R,8aS)-6-(8-amino-1-{4-[(1S)-1-hydroxy-1-(3-methoxyphenyl)ethyl]phenyl}imidazo[1,5-a]pyrazin-3-yl)hexahydroindolizin-3(2H)-one;

(6R,8aS)-6-(8-amino-1-{4-[(1R)-1-hydroxy-1-(3-methoxyphenyl)ethyl]phenyl}imidazo[1,5-a]pyrazin-3-yl)hexahydroindolizin-3(2H)-one;

(6R,8aS)-6-(8-amino-1-{4-[(1R)-1-hydroxy-1-(3-methylphenyl)ethyl]phenyl}imidazo[1,5-a]pyrazin-3-yl)hexahydroindolizin-3(2H)-one;

(6R,8aS)-6-(8-amino-1-{4-[(1S)-1-hydroxy-1-(2-methylphenyl)ethyl]phenyl}imidazo[1,5-a]pyrazin-3-yl)hexahydroindolizin-3(2H)-one;

(6R,8aS)-6-(8-amino-1-{4-[(1R)-1-hydroxy-1-(2-methylphenyl)ethyl]phenyl}imidazo[1,5-a]pyrazin-3-yl)hexahydroindolizin-3(2H)-one;

(6R,8aS)-6-(8-amino-1-{4-[(1S)-1-hydroxy-1-(2-methoxyphenyl)ethyl]phenyl}imidazo[1,5-a]pyrazin-3-yl)hexahydroindolizin-3(2H)-one;

(6R,8aS)-6-(8-amino-1-{4-[(1R)-1-hydroxy-1-(2-methoxyphenyl)ethyl]phenyl}imidazo[1,5-a]pyrazin-3-yl)hexahydroindolizin-3(2H)-one;

(6R,8aS)-6-(8-amino-1-{4-[(1S)-1-(3-cyclopropylphenyl)-1-hydroxyethyl]phenyl}imidazo[1,5-a]pyrazin-3-yl)hexahydroindolizin-3(2H)-one;

(6R,8aS)-6-(8-amino-1-{4-[(1R)-1-(3-chlorophenyl)-1-hydroxyethyl]phenyl}imidazo[1,5-a]pyrazin-3-yl)hexahydroindolizin-3(2H)-one;

(6R,8aS)-6-(8-amino-1-{4-[(1S)-1-hydroxy-1-(3-methylphenyl)ethyl]phenyl}imidazo[1,5-a]pyrazin-3-yl)hexahydroindolizin-3(2H)-one;

(6R,8aS)-6-[8-amino-1-(3-fluoro-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{1-hydroxy-1-[3-(trifluoromethyl)phenyl]propyl}phenyl)imidazo[1,5-a]pyrazin-3-yl]hexahydroindolizin-3(2H)-one;

(6R,8aS)-6-[8-amino-1-(4-{(1S)-1-hydroxy-1-[3-(trifluoromethoxy)phenyl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[3-(trifluoromethoxy)phenyl]ethyl}phenyl)imidazo[1,5-a]pyrazin-3-yl]hexahydroindolizin-3(2H)-one;

(6R,8aS)-6-(8-amino-1-{4-[(1S)-1-biphenyl-3-yl-1-hydroxyethyl]phenyl}imidazo[1,5-a]pyrazin-3-yl)hexahydroindolizin-3(2H)-one;

(6R,8aS)-6-(8-amino-1-{4-[(1R)-1-biphenyl-3-yl-1-hydroxyethyl]phenyl}imidazo[1,5-a]pyrazin-3-yl)hexahydroindolizin-3(2H)-one;

(6R,8aS)-6-[8-amino-1-(3-fluoro-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{1-hydroxy-1-[3-(trifluoromethyl)phenyl]propyl}phenyl)imidazo[1,5-a]pyrazin-3-yl]hexahydroindolizin-3(2H)-one;

(1R)-1-(4-{8-amino-3-[(6R,8aS)-octahydroindolizin-6-yl]imidazo[1,5-a]pyrazin-1-yl}phenyl)-1-[3-(trifluoromethyl)phenyl]ethanol;

(1S)-1-(4-{8-amino-3-[(6R,8aS)-octahydroindolizin-6-yl]imidazo[1,5-a]pyrazin-1-yl}phenyl)-1-[3-(trifluoromethyl)phenyl]ethanol;

(6R,8aS)-6-(8-amino-1-(4-{1-hydroxy-1-[3-(trifluoromethyl)phenyl]ethyl}-3-methoxyphenyl)imidazo[1,5-a]pyrazin-3-yl)hexahydroindolizin-3(2H)-one;

(6R,8aS)-6-(8-amino-1-(4-{1-hydroxy-1-[3-(trifluoromethyl)phenyl]ethyl}-3-methoxyphenyl)imidazo[1,5-a]pyrazin-3-yl)hexahydroindolizin-3(2H)-one;

(6R,8aS)-6-(8-amino-1-{4-[(1R)-1-hydroxy-1-(3-morpholin-4-ylphenyl)ethyl]phenyl}imidazo[1,5-a]pyrazin-3-yl)hexahydroindolizin-3(2H)-one;

(6R,8aS)-6-(8-amino-1-{4-[(1S)-1-hydroxy-1-(3-morpholin-4-ylphenyl)ethyl]phenyl}imidazo[1,5-a]pyrazin-3-yl)hexahydroindolizin-3(2H)-one;

(6R,8aS)-6-(8-amino-1-{4-[(1S)-1-(2-fluorophenyl)-1-hydroxyethyl]phenyl}imidazo[1,5-a]pyrazin-3-yl)hexahydroindolizin-3(2H)-one;

(6R,8aS)-6-(8-amino-1-{4-[(1R)-1-(2-fluorophenyl)-1-hydroxyethyl]phenyl}imidazo[1,5-a]pyrazin-3-yl)hexahydroindolizin-3(2H)-one;

(6R,8aS)-6-[8-amino-1-(4-{(1S)-1-[3-(difluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1R)-1-[3-(difluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{hydroxy[3-(trifluoromethyl)phenyl]methyl}phenyl)imidazo[1,5-a]pyrazin-3-yl]hexahydroindolizin-3(2H)-one;

(6R,8aS)-6-[8-amino-1-(4-{hydroxy[3-(trifluoromethyl)phenyl]methyl}phenyl)imidazo[1,5-a]pyrazin-3-yl]hexahydroindolizin-3(2H)-one;

(6R,8aS)-6-[8-amino-1-(4-{(1S)-1-hydroxy-1-[3-(1-methylethyl)phenyl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[3-(1-methylethyl)phenyl]ethyl}phenyl)imidazo[1,5-a]pyrazin-3-yl]hexahydroindolizin-3(2H)-one;

(6R,8aS)-6-[8-amino-1-(4-{1-hydroxy-2-methyl-1-[3-(trifluoromethyl)phenyl]propyl}phenyl)imidazo[1,5-a]pyrazin-3-yl]hexahydroindolizin-3(2H)-one;

(6R,8aS)-6-[8-amino-1-(4-{(1S)-1-hydroxy-1-[3-(2,2,2-trifluoroethyl)phenyl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[3-(2,2,2-trifluoroethyl)phenyl]ethyl}phenyl)imidazo[1,5-a]pyrazin-3-yl]hexahydroindolizin-3(2H)-one;

(6R,8aS)-6-[8-amino-1-(4-{1-hydroxy-2-methyl-1-[3-(trifluoromethyl)phenyl]propyl}phenyl)imidazo[1,5-a]pyrazin-3-yl]hexahydroindolizin-3(2H)-one;

(6R,8aS)-6-{8-amino-1-[2-(difluoromethyl)-4-{(1S)-1-hydroxy-1-[3-(trifluoromethyl)phenyl]ethyl}phenyl]imidazo[1,5-a]pyrazin-3-yl}hexahydroindolizin-3(2H)-one;

(6R,8aS)-6-{8-amino-1-[2-(difluoromethyl)-4-{(1R)-1-hydroxy-1-[3-(trifluoromethyl)phenyl]ethyl}phenyl]imidazo[1,5-a]pyrazin-3-yl}hexahydroindolizin-3(2H)-one;

(6R,8aS)-6-(8-amino-1-{4-[(1S)-1-(3-cyclobutylphenyl)-1-hydroxyethyl]phenyl}imidazo[1,5-a]pyrazin-3-yl)hexahydroindolizin-3(2H)-one;

(6R,8aS)-6-(8-amino-1-{4-[(1R)-1-(3-cyclobutylphenyl)-1-hydroxyethyl]phenyl}imidazo[1,5-a]pyrazin-3-yl)hexahydroindolizin-3(2H)-one;

3-[(1S)-1-(4-{8-amino-3-[(6R,8aS)-3-oxooctahydroindolizin-6-yl]imidazo[1,5-a]pyrazin-1-yl}phenyl)-1-hydroxyethyl]benzonitrile;

3-[(1R)-1-(4-{8-amino-3-[(6R,8aS)-3-oxooctahydroindolizin-6-yl]imidazo[1,5-a]pyrazin-1-yl}phenyl)-1-hydroxyethyl]benzonitrile;

(6R,8aS)-6-[8-amino-1-(4-{cyclopropyl(hydroxy)[3-(trifluoromethyl)phenyl]methyl}phenyl)imidazo[1,5-a]pyrazin-3-yl]hexahydroindolizin-3(2H)-one;

(6R,8aS)-6-[8-amino-1-(4-{cyclopropyl(hydroxy)[3-(trifluoromethyl)phenyl]methyl}phenyl)imidazo[1,5-a]pyrazin-3-yl]hexahydroindolizin-3(2H)-one;

(6R,8aS)-6-[8-amino-1-(2-cyclopropyl-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{(1R)-1-methoxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{(1S)-1-methoxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{1-hydroxy-1-[3-(trifluoromethyl)phenyl]ethyl}-2-methoxyphenyl)imidazo[1,5-a]pyrazin-3-yl]hexahydroindolizin-3(2H)-one;

(6R,8aS)-6-(8-amino-1-{4-[(1S)-1-(3-ethylphenyl)-1-hydroxyethyl]phenyl}imidazo[1,5-a]pyrazin-3-yl)hexahydroindolizin-3(2H)-one;

(6R,8aS)-6-(8-amino-1-{4-[(1R)-1-(3-ethylphenyl)-1-hydroxyethyl]phenyl}imidazo[1,5-a]pyrazin-3-yl)hexahydroindolizin-3(2H)-one;

(6R,8aS)-6-[8-amino-1-(4-{(1S)-1-[3-(cyclopropyloxy)phenyl]-1-hydroxyethyl}phenyl)imidazo[1,5-a]pyrazin-3-yl]hexahydroindolizin-3(2H)-one;

(6R,8aS)-6-[8-amino-1-(4-{(1R)-1-[3-(cyclopropyloxy)phenyl]-1-hydroxyethyl}phenyl)imidazo[1,5-a]pyrazin-3-yl]hexahydroindolizin-3(2H)-one;

2-(4-{8-amino-3-[(6R,8aS)-3-oxooctahydroindolizin-6-yl]imidazo[1,5-a]pyrazin-1-yl}phenyl)-2-hydroxy-2-[3-(trifluoromethyl)phenyl]acetamide;

2-(4-{8-amino-3-[(6R,8aS)-3-oxooctahydroindolizin-6-yl]imidazo[1,5-a]pyrazin-1-yl}phenyl)-2-hydroxy-2-[3-(trifluoromethyl)phenyl]acetamide;

(6R,8aS)-6-(8-amino-1-{4-[(1R)-1-(3-cyclopropylphenyl)-1-hydroxyethyl]-3-methoxyphenyl}imidazo[1,5-a]pyrazin-3-yl)hexahydroindolizin-3(2H)-one;

(6R,8aS)-6-(8-amino-1-{4-[(1S)-1-(3-cyclopropylphenyl)-1-hydroxyethyl]-3-methoxyphenyl}imidazo[1,5-a]pyrazin-3-yl)hexahydroindolizin-3(2H)-one;

(6R,8aS)-6-[8-amino-1-(2-chloro-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(2-fluoro-4-{(1S)-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(2-fluoro-4-{(1R)-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[3-(trifluoromethyl)phenyl]ethyl}-2-methylphenyl)imidazo[1,5-a]pyrazin-3-yl]hexahydroindolizin-3(2H)-one;

(6R,8aS)-6-[8-amino-1-(4-{(1S)-1-hydroxy-1-[3-(trifluoromethyl)phenyl]ethyl}-2-methylphenyl)imidazo[1,5-a]pyrazin-3-yl]hexahydroindolizin-3(2H)-one;

(6R,8aS)-6-{8-amino-1-[4-{1-hydroxy-1-[3-(trifluoromethyl)phenyl]ethyl}-2-(trifluoromethyl)phenyl]imidazo[1,5-a]pyrazin-3-yl}hexahydroindolizin-3(2H)-one;

(6R,8aS)-6-[8-amino-1-(4-{(1S)-1,2-dihydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{(1R)-1,2-dihydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{2,2-difluoro-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[3-(2,2,2-trifluoro-1,1-dimethylethyl)phenyl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[3-(2,2,2-trifluoro-1,1-dimethylethyl)phenyl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[5-(trifluoromethyl)thiophen-2-yl]ethyl}phenyl)imidazo[1,5-a]pyrazin-3-yl]hexahydroindolizin-3(2H)-one;

(6R,8aS)-6-[8-amino-1-(4-{2,2-difluoro-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[5-(trifluoromethyl)thiophen-2-yl]ethyl}phenyl)imidazo[1,5-a]pyrazin-3-yl]hexahydroindolizin-3(2H)-one;

(4aS,7R)-7-[8-amino-1-(4-{(1R)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one;

(4aS,7R)-7-[8-amino-1-(4-{(1S)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one;

(6R,8aS)-6-(8-amino-5-chloro-1-{4-[(1S)-1-(3-cyclopropylphenyl)-1-hydroxyethyl]phenyl}imidazo[1,5-a]pyrazin-3-yl)hexahydroindolizin-3(2H)-one;

(6R,8aS)-6-(8-amino-5-chloro-1-{4-[(1R)-1-(3-cyclopropylphenyl)-1-hydroxyethyl]phenyl}imidazo[1,5-a]pyrazin-3-yl)hexahydroindolizin-3(2H)-one;

(4aR,7S)-7-[8-amino-1-(4-{(1R)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one;

(7R,9aS)-7-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)octahydro-4H-pyrido[1,2-a]pyrazin-4-one;

(7S,9aR)-7-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)octahydro-4H-pyrido[1,2-a]pyrazin-4-one;

(6R,8aS)-6-[8-amino-5-chloro-1-(4-{(1R)-1-hydroxy-1-[3-(2,2,2-trifluoroethyl)phenyl]ethyl}phenyl)imidazo[1,5-a]pyrazin-3-yl]hexahydroindolizin-3(2H)-one;

(6R,8aS)-6-[8-amino-5-chloro-1-(4-{(1S)-1-hydroxy-1-[3-(2,2,2-trifluoroethyl)phenyl]ethyl}phenyl)imidazo[1,5-a]pyrazin-3-yl]hexahydroindolizin-3(2H)-one;

(6R,8aS)-6-[8-amino-5-chloro-1-(4-{(1S)-1-hydroxy-1-[3-(2,2,2-trifluoro-1,1-dimethylethyl)phenyl]ethyl}phenyl)imidazo[1,5-a]pyrazin-3-yl]hexahydroindolizin-3(2H)-one;

(6R,8aS)-6-[8-amino-5-chloro-1-(4-{(1R)-1-hydroxy-1-[3-(2,2,2-trifluoro-1,1-dimethylethyl)phenyl]ethyl}phenyl)imidazo[1,5-a]pyrazin-3-yl]hexahydroindolizin-3(2H)-one;

(6R,8aS)-6-[8-amino-1-(4-{[2-fluoro-5-(trifluoromethyl)phenyl](hydroxy)methyl}phenyl)imidazo[1,5-a]pyrazin-3-yl]hexahydroindolizin-3(2H)-one;

(6R,8aS)-6-[8-amino-5-chloro-1-(4-{[2-fluoro-5-(trifluoromethyl)phenyl](hydroxy)methyl}phenyl)imidazo[1,5-a]pyrazin-3-yl]hexahydroindolizin-3(2H)-one;

(6R,8aS)-6-[8-amino-1-(4-{hydroxy[2-methyl-5-(trifluoromethyl)phenyl]methyl}phenyl)imidazo[1,5-a]pyrazin-3-yl]hexahydroindolizin-3(2H)-one;

(6R,8aS)-6-[8-amino-1-(4-{[2-fluoro-5-(trifluoromethyl)phenyl](hydroxy)methyl}phenyl)imidazo[1,5-a]pyrazin-3-yl]hexahydroindolizin-3(2H)-one;

(6R,8aS)-6-[8-amino-5-chloro-1-(4-{[2-fluoro-5-(trifluoromethyl)phenyl](hydroxy)methyl}phenyl)imidazo[1,5-a]pyrazin-3-yl]hexahydroindolizin-3(2H)-one;

(6R,8aS)-6-[8-amino-1-(4-{hydroxy[2-methyl-5-(trifluoromethyl)phenyl]methyl}phenyl)imidazo[1,5-a]pyrazin-3-yl]hexahydroindolizin-3(2H)-one;

(6R,8aS)-6-[8-amino-1-(4-{(1S)-1-[3-(1,1-difluoroethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1R)-1-[3-(1,1-difluoroethyl)phenyl]-1-hydroxyethyl}phenyl)imidazo[1,5-a]pyrazin-3-yl]hexahydroindolizin-3(2H)-one;

(6R,8aS)-6-[8-amino-5-chloro-1-(4-{(1S)-1-[3-(difluoromethyl)phenyl]-1-hydroxyethyl}phenyl)imidazo[1,5-a]pyrazin-3-yl]hexahydroindolizin-3(2H)-one;

(6R,8aS)-6-[8-amino-5-chloro-1-(4-{(1R)-1-[3-(difluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1S)-1-hydroxy-1-[5-(trifluoromethyl)pyridin-3-yl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[5-(trifluoromethyl)pyridin-3-yl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[6-(trifluoromethyl)pyridin-2-yl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[6-(trifluoromethyl)pyridin-2-yl]ethyl}phenyl)imidazo[1,5-a]pyrazin-3-yl]hexahydroindolizin-3(2H)-one;

(6R,8aS)-6-[8-amino-5-chloro-1-(4-{(1S)-1-[3-(1,1-difluoroethyl)phenyl]-1-hydroxyethyl}phenyl)imidazo[1,5-a]pyrazin-3-yl]hexahydroindolizin-3(2H)-one;

(6R,8aS)-6-[8-amino-5-chloro-1-(4-{(1R)-1-[3-(1,1-difluoroethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1S)-1-hydroxy-1-[3-(trifluoromethyl)phenyl]ethyl}-2-methoxyphenyl)imidazo[1,5-a]pyrazin-3-yl]hexahydroindolizin-3(2H)-one;

(6R,8aS)-6-[8-amino-1-(4-{(1R)-1-hydroxy-1-[3-(trifluoromethyl)phenyl]ethyl}-2-methoxyphenyl)imidazo[1,5-a]pyrazin-3-yl]hexahydroindolizin-3(2H)-one;

(6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3(2H)-one;

(6R,8aS)-6-[8-amino-1-(4-{1-[3-(difluoromethoxy)phenyl]-1-hydroxyethyl}phenyl)imidazo[1,5-a]pyrazin-3-yl]hexahydroindolizin-3(2H)-one;

(6R,8aS)-6-[8-amino-1-(4-{1-[2-fluoro-5-(trifluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{1-[3,5-bis(trifluoromethyl)phenyl]-1-hydroxyethyl}phenyl)imidazo[1,5-a]pyrazin-3-yl]hexahydroindolizin-3(2H)-one;

(6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3(2H)-one;

(6R,8aS)-6-[8-amino-1-(4-{1-[3-(difluoromethoxy)phenyl]-1-hydroxyethyl}phenyl)imidazo[1,5-a]pyrazin-3-yl]hexahydroindolizin-3(2H)-one;

(6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3(2H)-one;

(6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3(2H)-one;

(6R,8aS)-6-[8-amino-1-(4-{1-[2-fluoro-5-(trifluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1R)-1-hydroxy-1-[3-(1H-imidazol-1-yl)phenyl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[3-(1H-imidazol-1-yl)phenyl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[2-(trifluoromethyl)pyridin-4-yl]ethyl}phenyl)imidazo[1,5-a]pyrazin-3-yl]hexahydroindolizin-3(2H)-one;

(6R,8aS)-6-[8-amino-1-(4-{(1R)-1-hydroxy-1-[2-(trifluoromethyl)pyridin-4-yl]ethyl}phenyl)imidazo[1,5-a]pyrazin-3-yl]hexahydroindolizin-3(2H)-one;

(7S,9aR)-7-[8-amino-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one;

(7R,9aS)-7-[8-amino-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one;

(6R,8aS)-6-[8-amino-5-fluoro-1-(4-{(1R)-1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one;

(6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one;

(6S,8aR)-6-[8-amino-1-(4-{(1R)-1-hydroxy-1-[3-(trifluoromethyl)phenyl]ethyl}phenyl)imidazo[1,5-a]pyrazin-3-yl]-1,1-dimethylhexahydroindolizin-3(2H)-one;

(6R,8aS)-6-[8-amino-1-(2-ethoxy-4-{1-hydroxy-1-[3-(trifluoromethyl)phenyl]ethyl}phenyl)imidazo[1,5-a]pyrazin-3-yl]hexahydroindolizin-3(2H)-one;

(6S,8aR)-6-[8-amino-1-(4-{(1R)-1-hydroxy-1-[3-(trifluoromethyl)phenyl]ethyl}phenyl)imidazo[1,5-a]pyrazin-3-yl]-1,1-dimethylhexahydroindolizin-3(2H)-one;

(6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one;

(6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one;

(6R,8aS)-6-(8-amino-1-{2-ethoxy-4-[1-hydroxy-1-(3-methylphenyl)ethyl]phenyl}imidazo[1,5-a]pyrazin-3-yl)hexahydroindolizin-3(2H)-one;

(6R,8aS)-6-[8-amino-1-(2-ethoxy-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-(8-amino-1-{2-ethoxy-4-[1-hydroxy-1-(3-methylphenyl)ethyl]phenyl}imidazo[1,5-a]pyrazin-3-yl)hexahydroindolizin-3(2H)-one;

(3R,8aR)-3-[8-amino-1-(4-{(1R)-1-hydroxy-1-[3-(trifluoromethyl)phenyl]ethyl}phenyl)imidazo[1,5-a]pyrazin-3-yl]hexahydro-6H-pyrrolo[2,1-c][1,4]oxazin-6-one;

(7R,9aR)-7-[8-amino-1-(4-{(1R)-1-hydroxy-1-[3-(trifluoromethyl)phenyl]ethyl}phenyl)imidazo[1,5-a]pyrazin-3-yl]-1,1-difluorooctahydro-4H-quinolizin-4-one;

(7S,9aS)-7-[8-amino-1-(4-{(1R)-1-hydroxy-1-[3-(trifluoromethyl)phenyl]ethyl}phenyl)imidazo[1,5-a]pyrazin-3-yl]-1,1-difluorooctahydro-4H-quinolizin-4-one;

(1S,6R,8aR)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3(2H)-one;

(6R,8aS)-6-[8-amino-1-(4-{(1R)-1-hydroxy-1-[3-(trifluoromethyl)phenyl]ethyl}phenyl)-5-(trifluoromethyl)imidazo[1,5-a]pyrazin-3-yl]hexahydroindolizin-3(2H)-one;

(7S,9aR)-7-[8-amino-5-chloro-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one;

(7R,9aS)-7-[8-amino-5-chloro-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one;

(7R,9aR)-7-[8-amino-1-(4-{(1R)-1-hydroxy-1-[3-(trifluoromethyl)phenyl]ethyl}phenyl)imidazo[1,5-a]pyrazin-3-yl]tetrahydro-1H-[1,4]oxazino[3,4-c][1,4]oxazin-4(3H)-one;

(6R,8aS)-6-[8-amino-1-(4-{(1R)-1-[3-(difluoromethyl)phenyl]-1-hydroxyethyl}phenyl)imidazo[1,5-a]pyrazin-3-yl]-1,1-dimethylhexahydroindolizin-3(2H)-one;

(6R,8aS)-6-[8-amino-1-(4-{(1R)-1-[3-(difluoromethyl)phenyl]-1-hydroxyethyl}phenyl)-5-fluoroimidazo[1,5-a]pyrazin-3-yl]-2,2-dimethylhexahydroindolizin-3(2H)-one;

(1R,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3(2H)-one;

(1R,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3(2H)-one;

(6R,8aS)-6-[8-amino-1-(4-{(1R)-1-[3-(difluoromethyl)phenyl]-1-hydroxyethyl}phenyl)imidazo[1,5-a]pyrazin-3-yl]-2,2-dimethylhexahydroindolizin-3(2H)-one;

(1R,6R,8aS)-6-[8-amino-1-(4-{(1R)-1-[3-(difluoromethyl)phenyl]-1-hydroxyethyl}phenyl)imidazo[1,5-a]pyrazin-3-yl]-1-(trifluoromethyl)hexahydroindolizin-3(2H)-one;

(6R,8aS)-6-[8-amino-5-fluoro-1-(2-fluoro-4-{1-hydroxy-1-[3-(trifluoromethyl)phenyl]ethyl}phenyl)imidazo[1,5-a]pyrazin-3-yl]hexahydroindolizin-3(2H)-one;

(1R,6R,8aS)-6-[8-amino-1-(4-{(1R)-1-[3-(difluoromethyl)phenyl]-1-hydroxyethyl}phenyl)imidazo[1,5-a]pyrazin-3-yl]-1-(trifluoromethyl)hexahydroindolizin-3(2H)-one;

(6R,8aS)-6-[8-amino-5-fluoro-1-(2-fluoro-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(2-ethoxy-4-{(1S)-1-hydroxy-1-[3-(trifluoromethyl)phenyl]ethyl}phenyl)imidazo[1,5-a]pyrazin-3-yl]-1,1-dimethylhexahydroindolizin-3(2H)-one;

(6R,8aS)-6-[8-amino-1-(4-{(1R)-1-[3-(difluoromethyl)phenyl]-1-hydroxyethyl}phenyl)imidazo[1,5-a]pyrazin-3-yl]-1,1-dimethyltetrahydro-1H-[1,3]oxazolo[4,3-c][1,4]oxazin-3-one;

(6'R,8a'S)-6'-[8-amino-1-(4-{(1R)-1-hydroxy-1-[3-(trifluoromethyl)phenyl]ethyl}phenyl)imidazo[1,5-a]pyrazin-3-yl]tetrahydro-5'H-spiro[cyclopropane-1,1'-indolizin]-3'(2'H)-one;

(6'R,8a'S)-6'-[8-amino-1-(4-{(1R)-1-[3-(difluoromethyl)phenyl]-1-hydroxyethyl}phenyl)imidazo[1,5-a]pyrazin-3-yl]tetrahydro-5'H-spiro[cyclopropane-1,1'-indolizin]-3'(2'H)-one;

(6R,8aS)-6-[8-amino-5-chloro-1-(2-fluoro-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-1,1-dimethylhexahydroindolizin-3(2H)-one;

(6R,8aS)-6-[8-amino-1-(4-{1-[3-(difluoromethyl)phenyl]-1-hydroxyethyl}-2-fluorophenyl)imidazo[1,5-a]pyrazin-3-yl]hexahydroindolizin-3(2H)-one;

(6R,8aS)-6-[8-amino-5-chloro-1-(2-fluoro-4-{1-hydroxy-1-[3-(trifluoromethyl)phenyl]ethyl}phenyl)imidazo[1,5-a]pyrazin-3-yl]hexahydroindolizin-3(2H)-one;

(6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-1,1-dimethylhexahydroindolizin-3(2H)-one;

(6R,8aS)-6-[8-amino-1-(4-{1-[3-(difluoromethyl)phenyl]-1-hydroxyethyl}-2-fluorophenyl)imidazo[1,5-a]pyrazin-3-yl]hexahydroindolizin-3(2H)-one;

(6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-2,2-dimethylhexahydroindolizin-3(2H)-one;

(6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-2,2-dimethylhexahydroindolizin-3(2H)-one;

(6R,8aS)-6-[8-amino-5-fluoro-1-(4-{(1R)-1-hydroxy-1-[3-(trifluoromethyl)phenyl]ethyl}phenyl)imidazo[1,5-a]pyrazin-3-yl]-2,2-dimethylhexahydroindolizin-3(2H)-one;

(6R,8aS)-6-[8-amino-1-(4-{(1R)-1-[3-(difluoromethyl)phenyl]-1-hydroxyethyl}phenyl)-5-fluoroimidazo[1,5-a]pyrazin-3-yl]hexahydroindolizin-3(2H)-one;

(6R,8aS)-6-[8-amino-1-(4-{1-[3-(difluoromethyl)phenyl]-1-hydroxyethyl}-2-fluorophenyl)imidazo[1,5-a]pyrazin-3-yl]-1,1-dimethylhexahydroindolizin-3(2H)-one;

(6R,8aS)-6-[8-amino-1-(4-{1-[3-(difluoromethyl)phenyl]-1-hydroxyethyl}-2-fluorophenyl)imidazo[1,5-a]pyrazin-3-yl]-2,2-dimethylhexahydroindolizin-3(2H)-one;

(6R,8aS)-6-[8-amino-1-(4-{1-[3-(difluoromethyl)phenyl]-1-hydroxyethyl}-2-fluorophenyl)imidazo[1,5-a]pyrazin-3-yl]-1,1-dimethylhexahydroindolizin-3(2H)-one;
(6R,8aS)-6-[8-amino-1-(4-{1-[3-(difluoromethyl)phenyl]-1-hydroxyethyl}-2-fluorophenyl)imidazo[1,5-a]pyrazin-3-yl]-2,2-dimethylhexahydroindolizin-3(2H)-one;
(6R,8aS)-6-[8-amino-1-(2-ethoxy-4-{(1S)-1-hydroxy-1-[3-(trifluoromethyl)phenyl]ethyl}phenyl)-5-fluoroimidazo[1,5-a]pyrazin-3-yl]hexahydroindolizin-3(2H)-one;
(6R,8aS)-6-[8-amino-1-(4-{1-hydroxy-1-[3-(trifluoromethyl)phenyl]ethyl}-2-methoxyphenyl)imidazo[1,5-a]pyrazin-3-yl]-1,1-dimethylhexahydroindolizin-3(2H)-one;
(6R,8aS)-6-[8-amino-1-(4-{(1S)-1-hydroxy-1-[3-(trifluoromethyl)phenyl]ethyl}-2-methoxyphenyl)imidazo[1,5-a]pyrazin-3-yl]-2,2-dimethylhexahydroindolizin-3(2H)-one;
(6R,8aS)-6-[8-amino-1-(4-{1-[3-(difluoromethyl)phenyl]-1-hydroxyethyl}-2-fluorophenyl)-5-fluoroimidazo[1,5-a]pyrazin-3-yl]hexahydroindolizin-3(2H)-one;
(6R,8aS)-6-[8-amino-1-(4-{1-[3-(difluoromethyl)phenyl]-1-hydroxyethyl}-2-fluorophenyl)-5-fluoroimidazo[1,5-a]pyrazin-3-yl]hexahydroindolizin-3(2H)-one;
(6R,8aS)-6-[8-amino-1-(4-{1-hydroxy-1-[3-(trifluoromethyl)phenyl]ethyl}-2-methoxyphenyl)imidazo[1,5-a]pyrazin-3-yl]-1,1-dimethylhexahydroindolizin-3(2H)-one;
(6R,8aS)-6-[8-amino-1-(4-{1-[3-(difluoromethyl)phenyl]-2,2,2-trifluoro-1-hydroxyethyl}-2-methoxyphenyl)imidazo[1,5-a]pyrazin-3-yl]hexahydroindolizin-3(2H)-one;
(6R,8aS)-6-[8-amino-1-(4-{1-[3-(difluoromethyl)phenyl]-2,2,2-trifluoro-1-hydroxyethyl}-2-methoxyphenyl)imidazo[1,5-a]pyrazin-3-yl]hexahydroindolizin-3(2H)-one;
(6R,8aS)-6-[8-amino-1-(2-ethoxy-6-fluoro-4-{(1S)-1-hydroxy-1-[3-(trifluoromethyl)phenyl]ethyl}phenyl)imidazo[1,5-a]pyrazin-3-yl]hexahydroindolizin-3(2H)-one;
(6R,8aS)-6-[8-amino-1-(2-ethoxy-6-fluoro-4-{(1R)-1-hydroxy-1-[3-(trifluoromethyl)phenyl]ethyl}phenyl)imidazo[1,5-a]pyrazin-3-yl]hexahydroindolizin-3(2H)-one;
(6R,8aS)-6-[8-amino-1-(2-ethoxy-4-{2,2,2-trifluoro-1-hydroxy-1-[3-(trifluoromethyl)phenyl]ethyl}phenyl)imidazo[1,5-a]pyrazin-3-yl]hexahydroindolizin-3(2H)-one;
(7'R,9a'S)-7'-[8-amino-1-(4-{(1R)-1-hydroxy-1-[3-(trifluoromethyl)phenyl]ethyl}phenyl)imidazo[1,5-a]pyrazin-3-yl]hexahydro-2'H-spiro[cyclopropane-1,3'-pyrido[1,2-a]pyrazin]-4'-one;
5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one (D1);
5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one (D2);
5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one (D3); and
5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one (D4).

The compounds of this invention include the salts, solvates, hydrates or prodrugs of the compounds. The use of the terms "salt", "solvate", "hydrate", "prodrug" and the like, is intended to equally apply to the salt, solvate, hydrate and prodrug of enantiomers, stereoisomers, rotamers, tautomers, positional isomers, or racemates of the inventive compounds.

Salts

The Btk inhibitor compounds of the present invention, which can be in the form of a free base, may be isolated from the reaction mixture in the form of a pharmaceutically acceptable salt.

The compounds of Formula I can form salts which are also within the scope of this invention. Reference to a compound of Formula I herein is understood to include reference to pharmaceutically acceptable salts thereof, unless otherwise indicated. The term "pharmaceutically acceptable salt(s)" or "salt", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Crystals

The Btk inhibitor compounds of the present invention may exist as amorphous forms or crystalline forms.

The compounds of Formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

Solvates

The compounds having Formula I or the pharmaceutically acceptable salts may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

One or more compounds of the invention having Formula I or the pharmaceutically acceptable salts or solvates thereof may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example IR spectroscopy, show the presence of the solvent (or water) in the crystals as a solvate (or hydrate).

Optical Isomers

The compounds of Formula I may contain asymmetric or chiral centers, and, therefore, exist in different stereoisomeric forms. It is intended that all stereoisomeric forms of the compounds of Formula I, as well as mixtures thereof, including racemic mixtures, form part of the present invention. In addition, the present invention embraces all geometric and positional isomers. For example, if a compound of Formula I incorporates a double bond or a fused ring, both the cis- and trans-forms, as well as mixtures, are embraced within the scope of the invention. Such stereoisomeric forms also include enantiomers and diastereoisomers, etc.

For chiral compounds, methods for asymmetric synthesis whereby the pure stereoisomers are obtained are well known in the art, e.g. synthesis with chiral induction, synthesis starting from chiral intermediates, enantioselective enzymatic conversions, separation of stereoisomers using chromatography on chiral media. Such methods are described in Chirality in Industry (edited by A. N. Collins, G. N. Sheldrake and J. Crosby, 1992; John Wiley). Likewise methods for synthesis of geometrical isomers are also well known in the art.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Also, some of the compounds of Formula I may be atropisomers (e.g. substituted biaryls) and are considered as part of this invention. Enantiomers can also be separated by use of chiral HPLC column.

It is also possible that the compounds of Formula I may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Prodrugs

A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of Formula I or a pharmaceutically acceptable salt, hydrate or solvate of the compound. The transformation may occur by various mechanisms (e.g. by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Isotopes

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula I (e.g. those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples hereinbelow, by substituting an appropriate isotopically labeled reagent for a non-isotopically labeled reagent.

Utilities

The compounds having Formula I and pharmaceutical compositions thereof can be used to treat or prevent a variety of conditions, diseases or disorders mediated by Bruton's Tyrosine kinase (Btk). Such Btk-mediated conditions, diseases or disorders include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g. precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors, myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; and (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula I and salts thereof for use in therapy, and particularly in the treatment of disorders, diseases and conditions mediated by inappropriate Btk activity.

The inappropriate Btk activity referred to herein is any Btk activity that deviates from the normal Btk activity expected in a particular mammalian subject. Inappropriate Btk activity may take the form of, for instance, an abnormal increase in activity, or an aberration in the timing and or control of Btk activity. Such inappropriate activity may result then, for example, from overexpression or mutation of the protein kinase leading to inappropriate or uncontrolled activation.

In one embodiment, the present invention provides for the use of a compound of Formula I, or a pharmaceutically acceptable salt thereof for the manufacture of a medicament for the treatment of a Btk-mediated disorder.

In another embodiment, the present invention provides methods of regulating, modulating, or inhibiting Btk for the prevention and/or treatment of disorders related to unregulated or inappropriate Btk activity.

In a further embodiment, the present invention provides a method for treating a subject suffering from a disorder mediated by Btk, which comprises administering to said subject a compound of Formula I or a pharmaceutically acceptable salt thereof in an amount effective to treat the Btk-mediated disorder.

A further aspect of the invention resides in the use of a compound of Formula I or a pharmaceutically acceptable salt thereof for the manufacture of a medicament to be used for the treatment of chronic B cell disorders in which T cells play a prominent role.

Thus, the compounds according to the invention may be used in therapies to treat or prevent Bruton's Tyrosine Kinase (Btk) mediated diseases, conditions and disorders. Btk mediated diseases, conditions and disorders as used herein, mean any disease, condition or disorder in which B cells, mast cells, myeloid cells or osteoclasts play a central role. These diseases include but are not limited to, immune, autoimmune and inflammatory diseases, allergies, infectious diseases, bone resorption disorders and proliferative diseases.

Immune, autoimmune and inflammatory diseases that may be treated or prevented with the compounds of the present invention include rheumatic diseases (e.g. rheumatoid arthritis, psoriatic arthritis, infectious arthritis, progressive chronic arthritis, deforming arthritis, osteoarthritis, traumatic arthritis, gouty arthritis, Reiter's syndrome, polychondritis, acute synovitis and spondylitis), glomerulonephritis (with or without nephrotic syndrome), Goodpasture's syndrome, (and associated glomerulonephritis and pulmonary hemorrhage), atherosclerosis, autoimmune hematologic disorders (e.g. hemolytic anemia, aplastic anemia, idiopathic thrombocytopenia, chronic idiopathic thrombocytopenic purpura (ITP), and neutropenia), autoimmune gastritis, and autoimmune inflammatory bowel diseases (e.g. ulcerative colitis and Crohn's disease), irritable bowel syndrome, host versus graft disease, allograft rejection, chronic thyroiditis, Graves' disease, Sjorgren's disease, scleroderma, diabetes (type I and type II), active hepatitis (acute and chronic), pancreatitis, primary billiary cirrhosis, myasthenia gravis, multiple sclerosis, systemic lupus erythematosis, psoriasis, atopic dermatitis, dermatomyositis, contact dermatitis, eczema, skin sunburns, vasculitis (e.g. Behcet's disease), ANCA-associated and other vasculitudes, chronic renal insufficiency, Stevens-Johnson syndrome, inflammatory pain, idiopathic sprue, cachexia, sarcoidosis, Guillain-Barré syndrome, uveitis, conjunctivitis, kerato conjunctivitis, otitis media, periodontal disease, Addison's disease, Parkinson's disease, Alzheimer's disease, diabetes, septic shock, myasthenia gravis, pulmonary interstitial fibrosis, asthma, bronchitis, rhinitis, sinusitis, pneumoconiosis, pulmonary insufficiency syndrome, pulmonary emphysema, pulmonary fibrosis, silicosis, chronic inflammatory pulmonary disease (e.g. chronic obstructive pulmonary disease) and other inflammatory or obstructive disease on airways.

Allergies that may be treated or prevented include, among others, allergies to foods, food additives, insect poisons, dust mites, pollen, animal materials and contact allergans, type I hypersensitivity allergic asthma, allergic rhinitis, allergic conjunctivitis.

Infectious diseases that may be treated or prevented include, among others, sepsis, septic shock, endotoxic shock, sepsis by Gram-negative bacteria, shigellosis, meningitis, cerebral malaria, pneumonia, tuberculosis, viral myocarditis, viral hepatitis (hepatitis A, hepatitis B and hepatitis C), HIV infection, retinitis caused by cytomegalovirus, influenza, herpes, treatment of infections associated with severe burns, myalgias caused by infections, cachexia secondary to infections, and veterinary viral infections such as lentivirus, caprine arthritic virus, visna-maedi virus, feline immunodeficiency virus, bovine immunodeficiency virus or canine immunodeficiency virus.

Bone resorption disorders that may be treated or prevented include, among others, osteoporosis, osteoarthritis, traumatic arthritis, gouty arthritis and bone disorders related with multiple myeloma.

Proliferative diseases that may be treated or prevented include, among others, non-Hodgkin lymphoma (in particular the subtypes diffuse large B-cell lymphoma (DLBCL) and mantle cell lymphoma (MCL)), B cell chronic lymphocytic leukemia and acute lymphoblastic leukemia (ALL) with mature B cell, ALL in particular.

In particular the compounds of Formula I or pharmaceutically acceptable salts may be used for the treatment of B cell lymphomas resulting from chronic active B cell receptor signaling.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Btk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

Combination Therapy

Included herein are methods of treatment and/or pharmaceutical compositions in which at least one compound of Formula I or a pharmaceutically acceptable salt thereof is administered in combination with at least one other active agent. The other active agent is an anti-inflammatory agent, an immunosuppressant agent, or a chemotherapeutic agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory agent is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant agent, such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been dMPLCvered that BTK inhibitors are useful as chemosensitizing agents, and, thus, are useful in combination with other chemotherapeutic agents, in particular, drugs that induce apoptosis. Examples of other chemotherapeutic agents that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. J. Exp. Med. 2005 201(11):1837-1852).

The compound(s) of Formula I and the other pharmaceutically active agent(s) may be administered together or separately and, when administered separately this may occur simultaneously or sequentially in any order. The amounts of the compound(s) of Formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) nonselective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2), p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for "triple combination" therapy, comprising a compound of Formula I or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol).

For the treatment of cancer a compound of Formula I may be combined with one or more of an anticancer agents. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpimase, IM862, acetyldinanaline, 5-amino-1-[[3,5-dichloro-4-(4-chlorobenzoyl)phenyl]methyl]-1H-1,2,3-triazole-4-carboxamide, CM 101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. No. 60/235, 708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PC132765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1l-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate;

levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent, carrier or excipient represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Pharmaceutical Compositions

While it is possible that, for use in therapy, a compound of Formula I, as well as salts, solvates and physiological functional derivatives thereof, may be administered as the raw chemical, it is possible to present the active ingredient as a pharmaceutical composition. Accordingly, the invention further provides a pharmaceutical composition which comprises a compound of Formula I and salts, solvates and physiological functional derivatives thereof, and one or more pharmaceutically acceptable carriers, diluents, or excipients. The compounds of the Formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula I, or salts, solvates and physiological functional derivatives thereof, with one or more pharmaceutically acceptable carriers, diluents or excipients.

Routes of Administration

Pharmaceutical compositions of the present invention may be presented in unit dose forms containing a predetermined amount of active ingredient per unit dose. Such a unit may contain, for example, 5 g to 1 g, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, sublingual, subcutaneous, local or parenteral (including intravenous and intramuscular) route, and the like, all in unit dosage forms for administration. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, Chronic Obstructive Pulmonary disease (COPD) or Acute Respiratory Distress Syndrome (ARDS).

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula I is in a particle-size-reduced form, and more preferably the size-reduced form is obtained or obtainable by micronisation. The preferable particle size of the size-reduced (e.g. micronised) compound or salt or solvate is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula I or salt or solvate thereof (preferably in particle-size-reduced form, e.g. in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula I or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (IVAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurized aerosols, nebulizers or insufflators.

For pharmaceutical compositions suitable and/or adapted for intranasal administration, the compound of Formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The invention further includes a pharmaceutical composition of a compound of Formula I or pharmaceutically acceptable salts thereof, as hereinbefore described, in combination with packaging material suitable for said composition, said packaging material including instructions for the use of the composition for the use as hereinbefore described.

The following are examples of representative pharmaceutical dosage forms for the compounds of this invention:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
| --- | --- |
| Compound of Formula I | 25 |
| Lactose Powder | 573.5 |
| Magnesium Stearate | 1.5 |
| | 600 |

| Aerosol | Per canister |
| --- | --- |
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the particular compound having Formula I, the nature of the formulation, and the route of administration, and will ultimately be at the discretion of the attendant physician or veterinarian. However, an effective amount of a compound of Formula I for the treatment of diseases or conditions associated with inappropriate Btk activity, will generally be in the range of 5 μg to 100 mg/kg body weight of recipient (mammal) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

In general parenteral administration requires lower dosages than other methods of administration which are more dependent upon absorption. However, a dosage for humans preferably contains 0.0001-25 mg of a compound of Formula I or pharmaceutically acceptable salts thereof per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

General Synthesis

The compounds of the present invention can be prepared by methods well known in the art of organic chemistry. See, for example, J. March, 'Advanced Organic Chemistry' $4^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts 'Protective Groups in Organic Synthesis' $3^{rd}$ Edition, John Wiley and Sons, 1999. The protective groups are optionally removed at a convenient subsequent stage using methods well known in the art.

The products of the reactions are optionally isolated and purified, if desired, using conventional techniques, but not limited to, filtration, distillation, crystallization, chromatography and the like. Such materials are optionally characterized using conventional means, including physical constants and spectral data.

The compounds of Formula I can be prepared by the general synthetic routes shown in the schemes below.

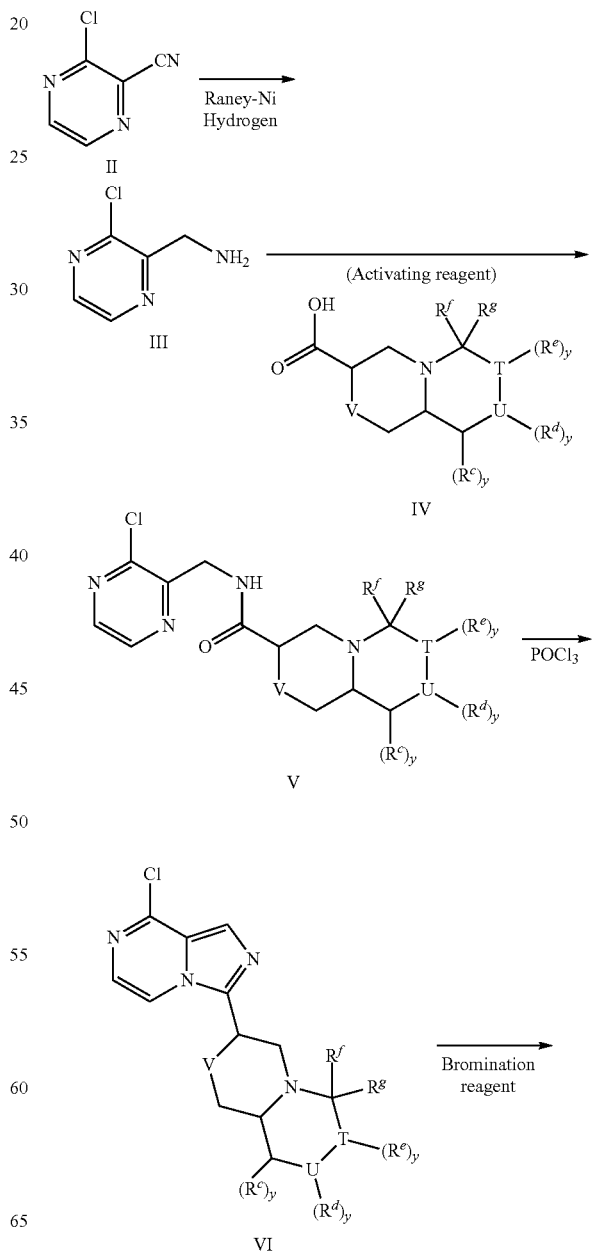

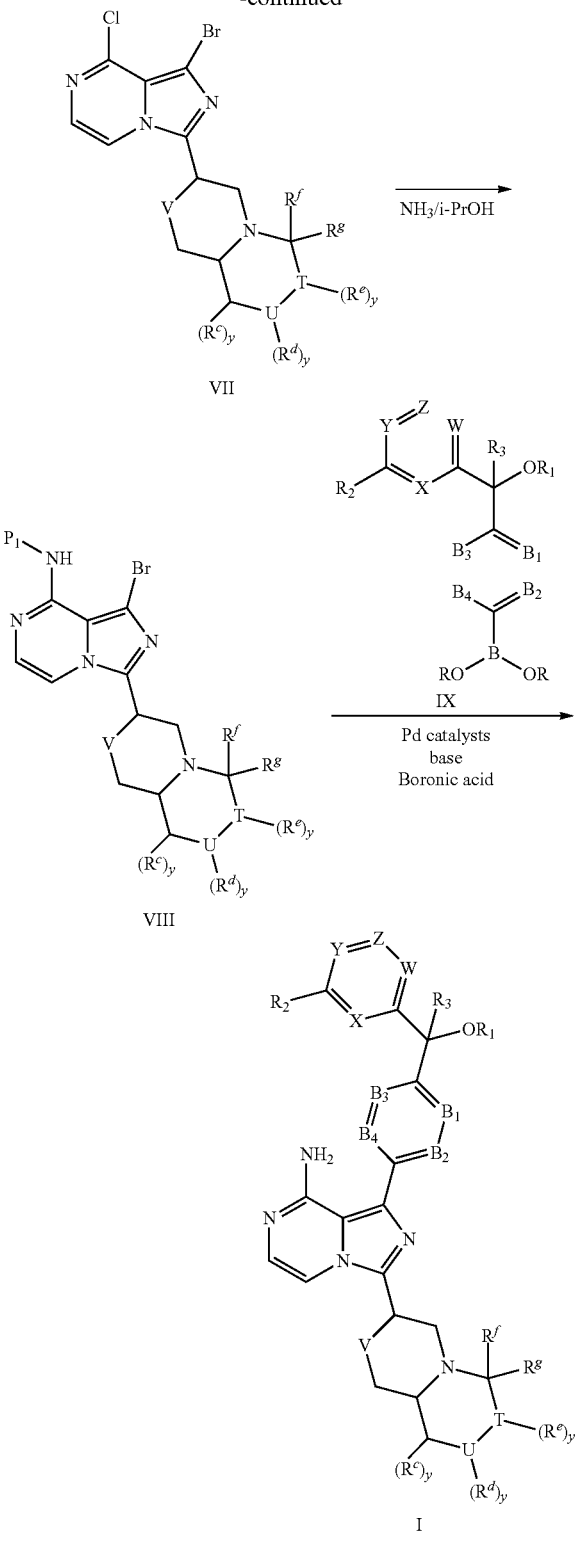

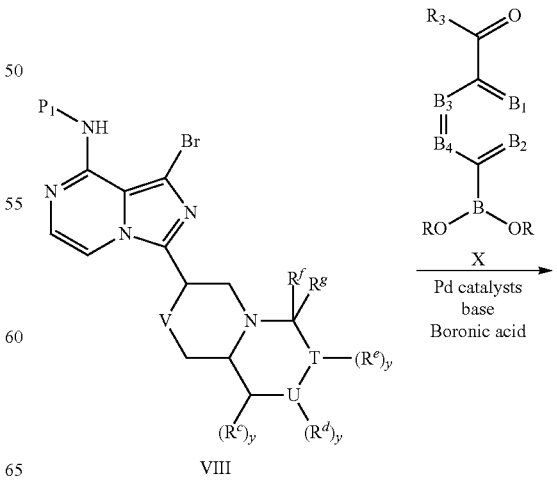

DIPEA, N-methylmorpholine, 4-DMAP or triethylamine and in the presence of a coupling reagent such as PyBOP, TBTU, EDCI or HATU to form N-((3-chloropyrazin-2-yl)methyl)amide (V). Cyclisation chloropyrazine (V) can be performed using condensation reagents like phosphorousoxychloride under heating conditions to provide the 8-chloroimidazo[1,5-a]pyrazine derivatives VI. Subsequent bromination can be accomplished using bromine or N-bromosuccinimide in a suitable solvent like DCM or DMF at appropriate temperature to obtain compounds of formula VII. 8-Aminoimidazo[1,5-a]pyrazine derivatives (VIII) can be prepared from compounds of formula VII using ammonia (gas) in isopropanol at elevated temperature in a pressure vessel (>4 atm). Compounds of formula I can be prepared from compounds of formula VIII using an appropriate boronic acid or pinacol ester (IX), in the presence of a suitable palladium catalyst system, for example bis(diphenylphosphino)ferrocene palladium(II)chloride complex or tetrakis(triphenylphosphine)palladium(0) in the presence of an inorganic base like potassium carbonate, cesium carbonate or potassium phosphate in a suitable solvent system like combinations of dioxane and water. Palladium catalysts and conditions to form either the pinacol esters or to couple the boronic acids or pinacol esters with the 1-bromoimidazo[1,5-a]pyrazin-8-amine are well known to the skilled organic chemist (see, for example, Ei-ichi Negishi (Editor), Armin de Meijere (Associate Editor), Handbook of Organopalladium Chemistry for Organic Synthesis, John Wiley and Sons, 2002). The bicyclic carboxylic compounds like IV can be readily prepared using methods well known to the skilled organic chemist, which are illustrated in the schemes.

Scheme II

Reduction of 3-chloropyrazine-2-carbonitrile (II) can be accomplished by hydrogenation in the presence of a suitable catalyst system and solvent, for example Raney-Nickel ethanol to provide (3-chloropyrazin-2-yl)methanamine (III). This can then be reacted with the bicyclic carboxylic acid (IV). The reaction of IV can be carried out in a solvent such as DMF, THF or DCM in the presence of a base such as

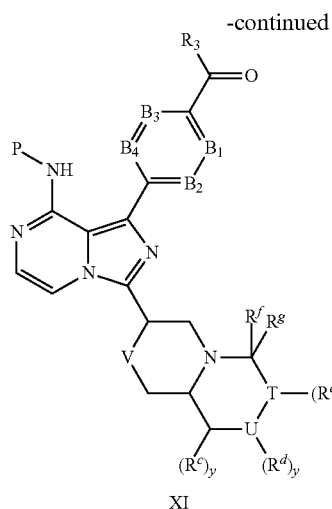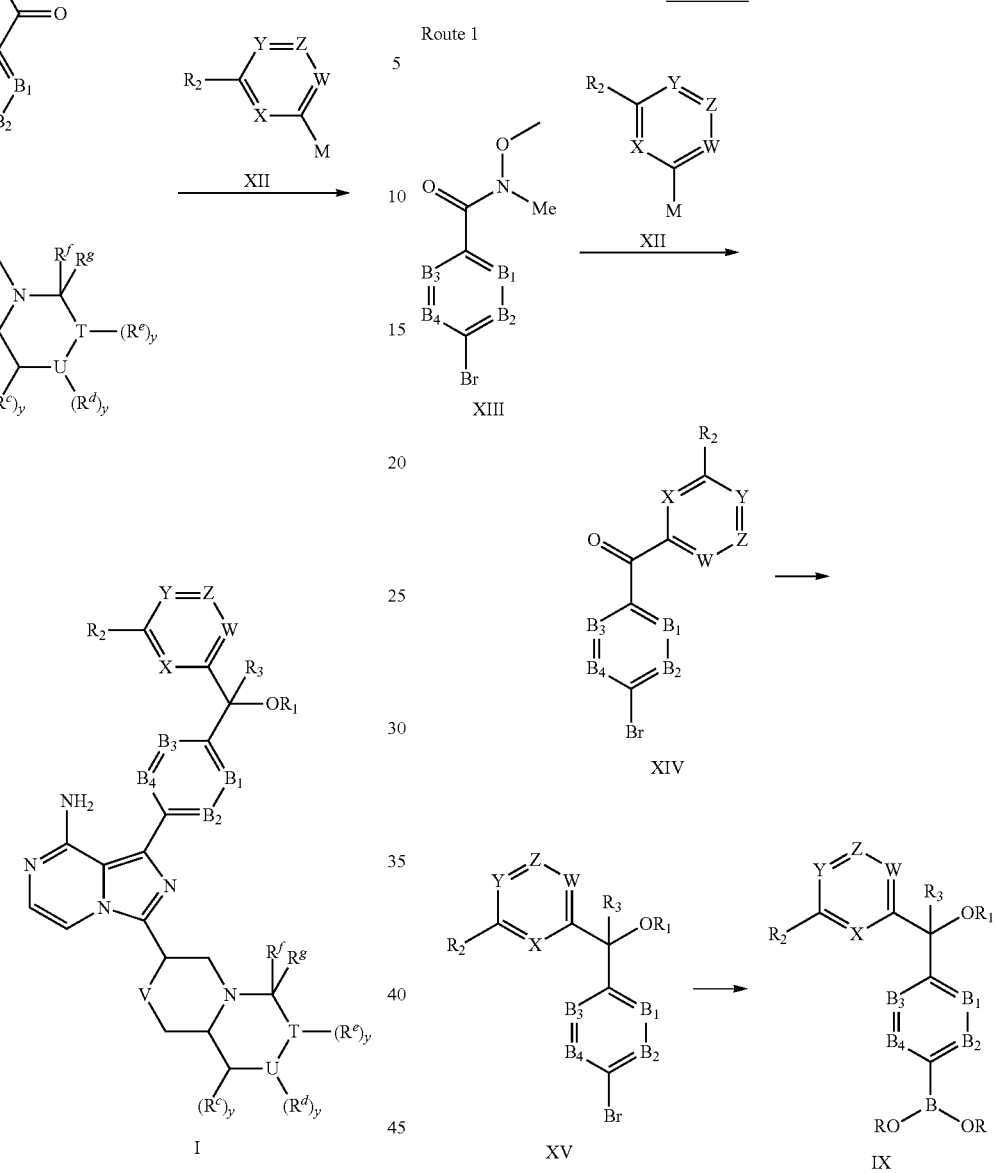

Scheme II shows an alternative route for the preparation of I. The intermediate VIII can be coupled with readily available boronic ester X under Suzuki coupling condition to provide ketone XI. An addition of an aromatic metallic reagent XII to the ketone in XI provide the final tertiary alcohol product I.

Several routes for the preparation of the biaryl tertiary alcohol boronic ester IX are shown in Scheme III. Route 1 use Weinreb amide XIII to react with the aromatic metallic reagent XII to provide ketone XIV, which then reacts with alkyl lithium or Grinard reagent to provide intermediate XV. The bromo in XV can be converted to boronic ester using palladium catalyzed conversion. The difference of Route 2 and Route 1 is that Route 2 utilizes the Weinreb amide XVI and metallic reagent XVII for the first step. Route 3 apply the commercially available or readily prepared methal ketone XVIII to react with the aromatic metallic reagent XII to form the tertiary alcohol XV, in which the bromo was later converted to the boronic ester.

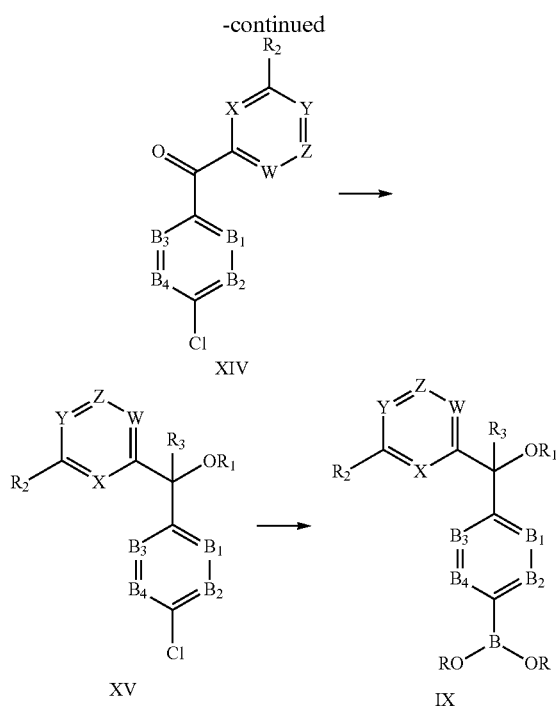

Route 3

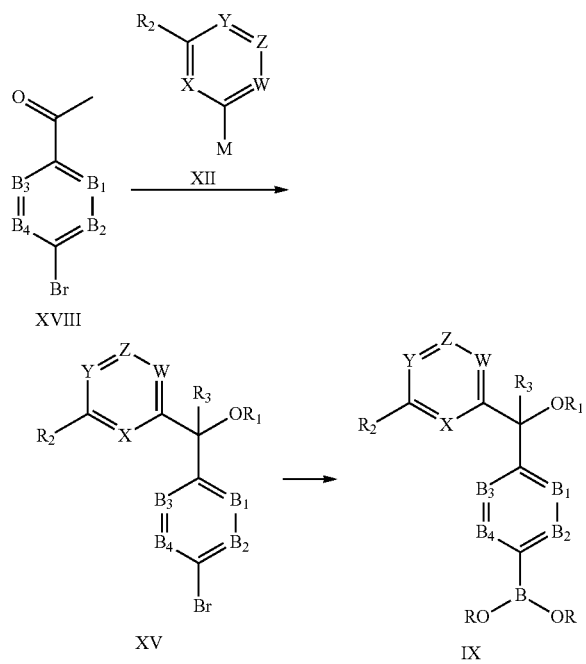

The invention is illustrated by the following examples.

EXAMPLES

The following examples are illustrative embodiments of the invention, not limiting the scope of the invention in any way. Reagents are commercially available or are prepared according to procedures in the literature.

Mass Spectrometry: Electron Spray spectra were recorded on the Applied Biosystems API-165 single quad mass spectrometer in alternating positive and negative ion mode using Flow Injection. The mass range was 120-2000 Da. and scanned with a step rate of 0.2 Da. and the capillary voltage was set to 5000 V. $N_2$ gas was used for nebulisation.

LC-MS spectrometer (Waters) Detector: PDA (200-320 nm), Mass detector: ZQ and Eluent:A: acetonitrile with 0.05% trifluoroacetic acid, B: acetonitrile/water=1/9 (v/v) with 0.05% trifluoroacetic acid.

| Method A: LC-MS | |
|---|---|
| Column | Ascentis Express C18, 100 × 3.0 mm, 2.7 μm |
| Mobile Phase | A : $H_2O$ (0.1% TFA) |
| | B: MeCN (0.05% TFA) |
| | Stop Time: 5.0 min |
| | Time (min) | B % |
| Gradient | 0.00 | 10 |
| | 3.50 | 99 |
| | 4.99 | 99 |
| | 5.00 | 10 |
| Sample injection volume | 2 μl |
| Flow Rate | 1.00 ml/min |
| Wavelength | 220 nm |
| Oven Tem. | 50° C. |
| MS polarity | ESI POS |

| Method B: LC-MS | |
|---|---|
| Column | Ascentis Express C18, 50 × 2.1 mm, 5 μm |
| Mobile Phase | A : $H_2O$ (0.1% TFA) |
| | B: MeCN (0.05% TFA) |
| | Stop Time: 2.0 min |
| | Time (min) | B% |
| Gradient | 0 | 10 |
| | 0.8 | 99 |
| | 1.99 | 99 |
| | 2.00 | 10 |
| Sample injection volume | 2 μl |
| Flow Rate | 1.25 ml/min |
| Wavelength | 220 nm |
| Oven Temp. | 50° C. |
| MS polarity | ESI POS |

Method C:
Sample Info: Easy-Access Method: '1-Short_TFA_Pos'
Method Info: B222 Column Agilent SBC (3.0×50 mm, 1.8 μm); Flow 1.0 mL/min; solvent A: $H_2O$—0.1% TFA; solvent B: MeCN-0.1% TFA;
GRADIENT TABLE: 0 min:10% B, 0.3 min:10% B, 1.5 min: 95% B, 2.70 min: 95% B, 2.76 min: 10% B stop time 3.60 min, PostTime 0.70 min.
Method D:
Sample Info: Easy-Access Method: '1_Fast'
Method Info: A330 Column Agilent Zorbax SB-C18 (2.1× 30 mm, 3.5 μm); Flow 2.0 mL/min;
solvent A: $H_2O$-0.1% TFA;
solvent B: MeCN-0.1% TFA;
GRADIENT TABLE: 0.01 min:10% B, 1.01 min:95% B, 1.37 min:95% B, 1.38 min:10% B, stop time 1.7 min, PostTime=OFF The following abbreviations are used throughout the application with respect to chemical terminology:
HATU O-(7-Azabenzotriazol-1-yl)-1,1,3,3-tetramethyluroniumhexafluoro phosphate
Cbz Benzyloxycarbonyl D Deuterated hydrogen
DMF N,N-Dimethylformamide
DCM Dichloromethane
EA Ethyl acetate
EtOAc Ethyl acetate
DIPEA N,N-Diisopropylethylamine
THF Tetrahydrofuran
EtOH Ethanol
EDCI.HCl 1-(3-Dimethylaminopropyl)-3-ethylcarbodiimide hydrochloride
4-DMAP 4-Dimethylaminopyridine
PyBOP O-Benzotriazole-1-yl-oxy-trispyrrolidinophosphonium hexafluorophosphate
TBTU O-Benzotriazol-1-yl-N,N,N',N'-tetramethyluronium tetrafluoroborate
HBr Hydrogen bromide
HCl Hydrogen chloride
HOAc Acetic acid
POCl$_3$ Phosphorous oxychloride
HPLC High Pressure Liquid Chromatography
UPLC Ultra Performance Liquid Chromatography
LiHMDS Lithium hexamethyldisilazide
MeOH Methanol
DCM Dichloromethane
n-BuLi n-Butyllithium
CO$_2$ Carbondioxide
NaHCO$_3$ Sodium bicarbonate
K$_3$PO$_4$ Potassium phosphate
P(Cy)$_3$ Tricyclohexylphosphine
Pd(OAc)$_2$ Palladium(II) acetate
Na$_2$SO$_4$ Sodium sulfate
Na$_2$CO$_3$ Sodium carbonate
DAST Diethylaminosulfur trifluoride
Cs$_2$CO$_3$ Cesium carbonate
Et$_2$O Diethylether
Na$_2$S$_2$O$_3$ Sodium thiosulfate
Na$_2$S$_2$O$_4$ Sodium hydrosulfite
NaCNBH$_3$ Sodium cyanoborohydride
NH$_4$Cl Ammonium chloride
MgSO$_4$ Magnesium sulfate
LiOH Lithium hydroxide
IPA Isopropylamine
TFA Trifluoroacetic acid
Cbz-Cl Benzylchloroformate
PE Petroleum ether
EA Ethyl acetate
NaHMDS Sodium hexamethyldisilazide
10% Pd/C 10% Palladium on carbon
TEA Triethylamine
CDI 1,1'-Carbonyl diimidazole
DMI 1,3-Dimethyl-2-imidazolidinone
NBS N-Bromosuccinimide
i-PrOH 2-Propanol
K$_2$CO$_3$ Potassium carbonate
Pd(dppf)Cl$_2$ 1,1'-Bis(diphenylphosphino)ferrocene palladium (II) chloride, complex with dichloromethane
Et$_3$N Triethylamine
2-BuOH 2-Butanol
LCMS Liquid Chromatography/Mass Spectrometry
MeCN Acetonitrile
NH$_3$ Ammonia
CD$_3$I Trideuteromethyl iodide
CD$_3$OD Tetradeuteromethanol
CH$_3$I Iodomethane
CBr$_4$ Carbon tetrabromide
Tris-HCl Tris(hydroxymethyl)aminomethane hydrochloride
MgCl$_2$ Magnesium chloride
NaN$_3$ Sodium azide
DTT Dithiothreitol
DMSO Dimethyl sulfoxide
IMAP Immobilized Metal Ion Affinity-Based Fluorescence Polarization
ATP Adenosine triphosphate
MnCl$_2$ Manganese(II) chloride
DMA Dimethylacetamide
IPA Isopropyl alcohol
TPP triphenylphosphine
DIAD Diisopropyl azodicarboxylate
DMB 2,4-dimethoxybenzyl
DCE Dichloroethane
DEAD Diethyl azodicarboxylate
ACN Acetonitrile
Ret. Time Retention Time
RT (rt) Room Temperature
Aq Aqueous
EtOH Ethanol
MPLC Medium Pressure Liquid Chromoatography
Xantphos 4,5-Bis(diphenylphosphino)-9,9-dimethylxanthene
X-phos 2-Dicyclohexylphosphino-2',4',6'-triisopropylbiphenyl

INTERMEDIATES

Intermediate 1

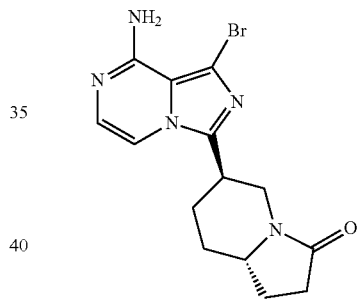

(6R,8aS)-6-(8-amino-1-bromoimidazo[1,5-a]pyrazin-3-yl)hexahydroindolizin-3(2H)-one (a) (E)-methyl 6-(3-ethoxy-3-oxoprop-1-en-1-yl)nicotinate A 1 L flask containing mixture of ethyl 2-oxoacetate (155 g, 0.76 mol) and methyl 6-methylnicotinate (50 g, 0.33 mol) in 300 mL of acetic anhydride was refluxed at 130° C. for two days and concentrated in vacuo. The resultant crude was purified by silica gel chromatography (eluent: 20% EA/hex) to afford (E)-methyl 6-(3-ethoxy-3-oxoprop-1-en-1-yl)nicotinate (57 g, 0.242 mol, 73. LCMS data: Ret. time.=1.42 min, m/z 236 (M+H)$^+$; $^1$HNMR (CDCl$_3$, 500 Hz): 9.24 (1H, d, J=2 Hz); 8.333 (1H, dd J=6 Hz); 7.20 (1H, d, J=16 Hz); 7.511 (1H, d, J=8 Hz); 7.042 (1H, d, J=15.5 Hz); 4.310 (q, J=7 Hz); 3.988 (3H, s), 1.366 (3H, t, J=7 Hz) ppm.

(b) Ethyl 6-(3-ethoxy-3-oxopropyl)piperidine-3-carboxylate

To a 500 ml vessel charged with (E)-methyl 6-(3-ethoxy-3-oxoprop-1-en-1-yl)nicotinate (10 g) in acetic acid (100 mL) was added palladium hydroxide on carbon (20%, 2.5 g). The vessel was loaded on ParShaker and the mixture was exposed to hydrogen at 40 psi for 18 hours. The catalyst was filtered under nitrogen stream and washed with ethyl acetate. The filtrate was then concentrated in vacuo to afford methyl 6-(3-ethoxy-3-oxopropyl)piperidine-3-carboxylate. LCMS data: Ret. time 0.22 min; m/z 244.3 (M+H)$^+$.

(c) Methyl 3-oxooctahydroindolizine-6-carboxylate

Methyl 6-(3-ethoxy-3-oxopropyl)piperidine-3-carboxylate (103.5 g, 0.425 mol) was refluxed in a mixture of TEA (100 ml, 0717 mol) and MeOH (500 ml) for 18 h and concentrated in vacuo. The residue was purified by silicagel chromatography (eluent: 3% 2N NH$_3$ in MeOH/DCM) to afford a mixture of cis/trans isomers methyl 3-oxooctahydroindolizine-6-carboxylate (4/1 ratio). LCMS data: Ret. time 1.07 min; m/z 198 (M+H)$^+$.

(d) Trans 3-oxooctahydroindolizine-6-carboxylic acid

A solution of methyl 3-oxooctahydroindolizine-6-carboxylate (94 g, 477 mmol) in methanol (1000 mL) was heated from rt to 50° C. While the solution was being heated, 25% NaOMe in methanol (215 mL, 940 mmol) was added in one portion. The reaction mixture was stirred at 50° C. for 4.5 h and concentrated in vacuo to afford a solid. This solid was dissolved in water (300 mL), resulting in the formation of a gray solid. This solid was filtered off, and the filtrate was then reconcentrated (water bath at 60° C.) to provide a white solid. This 60° C. solid was dissolved in water (100 mL) and cooled in an ice bath. Once the solution had reached 5° C., aq. 6 M HCl (165 mL, 990 mmol) was added dropwise while maintaining the temperature below 23° C. Solids formed as the addition continued. This mixture was stirred for ~30 min while the solution cooled to 5° C., and then it was filtered. The isolated solid was washed with cold water and then dried under a nitrogen flush overnight to afford the mixture of enantiomers trans 3-oxooctahydroindolizine-6-carboxylic acid. LCMS data: Ret. time 0.92 min; m/z 184.12 (M+H)$^+$. $^1$HNMR (CDCl$_3$, 500 MHz, ppm): δ=9.42 (1H, br), 4.38 (1H, ddd, J=13.2, 4.1, 1.6 Hz), 3.44 (1H, m), 2.76 (1H, t, J=12.7 Hz), 2.42 (3H, m), 2.24 (2H, m), 1.97 (1H, ddd, J=13.2, 6.8, 3.3 Hz), 1.61 (2H, m), 1.23 (1H, M) ppm.

(e) (6R,8aS) 3-oxooctahydroindolizine-6-carboxylic acid and (6S,8aR) 3-oxooctahydroindolizine-6-carboxylic acid The two enantiomers of trans 3-oxooctahydroindolizine-6-carboxylic acid were separated on Chiral HPLC (IC column, 4.6×150 mm, 50% IPA+TFA/CO$_2$, 2.5 ml/min. 100 bar, 35° C.) to give (6S,8aR)-3-oxooctahydroindolizine-6-carboxylic acid (E1, Ret. time=3.1 min, >99% ee) followed by (6R,8aS)-3-oxooctahydroindolizine-6-carboxylic acid (E2, Ret. time=4.2 min, >99% ee).

(f) (6R,8aS)-N-((3-chloropyrazin-2-yl)methyl)-3-oxooctahydroindolizine-6-carboxamide HATU (15.91 g, 41.8 mmol) was added to a stirred, cooled 0° C. mixture of (6R,8aS)-3-oxooctahydroindolizine-6-carboxylic acid (7.3 g, 39.8 mmol), (3-chloropyrazin-2-yl)methanamine hydrochloride (7.89 g, 43.8 mmol) and DIPEA (10.44 ml, 59.8 mmol) in CH$_2$Cl$_2$ (25 ml) and the mixture was stirred at room temperature for 1 h. and then concentrated. The residue was purified by column chromatography on silica gel (MPLC 240 g silica gel), eluting with CH$_2$Cl$_2$/MeOH (50/1) to give (6R,8aS)-N-((3-chloropyrazin-2-yl)methyl)-3-oxooctahydroindolizine-6-carboxamide. LC-MS: Ret. time 1.09 min; m/z 309.11 (M+H)$^+$; $^1$HNMR (CDCl$_3$, 500 Hz): 8.38 (1H, d, J=2 Hz), 8.25 (1H, d, J=2 Hz), 7.37 (1H, dd, J=4 and 4.5 Hz), 4.56-4.72 (2H, m, 1), 4.29 (1H, dd, J=13 and 4.5 Hz), 3.42-3.47 (m, 1), 2.81 (1H, t, J=13 Hz), 2.35 (2H, t, J=8 Hz), 2.17-2.23 (1H, m), 2.04 (1H, d, J=13.5 Hz), 1.94-1.96 (1H, m), 1.74-1.82 (1H, m), 1.55-1.62 (1H, m), 1.16-1.24 (1H, m) ppm.

(g) (6R,8aS)-6-(8-chloroimidazo[1,5-a]pyrazin-3-yl)hexahydroindolizin-3(2H)-one

POCl$_3$ (5.85 ml, 62.7 mmol) was added to a stirred, cooled 0° C. mixture of (6R,8aS)-N-((3-chloropyrazin-2-yl)methyl)-3-oxooctahydroindolizine-6-carboxamide (3228.2 mg, 10.46 mmol) in Acetonitrile (20 ml), to which DMF (0.810 ml, 10.46 mmol) was added. The mixture was stirred at room temperature for overnight, and poured into iced water, to which powdered NaHCO$_3$ was added until pH~8. The mixture was extracted with DCM, dried over MgSO$_4$, filtered and concentrated. The residue was purified by column chromatography on silica gel (MPLC, 40 g), eluting with CH$_2$Cl$_2$/MeOH (25/1) to give (6R,8aS)-6-(8-chloroimidazo[1,5-a]pyrazin-3-yl)hexahydroindolizin-3(2H)-one as an oil. Ret. time 1.15 min; m/z 291.12 (M+H)$^+$; $^1$HNMR (CDCl$_3$, 500 Hz): 7.72 (1H, d, J=4.5 Hz), 7.39 (1H, d, J=5 Hz), 4.40-4.42 (1H, m), 3.62-3.67 (1H, m), 3.03-3.08 (2H, m), 2.11-2.51 (8H, m), 1.70-1.77 (1H, m), 1.39-1.46 (1H, m) ppm.

(h) (6R,8aS)-6-(1-bromo-8-chloroimidazo[1,5-a]pyrazin-3-yl)hexahydroindolizin-3(2H)-one NBS (1.468 g, 8.25 mmol) was added to a stirred mixture of (6R,8aS)-6-(8-chloroimidazo[1,5-a]pyrazin-3-yl)hexahydroindolizin-3(2H)-one (1.9981 g, 6.87 mmol) in acetonitrile (25 ml) and the mixture was stirred at room temperature for 1 h. The reaction was quenched with sat. NaHCO$_3$, extracted with DCM, dried and concentrated in vacuo. The residue was purified by column chromatography on silica gel (MPLC gold 40 g), eluting with CH$_2$Cl$_2$/MeOH (40/1) to give (6R,8aS)-6-(1-bromo-8-chloroimidazo[1,5-a]pyrazin-3-yl)hexahydroindolizin-3(2H)-one. Ret. time 1.24 min; m/z 368.97 and 370.98 (M+H)$^+$.

(i) (6R,8aS)-6-(8-amino-1-bromoimidazo[1,5-a]pyrazin-3-yl)hexahydroindolizin-3(2H)-one A stirred mixture of (6R,8aS)-6-(1-bromo-8-chloroimidazo[1,5-a]pyrazin-3-yl)hexahydroindolizin-3(2H)-one (2.2109 g, 5.98 mmol) in 100 mL of 2N NH$_3$ in 2-propanol was heated in a sealed tube at 120° C. for 24 h. and concentrated in vacuo. The residue was purified by column chromatography on silica gel (MPLC, 80 g), eluting with CH$_2$Cl$_2$/MeOH (15/1) to afford (6R,8aS)-6-(8-amino-1-bromoimidazo[1,5-a]pyrazin-3-yl)hexahydroindolizin-3(2H)-one. Ret. time 1.16 min; m/z 350.0 and 352.0 (M+H)$^+$.

Intermediate 2

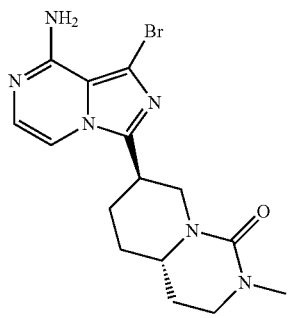 [SMILES: CN1CC[C@@H]2CC[C@@H](c3nc(Br)c4c(N)nccn34)CN2C1=O]

Trans-7-(8-amino-1-bromoimidazo[1,5-a]pyrazin-3-yl)-2-methyloctahydro-1H-pyrido[1,2-c]pyrimidin-1-one

(a) methyl 6-vinylnicotinate

To a solution of methyl 6-bromonicotinate (10 g, 46.5 mmol) in i-PrOH (100 mL) was added potassium vinyltrifluoroborate (12.4 g, 93 mmol), Et$_3$N (14.1 g, 140 mmol), and Pd(dppf)Cl$_2$.DCM (1.1 g). The mixture was stirred at 100° C. for 2 h under nitrogen. The reaction was complete detected by TLC. The mixture was concentrated and the residue was purified by column chromatography on silica gel eluted with PE/EA=15/1 to give methyl 6-vinylnicotinate. $^1$H-NMR (CDCl$_3$, 400 MHz) δ 3.94 (s, 3H), 5.55 (d, J=12.0 Hz, 1H), 6.36 (d, J=20.0 Hz, 1H), 6.85 (dd, J=17.41, 10.76 Hz, 1H), 7.39 (d, J=8.22 Hz, 1H), 8.23 (dd, J=8.22, 2.35 Hz, 1H), 9.15 (d, J=1.56 Hz, 1H) ppm.

(b) methyl 6-(2-((2,4-dimethoxybenzyl)amino)ethyl) nicotinate

To a solution of methyl 6-vinylnicotinate (7.2 g, 44.2 mmol) in MeOH (50 mL) was added (2,4-dimethoxyphenyl)methanamine (14.7 g, 88.3 mmol) and AcOH (50 mL). The mixture was heated to reflux overnight. The mixture was concentrated, basified with aq. NaHCO$_3$ and extracted with EA. The organic layer was dried and concentrated. The residue was purified by column chromatography on silica gel eluted with PE/EA=3/1 to give methyl 6-(2-((2,4-dimethoxybenzyl)amino)ethyl)nicotinate.

(c) methyl 6-(2-((2,4-dimethoxbenzyl)amino)ethyl) piperidine-3-carboxylate

To a solution of methyl 6-(2-((2,4-dimethoxybenzyl)amino)ethyl)nicotinate (3.6 g, 10.9 mmol) in AcOH (80 mL) was added NaBH$_3$CN (2.74 g, 43.6 mmol). The mixture was stirred at room temperature for 1 h, then heated to 70° C. and stirred overnight. The solvent was evaporated and the residue was dissolved in MeOH. The solution was alkalified with NaHCO$_3$ solution and purified by column chromatography on silica gel eluted with DCM/MeOH=20/1 to give methyl 6-(2-((2,4-dimethoxybenzyl)amino)ethyl)piperidine-3-carboxylate.
MS-ESI (m/z): 337 (M+1)+(LC-MS method D, Ret. time: 0.847 min).

(d) methyl 2-(2,4-dimethoxybenzyl)-1-oxooctahydro-1H-pyrido[1,2-c]pyrimidine-7-carboxylate To a solution of methyl 6-(2-((2,4-dimethoxybenzyl)amino)ethyl)piperidine-3-carboxylate (4 g, 11.9 mmol) in THF (130 mL) was added CDI (3.8 g, 23.8 mmol). The mixture was stirred at 70° C. for 6 h. The mixture was concentrated in vacuo and the residue was purified by column chromatography on silica gel eluted with DCM/THF=30/1 to give trans- and cis-(700 mg, yield 32%) methyl 2-(2,4-dimethoxybenzyl)-1-oxooctahydro-1H-pyrido[1,2-c]pyrimidine-7-carboxylate.

For trans isomers:
$^1$H NMR (CD$_3$OD, 400 MHz) δ 1.25-1.37 (m, 1H), 1.50-1.60 (m, 1H), 1.65-1.77 (m, 2H), 1.96-2.15 (m, 2H), 2.40-2.51 (m, 1H), 2.60 (t, J=12.0 Hz, 1H), 3.11-3.25 (m, 3H), 3.67 (s, 3H), 3.79 (s, 6H), 4.40-4.56 (m, 2H), 4.76-4.86 (m, 1H), 6.38-6.51 (m, 2H), 7.20 (d, J=8.0 Hz, 1H) ppm.

For cis isomers:
$^1$H NMR (CD$_3$OD, 400 MHz) δ 1.41-1.51 (m, 2H), 1.58-1.71 (m, 2H), 1.85-1.94 (m, 1H), 2.12-2.19 (m, 1H), 2.56-2.62 (m, 1H), 2.69-2.75 (m, 1H), 3.03-3.18 (m, 3H), 3.62 (s, 3H), 3.72 (d, J=2.74 Hz, 6H), 4.32-4.50 (m, 2H), 4.89-4.95 (m, 1H), 6.34-6.41 (m, 2H), 7.12 (d, J=8.0 Hz, 1H) ppm.

(e) trans-methyl 1-oxooctahydro-1H-pyrido[1,2-c]pyrimidine-7-carboxylate

A solution of trans-methyl 2-(2,4-dimethoxybenzyl)-1-oxooctahydro-1H-pyrido[1,2-c]pyrimidine-7-carboxylate (600 mg, 1.6 mmol) in TFA (4 mL) was stirred at 90° C. for 1 h. The solvent was evaporated and the residue was used in next step directly. MS-ESI (m/z): 213 (M+1)+ (LC-MS method D; Ret. time: 0.912 min).

(f) trans-methyl 2-methyl-1-oxooctahydro-1H-pyrido[1,2-c]pyrimidine-7-carboxylate A solution of trans-methyl 1-oxooctahydro-1H-pyrido[1,2-c]pyrimidine-7-carboxylate (1.6 mmol) in THF (30 mL) was cooled to 0-5° C. and NaH (199 mg, 5.0 mmol) was added portionwise. The mixture was stirred at room temperature for 30 min, and then MeI (706 mg, 5.0 mmol) was added. The reaction mixture was stirred at room temperature overnight. The reaction was quenched with H$_2$O (0.5 mL) and the volatiles were evaporated. The residue was used in next step directly.

(g) trans-2-methyl-1-oxooctahydro-1H-pyrido[1,2-c]pyrimidine-7-carboxylic acid To a solution of trans-methyl 2-methyl-1-oxooctahydro-1H-pyrido[1,2-c]pyrimidine-7-carboxylate (1.6 mmol) in MeOH/THF/H$_2$O (10 mL/10 mL/3 mL) was added LiOH*H$_2$O (83 mg, 2.0 mmol). The mixture was stirred at room temperature for 2 h. The volatiles were evaporated and the residue was used in next step directly. MS-ESI (m/z): 213 (M+1)+ (LC-MS method D; Ret. time: 0.917 min).

(h) trans-N-((3-chloropyrazin-2-yl)methyl)-2-methyl-1-oxooctahydro-1H-pyrido[1,2-c]pyrimidine-7-carboxamide To a solution of trans-2-methyl-1-oxooctahydro-1H-pyrido[1,2-c]pyrimidine-7-carboxylic acid (1.6 mmol) in DCM (20 mL) was added (3-chloropyrazin-2-yl) methanamine hydrochloride (356 mg, 2.0 mmol), EDC (477 mg, 2.5 mmol), HOBT (336 mg, 2.5 mmol) and TEA (670 mg, 6.6 mmol), and the resulting mixture was stirred at 50° C. overnight. The volatiles were evaporated and the residue was purified by column chromatography on silica gel eluted with DCM/THF=3/1 to give trans-N-((3-chloropyrazin-2-yl)methyl)-2-methyl-1-oxooctahydro-1H-pyrido[1,2-c]pyramidine-7-carboxamide. $^1$H NMR (CDCl$_3$, 400 MHz) δ 1.24-1.34 (m, 1H), 1.67-1.76 (m, 3H), 1.92-2.08 (m, 3H), 2.29-2.38 (m, 1H), 2.64 (t, J=12.0 Hz, 1H), 2.87 (s, 3H), 3.12-3.21 (m, 3H), 4.59-4.69 (m, 3H), 6.89-7.01 (m, 1H), 8.24 (d, J=4.0 Hz, 1H), 8.37 (d, J=4.0 Hz, 1H) ppm.

(i) trans-7-(8-chloroimidazo[1,5-a]pyrazin-3-yl)-2-methyloctahydro-1H-pyrido[1,2-c]pyrimidin-1-one To a solution of trans-N-((3-chloropyrazin-2-yl)methyl)-2-methyl-1-oxooctahydro-1H-pyrido[1,2-c]pyramidine-7-carboxamide (100 mg, 0.3 mmol) in MeCN (20 mL) was added PCl$_5$ (185 mg, 0.9 mmol). The mixture was stirred at 60° C. for 1 h, then another batch of PCl$_5$ (185 mg, 0.9 mmol) was added in portions during a period of 1 h, and the reaction mixture was stirred at 60° C. for further 20 min. The reaction was complete detected by LCMS. After cooling, the reaction solution was treated with DCM and aq. NaHCO$_3$. The organic layer was separated, dried and concentrated. The residue was purified by column chromatography on silica gel eluted with DCM/THF=5/1 to give trans-7-(8-chloroimidazo[1,5-a]pyrazin-3-yl)-2-methyl octahydro-1H-pyrido[1,2-c]pyrimidin-1-one. MS-ESI (m/z): 320 (M+1)$^+$ (LC-MS method D; Ret. time: 1.073 min).

(j) trans-7-(1-bromo-8-chloroimidazo[1,5-a]pyrazin-3-yl)-2-methyloctahydro-1H-pyrido[1,2-c]pyrimidin-1-one To a solution of trans-7-(8-chloroimidazo[1,5-a]pyrazin-3-yl)-2-methyloctahydro-1H-pyrido[1,2-c]pyrimidin-1-one (75 mg, 0.24 mmol) in DMF (1.5 mL) was added a solution of NBS (46 mg, 0.26 mmol) in DMF (0.5 mL). The mixture was stirred at room temperature for 1 h. The reaction mixture was treated with EA and water, the organic layer was separated, dried and concentrated. The residue was purified by column chromatography on silica gel eluted with DCM/THF=10/1 to give trans-7-(1-bromo-8-chloroimidazo[1,5-a]pyrazin-3-yl)-2-methylocta hydro-1H-pyrido[1,2-c]pyrimidin-1-one. MS-ESI (m/z): 400 (M+1)$^+$ (LC-MS method D; Ret. time: 1.205 min).

(k) trans-7-(8-amino-1-bromoimidazo[1,5-a]pyrazin-3-yl)-2-methyloctahydro-1H-pyrido[1,2-c]pyrimidin-1-one A solution of trans-7-(1-bromo-8-chloroimidazo[1,5-a]pyrazin-3-yl)-2-methyloctahydro-1H-pyrido[1,2-c]pyrimidin-1-one (75 mg, 0.2 mmol) in NH$_3$/i-PrOH (4 mL) was added in 30 mL seal tube, and the mixture was stirred at 100° C. overnight. The mixture was concentrated and the residue was purified by column chromatography on silica gel eluted with DCM/MeOH=30/1 to give the title compound. MS-ESI (m/z): 379 (M+1)$^+$ (LC-MS method D; Ret. time: 0.934 min).

Same procedure started from cis-methyl-2-(2,4-dimethoxybenzyl)-1-oxooctahydro-1H-pyrido[1,2-c]pyrimidine-7-carboxylate afforded cis-7-(8-amino-1-bromoimidazo[1,5-a]pyrazin-3-yl)-2-methyloctahydro-1H-pyrido[1,2-c]pyrimidin-1-one. MS-ESI (m/z): 379 (M+1)$^+$ (LC-MS method D; Ret. time: 0.954 min).

Intermediate 3

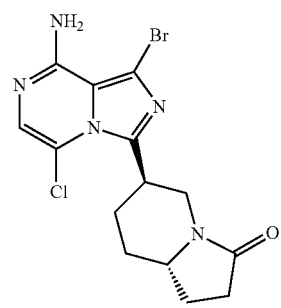 [SMILES: Nc1ncc(Cl)n2c([C@@H]3CC[C@H]4CCC(=O)N4C3)nc(Br)c12]

(6R,8aS)-6-(8-amino-1-bromo-5-chloroimidazo[1,5-a]pyrazin-3-yl)hexahydroindolizin-3(2H)-one N-chlorosuccinimide (1.906 g, 14.28 mmol) was added to a stirred mixture of (6R,8aS)-6-(8-amino-1-bromoimidazo[1,5-a]pyrazin-3-yl)hexahydroindolizin-3(2H)-one (Intermediate 1, 5 g, 14.28 mmol) in acetic acid (50 mL) and the mixture was stirred at 80° C. for 1 h, the reaction mixture was concentrated. The residue was purified by column chromatography on silica gel (MPLC, 80 g), eluting with 5% MeOH (2N NH$_3$)/methylene chloride to give (6R,8aS)-6-(8-amino-1-bromo-5-chloroimidazo[1,5-a]pyrazin-3-yl)hexahydroindolizin-3(2H)-one as a solid. LCMS [M+H]$^+$: found 386.

Intermediate 4

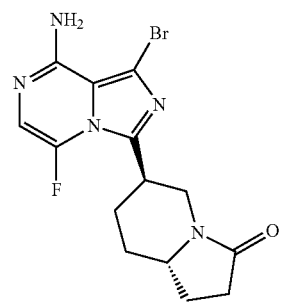 [SMILES: Nc1ncc(F)n2c([C@@H]3CC[C@H]4CCC(=O)N4C3)nc(Br)c12]

(6R,8aS)-6-(8-amino-1-bromo-5-fluoroimidazo[1,5-a]pyrazin-3-yl)hexahydroindolizin-3(2H)-one Step 1: (6R,8aS)-6-(8-amino-1-bromo-5-fluoro-6-methoxy-5,6-dihydroimidazo[1,5-a]pyrazin-3-yl)hexahydroindolizin-3(2H)-one 1-chloromethyl-4-fluoro-1,4-diazoniabicyclo[2.2.2]octanbis(tetrafluoroborate) (2.62 g, 7.40 mmol) was added to a stirred mixture of (6R,8aS)-6-(8-amino-1-bromoimidazo[1,5-a]pyrazin-3-yl)hexahydroindolizin-3(2H)-one (2.16 g, 6.17 mmol) in MeOH (25 ml) and acetonitrile (25 ml) in 250 ml round bottom flask. The mixture was stirred at room temperature for overnight and then concentrated. The residue was purified by column chromatography on silica gel (MPLC 80 g), eluting with $CH_2Cl_2$/MeOH (10/1) to give ((6R,8aS)-6-(8-amino-1-bromo-5-fluoro-6-methoxy-5,6-dihydroimidazo[1,5-a]pyrazin-3-yl)hexahydroindolizin-3(2H)-one.

Step 2: (6R,8aS)-6-(8-amino-1-bromo-5-fluoroimidazo[1,5-a]pyrazin-3-yl)hexahydroindolizin-3(2H)-one To 20 ml microwave reaction vessel was charged a mixture of (6R,8aS)-6-(8-amino-1-bromo-5-fluoro-6-methoxy-5,6 dihydroimidazo[1,5-a]pyrazin-3-yl)hexahydroindolizin-3(2H)-one (300 mg, 0.750 mmol) in pyridine (8 ml). The mixture was stirred under microwave irradiation at 180° C. for 15 min. and then concentrated. The residue was purified by column chromatography on silica gel (MPLC 80 g), eluting with $CH_2Cl_2$/MeOH (20/1) to give (6R,8aS)-6-(8-amino-1-bromo-5-fluoroimidazo[1,5-a]pyrazin-3-yl) hexahydroindolizin-3(2H)-one as a solid. LC-MS: $C_{14}H_{15}BrFN_5O$, found $[M+H]^+$ 370.0. LC-MS method E Ret. time=0.91 min.

Intermediate 5E1 and 5E2

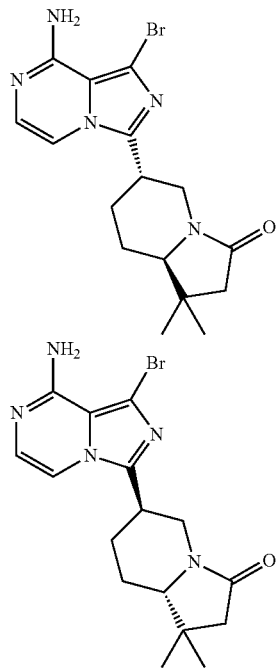

(6S,8aR)-6-(8-amino-1-bromoimidazo[1,5-a] pyrazin-3-yl)-1,1-dimethylhexahydroindolizin-3 (2H)-one (6R,8aS)-6-(8-amino-1-bromoimidazo[1,5-a] pyrazin-3-yl)-1-dimethylhexahydroindolizin-3(2H)-one Step (a) methyl 2-(5-bromopyridin-2-yl)-2-methylpropanoate A solution of diisopropylamine (18.05 mL, 127 mmol) in Tetrahydrofuran (360 mL) was cooled to −10° C. under nitrogen and treated with n-BuLi (50.7 mL, 127 mmol, 2.5 M hexane) over a five min period. After 30 min, the solution was cooled to −78° C. and treated with methyl isobutyrate (12.93 g, 127 mmol). After 45 min at −78° C., a solution of 2,5-dibromopyridine (20 g, 84 mmol) in Tetrahydrofuran (40 mL) was added via syringe, resulting in a bright yellow solution. After the addition was complete, the reaction was removed from the cooling bath and warmed to room temperature. After overnight at room temperature, the reaction was quenched by the addition of aqueous $NH_4Cl$ (100 mL) and the reaction mixture was extracted with EtOAc. The organic layer was dried over $Na_2SO_4$, filtered and concentrated. The crude product was purified by silica gel chromatography (Pet. Ether/EtOAc=90:10) to give methyl 2-(5-bromopyridin-2-yl)-2-methylpropanoate as an oil. MS (ESI) m/z $(M+H)^+$: 260. (LC-MS method D; RET. TIME=1.114 min).

Step (b) 2-(5-bromopyridin-2-yl)-2-methylpropanoic acid

To a solution of methyl 2-(5-bromopyridin-2-yl)-2-methylpropanoate (18.7 g, 72.4 mmol) and NaOH (39.8 ml, 80 mmol) in MeOH (180 mL) was stirred at 50° C. for overnight. The reaction was complete detected by TLC. The organic solvent was removed under reduced pressure, the residual was diluted with EtOAc, acidified with HCl to pH=5, extracted with EtOAc, dried over $Na_2SO_4$, concentrated to give 2-(5-bromopyridin-2-yl)-2-methylpropanoic acid as a light oil. MS (ESI) m/z $(M+H)^+$: 244. LC-MS method D (Ret time: 0.875 min).

Step (c) 2-(5-bromopyridin-2-yl)-2-methylpropanoyl chloride

To a solution of 2-(5-bromopyridin-2-yl)-2-methylpropanoic acid (1.1 g, 4.51 mmol) in DCM (30 mL) at 0° C. was added OXALYL CHLORIDE (1.183 mL, 13.52 mmol) and DMF (3.49 μL, 0.045 mmol). The mixture was stirred at r.t overnight. The mixture was detected by TLC, and concentrated in vacuo to give a yellow oil, which was used in next step.

Step (d) 3-(5-bromopyridin-2-yl)-1-diazo-3-methylbutan-2-one

This solution of 2-(5-bromopyridin-2-yl)-2-methylpropanoyl chloride (11 g, 41.9 mmol) in MeCN/THF (30 mL, 1:1) was added dropwise to an ice-water cooled solution of 2M TMS-Diazomethane (41.9 ml, 84 mmol) and $Et_3N$ (9.34 mL, 67.0 mmol) in a 1:1 solution of MeCN and THF (70 mL). The resulting yellow mixture was allowed to warm to ambient temperature overnight. The solvent was removed under reduced pressure and the residual was dissolved in EtOAc (50 mL) and washed with water (50 mL), $NaHCO_3$ (50 mL), and brine (50 mL). The combined organic phases was dried over $MgSO_4$ and concentrated to leave a gum, which was purified by chromatography (PE/AcOEt=10:1) to give 3-(5-bromopyridin-2-yl)-1-diazo-3-methylbutan-2-one.

$^1$H NMR (400 MHz, $CDCl_3$) δ=8.64 (d, J=1.57 Hz, 1H), 7.78 (dd, J=1.96, 8.61 Hz, 1H), 7.24 (d, J=8.61 Hz, 1H), 5.14 (s, 1H), 1.57 (s, 6H) ppm.

Step (e) methyl 3-(5-bromopyridin-2-yl)-3-methylbutanoate

To a solution of (benzoyloxy)silver (1.025 g, 4.48 mmol) and triethylamine (9.06 g, 90 mmol) in MeOH (50 mL) was added a solution of 3-(5-bromopyridin-2-yl)-1-diazo-3-methylbutan-2-one (6 g, 22.38 mmol) in MeOH (150 mL). The mixture was stirred at r.t. overnight, and then concentrated and diluted with EtOAc, washed with saturated NaHCO₃ solution and purified with silica gel chromatography (120 g, PE:THF=5:1). Methyl 3-(5-bromopyridin-2-yl)-3-methylbutanoate was obtained.

¹H NMR (400 MHz, CDCl₃) δ=8.58 (d, J=1.56 Hz, 1H), 7.75 (dd, J=1.96, 8.61 Hz, 1H), 7.27 (d, J=6.26 Hz, 1H), 3.55 (s, 3H), 2.83 (s, 2H), 1.44 (s, 6H) ppm.

MS (ESI) m/z (M+H)⁺: 272. (LC-MS method D; Ret. time=1.046 min).

Step (f) methyl 6-(4-methoxy-2-methyl-4-oxobutan-2-yl)nicotinate

A mixture of Methyl 3-(5-bromopyridin-2-yl)-3-methylbutanoate (4 g, 14.70 mmol), Et₃N (6.15 mL, 44.1 mmol), Pd(OAc)₂ (0.330 g, 1.470 mmol) and DPPF (1.630 g, 2.94 mmol) in MeOH (20 mL) and DMF (60 mL) was stirred at 90° C. under CO (50 psi) atmosphere overnight. It was detected by LCMS, concentrated and diluted with water, extracted with EtOAc, washed with water and brine, purified with silica gel chromatography (40 g, PE:EA=10:1) to give an oil methyl 6-(4-methoxy-2-methyl-4-oxobutan-2-yl)nicotinate.

¹H NMR (400 MHz, CDCl₃) δ=9.13 (s, 1H), 8.16-8.29 (m, 1H), 7.36-7.49 (m, 1H), 3.94 (s, 3H), 3.53 (s, 3H), 2.88 (s, 2H), 1.40-1.56 (m, 6H) ppm.

Step (g) methyl 1,1-dimethyl-3-oxooctahydroindolizine-6-carboxylate

To a mixture of methyl 6-(4-methoxy-2-methyl-4-oxobutan-2-yl)nicotinate (500 mg, 1.990 mmol) in AcOH (15 mL) was added NaCNBH₃ (375 mg, 5.97 mmol) at 0° C. After stirring at 25° C. overnight, the reaction was detected by TLC, concentrated to remove the solvent, quenched with NaHCO₃ solution (pH=8) and extracted with EtOAc (3 times). The organic phases were dried and concentrated to give a residual. It was dissolved in MeOH and stirred at 70° C. overnight. The reaction mixture was concentrated and purified with silica gel chromatography (PE:THF=1:1) to give an oil methyl 1,1-dimethyl-3-oxooctahydroindolizine-6-carboxylate.

¹H NMR (400 MHz, CDCl₃) δ=4.36 (dd, J=3.72, 13.11 Hz, 1H), 3.65-3.78 (m, 3H), 2.99 (dd, J=2.93, 11.93 Hz, 1H), 2.75 (t, J=12.33 Hz, 1H), 2.36 (tt, J=3.96, 11.88 Hz, 1H), 2.15-2.28 (m, 3H), 1.75 (dd, J=3.13, 12.91 Hz, 1H), 1.57 (dq, J=2.74, 12.91 Hz, 1H), 1.22-1.33 (m, 1H), 1.16 (s, 3H), 1.02 (s, 3H) ppm.

Step (h) 1,1-dimethyl-3-oxooctahydroindolizine-6-carboxylic acid

A mixture of methyl 1,1-dimethyl-3-oxooctahydroindolizine-6-carboxylate (1.7 g, 7.55 mmol) and LiOH.H₂O (0.633 g, 15.09 mmol) in MeOH (20 mL) and Water (7 mL) was stirred at 25° C. overnight. It was detected by TLC, concentrated and acidified with 1N HCl to pH=3, and extracted by DCM, dried over Na₂SO₄ and concentrated to give a white solid 1,1-dimethyl-3-oxooctahydroindolizine-6-carboxylic acid.

Step (i) N-((3-chloropyrazin-2-yl)methyl)-1,1-dimethyl-3-oxooctahydroindolizine-6-carboxamide To a mixture of 1,1-dimethyl-3-oxooctahydroindolizine-6-carboxylic acid (1.2 g, 5.68 mmol) in DMF (30 mL) was added (3-chloropyrazin-2-yl)methanamine HCl salt (1.023 g, 5.68 mmol), N-ethyl-N-isopropylpropan-2-amine (2.202 g, 17.04 mmol) and HATU (2.160 g, 5.68 mmol) at r.t. After stirring at 25° C. overnight, the reaction was detected by TLC and LCMS, quenched with water and extracted by DCM (3 times), Dried over Na₂SO₄ and concentrated to give a residual. It was purified with silica gel chromatography (40 g, DCM:MeOH=20:1) to give N-((3-chloropyrazin-2-yl)methyl)-1,1-dimethyl-3-oxooctahydroindolizine-6-carboxamide as a solid. MS (ESI) m/z (M+H)⁺: 337. (LC-MS method D; Ret. time=0.937 min).

Step (j) 6-(8-chloroimidazo[1,5-a]pyrazin-3-yl)-1,1-dimethylhexahydroindolizin-3(2H)-one PCl₅ (2.040 g, 9.80 mmol) was added to a stirred N-((3-chloropyrazin-2-yl)methyl)-1,1-dimethyl-3-oxooctahydroindolizine-6-carboxamide (1.1 g, 3.27 mmol) in acetonitrile (20 mL) and the mixture was stirred at 25° C. for overnight. The reaction was quenched with NaHCO₃, extracted with DCM, dried over Na₂SO₄ and concentrated to give 6-(8-chloroimidazo[1,5-a]pyrazin-3-yl)-1,1-dimethylhexahydroindolizin-3(2H)-one. MS (ESI) m/z (M+H)⁺: 319, (LC-MS method C; Ret. time=0.950 min).

Step (k) 6-(1-bromo-8-chloroimidazo[1,5-a]pyrazin-3-yl)-1,1-dimethylhexahydroindolizin-3(2H)-one NBS (0.860 g, 4.83 mmol) was added to a stirred 6-(8-chloroimidazo[1,5-a]pyrazin-3-yl)-1,1-dimethylhexahydroindolizin-3(2H)-one (1.4 g, 4.39 mmol) in Acetonitrile (30 mL) and the mixture was stirred at 25° C. for Overnight. It was detected LCMS, quenched with NaHCO₃, extracted with EtOAc, dried over Na₂SO₄ and concentrated to give 6-(1-bromo-8-chloroimidazo[1,5-a]pyrazin-3-yl)-1,1-dimethylhexahydroindolizin-3(2H)-one. MS (ESI) m/z (M+H)⁺: 399. Acq (LC-MS method D; RET. TIME=1.117 min).

Step (l) 6-(8-amino-1-bromoimidazo[1,5-a]pyrazin-3-yl)-1,1-dimethyylhexahydroindolizin-3(2H)-one 6-(1-bromo-8-chloroimidazo[1,5-a]pyrazin-3-yl)-1,1-dimethylhexahydroindolizin-3(2H)-one (1.7 g, 4.27 mmol) was added to a stirred NH₃.H₂O (15 mL, 94 mmol) in 2-Propanol (15 mL) and the mixture was stirred at 110° C. overnight. It was detected by LCMS, concentrated, extracted with DCM, dried over Na₂SO₄ and concentrated to give 6-(8-amino-1-bromoimidazo[1,5-a]pyrazin-3-yl)-1,1-dimethylhexahydroindolizin-3(2H)-one as a solid. MS (ESI) m/z (M+H)⁺: 380. (LC-MS method C; RET. TIME=0.854 min).

Step (m) 6-(8-amino-1-bromoimidazo[1,5-a]pyrazin-3-yl)-1,1-dimethyylhexahydroindolizin-3(2H)-one 6-(8-amino-1-bromoimidazo[1,5-a]pyrazin-3-yl)-1,1-dimethylhexahydroindolizin-3(2H)-one (1.5 g, 3.97 mmol, racemic) was separated by SFC separation under the following condition: Column: Chiralpak AS-H 250×4.6 mm I.D., 5 µm; Mobile phase: ethanol (0.05% DEA) in CO₂ from 5% to 40%; Flow rate: 2.35 mL/min; Wavelength: 220 nm. (6S,8aR)-6-(8-amino-1-bromoimidazo[1,5-a]pyrazin-3-yl)-1,1-dimethylhexahydroindolizin-3(2H)-one (RET. TIME=6.625) and (6R,8aS)-6-(8-amino-1-bromoimidazo[1, 5-a]pyrazin-3-yl)-1,1-dimethylhexahydroindolizin-3(2H)-one (Ret. time=8.268) were obtained.

Intermediate 6E1 and 6E2

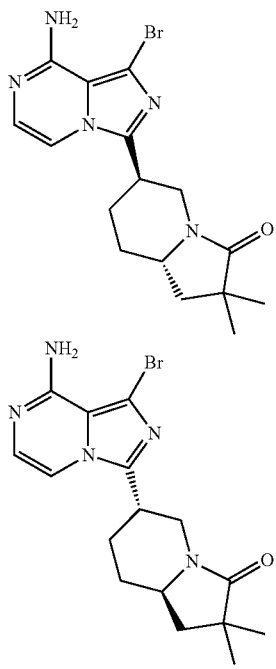

(6S,8aR)-6-(8-amino-1-bromoimidazo[1,5-a]pyrazin-3-yl)-2,2-dimethylhexahydroindolizin-3(2H)-one (6R,8aS)-6-(8-amino-1-bromoimidazo[1,5-a]pyrazin-3-yl)-2,2-dimethylhexahydroindolizin-3(2H)-one Step 1: 5-(methoxycarbonyl)-2-methylpyridine 1-oxide A solution of methyl 6-methylnicotinate (15 g, 99.34 mmol) and m-CPBA (18.8 g, 109.3 mmol) in DCM (100 mL) was stirred at room temperature for 4 hours. The reaction mixture was quenched with 200 mL of saturated aqueous $Na_2SO_3$ and 100 mL of saturated aqueous $NaHCO_3$. The resulting mixture was extracted with EA (200 mL×3). The combined EA layer was washed with brine and dried over $Na_2SO_4$. Filtered and the filtrate was concentrated. The residue was purified by column chromatography on silica gel (PE/EtOAc=5/1) to afford 5-(methoxycarbonyl)-2-methylpyridine 1-oxide as a solid. MS-ESI (m/z): 168.2 $(M+1)^+$ (LC-MS method D; Ret. time: 0.32 min).

Step 2: methyl 6-(hydroxymethyl)nicotinate

To a solution of 5-(methoxycarbonyl)-2-methylpyridine 1-oxide (12 g, 72 mmol) in DCM (50 mL) was added TFAA (25 mL) dropwise at 0° C. The mixture was stirred at reflux for 2 hours. The mixture was concentrated and the residue was adjusted to pH 9 with saturated aqueous $NaHCO_3$. The resulting mixture was extracted with EA. The solvent was removed and the residue was purified by column chromatography on silica gel (PE/EtOAc=1/1) to afford methyl 6-(hydroxymethyl)nicotinate.
MS-ESI (m/z): 168.2 $(M+1)^+$ (LC-MS method C; Rt: 0.25 min).

Step 3: methyl 6-formylnicotinate

A mixture of methyl 6-(hydroxymethyl)nicotinate (7 g, 37 mmol) and $MnO_2$ (32.3 g, 372 mmol) in DCM (200 mL) was stirred at 20° C. for 4 hours. The mixture was filtered and the filtrate was concentrated. The residue was purified by column chromatography on silica gel (PE/EtOAc=5/1) to afford methyl 6-formylnicotinate. MS-ESI (m/z): 166.2 $(M+1)^+$ (LC-MS method D; Ret. time: 0.36 min).

Step 4: methyl 6-(1-hydroxy-3-methoxy-2,2-dimethyl-3-oxopropyl)nicotinate

To a stirred solution of 1-methyl-1H-imidazole (296 mg, 3.6 mmol) and anhydrous LiCl (303 mg, 7.2 mmol) in DMF (150 mL) was added methyl 6-formylnicotinate (6 g, 36 mmol) and ((1-methoxy-2-methylprop-1-en-1-yl)oxy)trimethylsilane (9.4 g, 54 mmol) at room temperature under nitrogen atmosphere, and the resulting mixture was stirred for 10 h. The reaction was quenched by the addition of a little amount of 1 N aq HCl. The product was extracted with ethyl acetate twice. The combined organic layer was washed with water and brine, and evaporated to dryness. The residue was purified by column chromatography on silica gel (PE/EtOAc=10/1) to afford methyl 6-(1-hydroxy-3-methoxy-2,2-dimethyl-3-oxopropyl)nicotinate. MS-ESI (m/z): 268.0 $(M+1)^+$ (LC-MS method D; Ret. time: 0.888 min).

Step 5: methyl 6-(3-methoxy-2,2-dimethyl-1-((methylsulfonyl)oxy)-3-oxopropyl)nicotinate To a mixture of methyl 6-(1-hydroxy-3-methoxy-2,2-dimethyl-3-oxopropyl)nicotinate (5 g, 18.7 mmol) and TEA (3.78 g, 37.5 mmol) in DCM (200 mL) was added MsCl (5.15 g, 21 mmol) under ice-bath. The mixture was stirred at room temperature for 2 hours. The mixture was concentrated and the residue was purified by column chromatography on silica gel (PE/EtOAc=10/1) to afford methyl 6-(3-methoxy-2,2-dimethyl-1-((methylsulfonyl)oxy)-3-oxopropyl) nicotinate.
MS-ESI (m/z): 346.2 $(M+1)^+$ (LC-MS method D; Ret. time: 1.072 min).

Step 6: methyl 6-(3-methoxy-2,2-dimethyl-3-oxopropyl)nicotinate

A mixture of methyl 6-(3-methoxy-2,2-dimethyl-1-((methylsulfonyl)oxy)-3-oxopropyl)nicotinate (4 g, 11.6 mmol) and Pd/C (4 g) in MeOH (15 mL) was hydrogenated at room temperature for 2 hours. The mixture was filtered and the filtrate was concentrated, the residue was purified by column chromatography on silica gel (DCM/THF=5/1) to afford methyl 6-(3-methoxy-2,2-dimethyl-3-oxopropyl) nicotinate. MS-ESI (m/z): 252.2 $(M+1)^+$ (LC-MS method D; Ret. time: 1.059 min).

Step 7: methyl 2,2-dimethyl-3-oxooctahydroindolizine-6-carboxylate

To a solution of methyl 6-(3-methoxy-2,2-dimethyl-3-oxopropyl)nicotinate (1.2 g, 4.78 mmol) in AcOH (20 mL)

was added NaCNBH₃ (1.5 g, 24 mmol) in portions. The mixture was stirred at 60° C. for 16 hours. The mixture was concentrated and the residue was purified by column chromatography on silica gel PE/THF=10/1) to afford methyl 2,2-dimethyl-3-oxooctahydro indolizine-6-carboxylate. MS-ESI (m/z): 226.0 (M+1)⁺ (LC-MS method D; Ret. time: 0.918 min).

Step 8: 2,2-dimethyl-3-oxooctahydroindolizine-6-carboxylic acid

A mixture of methyl 2,2-dimethyl-3-oxooctahydroindolizine-6-carboxylate (530 mg, 2.36 mmol) and LiOH (495 mg, 11.8 mmol) in MeOH/THF/H₂O (5 mL/5 mL/2 mL) was stirred at 15° C. for 2 hours. The volatiles were removed and the mixture was adjusted to pH 4 with 1 N HCl. The resulting mixture was extracted with DCM/i-PrOH (10/1). The organic layer was dried over Na₂SO₄. The solvent was removed to give 2,2-dimethyl-3-oxooctahydroindolizine-6-carboxylic acid, which was used in the next step directly. MS-ESI (m/z): 212.0 (M+1)⁺ (LC-MS method D; Ret. time: 1.032 min).

Step 9: N-((3-chloropyrazin-2-yl)methyl)-2,2-dimethyl-3-oxooctahydroindolizine-6-carboxamide To a solution of 2,2-dimethyl-3-oxooctahydroindolizine-6-carboxylic acid (500 mg, 2.4 mmol) and (3-chloropyrazin-2-yl) methanamine (509 mg, 2.83 mmol) in THF (20 mL) was added HATU (1.075 g, 2.8 mmol) and TEA (596 mg, 5.9 mmol). The mixture was stirred at room temperature for 4 hours. Removed the volatiles under reduced pressure, and the rest mixture was extracted with DCM, the combined organic layer was washed with water, brine and dried over anhydrous Na₂SO₄. The organic layer was concentrated in vacuo and the residue was purified by silica gel column chromatography (PE/THF=10/1) to afford N-((3-chloropyrazin-2-yl)methyl)-2,2-dimethyl-3-oxooctahydroindolizine-6-carboxamide.
MS-ESI (m/z): 337.2 (M+1)⁺ (LC-MS method D; Ret. time: 0.935 min).

Step 10: 6-(8-chloroimidazo[1,5-a]pyrazin-3-yl)-2,2-dimethylhexahydroindolizin-3(2H)-one A mixture of N-((3-chloropyrazin-2-yl)methyl)-2,2-dimethyl-3-oxooctahydroindolizine-6-carboxamide (700 mg, 2.08 mmol) and PCl₅ (1.5 g, 7.3 mmol) in MeCN (40 mL) was stirred at 60° C. for 4 hours. The mixture was quenched with saturated NaHCO₃ solution and extracted with EA. The EA layer was washed with brine and dried over anhydrous Na₂SO₄. The mixture was filtered and the filtrate was concentrated. The residue was purified by silica gel column chromatography (DCM/THF=10/1) to afford 6-(8-chloroimidazo[1,5-a]pyrazin-3-yl)-2,2-dimethylhexahydroindolizin-3(2H)-one.
MS-ESI (m/z): 319.2 (M+1)⁺ (LC-MS method D; Ret. time: 1.04 min).

Step 11: 6-(1-bromo-8-chloroimidazo[1,5-a]pyrazin-3-yl)-2,2-dimethylhexahdroindolizin-3(2H)-one A mixture of 6-(8-chloroimidazo[1,5-a]pyrazin-3-yl)-2,2-dimethylhexahydroindolizin-3(2H)-one (200 mg, 0.63 mmol) and NBS (145 mg, 0.82 mmol) in DMF (5 mL) was stirred at 15° C. for 1 hour. The mixture was treated with water and extracted with EA. The EA layer was washed with brine and dried over anhydrous Na₂SO₄. Filtered and the filtrate was concentrated. The residue was purified by column chromatography on silica gel (PE/EtOAc=1/1) to afford 6-(1-bromo-8-chloroimidazo[1,5-a]pyrazin-3-yl)-2,2-dimethylhexahydroindolizin-3(2H)-one. MS-ESI (m/z): 398.9 (M+1)⁺ (LC-MS method D; Ret. time: 1.105 min).

Step 12: 6-(8-amino-1-bromoimidazo[1,5-a]pyrazin-3-yl)-2,2-dimethylhexahydroindolizin-3(2H)-one A solution of 6-(1-bromo-8-chloroimidazo[1,5-a]pyrazin-3-yl)-2,2-dimethylhexahydroindolizin-3(2H)-one (200 mg, 0.5 mol) in i-PrOH (10 mL) saturated with NH₃ was stirred at 80° C. for 16 hours in a 30 mL of sealed tube. The mixture was concentrated and the residue was purified by prep.TLC to give 6-(8-amino-1-bromoimidazo[1,5-a]pyrazin-3-yl)-2,2-dimethylhexahydro indolizin-3(2H)-one, which was separated by SFC to only afford two trans-isomers (6R,8aS)-6-(8-amino-1-bromoimidazo[1,5-a]pyrazin-3-yl)-2,2-dimethylhexahydroindolizin-3(2H)-one and (6S,8aR)-6-(8-amino-1-bromoimidazo[1,5-a]pyrazin-3-yl)-2,2-dimethyl hexahydroindolizin-3(2H)-one.

Intermediate 7

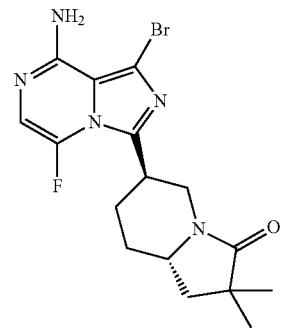 [SMILES: CC1(C)C[C@@H]2CC[C@@H](c3nc(Br)c4c(N)ncc(F)n34)CN2C1=O]

(6R,8aS)-6-(8-amino-1-bromo-5-fluoroimidazo[1,5-a]pyrazin-3-yl)-2,2-dimethylhexahydroindolizin-3 (2H)-one Step 1: (6R,8aS)-6-(8-amino-1-bromo-5-fluoro-6-methoxy-5,6-dihydroimidazo[1,5-a]pyrazin-3-yl)-2,2-dimethylhexahydroindolizin-3(2H)-one Selectfluor (412 mg, 1.163 mmol) was added to a stirred, cooled 0° C. (6R,8aS)-6-(8-amino-1-bromoimidazo[1,5-a]pyrazin-3-yl)-2,2-dimethylhexahydroindolizin-3(2H)-one (400 mg, 1.057 mmol) in MeCN (12 ml) and MeOH (12.00 ml) and the mixture was stirred at room temperature for Overnight. The reaction mixture was concentrated and purified by silica gel chromatography (40 g, DCM:MeOH=100%~90%) to give a (6R,8aS)-6-(8-amino-1-bromo-5-fluoro-6-methoxy-5,6-dihydroimidazo[1,5-a]pyrazin-3-yl)-2,2-dimethylhexahydroindolizin-3(2H)-one. C₁₇H₂₃BrFN₅O₂ [M/M+2]⁺ 428/430, found 428/430. ¹H NMR (400 MHz, CD₃OD) δ 6.82-6.57 (m, 1H), 5.14 (br. s., 1H), 4.16 (d, J=9.4 Hz, 1H), 3.63-3.52 (m, 1H), 3.49-3.42 (m, 3H), 3.19-3.11 (m, 1H), 3.02-2.88 (m, 1H), 2.20 (dd, J=7.2, 12.7 Hz, 1H), 2.09 (d, J=11.0 Hz, 2H), 1.93-1.81 (m, 1H), 1.57 (dd, J=8.0, 12.7 Hz, 1H), 1.45-1.33 (m, 1H), 1.19 (s, 3H), 1.16-1.07 (m, 3H).

Step 2: (6R,8aS)-6-(8-amino-1-bromo-5-fluoroimidazo[1,5-a]pyrazin-3-yl)-2,2-dimethylhexahydroindolizin-3(2H)-one To a solution of (6R,8aS)-6-(8-amino-1-bromo-5-fluoro-6-methoxy-5,6-dihydroimidazo[1,5-a]pyrazin-3-yl)-2,2-dimethylhexahydroindolizin-3(2H)-one (200 mg, 0.467 mmol) in Acetonitrile (8 ml) was added Cs2CO3 (1521 mg, 4.67 mmol) and heated to 90° C. for 0.5 h under Micwave for cooling condition. The reaction mixture (brown suspension) was cooled to room temperature (LCMS of the mixture examined), filtered, washed with acetonitrile and the solution was concentrated under reduced pressure. The residue was purified by column chromatography on 20 g silica gel [Column], eluting with $CH_2Cl_2$/MeOH (gradient 0% to 15%) to give the product (6R,8aS)-6-(8-amino-1-bromo-5-fluoroimidazo[1,5-a]pyrazin-3-yl)-2,2-dimethylhexahydroindolizin-3(2H)-one. C16H19BrFN5O $[M/M+2]^+$ 396/398, found 396/398. $^1$H NMR (400 MHz, $CDCl_3$) δ 7.75-7.41 (m, 1H), 6.14 (br. s., 2H), 4.82 (dd, J=3.1, 12.9 Hz, 1H), 3.89 (tdd, J=3.7, 7.2, 10.9 Hz, 1H), 3.76 (t, J=11.5 Hz, 1H), 3.53 (t, J=12.1 Hz, 1H), 2.67-2.52 (m, 3H), 2.47-2.36 (m, 1H), 1.98 (dd, J=7.8, 12.5 Hz, 1H), 1.88 (s, 3H), 1.82-1.72 (m, 1H), 1.68 (s, 3H) ppm.

Intermediate 8a and 8b

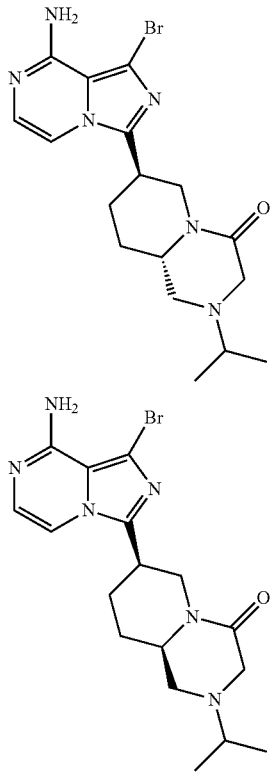

(7R,9aS)-7-(8-Amino-1-bromoimidazo[1,5-a]pyrazin-3-yl)-2-isopropylhexahydro-1H-pyrido[1,2-a]pyrazin-4(6H)-one (7R,9aR)-7-(8-Amino-1-bromoimidazo[1,5-a]pyrazin-3-yl)-2-isopropylhexahydro-1H-pyrido[1,2-a]pyrazin-4(6H)-one Step 1. Dimethyl pyridine-2,5-dicarboxylate $SOCl_2$ (855 g, 7.2 mol) was added dropwise into the solution of compound 1 (500 g, 3.0 mol) in MeOH (5 L) at room temperature. The mixture was stirred at 70° C. overnight. After cooling, the mixture was evaporated, and the residue was added EA (5 L), followed by $Na_2CO_3$ (sat.) until PH>7. The mixture was separated and the aqueous layer was extracted with EA (1 L*3). The combined organic layer was washed with brine, dried over $Na_2SO_4$, filtered and concentrated to give dimethyl pyridine-2,5-dicarboxylate as a solid. The product was used for next step without further purification.

Step 2. Methyl 6-(hydroxymethyl)nicotinate

The mixture of dimethyl pyridine-2,5-dicarboxylate (200 g, 1.03 mol) in MeOH (2400 ml) and THF (2200 ml) was added $CaCl_2$ (455 g, 4.10 mol) and $NaBH_4$ (97 g, 2.56 mol) below −10° C. The mixture was stirred below 0° C. for 3 hours. The mixture was added $NH_4Cl$ (15%, 2000 ml), and the temperature maintain below 5° C. Then, the solution was extracted with EA (500 ml×3). The combined organic layers were dried over $Na_2SO_4$, filtered and concentrated to give the crude product. The crude product was washed with PE:DCM=5:1 to give methyl 6-(hydroxymethyl) nicotinate as a solid. $^1$H NMR: 400 MHz $CDCl_3$: δ 8.052 (s, 1H), 8.315-8.290 (m, 1H), 7.381-7.359 (m, 1H), 4.845 (s, 2H), 3.969 (s, 3H) ppm.

Step 3. Methyl 6-(acetoxymethyl)nicotinate

The mixture of methyl 6-(hydroxymethyl) nicotinate (620 g, 3.7 mol) in DCM (6000 ml) was added $Et_3N$ (937 g, 9.3 mol), DMAP (31 g, 5%) and $Ac_2O$ (571 g, 5.5 mol). The mixture was stirred at room temperature for 3 hours. The mixture was added $H_2O$ (5000 ml), separated and the aqueous layer was extracted with DCM (1500 ml*3). The combined organic layers were dried over $Na_2SO_4$ and concentrated to give the crude product. The crude product was washed with PE:EA=5:1 to give methyl 6-(acetoxymethyl) piperidine-3-carboxylate. $^1$H NMR: 400 MHz $CDCl_3$ δ: 9.209-9.205 (s, 1H), 8.347-8.322 (m, 1H), 7.469-7.449 (d, J=8 Hz, 1H), 5.305 (s, 2H), 3.984 (s, 3H), 2.218 (s, 3H), 3.565-3.465 (m, 2H), 2.135-1.878 (m, 2H) ppm.

Step 4. Methyl 6-(acetoxymethyl)piperidine-3-carboxylate $NaBH_3CN$ (136 g, 2.15 mol) was added in portions to the solution of methyl 6-(acetoxymethyl)piperidine-3-carboxylate (100 g, 0.48 mol) in $CH_3COOH$ (500 ml) at 0° C. for 2 hours and the mixture was stirred at 30° C. for 2 hours, quenched with $H_2O$ (120 ml), evaporated in vacuum to give com methyl 6-(acetoxymethyl)piperidine-3-carboxylate (400 g, crude) as an oil, which was directly used for next step without further purification. LCMS: (M+1=216.2).

Step 5. trans-1-benzyl 3-methyl 6-(acetoxymethyl)piperidine-1,3-dicarboxylate NaHCO$_3$ (67.2 g, 0.8 mol) was added very slowly to the mixture of methyl 6-(acetoxymethyl)piperidine-3-carboxylate (133 g, 0.16 mol) in THF (300 ml) and H$_2$O (300 ml), followed by Cbz-Cl (270 g, 0.16 mol). The mixture was stirred at room temperature for 18 hours. The mixture was filtered, extracted with EA (600 ml×3). The combined organic layers were dried over Na$_2$SO$_4$, filtered and concentrated to give the crude product. Chromatograph column (EA in PE from 0% to 33%) gave an oil. Prep-HPLC gave trans-1-benzyl 3-methyl 6-(acetoxymethyl)piperidine-1,3-dicarboxylate. $^1$H NMR: 400 MHz CDCl$_3$ δ: 7.377-7.323 (m, 5H), 5.188-5.080 (m, 2H), 4.627-4.570 (m, 1H), 4.325-4.284 (m, 2H), 4.235-4.137 (s, 1H), 3.700 (s, 3H), 3.066-2.965 (m, 1H), 2.557-2.400 (m, 1H), 2.018-1.917 (m, 4H), 1.772-1.648 (m, 4H) ppm.

Step 6. (3 S,6R)-1-benzyl 3-methyl 6-(hydroxymethyl)piperidine-1,3-dicarboxylate and (3R,6S)-1-benzyl 3-methyl 6-(hydroxymethyl)piperidine-1,3-dicarboxylate The mixture of trans-1-benzyl 3-methyl 6-(acetoxymethyl)piperidine-1,3-dicarboxylate (25 g, 0.072 mmol), NaHCO$_3$ (54 g, 0.64 mol) and K$_2$CO$_3$ (4.94 g, 35.8 mmol) in MeOH (100 ml) was was stirred at room temperature for 1 hour, filtered, diluted with H$_2$O (100 ml), extracted with DCM (100 ml×3). The combined organic layers were washed with H$_2$O (100 ml), brine (100 ml), evaporated in vacuo to get crude product. Chromatograph column (EA in PE from 0% to 33%) gave colorless oil trans-1-benzyl 3-methyl 6-(hydroxymethyl)piperidine-1,3-dicarboxylate. The racemic mixture was further separated by SFC to obtain (3S,6R)-1-benzyl 3-methyl 6-(hydroxymethyl)piperidine-1,3-dicarboxylate (retention time=4.254 min) and (3R,6S)-1-benzyl 3-methyl 6-(hydroxymethyl)piperidine-1,3-dicarboxylate (retention time=4.607 min). SFC separation condition: Instrument: SFC Thar 200. Column: Chiralpak AD-H 250×50 mm I.D., 10 um filling. Mobile phase: A for CO$_2$ and B for ETOH (0.1% NH$_3$H$_2$O). Gradient: B 40% Flow rate: 200 mL/min. Back pressure: 100 bar. Column temperature: 35° C. Wavelength: 220 nm. $^1$H NMR: 400 MHz CDCl$_3$ δ: 7.379-7.311 (m, 5H), 5.227-5.195 (d, J=12.8 Hz, 1H), 5.121-5.089 (d, J=12.8 Hz, 1H), 4.248-4.169 (m, 2H), 3.846-3.818 (m, 1H), 3.721-3.679 (m, 1H), 3.625 (s, 3H), 3.450-3.322 (m, 1H), 2.617-2.594 (m, 1H), 1.999-1.899 (m, 1H), 1.855-1.831 (m, 2H), 1.616-1.582 (m, 1H) ppm.

Step 7: (3R,6S)-1-benzyl 3-methyl 6-(((tert-butyldiphenylsilyl)oxy)methyl)piperidine-1,3-dicarboxylate To a solution of (3R,6S)-1-benzyl 3-methyl 6-(hydroxymethyl)piperidine-1,3-dicarboxylate (2.00 g, 6.51 mmol), imidazole (0.532 g, 7.81 mmol) in DMF (10 ml) was added TBDPS-Cl (2.0 ml, 7.81 mmol). It was stirred at rt for 2 h. The reaction mixture was diluted with ethyl acetate, washed with water three times, then brine once. The organic layer was dried over sodium sulfate, filtered and concentrated. The residue was purified by MPLC (Gold 120 g, 0-50% ethyl acetate in hexane) to give the title compound as a solid. LC-MS: C$_{32}$H$_{39}$NO$_5$Si, calc.=546.27; found=546.29 (M+H)$^+$.

Step 8: (3R,6S)-1-((benzyloxy)carbonyl)-6-(((tert-butyldiphenylsilyl)oxy)methyl)piperidine-3-carboxylic acid To a solution of (3R,6S)-1-benzyl 3-methyl 6-(((tert-butyldiphenylsilyl)oxy)methyl)piperidine-1,3-dicarboxylate (3.40 g, 6.23 mmol) in THF (40 ml), MeOH (40.0 ml) and Water (40.0 ml) was added LiOH (5 M, 8 ml, 40.0 mmol) slowly. It was stirred at rt for 3 h and acidified by 1 M HCl (about 40 mL) to adjust pH to 5. The mixture was extracted with ethyl acetate (3×100 mL). The combined organic layers were washed with brine (100 mL), dried over sodium sulfate, filtered and concentrated under reduced pressure. The residue was used without purification. LC-MS: $C_{31}H_{37}NO_5Si$, calc.=532.25; found=532.34 (M+H)$^+$.

Step 9: (2S,5R)-benzyl 2-(((tert-butyldiphenylsilyl)oxy)methyl)-5-(((3-chloropyrazin-2-yl)methyl)carbamoyl)piperidine-1-carboxylate To a mixture of (3R,6S)-1-((benzyloxy)carbonyl)-6-(((tert-butyldiphenylsilyl)oxy)methyl)piperidine-3-carboxylic acid (3.3 g, 6.21 mmol), (3-chloropyrazin-2-yl)methanamine bis-hydrochloride salt (1.478 g, 6.83 mmol) and HATU (2.83 g, 7.45 mmol) in DMF (20 ml) was added DIEA (3.25 ml, 18.62 mmol). The mixture was stirred at rt for 1 h. Most solvent was removed under reduced pressure and the residue was diluted with ethyl acetate (100 mL), washed with water (3×50 mL), then brine (100 mL). The organic layer was separated and dried over sodium sulfate, filtered and concentrated under reduced pressure. The residue was purified by MPLC (Gold 80 g, 0-100% EtOAc/EtOH (3:1) in hexane) to give the title compound. LC-MS: C$_{36}$H$_{41}$ClN$_4$O$_4$Si, calc.=656.27; found=656.41 (M+H)$^+$.

Step 10: (2S,5R)-benzyl 2-(((tert-butyldiphenylsilyl)oxy)methyl)-5-(8-chloroimidazo[1,5-a]pyrazin-3-yl)piperidine-1-carboxylate To a mixture of (2S,5R)-benzyl 2-(((tert-butyldiphenylsilyl)oxy)methyl)-5-(((3-chloropyrazin-2-yl)methyl)carbamoyl)piperidine-1-carboxylate (2.2 g, 3.35 mmol) and sodium carbonate (2.84 g, 26.8 mmol) in acetonitrile (12 mL) and DMF (12.00 mL) at 0° C. was added POCl$_3$ (1 mL, 10.73 mmol) dropwise. It was warmed to 45° C. and stirred for 1 h. The mixture was diluted with 100 mL of ethyl acetate and washed with water (3×50 mL). The combined aqueous layers were extracted with ethyl acetate (100 mL). The combined organic layers were washed with brine, dried over sodium sulfate, filtered and concentrated. The residue was purified by MPLC (Gold 40 g, 0-100% EtOAc/EtOH (3:1) in hexane) to give the title compound. LC-MS: C36H39ClN4O3Si, calc.=639.26; found=656.41 (M+H)$^+$. (6R,8aS)-6-(8-Chloroimidazo[1,5-a]pyrazin-3-yl)tetrahydro-1H-oxazolo[3,4-a]pyridin-3(5H)-one was also isolated.

Step 11: (2S,5R)-benzyl 5-(1-bromo-8-chloroimidazo[1,5-a]pyrazin-3-yl)-2-(((tert-butyldiphenylsilyl)oxy)methyl)piperidine-1-carboxylate To a solution of (2S,5R)-benzyl 2-(((tert-butyldiphenylsilyl)oxy)methyl)-5-(8-chloroimidazo[1,5-a]pyrazin-3-yl)piperidine-1-carboxylate (1.33 g, 2.081 mmol) in acetonitrile (15 ml) was added NBS (0.444 g, 2.497 mmol). The mixture was stirred at rt for 15 min. It was concentrated and purified by MPLC (gold 40 g, 0-50% ethyl acetate in hexane) to give the title compound. LC-MS: C$_{36}$H$_{38}$BrClN$_4$O$_3$Si, calc.=717.17, 719.17; found=717.35, 719.30 (M+H)$^+$.

Step 12: (2S,5R)-benzyl 5-(1-bromo-8-((2,4-dimethoxybenzyl)amino)imidazo[1,5-a]pyrazin-3-yl)-2-(((tert-butyldiphenylsilyl)oxy)methyl)piperidine-1-carboxylate To a solution of (2S,5R)-benzyl 5-(1-bromo-8-chloroimidazo[1,5-a]pyrazin-3-yl)-2-(((tert-butyldiphenylsilyl)oxy)methyl)piperidine-1-carboxylate (1.35 g, 1.880 mmol) in DMF (6 ml) was added 2,4-dimethoxybenzylamine (0.40 g, 2.392 mmol) and triethylamine (0.42 ml, 3.01 mmol). The mixture was stirred at 60° C. for 4 h. It was diluted with ethyl acetate, washed with water three times and brine once. The organic layer was dried over sodium sulfate, filtered and concentrated under reduced pressure. The residue was purified by MPLC (Gold 40 g, 0-50% ethyl acetate in hexane) to give the title compound as a white solid. LC-MS: C$_{45}$H$_{50}$BrN$_5$O$_5$Si, calc.=848.36, 850.31; found=848.28, 850.29 (M+H)$^+$.

Step 13: (2S,5R)-benzyl 5-(1-bromo-8-((2,4-dimethoxybenzyl)amino)imidazo[1,5-a]pyrazin-3-yl)-2-(hydroxymethyl)piperidine-1-carboxylate A solution of (2S,5R)-benzyl 5-(1-bromo-8-((2,4-dimethoxybenzyl)amino)imidazo[1,5-a]pyrazin-3-yl)-2-(((tert-butyldiphenylsilyl)oxy)methyl)piperidine-1-carboxylate (880 mg, 1.037 mmol) in THF (5 ml) in a plastic vial was treated with HF (70 wt % in pyridine, 0.8 ml, 1.037 mmol) at rt for 3 h. It was diluted with ethyl acetate, washed with sodium bicarbonate, brine. The organic layer was dried over sodium sulfate, filtered and concentrated. The residue was purified by MPLC (Gold 40 g, 0-100% EtOAc/EtOH in hexane) to give the title compound. LC-MS: C$_{29}$H$_{32}$BrN$_5$O$_5$, calc.=610.17, 612.17; found=610.21, 612.16 (M+H)$^+$.

Step 14: (2S,5R)-benzyl 5-(1-bromo-8-((2,4-dimethoxybenzyl)amino)imidazo[1,5-a]pyrazin-3-yl)-2-formylpiperidine-1-carboxylate To a solution of (2S,5R)-benzyl 5-(1-bromo-8-((2,4-dimethoxybenzyl)amino)imidazo[1,5-a]pyrazin-3-yl)-2-(hydroxymethyl)piperidine-1-carboxylate (550 mg, 0.901 mmol) in DCM (9 mL) was added Dess-Martin periodinane (535 mg, 1.261 mmol). It was stirred at rt for 30 min. The reaction was quenched with aqueous sodium bicarbonate and sodium thiosulfate. The mixture was extracted with ethyl acetate. The organic layer was dried over sodium sulfate, filtered and concentrated under reduced pressure to give the title compound. It was used without further purification.

Step 15: (2S,5R)-benzyl 5-(1-bromo-8-((2,4-dimethoxybenzyl)amino)imidazo[1,5-a]pyrazin-3-yl)-2-((isopropyl(2-methoxy-2-oxoethyl)amino)methyl)piperidine-1-carboxylate A solution of (2S,5R)-benzyl 5-(1-bromo-8-((2,4-dimethoxybenzyl)amino)imidazo[1,5-a]pyrazin-3-yl)-2-formylpiperidine-1-carboxylate (548 mg, 0.901 mmol) and methyl 2-(isopropylamino)acetate (354 mg, 1.351 mmol) in DCM (6 ml) was stirred for 2 h. To the solution was added sodium triacetoxyborohydride (382 mg, 1.801 mmol) and the mixture was stirred for 30 min. It was directly purified by MPLC (gold 40 g, 0-10% methanol in DCM) to give the title compound. LC-MS: C$_{35}$H$_{43}$BrN$_6$O$_6$, calc.=723.25, 725.25; found=723.34, 725.21 (M+H)$^+$. $^1$H NMR (CDCl$_3$, 500 MHz): 0.99 (3H, d, J=6.51 Hz), 1.04 (3H, d, J=6.58 Hz), 1.80-1.76 (1H, m), 2.19-2.04 (3H, m), 2.45-2.35 (1H, m), 2.81 (2H, d, J=7.75 Hz), 3.06 (1H, t, J=6.60 Hz), 3.19 (1H, s), 3.33 (2H, s), 3.48 (1H, dd, J=13.89, 4.17 Hz), 3.69-3.65 (3H, m), 3.83 (3H, s), 3.91 (3H, s), 4.17 (1H, d, J=13.94 Hz), 4.29-4.24 (1H, m), 4.70 (2H, d, J=5.54 Hz), 5.04-4.98 (2H, m), 6.48 (1H, dd, J=8.24, 2.42 Hz), 6.53 (1H, d, J=2.37 Hz), 6.75 (1H, t, J=5.57 Hz), 6.98 (1H, d, J=5.05 Hz), 7.08 (1H, d, J=5.02 Hz), 7.19 (2H, d, J=7.34 Hz), 7.28-7.35 (3H, m) ppm.

Diastereomer (2R,5R)-benzyl 5-(1-bromo-8-((2,4-dimethoxybenzyl)amino)imidazo[1,5-a]pyrazin-3-yl)-2-((isopropyl(2-methoxy-2-oxoethyl)amino)methyl)piperidine-1-carboxylate was isolated also. LC-MS: C$_{35}$H$_{43}$BrN$_6$O$_6$, calc.=723.25, 725.25; found=723.32, 725.22 (M+H)$^+$. $^1$H NMR (CHCl$_3$-d, 500 MHz): 1.06-0.93 (6H, m), 1.72 (1H, br s), 2.19-1.98 (3H, m), 2.65 (1H, br s), 2.88 (1H, dd, J=13.49, 9.29 Hz), 3.15-2.98 (2H, m), 3.27 (1H, d, J=7.47 Hz), 3.40 (1H, s), 3.65 (1H, s), 3.71 (1H, s), 3.83 (3H, s), 3.91 (3H, d, J=2.75 Hz), 4.35-4.19 (2H, m), 4.70 (2H, t, J=6.16 Hz), 5.24-5.10 (2H, m), 6.47 (1H, d, J=8.34 Hz), 6.52 (1H, s), 6.75 (1H, s), 6.98 (1H, dd, J=31.21, 5.03 Hz), 7.18-7.14 (1H, m), 7.39-7.34 (5H, m) ppm.

Step 16: (7R,9aS)-7-(8-amino-1-bromoimidazo[1,5-a]pyrazin-3-yl)-2-isopropylhexahydro-1H-pyrido[1,2-a]pyrazin-4(6H)-one (2S,5R)-Benzyl 5-(1-bromo-8-((2,4-dimethoxybenzyl)amino)imidazo[1,5-a]pyrazin-3-yl)-2-((isopropyl(2-methoxy-2-oxoethyl)amino)methyl)piperidine-1-carboxylate (320 mg, 0.442 mmol) was treated with TFA (6 mL, 78 mmol) at 100° C. for 1 h. Most TFA was removed under reduced pressure and the residue was dissolved in DCM. It was concentrated again to give a crude product. It was used without purification. LC-MS: C$_{17}$H$_{23}$BrN$_6$O, calc.=407.12, 409.12; found=407.08, 409.01 (M+H)$^+$. $^1$H NMR (CDCl$_3$, 500 MHz): 1.08 (3H, d, J=4.17 Hz), 1.10 (3H, d, J=4.19 Hz), 1.70 (1H, t, J=11.40 Hz), 1.89 (1H, dd, J=13.45, 3.75 Hz), 2.20-2.18 (2H, m), 2.46 (1H, dd, J=11.87, 6.68 Hz), 2.78-2.73 (2H, m), 3.00-2.97 (2H, m), 3.19 (1H, d, J=5.39 Hz), 3.34 (1H, d, J=15.92 Hz), 3.48 (1H, br s), 4.92 (1H, dd, J=13.17, 4.04 Hz), 7.01 (1H, d, J=5.26 Hz), 7.30 (1H, d, J=5.29 Hz) ppm.

(7R,9aR)-7-(8-amino-1-bromoimidazo[1,5-a]pyrazin-3-yl)-2-isopropylhexahydro-1H-pyrido[1,2-a]pyrazin-4(6H)-one (2R,5R)-Benzyl 5-(1-bromo-8-((2,4-dimethoxybenzyl)amino)imidazo[1,5-a]pyrazin-3-yl)-2-((isopropyl(2-methoxy-2-oxoethyl)amino)methyl)piperidine-1-carboxylate (76 mg, 0.105 mmol) was treated with TFA (2 mL, 26.0 mmol) at 100° C. for 2 h. It was concentrated and the residue was dissolved in 2 mL DCM and added 1 mL of TEA. It was loaded on a silica gel sampler and purified by MPLC (Gold 12 g, 0-100% ethyl acetate/ethanol (3:1) in hexane with 2% TEA) to give the title compound. LC-MS: C$_{17}$H$_{23}$BrN$_6$O, calc.=407.12, 409.12; found=406.99, 408.95 (M+H)$^+$.

Intermediate 9

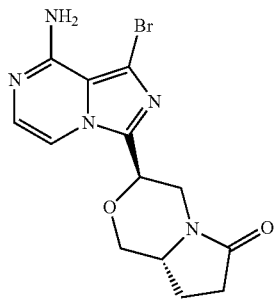 [SMILES: Nc1nccn2c([C@H]3CN4C(=O)CC[C@@H]4CO3)nc(Br)c12]

(3R,8aR)-3-(8-amino-1-bromoimidazo[1,5-a]
pyrazin-3-yl)tetrahydro-1H-pyrrolo[2,1-c][1,4]ox-
azin-6(7H)-one

Step 1: (R)-5-(((tert-butyldimethylsilyl)oxy)methyl)pyrrolidin-2-one

To a solution of (R)-5-(((tert-butyldimethylsilyl)oxy) methyl)pyrrolidin-2-one (25 g, 217.14 mmol) in anhydrous DMF (100 mL) was added TBSCl (49.09 g, 325.72 mmol) and 4H-imidazole (44.35 g, 651.43 mmol). The mixture was stirred at 25° C. for 3 hours. The mixture was quenched by the addition of water (100 mL), the mixture was then extracted with EtOAc (200 mL×4). The combined organic layers were washed with brine (100 mL×5), dried over sodium sulfate, filtered and concentrated to afford the crude product, which was purified on silica gel column chromatograph (THF/PE=5%~30%) to give (R)-5-(((tert-butyldimethylsilyl)oxy)methyl)pyrrolidin-2-one as an oil. $^1$H NMR (400 MHz, CDCl$_3$)=5.80 (s, 1H), 3.76-3.64 (m, 1H), 3.61 (d, J=2.8 Hz, 1H), 3.46-3.41 (m, 1H), 2.37-2.32 (m, 2H), 2.20-2.16 (m, 1H), 1.74-1.70 (m, 1H), 0.88 (s, 9H), 0.06 (s, 6H) ppm; (ESI): M/Z (M+1): 230.1 (LC-MS method C; RetTime: 1.466).

Step 2: (R)-5-(((tert-butyldimethylsilyl)oxy)methyl)-1-((R)-oxiran-2-ylmethyl)pyrrolidin-2-one To a solution of (R)-5-(((tert-butyldimethylsilyl)oxy)methyl)pyrrolidin-2-one (16 g, 69.75 mmol) in anhydrous THF (500 mL) was added NaH (60%, 3.07 g, 76.72 mmol) at 0° C. portionwise. The mixture was stirred at 25° C. for 1 hour, then (S)-2-(chloromethyl)oxirane (7.74 g, 83.70 mmol) was added and the mixture was heated to 80° C. stirred for another 10 hours. The mixture was quenched by the addition of sat. NH$_4$Cl (200 mL) at 0° C., the mixture was then extracted with EtOAc (100 mL×4), the combined organic layers were washed with brine (100 mL), dried over sodium sulfate, filtered and concentrated to afford the crude product, which was purified on silica gel column chromatograph (THF/PE=5%~35%) to give (R)-5-(((tert-butyldimethylsilyl)oxy)methyl)-1-((R)-oxiran-2-ylmethyl)pyrrolidin-2-one. $^1$H NMR (400 MHz, CDCl$_3$)=4.19 (dd, J=2.8, 14.8, 1H), 3.80-3.77 (m, 2H), 3.60-3.56 (m, 1H), 3.25-3.13 (m, 1H), 3.08-3.00 (m, 1H), 2.77 (d, J=8.8 Hz, 1H), 2.74-2.65 (m, 1H), 2.49-2.41 (m, 1H), 2.40-2.26 (m, 1H), 2.23-2.08 (m, 1H), 1.93-1.82 (m, 1H), 0.87 (s, 9H), 0.04 (s, 6H); (ESI): M/Z (M+1): 286.1 (LC-MS method D; R.T.: 0.804).

Step 3: (R)-5-(hydroxymethyl)-1-((R)-oxiran-2-ylmethyl)pyrrolidin-2-one

To a solution of (R)-5-(((tert-butyldimethylsilyl)oxy) methyl)-1-((R)-oxiran-2-ylmethyl)pyrrolidin-2-one (2.7 g, 9.46 mmol) in anhydrous THF (30 mL), TBAF (2.97 g, 11.35 mmol) was added portionwise. The reaction mixture was stirred at 25° C. for 2 hrs. The reaction was quenched by water (3 mL), then the mixture was concentrated to afford the crude product, which was purified on silica gel column chromatograph (THF/PE=20%~100%) to give (R)-5-(hydroxymethyl)-1-((R)-oxiran-2-ylmethyl)pyrrolidin-2-one. $^1$H NMR (400 MHz, CD$_3$OD)=3.99 (dd, J=2.8, 14.8, 1H), 3.90-3.82 (m, 1H), 3.80-3.74 (m, 1H), 3.57-3.53 (m, 1H), 3.07-3.04 (m, 1H), 2.95-2.86 (m, 1H), 2.77-2.75 (m, 1H), 2.58-2.56 (m, 1H), 2.45-2.41 (m, 1H), 2.36-2.30 (m, 1H), 2.22-2.13 (m, 1H), 1.99-1.92 (m, 1H) ppm; (ESI): M/Z (M+1): 172.1 (LC-MS method D; R.T.: 0.201).

Step 4: (3R,8aR)-3-(hydroxymethyl)tetrahydro-1H-pyrrolo[2,1-c][1,4]oxazin-6(7H)-one Na (1.93 g, 84.12 mmol) was added to EtOH (30 mL) and the mixture was stirred at 25° C. for 40 mins, then a solution of (R)-5-(hydroxymethyl)-1-((R)-oxiran-2-ylmethyl)pyrrolidin-2-one (2.4 g, 8.18 mmol) in anhydrous EtOH (30 mL) was added at 0° C. The mixture was stirred at 25° C. for 16 hours. The mixture was adjusted to pH=7 with 1M HCl and concentrated to afford a residue, which was diluted with DCM (100 mL) and stirred for 20 mins. The mixture was filtered and the filtrate was concentrated to give crude (3R,8aR)-3-(hydroxymethyl)tetrahydro-1H-pyrrolo[2,1-c][1,4]oxazin-6(7H)-one, which was immediately used in the next step. (ESI): M/Z (M+1): 172.1 (LC-MS method D; R.T.: 0.100).

Step 5: (3R,8aR)-6-oxohexahydro-1H-pyrrolo[2,1-c][1,4]oxazine-3-carboxylic acid To a solution of (3R,8aR)-3-(hydroxymethyl)tetrahydro-1H-pyrrolo[2,1-c][1,4]oxazin-6(7H)-one (1.1 g, 6.43 mmol) in acetone (50 mL) and Sat.NaHCO$_3$ (15 mL) was added TEMPO (50.2 mg, 0.321 mmol) and NaBr (198.3 mg, 1.93 mol). Then 1,3,5-trichloro-1,3,5-triazinane-2,4,6-trione (3 g, 12.85 mmol) was added portionwise at 0° C. The reaction mixture was stirred at 25° C. for 12 hrs. The reaction was quenched by i-PrOH (20 mL) and stirred for another 60 mins. The mixture was filtered and filtrate was adjusted to basic to PH=8 with sat. NaHCO$_3$. It was extracted with DCM (100 mL), the aqueous layer was adjust acid to PH=4 with 2M HCl. It was extracted with DCM/i-PrOH (3:1, 100 mL×4), the combined organic layers were washed with brine (30 mL), dried over sodium sulfate, filtered and concentrated to give (3R,8aR)-6-oxohexahydro-1H-pyrrolo[2,1-c][1,4]oxazine-3-carboxylic acid as an oil, which was immediately used in the next step. (ESI): M/Z (M+1): 186.1 (LC-MS method D; R.T.: 0.205)

Step 6: (3R,8aR)-N-((3-chloropyrazin-2-yl)methyl)-6-oxohexahydro-1H-pyrrolo[2,1-c][1,4]oxazine-3-carboxamide To a solution of (3R,8aR)-6-oxohexahydro-1H-pyrrolo[2,1-c][1,4]oxazine-3-carboxylic acid (600 mg, 3.24 mmoL) in DCM (20 mL) was added isobutyl carbonochloridate (531 mg, 3.56 mmol) and TEA (0.53 mL, 3.78 mmol), the mixture was stirred at 0° C. for 1 hour, then (3-chloropyrazin-2-yl)

methanamine hydrochloride (641 mg, 3.56 mmol) and TEA (1.1 mL, 7.56 mmol) was added at 0° C. The mixture was stirred at 25° C. for 3 hours. To the mixture was added water (20 mL) and DCM (50 mL), the mixture was then separated and the aqueous layer was extracted with DCM (50 mL×3), the combined organic layers were washed with brine (20 mL), dried over sodium sulfate, filtered and concentrated to afford the crude product, which was purified on silica gel column chromatograph (MeOH/DCM=0-10%) to give (3R, 8aR)-N-((3-chloropyrazin-2-yl)methyl)-6-oxohexahydro-1H-pyrrolo[2,1-c][1,4]oxazine-3-carboxamide. $^1$H NMR (400 MHz, CDCl$_3$) d=8.50 (d, J=2.5 Hz, 1H), 8.36 (d, J=2.0 Hz, 1H), 7.78 (br. s., 1H), 4.74 (d, J=5.0 Hz, 2H), 4.52 (dd, J=3.1, 13.4 Hz, 1H), 4.23 (dd, J=3.8, 11.3 Hz, 1H), 3.97 (dd, J=3.0, 11.0 Hz, 1H), 3.75 (dtd, J=4.0, 7.3, 10.8 Hz, 1H), 3.30 (t, J=11.0 Hz, 1H), 2.86 (t, J=12.3 Hz, 1H), 2.60-2.43 (m, 2H), 2.29-2.13 (m, 1H), 1.70-1.54 (m, 1H) ppm.

Step 7: (3R,8aR)-3-(8-chloroimidazo[1,5-a]pyrazin-3-yl)tetrahydro-1H-pyrrolo[2,1-c][1,4]oxazin-6(7H)-one To a solution of (3R,8aR)-N-((3-chloropyrazin-2-yl)methyl)-6-oxohexahydro-1H-pyrrolo[2,1-c][1,4]oxazine-3-carboxamide (600 mg, 1.93 mmol) in anhydrous MeCN (15 mL) was added PCl$_5$ (2 g, 9.65 mmol) at 0° C. The mixture was stirred at 15° C. for 15 hours. The mixture was poured into ice-water, adjust basic with Sat. NaHCO$_3$, then separated and the aqueous layer was extracted with DCM (50 mL×3), the combined organic layers were washed with brine (20 mL), dried over sodium sulfate, filtered and concentrated to afford the crude product, which was purified on silica gel column chromatography (MeOH/DCM=0-10%) to give (3R,8aR)-3-(8-chloroimidazo[1,5-a]pyrazin-3-yl)tetrahydro-1H-pyrrolo[2,1-c][1,4]oxazin-6(7H)-one. (ESI): M/Z (M+1): 293.0 (LC-MS method D; R.T.: 0.585).

Step 8: (3R,8aR)-3-(1-bromo-8-chloroimidazo[1,5-a]pyrazin-3-yl)tetrahydro-1H-pyrrolo[2,1-c][1,4]oxazin-6(7H)-one To a solution of (3R,8aR)-3-(8-chloroimidazo[1,5-a]pyrazin-3-yl)tetrahydro-1H-pyrrolo[2,1-c][1,4]oxazin-6(7H)-one (300 mg, 1.02 mmol) in anhydrous MeCN (10 mL) was added 1-bromopyrrolidine-2,5-dione (219 mg, 1.23 mmol). The mixture was stirred at 25° C. for 1 hour. The mixture was quenched by the addition of water (10 mL) at 0° C., the mixture was then extracted with DCM/i-PrOH (3:1, 30 mL×4), the combined organic layers were washed with brine (10 mL), dried over sodium sulfate, filtered and concentrated to give (3R,8aR)-3-(1-bromo-8-chloroimidazo[1,5-a]pyrazin-3-yl)tetrahydro-1H-pyrrolo[2,1-c][1,4]oxazin-6(7H)-one, which was immediately used in the next step. (ESI): M/Z (M+1): 370.8 (LC-MS method D; R.T.: 1.133).

Step 9: (3R,8aR)-3-(8-amino-1-bromoimidazo[1,5-a]pyrazin-3-yl)tetrahydro-1H-pyrrolo[2,1-c][1,4]oxazin-6(7H)-one To a solution of (3R,8aR)-3-(1-bromo-8-chloroimidazo[1,5-a]pyrazin-3-yl)tetrahydro-1H-pyrrolo[2,1-c][1,4]oxazin-6(7H)-one (300 mg, 0.807 mmol) in NH$_3$.H$_2$O (4 mL) was added i-PrOH (4 mL). The mixture was stirred at 100° C. for 12 hour under a sealed tube. The mixture was concentrated to give crude (3R,8aR)-3-(8-amino-1-bromoimidazo[1,5-a]pyrazin-3-yl)tetrahydro-1H-pyrrolo[2,1-c][1,4]oxazin-6(7H)-one, which was immediately used in the next step. (ESI): M/Z (M+1): 351.8 (LC-MS method D; R.T.: 1.239).

Intermediate 10E1 and 10E2

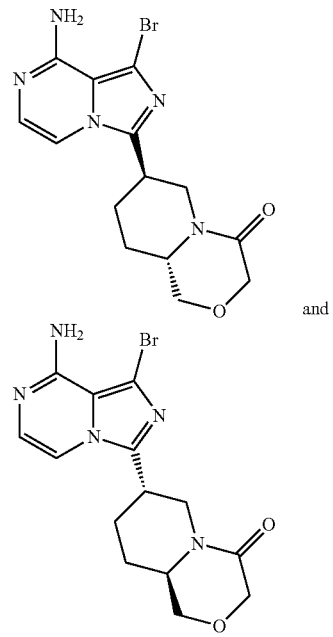

and (7R,9aS)-7-(8-amino-1-bromoimidazo[1,5-a]pyrazin-3-yl)hexahydropyrido[2,1-c][1,4]oxazin-4(3H)-one & (7S,9aR)-7-(8-amino-1-bromoimidazo[1,5-a]pyrazin-3-yl)hexahydropyrido[2,1-c][1,4]oxazin-4(3H)-one Step 1: methyl 6-((2-ethoxy-2-oxoethoxy)methyl)nicotinate To a solution of methyl 6-(hydroxymethyl)nicotinate (15.0 g, 89.7 mmol) in tetrahydrofuran (300 mL) was added NaH (4.7 g, 10.4 mmol, 60%) in one portion at 0° C. After 30 min, ethyl 2-bromoacetate (14.9 mL, 134.6 mmol) was added to the reaction mixture. The reaction mixture was heated to 70° C. overnight and quenched with saturated NaHCO$_3$ and extracted with ethyl acetate (150 mL×3). The combined organic layers were washed with brine, dried over sodium sulfate, filtered and concentrated in vacuo to afford the crude product, which was purified by silica gel column chromatography (EA: PE=10%~70%) to give methyl 6-((2-ethoxy-2-oxoethoxy)methyl)nicotinate. $^1$HNMR (400 MHz, CDCl$_3$): δ=9.12 (d, J=1.5 Hz, 1H), 8.29 (dd, J=8.2, 2.1 Hz, 1H), 7.60 (d, J=8.0 Hz, 1H), 4.79 (s, 2H), 4.20-4.25 (m, 4H), 3.93 (s, 3H), 1.25-1.30 ppm (m, 3H). MS (ESI): M/Z (M+1): 253.9.

Step 2: trans-methyl 4-oxooctahydropyrido[2,1-c][1,4]oxazine-7-carboxylate

To a solution of methyl 6-((2-ethoxy-2-oxoethoxy)methyl)nicotinate (8.0 g, 31.6 mmol) in AcOH (100 ml) was added NaBH$_3$CN (6.0 g, 94.8 mmol) portionwise at 0° C. and the reaction mixture was stirred at rt overnight. The reaction mixture was concentrated in vacuo and the residue was dissolved in H₂O (100 ml) and basified with aqueous NaHCO₃ to pH 8. The reaction mixture was extracted with EA (100 mL×3). The organic layer was dried over Na₂SO₄ and concentrated in vacuo. The residue was dissolved into MeOH (300 ml) and the resulting mixture was refluxed for 4 h and concentrated in vacuo to afford the crude product, which was purified by silica gel column chromatography (THF:PE=10%~80%) to give trans-methyl 4-oxooctahydropyrido[2,1-c][1,4]oxazine-7-carboxylate. ¹HNMR (400 MHz, CDCl₃): δ=4.85-4.97 (m, 1H), 4.05-4.19 (m, 2H), 3.96 (dd, J=11.9, 4.4 Hz, 1H), 3.67 (s, 3H), 3.50 (dd, J=11.9, 6.9 Hz, 1H), 3.36 (qd, J=7.3, 4.1 Hz, 1H), 2.52-2.62 (m, 1H), 2.43 (tt, J=12.0, 3.8 Hz, 1H), 2.18 (dt, J=13.5, 2.4 Hz, 1H), 1.69-1.82 (m, 1H), 1.55-1.67 (m, 1H), 1.33-1.46 ppm (m, 1H). MS (ESI): M/Z (M+1): 213.9.

Step 3: trans-4-oxooctahydropyrido[2,1-c][1,4]oxazine-7-carboxylic acid

To a solution of methyl 4-oxooctahydropyrido[2,1-c][1,4]oxazine-7-carboxylate (2.55 g, 12.0 mmol) in tetrahydrofuran (100 mL) was added a solution of lithium hydroxide monohydrate (1.0 g) in H₂O (24 mL) and the reaction mixture was stirred at room temperature overnight under N₂ atmosphere. The organic layer was evaporated under vacuum. The aqueous layer was acidified to pH 2 with 2M HCl and lyophilized to afford the crude trans-4-oxooctahydropyrido[2,1-c][1,4]oxazine-7-carboxylic acid, which was used in next step without purification. ¹HNMR (400 MHz, D₂O): δ=3.86-4.01 (m, 2H), 3.67 (dd, J=11.2, 3.4 Hz, 1H), 3.51 (dd, J=11.3, 7.8 Hz, 2H), 3.23-3.33 (m, 1H), 2.90-2.99 (m, 1H), 2.52-2.63 (m, 1H), 2.11 (d, J=10.0 Hz, 1H), 1.82-1.92 (m, 1H), 1.44-1.62 ppm (m, 2H). MS (ESI): M/Z (M+1): 199.9.

Step 4: trans-N-((3-chloropyrazin-2-yl)methyl)-4-oxooctahydropyrido[2,1-c][1,4]oxazine-7-carboxamide A mixture of trans-4-oxooctahydropyrido[2,1-c][1,4]oxazine-7-carboxylic acid (2.2 g, 11.0 mmol), (3-chloropyrazin-2-yl)methanamine hydrochloride (2.2 g, 3.70 mmol), HATU (6.3 g, 16.6 mmol) and triethylamine (4.7 mL, 33.1 mmol) in dichloromethane (100 mL) was stirred at room temperature for 4 hours. The reaction mixture was washed with water (150 mL) and extracted with dichloromethane (50 mL×3) and the combined organic layers were concentrated in vacuo to afford the crude product, which was purified by silica gel column chromatography (THF:PE=10%~100%) to give trans-N-((3-chloropyrazin-2-yl)methyl)-4-oxooctahydropyrido[2,1-c][1,4]oxazine-7-carboxamide. ¹HNMR (400 MHz, CD₃OD): δ=8.54 (d, J=2.4 Hz, 1H), 8.34 (d, J=2.3 Hz, 1H), 4.74 (dt, J=12.9, 1.9 Hz, 1H), 4.60-4.67 (m, 2H), 4.11 (s, 2H), 4.02 (dd, J=11.9, 4.3 Hz, 1H), 3.56-3.65 (m, 2H), 3.43-3.53 (m, 1H), 2.67-2.76 (m, 1H), 2.49 (tt, J=11.8, 3.7 Hz, 1H), 2.05-2.15 (m, 1H), 1.77-1.88 (m, 2H), 1.50 ppm (dd, J=11.8, 3.9 Hz, 1H). MS (ESI): M/Z (M+1): 325.1.

Step 5: trans-7-(8-chloroimidazo[1,5-a]pyrazin-3-yl)hexahydropyrido[2,1-c][1,4]oxazin-4(3H)-one To a solution of trans-N-((3-chloropyrazin-2-yl)methyl)-4-oxooctahydropyrido[2,1-c][1,4]oxazine-7-carboxamide (1.3 g, 4.0 mmol) in anhydrous dichloromethane (100 mL) at 0° C. was added dimethylformamide (52 uL, 0.68 mmol), pyridine (3.25 mL, 40.0 mmol) and followed by POCl₃ (1.82 mL, 20.0 mmol). The resulting mixture was stirred at 25° C. for 5 h under a stream of nitrogen. The reaction mixture was poured into an ice-water mixture, neutralized with powdered sodium bicarbonate and extracted with DCM. The organic layer was washed with brine, dried over anhydrous Na₂SO₄ and concentrated under vacuum to give a crude product. The crude product was purified by column chromatography on silica gel eluting with (THF:PE=10%~100%) to give trans-7-(8-chloroimidazo[1,5-a]pyrazin-3-yl)hexahydropyrido[2,1-c][1,4]oxazin-4(3H)-one. ¹H NMR (400 MHz, CDCl₃) δ=7.81 (s, 1H), 7.72 (dd, J=5.0, 0.8 Hz, 1H), 7.37 (d, J=5.0 Hz, 1H), 4.93 (dt, J=13.3, 2.1 Hz, 1H), 4.20 (d, J=4.0 Hz, 2H), 4.07 (dd, J=12.0, 4.3 Hz, 1H), 3.66 (dd, J=12.0, 6.0 Hz, 1H), 3.52-3.60 (m, 1H), 3.07-3.17 (m, 1H), 2.78-2.89 (m, 1H), 2.17-2.28 (m, 2H), 1.92 (dq, J=13.4, 3.2 Hz, 1H), 1.62-1.70 ppm (m, 1H). MS (ESI): M/Z (M+1): 307.1.

Step 6: trans-7-(1-bromo-8-chloroimidazo[1,5-a]pyrazin-3-yl)hexahydropyrido[2,1-c][1,4]oxazin-4(3H)-one N-bromosuccinimide (0.26 g, 1.43 mmol) was added to a solution of trans-7-(8-chloroimidazo[1,5-a]pyrazin-3-yl)hexahydropyrido[2,1-c][1,4]oxazin-4(3H)-one (0.40 g, 1.30 mmol) in dimethylformamide (4 mL) and stirred at 25° C. for 2 h under a stream of nitrogen. The reaction was quenched with aqueous NaHCO₃ (40 mL), and extracted with EA (20 mL×3). The combined organic phase was washed with water (10 mL×5), followed by brine (10 mL). The organic phase was dried over anhydrous Na₂SO₄ and concentrated under vacuum to afford trans-7-(1-bromo-8-chloroimidazo[1,5-a]pyrazin-3-yl) hexahydropyrido[2,1-c][1,4]oxazin-4(3H)-one. ¹H NMR (400 MHz, CD₃OD) δ=8.20 (d, J=5.0 Hz, 1H), 7.36 (d, J=5.3 Hz, 1H), 4.77-4.82 (m, 1H), 4.15 (s, 2H), 4.08 (dd, J=11.5, 4.0 Hz, 1H), 3.58-3.75 (m, 3H), 2.95 (t, J=12.4 Hz, 1H), 2.15-2.24 (m, 1H), 1.94-2.03 (m, 1H), 1.91 (d, J=3.3 Hz, 1H), 1.64-1.78 ppm (m, 1H). MS (ESI): M/Z (M/M+2=1/1) 385.0/387.0.

Step 7: trans-7-(8-amino-1-bromoimidazo[1,5-a]pyrazin-3-yl)hexahydropyrido[2,1-c][1,4]oxazin-4(3H)-one Trans-7-(1-bromo-8-chloroimidazo[1,5-a]pyrazin-3-yl) hexahydropyrido[2,1-c][1,4]oxazin-4(3H)-one (0.50 g, 1.30 mmol) was dissolved in NH₄OH (6 mL) and i-PrOH (6 mL) and stirred at 110° C. for 12 h in a sealed tube. Then the reaction was cooled and concentrated at reduced pressure to afford trans-7-(8-amino-1-bromoimidazo[1,5-a]pyrazin-3-yl)hexahydropyrido[2,1-c][1,4]oxazin-4(3H)-one, which was used directly in the next step without further purification. MS (ESI): M/Z (M/M+2=10/8) 366.0/368.0. (R.T.: 0.29)

Step 8: (7R,9aS)-7-(8-amino-1-bromoimidazo[1,5-a]pyrazin-3-yl)hexahydropyrido[2,1-c][1,4]oxazin-4(3H)-one Trans-7-(8-amino-1-bromoimidazo[1,5-a]pyrazin-3-yl) hexahydropyrido[2,1-c][1,4]oxazin-4(3H)-one (0.47 g, 1.3 mmol) were separated by chiral separation (Instrument: Berger MultiGram™ SFC, Mettler Toledo Co, Ltd; Column: OD 250 mm*30 mm, 5 um; Mobile phase: A: Supercritical CO₂, B: MeOH, A:B=65:35 at 50 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to obtain the compounds 10E1: ((7R,9aS)-7-(8-amino-1-bromoimidazo[1,5-a]pyrazin-3-yl)hexahydropyrido[2,1-c][1,4]oxazin-4(3H)-one, (Ret. time=6.29 min). ¹H NMR (400 MHz, CD₃OD) δ=7.60 (d, J=5.5 Hz, 1H), 7.00 (d, J=5.0 Hz, 1H), 4.80 (dt, J=12.8, 1.9 Hz, 1H), 4.16 (s, 2H), 4.09 (dd, J=11.5, 4.0 Hz, 1H), 3.64-3.68 (m, 1H), 3.57 (br. s., 1H), 3.22-3.30 (m, 1H), 2.91 (t, J=12.5 Hz, 1H), 2.20 (d, J=13.1 Hz, 1H), 1.87-2.00 (m, 2H), 1.67-1.77 ppm (m, 1H). MS (ESI): M/Z (M+1): 367.2.

(7 S,9aR)-7-(8-amino-1-bromoimidazo[1,5-a]pyrazin-3-yl)hexahydropyrido[2,1-c][1,4]oxazin-4(3H)-one Intermediate 10E2: ((7S,9aR)-7-(8-amino-1-bromoimidazo[1,5-a]pyrazin-3-yl)hexahydropyrido[2,1-c][1,4]oxazin-4(3H)-one (Ret. time=6.83 min)) was prepared by following the procedure of intermediate 11. ¹H NMR (400 MHz, CD₃OD)) δ=7.60 (d, J=5.5 Hz, 1H), 7.00 (d, J=5.0 Hz, 1H), 4.80 (dt, J=12.8, 1.9 Hz, 1H), 4.16 (s, 2H), 4.09 (dd, J=11.5, 4.0 Hz, 1H), 3.64-3.68 (m, 1H), 3.57 (br. s., 1H), 3.22-3.30 (m, 1H), 2.91 (t, J=12.5 Hz, 1H), 2.20 (d, J=13.1 Hz, 1H), 1.87-2.00 (m, 2H), 1.67-1.77 ppm (m, 1H). MS (ESI): M/Z (M+1): 367.2.

Intermediate 11E1 and 11E2

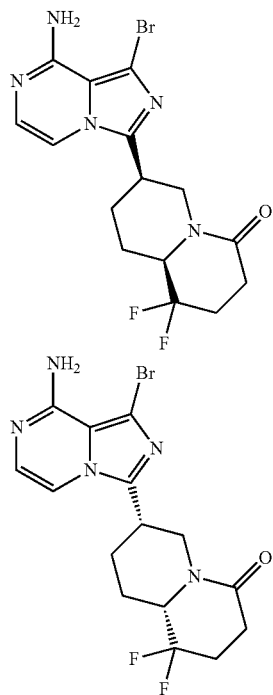

(7R,9aR)-7-(8-amino-1-bromoimidazo[1,5-a]pyrazin-3-yl)-1,1-difluorohexahydro-1H-quinolizin-4(6H)-one (7S,9aS)-7-(8-amino-1-bromoimidazo[1,5-a]pyrazin-3-yl)-1,1-difluorohexahydro-1H-quinolizin-4(6H)-one Step 1: methyl 6-formylnicotinate To a solution of methyl 6-(hydroxymethyl)nicotinate (30 g, 179.6 mmol) in DCM (500 mL) was added MnO2 (93.8 g, 1077.8 mmol). The mixture was stirred at room temperature overnight. The reaction mixture was filtered and concentrated. The residue was purified by column chromatography on silica gel eluted with PE/EA=10/1 to give methyl 6-formylnicotinate. ¹H NMR (400 MHz, CDCl₃) δ ppm 3.98 (d, J=0.78 Hz, 3H), 8.01 (d, J=8.0 Hz, 1H), 8.40-8.49 (m, 1H), 9.29-9.38 (m, 1H), 10.11 (s, 1H).

Step 2: methyl 6-(4-methoxy-4-oxobutanoyl)nicotinate

To a suspension of 3-benzyl-5-(2-hydroxyethyl)-4-methylthlazolium chloride (CAS: 4568-71-2, 5.9 g, 21.8 mmol) in [bmim][PF6] (CAS: 174501-64-5, 15 mL) was added TEA (11 g, 109 mmol), methyl acrylate (18.8 g, 218 mmol) and methyl 6-formylnicotinate (18 g, 109 mmol) at room temperature. The mixture was stirred at 80° C. for 3 hrs. The reaction mixture was treated with EA and water. The organic layer was dried and concentrated. The residue was purified by column chromatography on silica gel eluted with PE/EA=15/1 to give methyl 6-(4-methoxy-4-oxobutanoyl)nicotinate. ¹H NMR (400 MHz, CDCl₃) δ ppm 2.74 (t, J=8.0 Hz, 2H), 3.54 (t, J=8.0 Hz, 2H), 3.66 (s, 3H), 3.95 (s, 3H), 8.06 (d, J=8.0 Hz, 1H), 8.35-8.41 (m, 1H), 9.20-9.25 (m, 1H).

Step 3: methyl 6-(1,1-difluoro-4-methoxy-4-oxobutyl)nicotinate

To a solution of methyl 6-(4-methoxy-4-oxobutanoyl)nicotinate (10 g, 39.8 mmol) in DCM (100 mL) was added DAST (25.6 g, 159.4 mmol). The mixture was stirred at room temperature overnight. Then another batch of DAST (25.6 g, 159.4 mmol) was added and the mixture was stirred overnight again. The reaction mixture was treated with NaHCO₃ aqueous solution and DCM. The organic layer was dried and concentrated, and the residue was purified by column chromatography on silica gel eluted with PE/EA=25/1 to give methyl 6-(1,1-difluoro-4-methoxy-4-oxobutyl)nicotinate. ¹H NMR (400 MHz, CDCl₃) δ ppm 2.52-2.58 (m, 2H), 2.61-2.75 (m, 2H), 3.66 (s, 3H), 3.96 (s, 3H), 7.70 (d, J=8.0 Hz, 1H), 8.36-8.43 (m, 1H), 9.20 (s, 1H).

Step 4: methyl 6-(1,1-difluoro-4-methoxy-4-oxobutyl)piperidine-3-carboxylate

A mixture of methyl 6-(1,1-difluoro-4-methoxy-4-oxobutyl)nicotinate (5.5 g, 20.1 mmol) and PtO₂ (1 g) in MeOH/HCl (100 mL/10 mL) was hydrogenated under 50 Psi at 50° C. overnight. The suspension was filtered through a pad of Celite and the filter cake was washed with MeOH. The combined filtrates were concentrated to give methyl 6-(1,1-difluoro-4-methoxy-4-oxobutyl)piperidine-3-carboxylate which was used in next step directly. MS-ESI (m/z): 280 (M+1)+(Acq Method D: Rt: 0.769 min).

Step 5: methyl 9,9-difluoro-6-oxooctahydro-1H-quinolizine-3-carboxylate

A solution of methyl 6-(1,1-difluoro-4-methoxy-4-oxobutyl)piperidine-3-carboxylate (5.61 g, 20.1 mmol) in 1,4-Dioxane (100 ml) was stirred at 100° C. overnight. The solvent was evaporated. The residue was purified by column chromatography on silica gel, eluting with PE/EA=1/1 to give methyl 9,9-difluoro-6-oxooctahydro-1H-quinolizine-3-carboxylate. ¹H NMR (400 MHz, CDCl₃) δ ppm 1.63-1.76

(m, 1H), 1.83-1.92 (m, 2H), 2.09-2.36 (m, 3H), 2.53-2.60 (m, 2H), 2.66-2.73 (m, 2H), 3.47-3.58 (m, 1H), 3.68 (s, 3H), 5.07-5.17 (m, 1H).

Step 6: 9,9-difluoro-6-oxooctahydro-1H-quinolizine-3-carboxylic acid

To a solution of methyl 9,9-difluoro-6-oxooctahydro-1H-quinolizine-3-carboxylate (2.8 g, 11.33 mmol) in THF/MeOH/water (30 mL/30 mL/9 mL) was added LiOH.H$_2$O (1.426 g, 34.0 mmol). The mixture was stirred at room temperature for 2 hrs. The reaction mixture was acidified by 1 M HCl, and extracted with EA. The organic layer was dried and concentrated to give 9,9-difluoro-6-oxooctahydro-1H-quinolizine-3-carboxylic acid, which was used in next step directly. MS-ESI (m/z): 234 (M+1)+(Acq Method: 10-80AB_2 min; Rt: 0.296/0.381 min).

Step 7: N-((3-chloropyrazin-2-yl)methyl)-9,9-difluoro-6-oxooctahydro-1H-quinolizine-3-carboxamide To a solution of 9,9-difluoro-6-oxooctahydro-1H-quinolizine-3-carboxylic acid (1.9 g, 8.15 mmol) in THF (40 ml) was added (3-chloropyrazin-2-yl)methanamine hydrochloride (2.2 g, 12.22 mmol), HATU (4.65 g, 12.22 mmol) and TEA (6.81 ml, 48.9 mmol). The mixture was stirred at RT overnight. The reaction mixture was treated with EA (200 ml) and water (200 ml), the organic layer was dried over Na$_2$SO$_4$, filtered and concentrated. The residue was purified by column chromatography on silica gel eluted with PE/DCM/THF=1/1/1 to give N-((3-chloropyrazin-2-yl)methyl)-9,9-difluoro-6-oxooctahydro-1H-quinolizine-3-carboxamide. $^1$H NMR (400 MHz, CDCl$_3$) δ ppm 1.63-1.85 (m, 2H), 1.99-2.29 (m, 3H), 2.32-2.81 (m, 5H), 3.46-3.62 (m, 1H), 4.33-4.98 (m, 3H), 8.15-8.24 (m, 1H), 8.30-8.40 (m, 1H).

Step 8: 7-(8-chloroimidazo[1,5-a]pyrazin-3-yl)-1,1-difluorohexahydro-H-quinolizin-4(6H)-one To a solution of N-((3-chloropyrazin-2-yl)methyl)-9,9-difluoro-6-oxooctahydro-1H-quinolizine-3-carboxamide (2.4 g, 6.69 mmol) in acetonitrile (20 ml) was added PCl$_5$ (2.79 g, 13.38 mmol). The mixture was stirred at RT for 2 hrs. The reaction mixture was poured into NaHCO$_3$ aqueous solution (300 ml) and extracted with DCM (200 ml). The organic layer was dried over Na$_2$SO$_4$, filtered and the filtrate was evaporated under reduced pressure. The residue was purified by column chromatography on silica gel eluting with DCM/THF=10/1 to give 7-(8-chloroimidazo[1,5-a]pyrazin-3-yl)-1,1-difluorohexahydro-1H-quinolizin-4(6H)-one. MS-ESI (m/z): 341 (M+1)+(Acq Method: 0-60AB_2 min; Rt: 1.119 min).

Step 9: 7-(1-bromo-8-chloroimidazo[1,5-a]pyrazin-3-yl)-1,1-difluorohexahydro-1H-quinolizin-4(6H)-one To a solution of 7-(8-chloroimidazo[1,5-a]pyrazin-3-yl)-1,1-difluorohexahydro-1H-quinolizin-4(6H)-one (1.07 g, 3.14 mmol) in acetonitrile (40 ml) was added a solution of NBS (0.615 g, 3.45 mmol) in acetonitrile (10 ml). The mixture was stirred at room temperature for 1 hr. The reaction mixture was treated with EA (100 ml) and water (100 ml), the organic layer was dried over Na$_2$SO$_4$ and concentrated. The residue was purified by column chromatography on silica gel, eluting with DCM/THF=10/1 to give 7-(1-bromo-8-chloroimidazo[1,5-a]pyrazin-3-yl)-1,1-difluorohexahydro-1H-quinolizin-4(6H)-one. MS-ESI (m/z): 421 (M+1)+(Acq Method: 10-80AB_2 min; Rt: 1.027 min).

Step 10: 7-(8-amino-1-bromoimidazo[1,5-a]pyrazin-3-yl)-1,1-difluorohexahydro-1H-quinolizin-4(6H)-one To a solution of 7-(1-bromo-8-chloroimidazo[1,5-a]pyrazin-3-yl)-1,1-difluorohexahydro-1H-quinolizin-4(6H)-one (0.6 g, 1.430 mmol) in 2-Propanol (5 ml) was added ammonia and i-PrOH (3.57 ml, 14.30 mmol) in 100 mL seal tube, and the resulting mixture was stirred at 95° C. overnight. The valotiles were evaporated, and the residue was purified by column chromatography on silica gel eluting with DCM/MeOH=30/1 to give 7-(8-amino-1-bromoimidazo[1,5-a]pyrazin-3-yl)-1,1-difluorohexahydro-1H-quinolizin-4(6H)-one.

Step 11

(7R,9aR)-7-(8-amino-1-bromoimidazo[1,5-a]pyrazin-3-yl)-1,1-difluorohexahydro-1H-quinolizin-4(6H)-one (7S,9aS)-7-(8-amino-1-bromoimidazo[1,5-a]pyrazin-3-yl)-1,1-difluorohexahydro-1H-quinolizin-4(6H)-one (7R,9aS)-7-(8-amino-1-bromoimidazo[1,5-a]pyrazin-3-yl)-1,1-difluorohexahydro-1H-quinolizin-4(6H)-one (7S,9aR)-7-(8-amino-1-bromoimidazo[1,5-a]pyrazin-3-yl)-1,1-difluorohexahydro-1H-quinolizin-4(6H)-one 7-(8-amino-1-bromoimidazo[1,5-a]pyrazin-3-yl)-1,1-difluorohexahydro-1H-quinolizin-4(6H)-one was separated by SFC condition: ["Column: Chiralpak AS-H 250×4.6 mm I.D., 5 um Mobile phase: methanol (0.05% DEA) in CO2 from 5% to 40% Flow rate: 2.5 mL/min Wavelength: 220 nm"] to give P1 ((7R,9aR)-7-(8-amino-1-bromoimidazo[1,5-a]pyrazin-3-yl)-1,1-difluorohexahydro-1H-quinolizin-4(6H)-one), P2 (trans: (7R,9aS)-7-(8-amino-1-bromoimidazo[1,5-a]pyrazin-3-yl)-1,1-difluorohexahydro-1H-quinolizin-4(6H)-one), P3 ((7S,9aR)-7-(8-amino-1-bromoimidazo[1,5-a]pyrazin-3-yl)-1,1-difluorohexahydro-1H-quinolizin-4(6H)-one), P4 ((7S,9aS)-7-(8-amino-1-bromoimidazo[1,5-a]pyrazin-3-yl)-1,1-difluorohexahydro-1H-quinolizin-4(6H)-one).

For cis-products:
$^1$H NMR (400 MHz, CDCl$_3$) δ ppm 1.89-2.26 (m, 3H), 2.32-2.52 (m, 4H), 2.60-2.75 (m, 1H), 2.83-2.93 (m, 1H), 3.23-3.35 (m, 1H), 3.63-3.78 (m, 1H), 4.87 (d, J=12.0 Hz, 1H), 5.71 (br. s., 2H), 7.03 (d, J=5.09 Hz, 1H), 7.11 (d, J=5.09 Hz, 1H).

For trans-products:
$^1$H NMR (400 MHz, CDCl$_3$) δ ppm 1.54-1.64 (m, 1H), 2.08-2.41 (m, 5H), 2.58-2.78 (m, 3H), 2.93-3.07 (m, 1H), 3.59-3.75 (m, 1H), 4.89 (d, J=12.0 Hz, 1H), 5.69 (br. s., 2H), 7.05 (d, J=5.09 Hz, 1H), 7.26 (d, J=5.09 Hz, 1H).

Intermediate 12

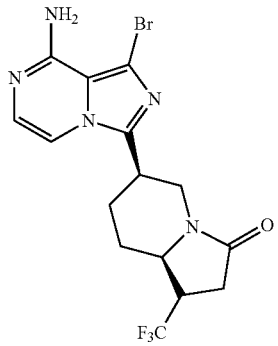

(1S,6R,8aR)-6-(8-amino-1-bromoimidazo[1,5-a]
pyrazin-3-yl)-1-(trifluoromethyl)hexahydroindolizin-
3(2H)-one Step 1: (3R,6R)-1-benzyl 3-methyl
6-formylpiperidine-1,3-dicarboxylate To a mixture of (3R,6R)-1-benzyl 3-methyl 6-(hydroxymethyl)piperidine-1,3-dicarboxylate (10 g, 32 mmol) in DCM (100 mL) was added DMP (16 g, 38 mmol) in portions with stirring at 0° C. and then stirred at room temperature for 3 h, the mixture was quenched with sat. Na$_2$SO$_3$, extracted with DCM. After concentrated in vacuo to give (3R,6R)-1-benzyl 3-methyl 6-formylpiperidine-1,3-dicarboxylate as an oil.

Step 2: (3R,6R)-1-benzyl 3-methyl 6-((S)-2,2,2-
trifluoro-1-(((trimethylsilyl)oxy)ethyl)piperidine-1,3-
dicarboxylate To a mixture of (3R,6R)-1-benzyl 3-methyl 6-formylpiperidine-1,3-dicarboxylate (8.9 g, 29 mmol) in DMF (50 mL) was added TMSCF$_3$ (8.3 g, 29 mmol) and LiOAc (970 mg, 14 mmol). The mixture was stirring at room temperature for 4 h, TLC detected the reaction was complete. The organic phase was washed 2 times with water, extracted with EtOAc. The combined organic phases were dried over Na$_2$SO$_4$, and the solvent was removed under reduced pressure. The resulting mixture was purified by column chromatography on silica gel eluted with Pet.ether:EtOAc=10:1 to afford (3R,6R)-1-benzyl 3-methyl 6-((S)-2,2,2-trifluoro-1-((trimethylsilyl)oxy)ethyl)piperidine-1,3-dicarboxylate as an oil. MS: 448 (M+1).

Step 3: (3R,6R)-1-benzyl 3-methyl 6-((S)-2,2,2-
trifluoro-1-hydroxyethyl)piperidine-1,3-dicarboxylate To a mixture of (3R,6R)-1-benzyl 3-methyl 6-((S)-2,2,2-trifluoro-1-((trimethylsilyl)oxy)ethyl)piperidine-1,3-dicarboxylate (8.9 g, 29 mmol) in THF (50 mL) was added TBAF (4.4 g, 31 mmol). The mixture was stirring at room temperature overnight. The organic phase was washed twice with water, extracted with EtOAc. The combined organic phases were dried over Na$_2$SO$_4$, and concentrated in vacuo to afford (3R,6R)-1-benzyl 3-methyl 6-((S)-2,2,2-trifluoro-1-hydroxyethyl)piperidine-1,3-dicarboxylate as an oil. MS: 376 (M+1).

Step 4: (3R,6R)-1-benzyl 3-methyl 6-(2,2,2-trifluoroacetyl)piperidine-1,3-dicarboxylate To a mixture of (3R,6R)-1-benzyl 3-methyl 6-((S)-2,2,2-trifluoro-1-hydroxyethyl)piperidine-1,3-dicarboxylate (6.2 g, 16.5 mmol) in DCM (100 mL) was added DMP (8.4 g, 19.8 mmol) in portions with stirring at 0° C. and then stirred at room temperature for 3 h, TLC detected the reaction was complete. The mixture was quenched with sat Na$_2$SO$_3$, extracted with DCM. After concentrated in vacuo, the residual was purified by column chromatography on silica gel eluted with Pet.ether:EtOAc=5:1 to afford (3R,6R)-1-benzyl 3-methyl 6-(2,2,2-trifluoroacetyl)piperidine-1,3-dicarboxylate as an oil.

Step 5: (3R,6R)-1-benzyl 3-methyl 6-((E)-4-ethoxy-
1,1,1-trifluoro-4-oxobut-2-en-2-yl)piperidine-1,3-
dicarboxylate To the solution of t-BuOK (20 mL, 20 mmol) in THF (20 mL) was added ethyl 2-(diethoxyphosphoryl)acetate (4.7 g, 20 mmol). The reaction was stirred at room temperature for 0.5 hour. Then to the reaction mixture was added (3R,6R)-1-benzyl 3-methyl 6-(2,2,2-trifluoroacetyl)piperidine-1,3-dicarboxylate (3.9 g, 10 mmol) in 10 mL THF dropwise. The reaction mixture was stirred at room temperature for overnight. The reaction mixture was quenched with water and extracted with EtOAc, the combined organic phases were dried over Na$_2$SO$_4$, and the solvent was removed under reduced pressure. The resulting mixture was purified by column chromatography on silica gel eluted with Pet.ether: THF=5:1 to afford an oil (3R,6R)-1-benzyl 3-methyl 6-((E)-4-ethoxy-1,1,1-trifluoro-4-oxobut-2-en-2-yl)piperidine-1,3-dicarboxylate. MS: 444.3 (M+1).

Step 6: (1S,6R,8aR)-methyl 3-oxo-1-(trifluoromethyl)octahydroindolizine-6-carboxylate To the solution of (3R,6R)-1-benzyl 3-methyl 6-((E)-4-ethoxy-1,1,1-trifluoro-4-oxobut-2-en-2-yl)piperidine-1,3-dicarboxylate (2.4 g, 5.4 mmol) in MeOH (50 mL) was added Pd(OH)$_2$ (200 mg). The reaction was purged with nitrogen then was stirred under H$_2$ balloon overnight at room temperature. The reaction was filtered though celite concentrated to give (1S,6R,8aR)-methyl 3-oxo-1-(trifluoromethyl) octahydroindolizine-6-carboxylate as an oil. MS: 444.3 (M+1).

Step 7: (1S,6R,8aR)-3-oxo-1-(trifluoromethyl)octahydroindolizine-6-carboxylic acid To a solution of (1S,6R,8aR)-methyl 3-oxo-1-(trifluoromethyl)octahydroindolizine-6-carboxylate (1.1 g, 4.1 mmol) in MeOH/H$_2$O (30 mL) was added LiOH (504 mg, 12 mmol). The resulting mixture was stirred at room temperature overnight. TLC detected the reaction was complete. Adjust the pH of this mixture to 2 with 1N HCl and extracted with DCM, and the combined organic layers were dried over anhydrous sodium sulfate. Then it was concentrated in vacuum to give (1S,6R,8aR)-3-oxo-1-(trifluoromethyl)octahydroindolizine-6-carboxylic acid.

Step 8: (1S,6R,8aR)-N-((3-chloropyrazin-2-yl)
methyl)-3-oxo-1-(trifluoromethyl) octahydroindolizine-6-carboxamide To a solution of (1S,6R,8aR)-3-oxo-1-(trifluoromethyl) octahydroindolizine-6-carboxylic acid (0.7 g, 2.8 mmol) in THF (100 mL) was added (3-chloropyrazin-2-yl)methanamine (0.5 g, 2.8 mmol), DIEA (1.1 g, 8.4 mmol) and HATU (1 g, 2.8 mmol). The mixture was stirred at room temperature for 2 hrs. The reaction was complete detected by LCMS. The reaction mixture was extracted with DCM and water, the organic layer was dried and concentrated to give the crude product which was purified by column chromatography on silica gel eluted with Pet. ether:EtOAc=1:1 to afford (1S,6R,8aR)-N-((3-chloropyrazin-2-yl)methyl)-3-oxo-1-(trifluoromethyl)octahydroindolizine-6-carboxamide as an oil. MS: 377 (M+1).

Step 9: (1S,6R,8aR)-6-(8-chloroimidazo[1,5-a]pyrazin-3-yl)-1-(trifluoromethyl) hexahydroindolizin-3(2H)-one To a solution of (1S,6R,8aR)-N-((3-chloropyrazin-2-yl)methyl)-3-oxo-1-(trifluoromethyl)octahydroindolizine-6-carboxamide (730 mg, 1.9 mmol) in MeCN (30 mL) was added PCl$_5$ (1.2 g, 5.8 mmol). The mixture was stirred at room temperature overnight. The reaction was complete detected by LCMS. Then it was quenched by pouring into sat. NaHCO$_3$ aqueous, and extracted with DCM. The organic layer was dried and concentrated to afford (1S,6R,8aR)-6-(8-chloroimidazo[1,5-a]pyrazin-3-yl)-1-(trifluoromethyl)hexahydroindolizin-3(2H)-one. MS: 359 (M+1).

Step 10: (1S,6R,8aR)-6-(1-bromo-8-chloroimidazo[1,5-a]pyrazin-3-yl)-1-(trifluoromethyl) hexahydroindolizin-3(2H)-one To a solution of (1S,6R,8aR)-6-(8-chloroimidazo[1,5-a]pyrazin-3-yl)-1-(trifluoromethyl)hexahydroindolizin-3(2H)-one (375 g, 1 mmol) in MeCN (10 mL) was added NBS (203 mg, 1.1 mmol). The mixture was stirred at room temperature for 1 h. The reaction solution was poured into Na$_2$SO$_3$ solution and extracted with DCM. The organic layer was washed with water and brine, dried over Na$_2$SO$_4$, concentrated to afford (1S,6R,8aR)-6-(1-bromo-8-chloroimidazo[1,5-a]pyrazin-3-yl)-1-(trifluoromethyl)hexahydroindolizin-3(2H)-one, which was used in next step without further purification. MS: 439 (M+1).

Step 11: (1S,6R,8aR)-6-(8-amino-1-bromoimidazo[1,5-a]pyrazin-3-yl)-1-(trifluoromethyl) hexahydroindolizin-3(2H)-one In 30 mL seal tube, added a solution of (1S,6R,8aR)-6-(1-bromo-8-chloroimidazo[1,5-a]pyrazin-3-yl)-1-(trifluoromethyl)hexahydroindolizin-3(2H)-one (320 mg, 0.7 mmol) in NH$_3$.H$_2$O/i-PrOH (10 mL/10 mL), and stirred at 110° C. overnight. After cooled to room temperature, the mixture was diluted with EtOAc, washed with water and brine, dried over Na$_2$SO$_4$. After concentrated in vacuum, the resulting mixture was purified by pre-HPLC to afford (1S,6R,8aR)-6-(8-amino-1-bromoimidazo[1,5-a]pyrazin-3-yl)-1-(trifluoromethyl) hexahydroindolizin-3(2H)-one as a solid. MS: 418 (M+1). MS-ESI (m/z): 418 (M+1)$^+$ (Acq Method D: Rt: 1.067 min).

Step 12: (single) (1S,6R,8aR)-6-(8-amino-1-bromoimidazo[1,5-a]pyrazin-3-yl)-1-(trifluoromethyl) hexahydroindolizin-3(2H)-one (1S,6R,8aR)-6-(8-amino-1-bromoimidazo[1,5-a]pyrazin-3-yl)-1-(trifluoromethyl)hexahydro indolizin-3(2H)-one, which was the major isomer, was obtained from (1S,6R,8aR)-6-(8-amino-1-bromoimidazo[1,5-a]pyrazin-3-yl)-1-(trifluoromethyl)hexahydroindolizin-3(2H)-one as a solid with SFC by the following condition: Column: Chiralpak AS-H 250×4.6 mm I.D., 5 um; Mobile phase: methanol (0.05% DEA) in CO$_2$ from 5% to 40%; Flow rate: 2.35 mL/min; Wavelength: 220 nm.

Intermediate 13

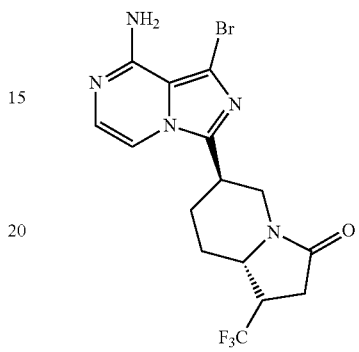

(1R,6R,8aS)-6-(8-amino-1-bromoimidazo[1,5-a]pyrazin-3-yl)-1-(trifluoromethyl)hexahydroindolizin-3(2H)-one In the same procedure as the preparation of intermediate 12, starting from (3R,6S)-1-benzyl 3-methyl 6-(hydroxymethyl)piperidine-1,3-dicarboxylate, the title intermediate (1R,6R,8aS)-6-(8-amino-1-bromoimidazo[1,5-a]pyrazin-3-yl)-1-(trifluoromethyl)hexahydro indolizin-3(2H)-one was prepared. MS: 420 (M+1).

Intermediate 14

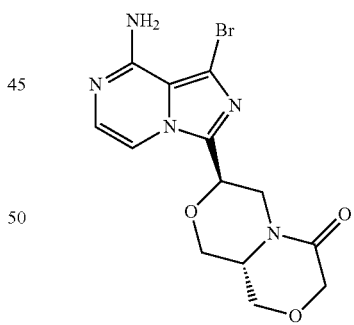

(7R,9aR)-7-(8-amino-1-bromoimidazo[1,5-a]pyrazin-3-yl)tetrahydro-1H-[1,4]oxazino[3,4-c][1,4]oxazin-4(3H)-one Step 1: methyl (2R)-3-hydroxy-2-[benzylamino]propanoate (R)-methyl 2-amino-3-hydroxypropanoate (1000 g, 6.43 mol) was dissolved in 5 L of anhydrous methanol and cooled to 0° C. Triethylamine (900 mL, 6.43 mol) was added, the reaction was stirred for 40 min, and 650 mL of benzaldehyde (6.43 mol) was added. The reaction mixture was stirred for 4 h, at which time sodium borohydride (480 g, 12.6 mol) was added portionwise to the reaction mixture over a period of 3 h. The solution was partitioned between 5 L of 20% HCl and 5 L of diethyl ether. The organic phase was extracted twice with 2 L portions of 20% HCl. The combined aqueous layers were washed with an additional diethyl ether and the organic layers were discarded. The aqueous layers were carefully neutralized with solid sodium carbonate and extracted three times with diethyl ether. After extraction with brine, the combined ether extracts were dried over $Na_2SO_4$ and evaporated to afford methyl (2R)-3-hydroxy-2-[benzylamino]propanoate, which was used directly in next step without further purification.

Step 2: methyl (2R)-3-(2,2-dimethyl-1,1-diphenyl-1-silapropoxy)-2-[benzylamino]propanoate To methyl (2R)-3-hydroxy-2-[benzylamino]propanoate (500 g, 2.39 mol) in 2 L $CH_2Cl_2$ were added $NEt_3$ (290 g, 2.87 mol) and cat. DMAP (15 g, 0.12 mol). Cooled to 0° C. and TBDPS-Cl (690 g, 2.51 mol) was added dropwise. Water (3 L) and $CH_2Cl_2$ (3 L) were added, layers were separated, combined organic layers were washed with sat $NH_4Cl$, dried over $Na_2SO_4$ and concentrated to give methyl (2R)-3-(2,2-dimethyl-1,1-diphenyl-1-silapropoxy)-2-[benzylamino]propanoate, which was used as such for the next step without any further purification.

Step 3: (2S)-3-(2,2-dimethyl-1,1-diphenyl-1-silapropoxy)-2-[benzylamino]propan-1-ol To methyl (2R)-3-(2,2-dimethyl-1,1-diphenyl-1-silapropoxy)-2-[benzylamino]propanoate (250 g, 0.559 mol) in 5 L THF was added MeOH (25 ml) and then 2.0 M $LiBH_4$ in THF (335 mL) stirred at rt for 16 hrs, quenched with slow addition of sat. aq $NH_4Cl$ (5 L), extracted with EtOAc (3×2 L), dried over $Na_2SO_4$, filtered and concentrated to give crude, which was purified by FCC (PE:AE=10:1) to afford (2S)-3-(2,2-dimethyl-1,1-diphenyl-1-silapropoxy)-2-[benzylamino]propan-1-ol.

Step 4: {(5S,2R)-5-[(2,2-dimethyl-1,1-diphenyl-1-silapropoxy)methyl]-4-benzylmorpholin-2-yl}methan-1-ol (2S)-3-(2,2-dimethyl-1,1-diphenyl-1-silapropoxy)-2-[benzylamino]propan-1-ol (600 g, 1.43 mol) was dissolved in 10 L toluene, (S)-(+)-epichlorohydrin (5, 158 g, 1.72 mol) was added and followed then by the slow addition of lithium perchlorate (182 g, 1.72 mol) over 60 min, stirred at rt for 3 days. A solution of sodium methoxide (25 wt % in $CH_3OH$, 2.5 L) was then added and the mixture was stirred for another 4 days. Saturated aq $NH_4Cl$ (5 L) was added, and the product was extracted with EtOAc (3×10 L). The combined organics were washed with brine, dried ($MgSO_4$), filtered, and evaporated to give the crude product, which was purified by chromatography eluting with 20-50% EtOAc in hexanes to afford {(5S,2R)-5-[(2,2-dimethyl-1,1-diphenyl-1-silapropoxy)methyl]-4-benzylmorpholin-2-yl}methan-1-ol.

Step 5: tert-butyl (5 S,2R)-5-[(2,2-dimethyl-1,1-diphenyl-1-silapropoxy)methyl]-2-(hydroxymethyl)morpholine-4-carboxylate {(5 S,2R)-5-[(2,2-dimethyl-1,1-diphenyl-1-silapropoxy)methyl]-4-benzylmorpholin-2-yl}methan-1-ol (400 g, 841 mmol) was dissolved in 10 L ethanol, $(Boc)_2O$ (220 g, 1.0 mol) was added followed by $Et_3N$ (86 g, 841 mmol). Then $Pd(OH)_2$ (120 g, 168 mmol) was added. Hydrogenated at 45-50 psi (4 days), filtered on a pad of celite, rinsed with EtOH (4 L), concentrated. EtOAc was added (4 L), washed with water (2×500 mL), dried over $MgSO_4$, filtered and concentrated, column purified using 5-20% MeoH in DCM to give tert-butyl (5S,2R)-5-[(2,2-dimethyl-1,1-diphenyl-1-silapropoxy)methyl]-2-(hydroxymethyl)morpholine-4-carboxylate.

Step 6: (5S,2R)-5-[(2,2-dimethyl-1,1-diphenyl-1-silapropoxy)methyl]-4-[(tert-butyl)oxycarbonyl]morpholine-2-carboxylic acid To tert-butyl (5 S,2R)-5-[(2,2-dimethyl-1,1-diphenyl-1-silapropoxy)methyl]-2-(hydroxymethyl)morpholine-4-carboxylate (200 g, 412 mmol) in 10 L $CH_2Cl_2$ that was cooled to 0° C. were added TEMPO (13 g, 82 mmol) and (diacetoxyiodo)benzene (265 g, 824 mmol). The ice bath was removed, and the reaction was allowed to warm to room temperature and stirred overnight. The mixture was diluted with 10 L ethyl acetate and washed with 10% $Na_2S_2O_3$, aq. satd. $NaHCO_3$, and brine, dried with $Na_2SO_4$, filtered and concentrated to give crude, which was purified by MPLC (DCM/MeOH=20/1) to (5S,2R)-5-[(2,2-dimethyl-1,1-diphenyl-1-silapropoxy)methyl]-4-[(tert-butyl)oxycarbonyl]morpholine-2-carboxylic acid.

Step 7: tert-butyl (5S,2R)-5-[(2,2-dimethyl-1,1-diphenyl-1-silapropoxy)methyl]-2-{N-[(3-chloropyrazin-2-yl)methyl]carbamoyl}morpholine-4-carboxylate (5S,2R)-5-[(2,2-dimethyl-1,1-diphenyl-1-silapropoxy)methyl]-4-[(tert-butyl)oxycarbonyl]morpholine-2-carboxylic acid (322.7 g, 645 mmol) and (3-chloropyrazin-2-yl)methanamine hydrochloride (116.2 g, 645 mmol) were dissolved in DMF 20 L. To the reaction mixture was added $Et_3N$ (163.5 g, 1.29 mol) and then HATU (294.7 g, 774 mmol) slowly at 0° C. The crude was stirred at rt for 1 day under nitrogen before quenching with sat. $NaHCO_3$ (10 L) at rt. The crude was diluted in EtOAc (2×10 L). The organic layer was washed with water, brine, dried over $Na_2SO_4$, filtered, and evaporated. The crude was purified by column chromatography on silica gel (PE:EA=5:1) to give tert-butyl (5S,2R)-5-[(2,2-dimethyl-1,1-diphenyl-1-silapropoxy)methyl]-2-{N-[(3-chloropyrazin-2-yl)methyl]carbamoyl}morpholine-4-carboxylate.

Step 8: [(3R)-2-({3-[(benzo[3,4-c]1,2,5-thiadiazol-5-ylamino)methyl](2-furyl)}carbonyl) (1,2,3,4-tetrahydrobeta-carbolin-3-yl)]-N-methylcarboxamide tert-butyl (5S,2R)-5-[(2,2-dimethyl-1,1-diphenyl-1-silapropoxy)methyl]-2-{N-[(3-chloropyrazin-2-yl)methyl]carbamoyl}morpholine-4-carboxylate (183 g, 293 mmol) was dissolved in 1:1 (4 L) mixture of acetonitrile: DMF. $POCl_3$ (93.6 mL, 1.03 mol) was added slowly at 0° C. The reaction mixture was stirred at 40° C. for 45 mins under nitrogen, and then cooled in an ice bath and poured into $NH_3H2O$ (5 L) solution cooled in an ice bath. The resultant mixture was extracted with EtOAc (3×5 L), dried over $Na_2SO_4$, filtered, and evaporated to give crude product, which was purified by column chromatography on silica gel (PE:EA=2:1) to give [(3R)-2-({3-[(benzo[3,4-c]1,2,5-thiadiazol-5-ylamino)methyl](2-furyl)}carbonyl) (1,2,3,4-tetrahydrobeta-carbolin-3-yl)]-N-methylcarboxamide. $^{1}$H-NMR (300 MHz, DMSO-d6 δ: 8.26-8.24 (m, 1H), 7.87 (s, 1H), 7.65-7.60 (m, 4H), 7.48-7.40 (m, 7H), 5.41-5.40 (m, 1H), 4.50-4.45 (m, 1H), 3.94-3.91 (m, 2H), 3.76-3.73 (m, 2H), 3.41-3.27 (m, 2H), 1.99-1.97 (m, 1H), 1.37 (s, 9H), 0.99 (s, 9H) ppm. LCMS [mobile phase: from 90% water (0.02% NH$_4$OAc) and 10% CH$_3$CN to 5% water (0.02% NH$_4$OAc) and 95% CH$_3$CN in 6.5 min, finally under these conditions for 0.5 min.] purity is >97%, Rt=2.640 min; MS Calcd.: 606; MS Found: 67 ([M+H]$^+$).

Step 9: (2R,5R)-tert-butyl 2-(8-chloroimidazo[1,5-a]pyrazin-3-yl)-5-(hydroxymethyl)morpholine-4-carboxylate To a solution of (2R,5S)-tert-butyl 5-(((tert-butyldiphenylsilyl)oxy)methyl)-2-(8-chloroimidazo[1,5-a]pyrazin-3-yl)morpholine-4-carboxylate (0.5 g, 0.823 mmol) in THF (15 mL) was added TBAF (2.47 mL, 2.47 mmol, 1.0 M in THF) at 0° C. The reaction was warmed to 18° C. and stirred for 18 h. The reaction mixture was diluted with H$_2$O (40 mL), extracted with ethyl acetate (10 mL×2). The combined organic layers were dried over anhydrous sodium sulfate, filtered and concentrated and purified by combi flash (DCM:THF=10-30%) to give (2R,5R)-tert-butyl 2-(8-chloroimidazo[1,5-a]pyrazin-3-yl)-5-(hydroxymethyl)morpholine-4-carboxylate. MS (ESI) m/z (M+H)$^+$: 369.0. Acq Method D: (1.065 min) $^{1}$H NMR (400 MHz, CDCl$_3$) δ=8.02 (d, J=5.1 Hz, 1H), 7.80 (s, 1H), 7.34 (d, J=5.1 Hz, 1H), 5.14 (br. s., 1H), 4.59 (d, J=13.3 Hz, 1H), 3.89 (br. s., 3H), 3.76 (d, J=11.7 Hz, 2H), 3.39 (d, J=10.6 Hz, 1H), 2.55 (br. s., 2H), 1.48 (s, 9H) ppm.

Step 10: (2R,5R)-tert-butyl 5-((2-(tert-butoxy)-2-oxoethoxy)methyl)-2-(8-chloroimidazo[1,5-a]pyrazin-3-yl)morpholine-4-carboxylate To a vigorously stirred mixture of (2R,5R)-tert-butyl 2-(8-chloroimidazo[1,5-a]pyrazin-3-yl)-5-(hydroxymethyl)morpholine-4-carboxylate (1.4 g, 3.80 mmol) and TBAF (0.070 g, 0.190 mmol) in Toluene (12 mL) at 0° C. was added dropwise 25% w/v NaOH (12 mL). Following complete addition, to the vigorously stirred reaction mixture at 0° C. was added dropwise a 1:1 (v/v) mixture of tert-butyl 2-bromoacetate (2.221 g, 11.39 mmol) and toluene (1 mL). The reaction mixture was allowed to warm to ambient temperature overnight. TLC (Pet.ether:THF=1:1) showed the reaction was complete. The organic layer was separated, washed with sequential portions of water until the washings were neutral, dried over Na$_2$SO$_4$ and concentrated in vacuo. The residue was purified by flash column chromatography (PE: THF=0-30%) to give (2R,5R)-tert-butyl 5-((2-(tert-butoxy)-2-oxoethoxy)methyl)-2-(8-chloroimidazo[1,5-a]pyrazin-3-yl)morpholine-4-carboxylate. $^{1}$H NMR (400 MHz, CDCl$_3$) δ=8.07 (d, J=5.1 Hz, 1H), 7.82 (s, 1H), 7.34 (d, J=5.1 Hz, 1H), 5.23 (d, J=3.5 Hz, 1H), 4.83 (d, J=13.7 Hz, 1H), 4.08 (br. s., 1H), 4.01 (s, 2H), 3.94-3.84 (m, 2H), 3.66 (dd, J=5.7, 8.8 Hz, 1H), 3.57 (dd, J=4.5, 13.9 Hz, 1H), 3.25 (dd, J=3.1, 11.7 Hz, 1H), 1.49 (d, J=4.7 Hz, 18H) ppm.

Step 11: (2R,5R)-tert-butyl 2-(1-bromo-8-chloroimidazo[1,5-a]pyrazin-3-yl)-5-((2-(tert-butoxy)-2-oxoethoxy)methyl)morpholine-4-carboxylate To the solution of (2R,5R)-tert-butyl 5-((2-(tert-butoxy)-2-oxoethoxy)methyl)-2-(8-chloroimidazo[1,5-a]pyrazin-3-yl)morpholine-4-carboxylate (0.2 g, 0.414 mmol) in DMF (5 mL) was added NBS (0.088 g, 0.497 mmol). The resulting mixture was stirred at 30° C. for 1.5 h. The mixture was diluted with H$_2$O (40 mL), extracted with ethyl acetate (10 mL×2). The combined organic layers were dried over anhydrous sodium sulfate, filtered and concentrated in vacuo to give crude (2R,5R)-tert-butyl 2-(1-bromo-8-chloroimidazo[1,5-a]pyrazin-3-yl)-5-((2-(tert-butoxy)-2-oxoethoxy)methyl)morpholine-4-carboxylate. MS (ESI) m/z (M+H)$^+$: 563.2. Acq Method D (1.358 min)$^{1}$H NMR (400 MHz, CDCl$_3$) δ=8.07 (d, J=5.1 Hz, 1H), 7.34 (d, J=4.7 Hz, 1H), 5.15 (d, J=3.5 Hz, 1H), 4.79 (d, J=14.1 Hz, 1H), 4.14 (br. s., 1H), 4.01 (s, 2H), 3.93-3.84 (m, 2H), 3.66 (dd, J=5.9, 9.0 Hz, 1H), 3.58 (dd, J=4.3, 13.7 Hz, 1H), 3.27 (dd, J=3.5, 12.1 Hz, 1H), 1.57-1.44 (m, 18H) ppm.

Step 12: (2R,5R)-tert-butyl 2-(1-bromo-8-((2,4-dimethoxybenzyl)amino)imidazo[1,5-a]pyrazin-3-yl)-5-((2-(tert-butoxy)-2-oxoethoxy)methyl)morpholine-4-carboxylate To a solution of (2R,5R)-tert-butyl 2-(1-bromo-8-chloroimidazo[1,5-a]pyrazin-3-yl)-5-((2-(tert-butoxy)-2-oxoethoxy)methyl)morpholine-4-carboxylate (0.22 g, 0.392 mmol) in DMF (5 mL) was added the (2,4-dimethoxyphenyl)methanamine (0.079 g, 0.470 mmol), K$_2$CO$_3$ (0.162 g, 1.175 mmol). The resulting mixture was stirred at 85° C. for 2.5 h. TLC (Pet.ether:EtOAc=2:1) showed the reaction was complete. The mixture was washed with H$_2$O (50 mL), extracted with EtOAc (10 mL×2). The EA layer was dried over sodium sulfate, filtered concentrated, purified by combi flash (Pet.ether:THF=0-50%) to give (2R,5R)-tert-butyl 2-(1-bromo-8-((2,4-dimethoxybenzyl)amino)imidazo[1,5-a]pyrazin-3-yl)-5-((2-(tert-butoxy)-2-oxoethoxy)methyl)morpholine-4-carboxylate. MS (ESI) m/z (M+H)$^+$: 694.1. Acq Method D1.142 min). $^{1}$H NMR (400 MHz, CDCl$_3$) δ=7.45 (d, J=5.1 Hz, 1H), 7.10 (d, J=5.1 Hz, 1H), 6.82-6.71 (m, 1H), 6.54-6.40 (m, 2H), 5.04 (d, J=3.1 Hz, 1H), 4.76-4.62 (m, 3H), 4.12 (br. s., 1H), 4.00 (s, 2H), 3.90-3.84 (m, 4H), 3.84-3.77 (m, 4H), 3.67 (dd, J=6.1, 8.8 Hz, 1H), 3.51 (dd, J=4.3, 13.7 Hz, 1H), 3.32 (dd, J=3.1, 12.1 Hz, 1H), 1.52 (s, 9H), 1.48 (s, 9H) ppm.

Step 13: 2-(((3R,6R)-6-(1-bromo-8-((2,4-dimethoxybenzyl)amino)imidazo[1,5-a]pyrazin-3-yl)morpholin-3-yl)methoxy)acetic acid The solution of (2R,5R)-tert-butyl 2-(1-bromo-8-((2,4-dimethoxybenzyl)amino)imidazo[1,5-a]pyrazin-3-yl)-5-((2-(tert-butoxy)-2-oxoethoxy)methyl)morpholine-4-carboxylate (0.25 g, 0.361 mmol) in TFA (3.5 mL) was stirred at 18° C. for 2.5 h. The reaction solution was concentrated in vacuo to give 2-(((3R,6R)-6-(1-bromo-8-((2,4-dimethoxybenzyl)amino)imidazo[1,5-a]pyrazin-3-yl)morpholin-3-yl)methoxy)acetic acid which was used in next step without further purification. MS (ESI) m/z (M+H)$^+$: 536.2. Acq Method D0.854 min).

Step 14: (7R,9aR)-7-(1-bromo-8-((2,4-dimethoxybenzyl)amino)imidazo[1,5-a]pyrazin-3-yl)tetrahydro-1H-[1,4]oxazino[3,4-c][1,4]oxazin-4(3H)-one To the solution of 2-(((3R,6R)-6-(1-bromo-8-((2,4-dimethoxybenzyl)amino)imidazo[1,5-a]pyrazin-3-yl)morpholin-3-yl)methoxy)acetic acid (1.5 g, 2.80 mmol) in DCM (20 mL) was added EDCI (0.804 g, 4.19 mmol), followed by DMAP (0.512 g, 4.19 mmol). The residue was stirred at 30° C. for 18 h. The mixture was diluted with H$_2$O (100 mL), extracted with DCM (30 mL×2). The DCM layer was dried over sodium sulfate, filtered, concentrated, purified by combi flash (PE: THF=0-50%) to give (7R,9aR)-7-(1-bromo-8-((2,4-dimethoxybenzyl)amino)imidazo[1,5-a]pyrazin-3-yl)tetrahydro-1H-[1,4]oxazino[3,4-c][1,4]oxazin-4(3H)-one. MS (ESI) m/z (M+H)+: 520.1. Acq Method D1.065 min). ¹H NMR (400 MHz, CDCl₃) δ=7.30-7.27 (m, 1H), 7.15 (d, J=5.1 Hz, 1H), 6.79 (br. s., 1H), 6.54-6.39 (m, 2H), 4.94 (dd, J=2.5, 13.9 Hz, 1H), 4.73 (dd, J=2.3, 11.0 Hz, 1H), 4.68 (d, J=5.5 Hz, 2H), 4.28-4.14 (m, 2H), 4.07-3.96 (m, 2H), 3.88 (s, 3H), 3.83-3.75 (m, 4H), 3.64-3.52 (m, 2H), 3.38 (dd, J=11.3, 13.7 Hz, 1H) ppm.

Step 15: (7R,9aR)-7-(8-amino-1-bromoimidazo[1,5-a]pyrazin-3-yl)tetrahydro-1H-[1,4]oxazino[3,4-c][1,4]oxazin-4(3H)-one The solution of (7R,9aR)-7-(1-bromo-8-((2,4-dimethoxybenzyl)amino)imidazo[1,5-a]pyrazin-3-yl)tetrahydro-1H-[1,4]oxazino[3,4-c][1,4]oxazin-4(3H)-one (134 mg, 0.259 mmol) in TFA (2 mL) was heated to reflux for 3 hs. LCMS showed the reaction was complete. The reaction solution was cooled and concentrated in vacuo to give (7R,9aR)-7-(8-amino-1-bromoimidazo[1,5-a]pyrazin-3-yl)tetrahydro-1H-[1,4]oxazino[3,4-c][1,4]oxazin-4(3H)-one, which was used in next step without further purification. MS (ESI) m/z (M+H)+: 370.1. Acq Method D0.922 min).

Intermediate 15

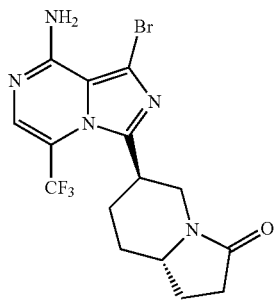 [SMILES: Nc1ncc(C(F)(F)F)n2c([C@@H]3CC[C@H]4CCC(=O)N4C3)nc(Br)c12]

(6R,8aS)-6-(8-amino-1-bromo-5-(trifluoromethyl)imidazo[1,5-a]pyrazin-3-yl)hexahydroindolizin-3(2H)-one (6R,8aS)-6-(8-amino-1-bromoimidazo[1,5-a]pyrazin-3-yl)hexahydroindolizin-3(2H)-one (400 mg, 1.142 mmol) was added to a stirred mixture of 2-chloro-1,1,1,3,3,3-hexamethyl-2-(trimethylsilyl)trisilane (485 mg, 1.713 mmol) and 3,3-dimethyl-1-(trifluoromethyl)-1,2-benziodoxole (754 mg, 2.28 mmol) in acetonitrile (20 ml) and the mixture was stirred at 80° C. for 2 h. The mixture was then concentrated. The residue was purified by column chromatography on silica gel (MPLC 80 g), eluting with CH₂Cl₂/MeOH (30/1) to give (6R,8aS)-6-(8-amino-1-bromo-5-(trifluoromethyl)imidazo[1,5-a]pyrazin-3-yl)hexahydroindolizin-3(2H)-one. LC-MS: (M+1)+418.0, 420.0, retention time=1.15 min.

Intermediate 16D1 and 16 D2

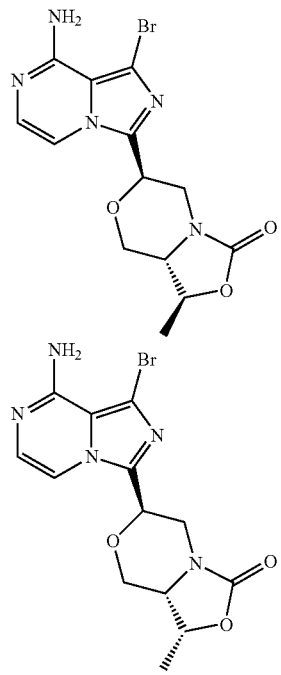

4-(8-amino-3-((6R,8aS)-1-methyl-3-oxohexahydrooxazolo[4,3-c][1,4]oxazin-6-yl)imidazo[1,5-a]pyrazin-1-yl)-3-ethoxy-N-(4-(trifluoromethyl)pyridin-2-yl)benzamide (isomer 1) and 4-(8-amino-3-((6R,8aS)-1-methyl-3-oxohexahydrooxazolo[4,3-c][1.4]oxazin-6-yl)imidazo[1,5-a]pyrazin-1-yl)-3-ethoxy-N-(4-(trifluoromethyl)pyridin-2-yl)benzamide (isomer 2)

Step 1: (2R,5S)-tert-butyl 2-(1-bromo-8-chloroimidazo[1,5-a]pyrazin-3-yl)-5-(((tert-butyldiphenylsilyl)oxy)methyl)morpholine-4-carboxylate To a solution of (2R,5S)-tert-butyl 5-(((tert-butyldiphenylsilyl)oxy)methyl)-2-(8-chloroimidazo[1,5-a]pyrazin-3-yl)morpholine-4-carboxylate (5 g, 8.23 mmol) in MeCN (60 mL) was added NBS (1.612 g, 9.06 mmol). The resulting mixture was stirred at room temperature (10° C.) for 1.5 h under N₂ (g). The mixture was diluted with water (10 mL), extracted with ethyl acetate (10 mL×3). The combined organic layers were washed with brine (10 mL), dried over with Na₂SO₄, filtered and the filtrate was concentrated to afford the crude product (2R,5S)-tert-butyl 2-(1-bromo-8-chloroimidazo[1,5-a]pyrazin-3-yl)-5-(((tert-butyldiphenylsilyl)oxy)methyl)morpholine-4-carboxylate which was purified by silica gel column chromatography (EtOAc: Pet.ether=0-30%) as faint yellow solid. MS: 593.2 (M+1). Acq Method D0.815 min).

Step 2: (2R,5S)-tert-butyl 2-(1-bromo-8-((2,4-dimethoxybenzyl)amino)imidazo[1,5-a]pyrazin-3-yl)-5-(((tert-butyldiphenylsilyl)oxy)methyl)morpholine-4-carboxylate To the mixture of (2R,5S)-tert-butyl 2-(1-bromo-8-chloroimidazo[1,5-a]pyrazin-3-yl)-5-(((tert-butyldiphenylsilyl)

oxy)methyl)morpholine-4-carboxylate (5 g, 7.29 mmol) in DMF (50 mL) were added K$_2$CO$_3$ (3.02 g, 21.86 mmol) and 2,4-dimethoxybenzylamine (1.462 g, 8.74 mmol), then stirred at 80° C. for 2 h. The mixture turned black. Then the mixture was partitioned between ethyl acetate (55 mL) and water (50 mL). The aqueous layer was extracted with ethyl acetate (30 mL×3). The organic layers were concentrated in vacuo, the residue was purified by chromatography (EtOAc: Pet.ether=0-30%) to get the product (2R,5S)-tert-butyl 2-(1-bromo-8-((2,4-dimethoxybenzyl)amino)imidazo[1,5-a]pyrazin-3-yl)-5-(((tert-butyldiphenylsilyl)oxy)methyl) morpholine-4-carboxylate. $^1$H NMR (400 MHz, CD$_3$OD) δ=7.67 (d, J=7.0 Hz, 4H), 7.50 (d, J=5.1 Hz, 1H), 7.48-7.32 (m, 6H), 7.19 (d, J=8.6 Hz, 1H), 7.00 (d, J=5.1 Hz, 1H), 6.55 (d, J=2.0 Hz, 1H), 6.44 (dd, J=2.0, 8.2 Hz, 1H), 5.08 (br. s., 1H), 4.63-4.45 (m, 3H), 4.15-4.07 (m, 2H), 3.95-3.79 (m, 5H), 3.76 (s, 3H), 3.39-3.31 (m, 2H), 1.47 (s, 9H), 1.02 (s, 9H) ppm.

Step 3: (2R,5R)-tert-butyl 2-(1-bromo-8-((2,4-dimethoxybenzyl)amino)imidazo[1,5-a]pyrazin-3-yl)-5-(hydroxymethyl)morpholine-4-carboxylate To the mixture of (2R,5S)-tert-butyl 2-(1-bromo-8-((2,4-dimethoxybenzyl)amino)imidazo[1,5-a]pyrazin-3-yl)-5-(((tert-butyldiphenylsilyl)oxy)methyl)morpholine-4-carboxylate (4.5 g, 5.51 mol) in DCM (70 mL) was added triethylamine hydrofluoride (2.003 g, 17 mmol) and stirred at 50° C. for 24 h under N$_2$ atmosphere. The extra triethylamine hydrofluoride (2.003 g, 17 mmol) was added and stirred at 50° C. for 24 h under N$_2$. Then the mixture was concentrated in vacuo, the residue was purified by silica gel. chromatography (THF/Pet.ether=0-50%) to get the (2R,5R)-tert-butyl 2-(1-bromo-8-((2,4-dimethoxybenzyl)amino)imidazo[1,5-a]pyrazin-3-yl)-5-(hydroxymethyl)morpholine-4-carboxylate. MS: 578/580 (M+1). Acq Method D0.951 min). $^1$H NMR (400 MHz, CD$_3$OD) δ=7.58 (d, J=5.3 Hz, 1H), 7.24 (d, J=8.3 Hz, 1H), 7.06 (d, J=5.0 Hz, 1H), 6.60 (d, J=2.0 Hz, 1H), 6.49 (dd, J=2.4, 8.2 Hz, 1H), 5.20 (d, J=4.3 Hz, 1H), 4.62 (s, 2H), 3.96 (br. s., 1H), 3.92 (s, 3H), 3.89-3.83 (m, 1H), 3.80 (s, 3H), 3.78-3.73 (m, 3H), 3.57 (dd, J=4.5, 14.1 Hz, 1H), 1.89 (td, J=3.3, 6.5 Hz, 2H), 1.52 (s, 9H) ppm.

Step 4: (2R,5S)-tert-butyl 2-(1-bromo-8-((2,4-dimethoxybenzyl)amino)imidazo[1,5-a]pyrazin-3-yl)-5-formylmorpholine-4-carboxylate To the solution of (2R,5R)-tert-butyl 2-(1-bromo-8-((2,4-dimethoxybenzyl)amino)imidazo[1,5-a]pyrazin-3-yl)-5-(hydroxymethyl)morpholine-4-carboxylate (900 mg, 1.556 mmol) in DCM (5 mL) was added Dess-MartinPeriodinane (792 mg, 1.867 mmol) at 0° C. and stirred at 0-25° C. for 3 h. Then the NaHCO$_3$ (aq.) (10 mL) and Na$_2$S$_2$O$_4$ (aq.) (10 mL) was added sequentially. The aqueous layer was extracted with DCM (5 mL×4), and the combined organic layers were washed with brine (10 mL), dried over sodium sulfate, filtered and concentrated to afford the crude product, which was purified on silica gel column chromatography (THF/PE=0-40%) to give (2R,5S)-tert-butyl 2-(1-bromo-8-((2,4-dimethoxybenzyl)amino)imidazo[1,5-a]pyrazin-3-yl)-5-formylmorpholine-4-carboxylate as a solid. MS: 576/578 (M+1), Method D1.045 min). $^1$H NMR (400 MHz, CDCl$_3$) δ=9.58 (s, 1H), 7.28 (d, J=5.1 Hz, 1H), 7.07 (d, J=4.7 Hz, 1H), 6.71 (br. s., 1H), 6.43 (d, J=8.2 Hz, 1H), 6.38 (d, J=8.2 Hz, 1H), 4.88 (br. s., 1H), 4.61 (d, J=4.3 Hz, 2H), 4.32 (dd, J=4.3, 13.7 Hz, 1H), 4.23 (br. s., 1H), 3.98 (d, J=9.0 Hz, 1H), 3.82 (s, 3H), 3.74 (s, 3H), 3.71-3.64 (m, 2H), 3.57 (d, J=11.0 Hz, 1H), 1.47 (br. s., 9H) ppm.

Step 5: (2R,5S)-tert-butyl 2-(1-bromo-8-((2,4-dimethoxbenzyl)amino)imidazo[1,5-a]pyrazin-3-yl)-5-(1-hydroxyethyl)morpholine-4-carboxylate To a solution of (2R,5S)-tert-butyl 2-(1-bromo-8-((2,4-dimethoxybenzyl)amino)imidazo[1,5-a]pyrazin-3-yl)-5-formylmorpholine-4-carboxylate (750 mg, 1.301 mmol) in anhydrous THF (10 mL) at −78° C., methylmagnesium bromide (0.651 ml, 1.952 mmol) 3M in ether was added dropwise. The reaction mixture was stirred at −78° C. to 15° C. for 3 h. The reaction was quenched by saturated ammonium chloride (10 mL), then the mixture was extracted with ethyl acetate (5 mL×4), the combined organic layers were washed with brine (10 mL), dried over sodium sulfate, filtered and concentrated to afford the crude product, which was purified on silica gel column chromatography (THF/PE=5-50%) to give (2R,5S)-tert-butyl 2-(1-bromo-8-((2,4-dimethoxybenzyl)amino)imidazo[1,5-a]pyrazin-3-yl)-5-(1-hydroxyethyl)morpholine-4-carboxylate as a solid. MS: 592/594 (M+1). Acq Method D1.082 min). $^1$H NMR (400 MHz, CD$_3$OD) δ=7.52 (d, J=3.9 Hz, 1H), 7.20 (d, J=8.2 Hz, 2H), 7.05-6.97 (m, 2H), 6.56 (s, 1H), 6.45 (d, J=8.2 Hz, 2H), 5.15 (d, J=3.9 Hz, 1H), 4.63-4.55 (m, 3H), 4.27-4.11 (m, 2H), 3.87 (s, 4H), 3.76 (s, 4H), 3.73-3.67 (m, 3H), 1.85 (t, J=6.3 Hz, 3H), 1.48 (d, J=7.0 Hz, 9H) ppm.

Step 6: 1-((3S,6R)-6-(1-bromo-8-((2,4-dimethoxybenzyl)amino)imidazo[1,5-a]pyrazin-3-yl)morpholin-3-yl)ethanol (2R,5S)-tert-butyl 2-(1-bromo-8-((2,4-dimethoxybenzyl)amino)imidazo[1,5-a]pyrazin-3-yl)-5-((S)-1-hydroxyethyl)morpholine-4-carboxylate was added into in TFA/CH$_2$Cl$_2$ (1 mL/10 mL) and then stirring at 25° C. for 1 h. The mixture was concentrated in vacuo and based with sat. NaHCO$_3$ (aq) to pH=8, which was extracted with DCM (2 mL×3). Then the organic layers were concentrated in vacuo to get the crude product 1-((3S,6R)-6-(1-bromo-8-((2,4-dimethoxybenzyl)amino)imidazo[1,5-a]pyrazin-3-yl)morpholin-3-yl)ethanol and directed to use in the next step. MS: 492/494 (M+1). Acq Method D 0.798 min). $^1$H NMR (400 MHz, CD$_3$OD) δ=7.85 (s, 1H), 7.59 (d, J=5.1 Hz, 1H), 7.19 (d, J=8.2 Hz, 1H), 7.03 (d, J=5.1 Hz, 1H), 6.55 (br. s., 1H), 6.45 (d, J=8.2 Hz, 1H), 5.45 (s, 1H), 4.80-4.70 (m, 1H), 4.58 (s, 2H), 4.14 (d, J=11.3 Hz, 1H), 3.87 (s, 3H), 3.79-3.69 (m, 3H), 3.66-3.49 (m, 2H), 3.24 (d, J=5.9 Hz, 1H), 2.72 (d, J=6.7 Hz, 1H), 1.38 (s, 1H), 1.19 (dd, J=6.5, 14.3 Hz, 3H) ppm.

Step 7: (6R,8aS)-6-(1-bromo-8-((2,4-dimethoxybenzyl)amino)imidazo[1,5-a]pyrazin-3-yl)-1-methyltetrahydrooxazolo[4,3-c][1,4]oxazin-3(1H)-one To a solution of 1-((3S,6R)-6-(1-bromo-8-((2,4-dimethoxybenzyl)amino)imidazo[1,5-a]pyrazin-3-yl)morpholin-3-yl)ethanol (500 mg, 1.016 mmol) in DCM (20 mL) was added CDI (181 mg, 1.117 mmol) and stirred at 25° C. for 12 h under nitrogen protected. There was a part material and extra CDI (181 mg, 1.117 mmol) was added and stirred at 25° C. for another 12 h. The mixture was quenched with water (2 mL), the organic layer was washed with NaCl (10 mL), dried over Na$_2$SO$_4$ and concentrated in vacuo. The residue was purified by chromatography (THF/Pet.ether=0-

50%) to get the product (6R,8aS)-6-(1-bromo-8-((2,4-dimethoxybenzyl)amino)imidazo[1,5-a]pyrazin-3-yl)-1-methyltetrahydrooxazolo[4,3-c][1,4]oxazin-3(1H)-one. MS: 518/520 (M+1). ¹H NMR (400 MHz, CDCl₃) δ=7.23 (br. s., 1H), 7.13 (d, J=4.7 Hz, 1H), 6.77 (br. s., 1H), 6.48 (br. s., 1H), 6.43 (d, J=7.8 Hz, 1H), 4.85-4.70 (m, 1H), 4.66 (d, J=5.5 Hz, 2H), 4.24 (d, J=5.9 Hz, 1H), 4.19-4.06 (m, 1H), 4.03-3.94 (m, 1H), 3.93-3.83 (m, 3H), 3.78 (s, 3H), 3.73 (br. s., 2H), 3.59-3.52 (m, 1H), 1.83 (br. s., 3H) ppm.

Step 8: (6R,8aS)-6-(8-amino-1-bromoimidazo[1,5-a]pyrazin-3-yl)-1-methyltetrahydrooxazolo[4,3-c][1.4]oxazin-3(1H)-one A solution of (6R,8aS)-6-(1-bromo-8-((2,4-dimethoxybenzyl)amino)imidazo[1,5-a]pyrazin-3-yl)-1-methyltetrahydrooxazolo[4,3-c][1,4]oxazin-3(1H)-one (350 mg, 0.675 mmol)) in TFA (4 mL) was stirred at 80° C. for 2 hours under N₂. The mixture was concentrated in vacuo and the residue was based with sat. NaHCO₃ (aq, 3 mL). After partitioned between water (2 mL) and DCM (5 mL), the water layer was extracted with DCM (2×3 mL). The organic layers were concentrated in vacuo to get the crude product (6R,8aS)-6-(8-amino-1-bromoimidazo[1,5-a]pyrazin-3-yl)-1-methyltetrahydrooxazolo[4,3-c][1,4]oxazin-3(1H)-one as a mixture of two diastereomers. LC-MS: 368/370 (M+1).

Intermediate 17

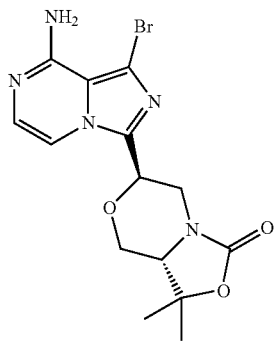 [SMILES: CC1(C)OC(=O)N2C[C@H](c3nc(Br)c4c(N)nccn34)OC[C@H]21]

(6R,8aS)-6-(8-amino-1-bromoimidazo[1,5-a]pyrazin-3-yl)-1,1-dimethyltetrahydrooxazolo[4,3-c][1,4]oxazin-3(1H)-one Step 1: (2R,5S)-tert-butyl 5-acetyl-2-(1-bromo-8-((2,4-dimethoxybenzyl)amino)imidazo[1,5-a]pyrazin-3-yl)morpholine-4-carboxylate To the solution of (2R,5S)-tert-butyl 2-(1-bromo-8-((2,4-dimethoxybenzyl)amino)imidazo[1,5-a]pyrazin-3-yl)-5-(1-hydroxyethyl)morpholine-4-carboxylate (1 g, 1.688 mmol) in DCM (20 mL) was added Dess-MartinPeriodinane (1.432 g, 3.38 mmol) at 0° C. and stirred at 0-25° C. for 3 h. Then the mixture was quenched with NaHCO₃ (aq.) (10 mL) and Na₂S₂O₄(aq.) (10 mL). The aqueous layer was extracted with DCM (5 mL×4), and the combined organic layers were washed with brine (10 mL), dried over sodium sulfate, filtered and concentrated to afford the crude product, which was purified on silica gel column chromatograph (THF/DCM=0%-40%) to give (2R,5S)-tert-butyl 5-acetyl-2-(1-bromo-8-((2,4-dimethoxybenzyl)amino)imidazo[1,5-a]pyrazin-3-yl)morpholine-4-carboxylate. ¹H NMR (400 MHz, CD₃OD) δ=7.50 (d, J=5.1 Hz, 1H), 7.20 (d, J=8.6 Hz, 1H), 7.03 (d, J=5.1 Hz, 1H), 6.56 (d, J=2.0 Hz, 1H), 6.45 (dd, J=2.0, 8.2 Hz, 1H), 5.11 (br. s., 1H), 4.58 (s, 2H), 4.43 (br. s., 1H), 4.16 (d, J=11.3 Hz, 1H), 3.88 (s, 3H), 3.76 (s, 3H), 3.71 (t, J=5.9 Hz, 1H), 3.62 (br. s., 1H), 3.49 (d, J=8.6 Hz, 1H), 2.21 (s, 3H), 1.57-1.37 (m, 9H) ppm.

Step 2: 1-((3S,6R)-6-(1-bromo-8-((2,4-dimethoxybenzyl)amino)imidazo[1,5-a]pyrazin-3-yl)morpholin-3-yl)ethanone The mixture of (2R,5S)-tert-butyl 5-acetyl-2-(1-bromo-8-((2,4-dimethoxybenzyl)amino)imidazo[1,5-a]pyrazin-3-yl)morpholine-4-carboxylate (100 mg, 0.169 mmol) in 2,2,2-trifluoroacetic acid, CH₂Cl₂ (0.228 mL, 0.169 mmol) was stirred at 10° C. for 1 h. The mixture was concentrated in vacuo and the residue was based with NaHCO₃ (aq., 3 mL) and parted between water (2 mL) and DCM (5 mL). The water layer was extracted with DCM (3 mL×2). The organic layers were concentrated in vacuo to get 1-((3S,6R)-6-(1-bromo-8-((2,4-dimethoxybenzyl)amino)imidazo[1,5-a]pyrazin-3-yl)morpholin-3-yl)ethanone. ¹H NMR (400 MHz, CD₃OD) δ=7.51 (d, J=5.1 Hz, 1H), 7.12 (d, J=8.2 Hz, 1H), 6.96 (d, J=5.1 Hz, 1H), 6.48 (s, 1H), 6.40-6.34 (m, 1H), 4.67 (dd, J=4.7, 8.2 Hz, 1H), 4.51 (s, 2H), 4.23 (d, J=3.1 Hz, 1H), 4.20 (d, J=3.5 Hz, 1H), 3.80 (s, 3H), 3.75-3.63 (m, 4H), 3.47 (t, J=10.8 Hz, 2H), 2.16-2.07 (m, 3H) ppm.

Step 3: 2-((3S,6R)-6-(1-bromo-8-((2,4-dimethoxybenzyl)amino)imidazo[1,5-a]pyrazin-3-yl)morpholin-3-yl)propan-2-ol To a solution of 1-((3S,6R)-6-(1-bromo-8-((2,4-dimethoxybenzyl)amino)imidazo[1,5-a]pyrazin-3-yl)morpholin-3-yl)ethanone (400 mg, 0.816 mmol) in anhydrous THF (5 mL) at −78° C., methylmagnesium bromide (1.360 mL, 4.08 mmol) 3M in ether was added dropwise. The reaction mixture was stirred at −78° C. to room temperature for 3 hours. The reaction was quenched by saturated ammonium chloride (10 mL), then the mixture was extracted with ethyl acetate (5 mL×4), the combined organic layers were washed with brine (10 mL), dried over sodium sulfate, filtered and concentrated to afford the crude product, which was purified on silica gel column chromatograph (THF/DCM=5%-50%) to give 2-((3S,6R)-6-(1-bromo-8-((2,4-dimethoxybenzyl)amino)imidazo[1,5-a]pyrazin-3-yl)morpholin-3-yl)propan-2-ol. ¹H NMR (400 MHz, CD₃OD) δ=7.60 (d, J=5.1 Hz, 1H), 7.19 (d, J=8.6 Hz, 1H), 7.05-6.98 (m, 1H), 6.56 (br. s., 1H), 6.48-6.42 (m, 1H), 4.75 (dd, J=4.7, 8.2 Hz, 1H), 4.58 (s, 2H), 4.10-4.03 (m, 1H), 3.94-3.80 (m, 4H), 3.79-3.66 (m, 4H), 3.60 (t, J=10.8 Hz, 1H), 2.80-2.70 (m, 1H), 1.29-1.10 (m, 6H) ppm.

Step 4: (6R,8aS)-6-(1-bromo-8-((2,4-dimethoxybenzyl)amino)imidazo[1,5-a]pyrazin-3-yl)-1,1-dimethyltetrahydrooxazolo[4,3-c][1,4]oxazin-3(1H)-one To the mixture of 2-((3S,6R)-6-(1-bromo-8-((2,4-dimethoxybenzyl)amino)imidazo[1,5-a]pyrazin-3-yl)morpholin-3-yl)propan-2-ol (25 mg, 0.049 mmol) in DCM (1 mL) was added CDI (8.81 mg, 0.054 mmol) and stirred at 25° C. for 12 h under N₂ protected. Then extra CDI (8.81 mg, 0.054 mmol) was added for 8 times, and the mixture was stirred at 28° C. for another 4 days. The mixture was parted between water (1 mL) and DCM (1 mL), and the organic layers were washed with sat. NaHCO₃ (1 mL) and concentrated in vacuo. The residue was purified by prep-TLC (THF:PE=1:1) to get the product (6R,8aS)-6-(1-bromo-8-((2,4-dimethoxybenzyl)amino)imidazo[1,5-a]pyrazin-3-yl)-1,1-dimethyltetrahydrooxazolo[4,3-c][1,4]oxazin-3(1H)-one. MS: 532/534 (M+1). $^1$H NMR (400 MHz, CD$_3$OD) δ=7.47 (d, J=4.7 Hz, 1H), 7.11 (d, J=7.8 Hz, 1H), 6.96 (d, J=4.7 Hz, 1H), 6.48 (br. s., 1H), 6.36 (d, J=7.8 Hz, 1H), 4.73 (d, J=11.0 Hz, 1H), 4.50 (br. s., 2H), 3.96-3.92 (m, 1H), 3.79 (s, 3H), 3.75-3.65 (m, 4H), 3.64-3.51 (m, 3H), 1.41 (br. s., 3H), 1.29 (br. s., 3H) ppm.

Step 5: (6R,8aS)-6-(8-amino-1-bromoimidazo[1,5-a]pyrazin-3-yl)-1,1-dimethyltetrahydrooxazolo[4,3-c][1,4]oxazin-3(1H)-one To a suspension of (6R,8aS)-6-(1-bromo-8-((2,4-dimethoxybenzyl)amino)imidazo[1,5-a]pyrazin-3-yl)-1,1-dimethyltetrahydrooxazolo[4,3-c][1,4]oxazin-3(1H)-one (180 mg, 0.338 mmol) in TFA (1.302 mL, 16.90 mmol) was heated to 80° C. for 2 h. The mixture was concentrated in vacuo to give the residue which was poured into aq.NaHCO$_3$ (30 mL) and extracted with DCM/MeOH (10/1) (30 mL×3). The combined organic layers were washed with brine (20 mL), dried over Na$_2$SO$_4$ and concentrated under reduced pressure to give the product (6R,8aS)-6-(8-amino-1-bromoimidazo[1,5-a]pyrazin-3-yl)-1,1-dimethyltetrahydrooxazolo[4,3-c][1,4]oxazin-3(1H)-one, which was used to the next step without future purification. MS: 382/384 (M+1). $^1$H NMR (400 MHz, CDCl$_3$): δ=7.39 (d, J=5.1 Hz, 1H), 7.09 (d, J=5.1 Hz, 1H), 5.71 (br. s., 2H), 4.71 (dd, J=3.1, 11.0 Hz, 1H), 4.21 (dd, J=2.9, 13.9 Hz, 1H), 4.03 (dd, J=3.3, 10.8 Hz, 1H), 3.69 (dd, J=6.1, 10.4 Hz, 2H), 3.61-3.54 (m, 1H), 1.53 (s, 3H), 1.39 (s, 3H) ppm.

Intermediate 18

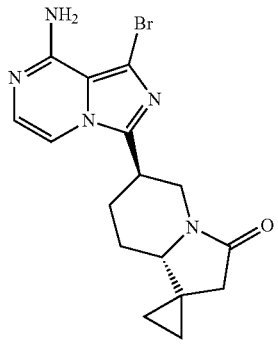 [SMILES: Nc1nccn2c([C@@H]3CC[C@@H]4N(C3)C(=O)CC43CC3)nc(Br)c12]

Trans-6'-(8-amino-1-bromoimidazo[1,5-a]pyrazin-3-yl)tetrahydro-2'H-spiro[cyclopropane-1,1'-indolizin]-3'(5'H)-one Step 1: 1-(5-bromopyridin-2-yl)cyclopropanecarbonitrile To a stirred solution of cyclopropanecarbonitrile (19.06 g, 284 mmol) and 5-bromo-2-fluoropyridine (50 g, 284 mmol) in toluene (400 mL) added dropwise potassium bis(trimethylsilyl)amide (500 ml, 500 mmol) in THF under ice-cooling, the reaction mixture was stirred at 10° C. for 16 hours. The TLC analyses showed completion of the reaction. Quenching was carried out with a saturated aqueous solution of ammonium chloride (500 mL) and extracted with EtOAc (200 mL×3). The combined organic layers were washed with brine (500 mL). The extracts were dried over Na$_2$SO$_4$, filtered and concentrated under reduced pressure. The residue was purified by silica gel column chromatography (polyethylene/ethyl acetate=0%~20%) to afford 1-(5-bromopyridin-2-yl)cyclopropanecarbonitrile. $^1$H NMR (CDCl$_3$ 400 MHz) δ=8.48 (d, J=1.6 Hz, 1H), 7.79 (dd, J=2.0, 8.2 Hz, 1H), 7.59 (d, J=8.2 Hz, 1H), 1.80-1.75 (m, 2H), 1.74-1.69 (m, 2H) ppm.

Step 2: 1-(5-bromopyridin-2-yl)cyclopropanecarboxylic acid

To a solution of 1-(5-bromopyridin-2-yl)cyclopropanecarbonitrile (58 g, 260 mmol) in ethanol (500 mL) was added a solution of NaOH (31.2 g, 780 mmol) in water (100 mL), then was heated to 100° C. for 24 hours. After the LCMS showed completion of the reaction. After cooling to room temperature, the solution was poured into an ice-cold saturated aqueous Na$_2$HPO$_4$ solution (500 mL) and the resulting mixture was adjusted to pH 4 by the addition of 1 M aqueous hydrochloric acid. The mixture was extracted with EtOAc (300 mL×4). The combined organic layers were washed with brine (500 mL). The extracts were dried over Na$_2$SO$_4$, filtered and concentrated under reduced pressure to give 1-(5-bromopyridin-2-yl)cyclopropanecarboxylic acid. $^1$H NMR (CDCl$_3$ 400 MHz) δ=8.50 (d, J=1.6 Hz, 1H), 7.87 (dd, J=2.0, 8.6 Hz, 1H), 6.80 (d, J=8.6 Hz, 1H), 2.09 (q, J=4.0 Hz, 2H), 1.43-1.34 (m, 2H) ppm.

Step 3: 1-(5-bromopyridin-2-yl)-N-methoxy-N-methylcyclopropanecarboxamide

To a solution of 1-(5-bromopyridin-2-yl)cyclopropanecarboxylic acid (60 g, 248 mmol) in anhydrous DMF (600 mL) was added HATU (113 g, 297 mmol) and the mixture was stirred for 30 mins under nitrogen. Et3N (104 ml, 744 mmol) was added and followed by N,O-dimethylhydroxylamine, HCl (26.6 g, 273 mmol). The mixture was stirred for 16 hrs at 10° C. After TLC (Pet. ether/EtOAc=1/1) showed the reaction finished, the mixture was diluted with water (1500 mL) and extracted with ethyl acetate (500 mL×5). The combined organic layers were washed with water (200 mL×2), brine (1000 mL), dried over Na$_2$SO$_4$ and evaporated to get the crude product, which was purified on flash chromatography (Pet. ether/EtOAc=100~50%) to give 1-(5-bromopyridin-2-yl)-N-methoxy-N-methylcyclopropanecarboxamide. $^1$H NMR (CDCl$_3$ 400 MHz) δ=8.49 (d, J=1.6 Hz, 1H), 7.68 (dd, J=2.2, 8.4 Hz, 1H), 7.06 (d, J=8.6 Hz, 1H), 3.43 (br. s., 3H), 3.19 (s, 3H), 1.49-1.38 (m, 4H) ppm.

Step 4: (1-(5-bromopyridin-2-yl)cyclopropyl)methanol

To a solution of 1-(5-bromopyridin-2-yl)-N-methoxy-N-methylcyclopropanecarboxamide (60 g, 210 mmol) in EtOH (600 ml) was added NaBH$_4$ (23.88 g, 631 mmol) in portions at 0° C. After an additional stirring at 30° C. for 20 hours, the LCMS showed completion of the reaction. Then the reaction mixture was poured into a saturated aqueous solution of NH$_4$Cl (1000 mL) and concentrated. The mixture was extracted with EtOAc (300 mL×4). The combined organic layers were washed with brine (500 mL). The extracts were dried over Na$_2$SO$_4$, filtered and concentrated under reduced pressure. The residue was purified by silica gel column chromatography (polyethylene/ethyl acetate=0%~50%) to afford (1-(5-bromopyridin-2-yl)cyclopropyl)methanol. $^1$H NMR (CDCl$_3$ 400 MHz) δ=8.51 (d, J=2.3 Hz, 1H), 7.71 (dd, J=2.5, 8.5 Hz, 1H), 6.88 (d, J=8.5 Hz, 1H), 3.82 (s, 2H), 3.75 (br. s., 1H), 1.07 (d, J=3.3 Hz, 4H) ppm.

Step 5: 2-(1-(5-bromopyridin-2-yl)cyclopropyl)acetonitrile

To a solution of (1-(5-bromopyridin-2-yl)cyclopropyl)methanol (20 g, 88 mmol) and Et$_3$N (36.7 ml, 263 mmol) in CH$_2$Cl$_2$ (200 mL) was added methanesulfonyl chloride (20.07 ml, 258 mmol) dropwise at 0° C. under nitrogen atmosphere. After an additional stirring at 0° C. for 4 hours, the mixture was washed with saturate aqueous NaHCO$_3$ (50 mL), brine (50 mL), dried over Na$_2$SO$_4$ and concentrated under reduced pressure. The residue was dissolved in DMF (200 mL) and then added NaCN (13.21 g, 270 mmol). The mixture was stirred at 70° C. for 18 hours. The mixture was added water (600 mL) and extracted with EtOAt (200 mL×4). The combined organic layers were washed with water (100 mL×3), brine (200 mL), dried over Na$_2$SO$_4$, filtered and concentrated under reduced pressure. The residue was purified by silica gel column chromatography (polyethylene/ethyl acetate=0%~40%) to give 2-(1-(5-bromopyridin-2-yl)cyclopropyl)acetonitrile. $^1$H NMR (CDCl$_3$ 400 MHz) δ=8.56 (d, J=2.0 Hz, 1H), 7.74 (dd, J=2.3, 8.6 Hz, 1H), 6.96 (d, J=8.2 Hz, 1H), 2.92 (s, 2H), 1.30-1.21 (m, 2H), 1.20-1.11 (m, 2H) ppm.

Step 6: 2-(1-(5-bromopyridin-2-yl)cyclopropyl)acetic acid

To a solution of 2-(1-(5-bromopyridin-2-yl)cyclopropyl)acetonitrile (13.5 g, 56.9 mmol) in ethanol (130 mL) was added a solution of sodium hydroxide (6.83 g, 171 mmol) in water (30 mL) was heated to 100° C. for 24 hours. After the LCMS showed completion of the reaction. After cooling to room temperature, the solution was poured into ice-cold saturated aqueous Na$_2$HPO$_4$ solution (50 mL) and the resulting mixture was adjusted to pH 4 by the addition of 1 M aqueous hydrochloric acid. The mixture was extracted with EtOAc (200 mL×4). The combined organic layers were washed with brine (200 mL). The extracts were dried over Na$_2$SO$_4$, filtered and concentrated under reduced pressure to give 2-(1-(5-bromopyridin-2-yl)cyclopropyl)acetic acid.

$^1$H NMR 0351907-0092-1A (CDCl$_3$ 400 MHz) δ=8.54 (d, J=2.0 Hz, 1H), 7.82 (dd, J=2.3, 8.6 Hz, 1H), 6.92 (d, J=8.6 Hz, 1H), 2.81 (s, 2H), 1.17 (s, 4H) ppm.

Step 7: methyl 2-(1-(5-bromopyridin-2-yl)cyclopropyl)acetate

A solution of 2-(1-(5-bromopyridin-2-yl)cyclopropyl)acetic acid (30 g, 117 mmol) was dissolved in HCl/CH3OH (250 mL)(4M), and stirring at 15° C. for 2 hours. The TLC showed completion of the reaction. The mixture was concentrated under reduced pressure. The residue was dissolved in EtOAc (100 mL) and neutralized with sat. NaHCO$_3$ (200 mL) (aq.). The aqueous was extracted with EtOAc (100 mL×4). The combined organic layers were washed with brine (200 mL). The extracts were dried over Na$_2$SO$_4$ and concentrated under reduced pressure. The residue was purified by silica gel column chromatography (EtOAc: Pet. ether=0%~30%) to give methyl 2-(1-(5-bromopyridin-2-yl)cyclopropyl)acetate. H NMR (CDCl$_3$ 400 MHz) δ=8.48 (br. s., 1H), 7.65 (d, J=6.7 Hz, 1H), 6.99 (d, J=8.2 Hz, 1H), 3.75-3.53 (m, 3H), 2.76 (s, 2H), 1.22 (br. s., 1H), 1.01 (br. s., 1H) ppm.

Step 8: methyl 6-(1-(2-methoxy-2-oxoethyl)cyclopropyl)nicotinate

To a solution of methyl 2-(1-(5-bromopyridin-2-yl)cyclopropyl)acetate (10 g, 37.0 mmol) in MeOH (100 mL) and DMF (100 mL) was added Et$_3$N (15.48 ml, 111 mmol), DPPF (4.10 g, 7.40 mmol) and diacetoxypalladium (0.831 g, 3.70 mmol). The mixture was stirred at 80° C. for 48 hours under CO (50 psi). The reaction mixture was filtered, and the filtrate was concentrated under reduced pressure. Then the residue was diluted with water (300 mL) and extracted with EtOAc (100 mL×4). The combined organic layers were washed with water (50 mL×3), brine (100 mL), dried over Na$_2$SO$_4$, and concentrated under reduced pressure. The residue was purified by silica gel column chromatography (EtOAc: Pet. ether=0%~40%) to afford methyl 6-(1-(2-methoxy-2-oxoethyl)cyclopropyl)nicotinate. H NMR (CDCl$_3$ 400 MHz) δ=9.05 (br. s., 1H), 8.14 (d, J=6.7 Hz, 1H), 7.14 (d, J=8.2 Hz, 1H), 4.00-3.86 (m, 3H), 3.75-3.59 (m, 3H), 2.83 (br. s., 2H), 1.36 (br. s., 2H), 1.10 (br. s., 2H) ppm.

Step 9: methyl 6-(1-(2-methoxy-2-oxoethyl)cyclopropyl)piperidine-3-carboxylate

To a solution of methyl 6-(1-(2-methoxy-2-oxoethyl)cyclopropyl)nicotinate (8.5 g, 34.1 mmol) in AcOH (100 ml) was added NaCNBH4 (6.43 g, 102 mmol) in portions and stirred at 40° C. for 24 hours. Then the mixture was concentrated under reduced pressure. The residue was dissolved in EtOAc (50 ml) and adjusted with a saturated aqueous solution of NaHCO$_3$ (5 mL) to pH=9, then extracted with EtOAc (50 mL×4). The combined organic layers were washed with brine (100 mL). The extracts were dried over Na$_2$SO$_4$, filtered and concentrated under reduced pressure to give crude methyl 6-(1-(2-methoxy-2-oxoethyl)cyclopropyl)piperidine-3-carboxylate. MS: 256.0 (M+1) ppm.

Step 10: methyl 3'-oxohexahydro-2'H-spiro[cyclopropane-1,1'-indolizine]-6'-Carboxylate A solution of methyl 6-(1-(2-methoxy-2-oxoethyl)cyclopropyl)piperidine-3-carboxylate (10 g, 39.2 mmol) in MeOH (100 ml) was stirred at refluxed for 16 hours. The LCMS showed completion of the reaction. Then the reaction mixture was concentrated under reduced pressure. The residue was purified by silica gel column chromatography (polyethylene/THF=100%~20%) to afford methyl 3'-oxohexahydro-2'H-spiro[cyclopropane-1,1'-indolizine]-6'-Carboxylate 1,1'-indolizine]-6'-carboxylate (trans isomer). $^1$H NMR (CDCl$_3$ 400 MHz) δ=4.46 (dd, J=3.3, 13.1 Hz, 1H), 3.74-3.61 (m, 3H), 3.18 (dd, J=2.7, 11.7 Hz, 1H), 2.78 (t, J=12.3 Hz, 1H), 2.50-2.31 (m, 3H), 2.19 (d, J=12.9 Hz, 1H), 1.64-1.51 (m, 2H), 1.28-1.15 (m, 1H), 0.72 (dtd, J=5.5, 9.8, 19.2 Hz, 2H), 0.65-0.56 (m, 1H), 0.56-0.46 (m, 1H) ppm.

Step 11: trans-3'-oxohexahydro-2'H-spiro[cyclopropane-1,1'-indolizine]-6'-carboxylic acid To a solution of methyl 3'-oxohexahydro-2'H-spiro[cyclopropane-1,1'-indolizine]-6'-Carboxylate (trans isomer) (1.5 g, 6.72 mmol) in THF (10 mL) was added a solution of LiOH (0.483 g, 20.16 mmol) in water (10 mL) and stirred at 10° C. for 3 hours. After the LCMS showed completion of the reaction. The mixture was adjusted to pH 4 by the addition of aqueous hydrochloric acid (1 M). The mixture was extracted with EtOAc (10 mL×4). The combined organic layers were washed with brine (30 mL). The extracts were dried over $Na_2SO_4$, filtered and concentrated under reduced pressure to give 3'-oxohexahydro-2'H-spiro[cyclopropane-1,1'-indolizine]-6'-carboxylic acid (trans isomer). $^1$H NMR (CDCl$_3$ 400 MHz) δ=4.49 (dd, J=3.3, 13.5 Hz, 1H), 3.22-3.14 (m, 1H), 2.79 (t, J=12.3 Hz, 1H), 2.50-2.35 (m, 3H), 2.23 (d, J=12.1 Hz, 1H), 1.66-1.53 (m, 2H), 1.21 (d, J=3.5 Hz, 1H), 0.72 (ddd, J=4.7, 9.8, 18.0 Hz, 2H), 0.60 (td, J=5.0, 9.9 Hz, 1H), 0.52 (dd, J=4.5, 9.6 Hz, 1H) ppm.

Step 12: N-((3-chloropyrazin-2-yl)methyl)-3'-oxohexahydro-2'H-spiro[cyclopropane-1,1'-indolizine]-6'-carboxamide (trans isomer)

To a solution of (6'R,8a'S)-3'-oxohexahydro-2'H-spiro[cyclopropane-1,1'-indolizine]-6'-carboxylic acid (100 mg, 0.478 mmol) in DMF (2 mL) were added HATU (113 g, 297 mmol), DIEA (0.250 ml, 1.434 mmol) and (3-chloropyrazin-2-yl)methanamine hydrochloride (86 mg, 0.478 mmol) and the mixture was stirred for 16 hrs at 15° C. The mixture was diluted with water (10 mL) and extracted with ethyl acetate (5 mL×4). The combined organic layers were washed with water (5 mL×3), brine (10 mL), dried over $Na_2SO_4$, evaporated to get the crude product, which was purified on flash chromatography (Pet. ether/EtOAc=100-60%) to give N-((3-chloropyrazin-2-yl)methyl)-3'-oxohexahydro-2'H-spiro[cyclopropane-1,1'-indolizine]-6'-carboxamide (trans isomer). $^1$H NMR (400 MHz, CDCl$_3$ δ=8.44 (d, J=2.0 Hz, 1H), 8.33 (s, 1H), 6.87 (br. s., 1H), 4.76-4.60 (m, 2H), 4.41 (dd, J=3.1, 12.9 Hz, 1H), 3.21 (dd, J=2.9, 11.5 Hz, 1H), 2.91 (t, J=12.3 Hz, 1H), 2.52-2.28 (m, 3H), 2.16-2.01 (m, 1H), 1.86-1.72 (m, 1H), 1.62 (dd, J=3.1, 13.3 Hz, 1H), 1.31-1.19 (m, 1H), 0.79-0.65 (m, 2H), 0.62 (td, J=5.0, 9.9 Hz, 1H), 0.56-0.47 (m, 1H) ppm.

Step 13: 6'-(8-chloroimidazo[1,5-a]pyrazin-3-yl)tetrahydro-2'H-spiro[cyclopropane-1,1'-indolizin]-3'(5'H)-one (trans isomer)

To a stirred solution of N-((3-chloropyrazin-2-yl)methyl)-3'-oxohexahydro-2'H-spiro[cyclopropane-1,1'-indolizine]-6'-carboxamide (1.8 g, 5.38 mmol) in acetonitrile (20 ml) was added PCl$_5$ (3.36 g, 16.13 mmol), the reaction mixture was stirred at 10° C. for 3 hours. After cooled to 0° C., the mixture was added into a saturated aqueous solution of NaHCO$_3$(50 mL) at 0° C. and extracted with EtOAc (30 mL×4). The combined organic layers were washed with brine (50 mL). The extracts were dried over Na$_2$SO$_4$, filtered and concentrated under reduced pressure. The residue was purified by silica gel column chromatography (CH$_2$Cl$_2$/MeOH=100%~80%) to afford 6'-(8-chloroimidazo[1,5-a]pyrazin-3-yl)tetrahydro-2'H-spiro[cyclopropane-1,1'-indolizin]-3'(5'H)-one (trans isomer). $^1$H NMR (CDCl$_3$400 MHz) δ=7.79 (s, 1H), 7.68 (d, J=4.7 Hz, 1H), 7.35 (d, J=4.7 Hz, 1H), 4.51-4.42 (m, 1H), 3.32 (dd, J=3.1, 11.3 Hz, 1H), 3.03 (d, J=9.0 Hz, 2H), 2.58-2.40 (m, 2H), 2.24-2.16 (m, 1H), 2.14-2.02 (m, 1H), 1.76 (dd, J=3.1, 12.9 Hz, 1H), 1.48-1.35 (m, 1H), 0.85-0.63 (m, 3H), 0.62-0.53 (m, 1H) ppm.

Step 14: 6'-(1-bromo-8-chloroimidazo[1,5-a]pyrazin-3-yl)tetrahydro-2'H-spiro[cyclopropane-1,1'-indolizin]-3'(5'H)-one (trans isomer)

To a solution of (6'R, 8a'S)-6'-(8-chloroimidazo[1,5-a]pyrazin-3-yl)tetrahydro-2'H-spiro[cyclopropane-1,1'-indolizin]-3'(5'H)-one (trans isomer) (1.3 g, 4.10 mmol) in acetonitrile (20 ml) was added NBS (0.803 g, 4.51 mmol). The resulting mixture was stirred at 10° C. for 1 hour. LCMS showed that the reaction was complete, the mixture was filtered to afford a white solid and the filtrate was poured into a saturated aqueous solution of NaHCO$_3$ (30 mL) and extracted with EtOAc (40 mL×3). The combined organic layers were washed with brine (50 mL), dried over Na$_2$SO$_4$, filtered and concentrated under reduced pressure. The residue was purified by silica gel column chromatography to afford 6'-(1-bromo-8-chloroimidazo[1,5-a]pyrazin-3-yl)tetrahydro-2'H-spiro[cyclopropane-1,1'-indolizin]-3'(5'H)-one (trans isomer). $^1$H NMR (CDCl$_3$ 400 MHz) δ=7.69 (d, J=5.1 Hz, 1H), 7.36 (d, J=5.1 Hz, 1H), 4.45 (d, J=8.6 Hz, 1H), 3.31 (dd, J=2.9, 11.5 Hz, 1H), 3.07-2.95 (m, 2H), 2.61-2.42 (m, 2H), 2.23-2.08 (m, 2H), 1.77 (dd, J=3.1, 13.3 Hz, 1H), 1.47-1.35 (m, 1H), 0.84-0.66 (m, 3H), 0.60 (dd, J=4.5, 9.6 Hz, 1H) ppm.

Step 15: 6'-(8-amino-1-bromoimidazo[1,5-a]pyrazin-3-yl)tetrahydro-2'H-spiro[cyclopropane-1,1'-indolizin]-3'(5'H)-one (trans isomer)

To a solution of (6'R,8a'S)-6'-(1-bromo-8-chloroimidazo[1,5-a]pyrazin-3-yl)tetrahydro-2'H-spiro[cyclopropane-1,1'-indolizin]-3'(5'H)-one (trans isomer) (1.5 g, 3.79 mmol) in 2-Propanol (15 ml) was added ammonia, H$_2$O (30 ml, 189 mmol). The mixture was stirred at 120° C. for 18 hours in a 100 mL of autoclave. The reaction mixture was concentrated and the residue was purified by silica gel column chromatography (DCM/MeOH=0%~20%) to afford 6'-(8-amino-1-bromoimidazo[1,5-a]pyrazin-3-yl)tetrahydro-2'H-spiro[cyclopropane-1,1'-indolizin]-3'(5'H)-one (trans isomer). H NMR (CDCl$_3$ 400 MHz) δ=7.25 (d, J=5.1 Hz, 1H), 7.06 (d, J=4.7 Hz, 1H), 5.67 (br. s., 2H), 4.46 (d, J=11.0 Hz, 1H), 3.30 (dd, J=2.9, 11.5 Hz, 1H), 3.06-2.91 (m, 2H), 2.60-2.42 (m, 2H), 2.22-2.13 (m, 1H), 2.11-1.99 (m, 1H), 1.74 (dd, J=2.9, 13.1 Hz, 1H), 1.39 (dq, J=3.1, 12.7 Hz, 1H), 0.85-0.64 (m, 3H), 0.63-0.54 (m, 1H) ppm.

Step 16: 6'-(8-amino-1-bromoimidazo[1,5-a]pyrazin-3-yl)tetrahydro-2'H-spiro[cyclopropane-1,1'-indolizin]-3'(5'H)-one (trans isomer1) and 6'-(8-amino-1-bromoimidazo[1,5-a]pyrazin-3-yl)tetrahydro-2'H-spiro[cyclopropane-1,1'-indolizin]-3'(5'H)-one (trans isomer2)

Instrument and Condition
Instrument: Thar 200
Column: OJ 250 mm*50 mm, 10 um
Mobile phase: A: Supercritical CO$_2$, B: EtOH (0.05% NH3H2O), A:B=70:30 at 200 ml/min
Column Temp: 38° C.
Nozzle Pressure: 100 Bar
Nozzle Temp: 60° C.
Evaporator Temp: 20° C.
Trimmer Temp: 25° C.
Wavelength: 220 nm
6'-(8-amino-1-bromoimidazo[1,5-a]pyrazin-3-yl)tetrahydro-2'H-spiro[cyclopropane-1,1'-indolizin]-3'(5'H)-one (trans isomer1). Retention time: 1.203 min. $^1$H NMR CDCl$_3$ 400 MHz δ=7.24 (d, J=5.1 Hz, 1H), 7.06 (d, J=5.1 Hz, 1H), 5.68 (br. s., 2H), 4.45 (d, J=11.0 Hz, 1H), 3.29 (dd, J=2.7, 11.7 Hz, 1H), 2.99 (q, J=12.3 Hz, 2H), 2.58-2.42 (m, 2H), 2.21-2.12 (m, 1H), 2.10-1.98 (m, 1H), 1.78-1.72 (m, 1H), 1.45-1.33 (m, 1H), 0.82-0.64 (m, 3H), 0.58 (dd, J=4.5, 9.6 Hz, 1H) ppm.

6'-(8-amino-1-bromoimidazo[1,5-a]pyrazin-3-yl)tetrahydro-2'H-spiro[cyclopropane-1,1'-indolizin]-3'(5'H)-one (trans isomer2). Retention time: 1.362 min. ¹H NMR (CDCl₃ 400 MHz) δ=7.17 (d, J=5.1 Hz, 1H), 6.97 (d, J=5.1 Hz, 1H), 5.85 (br. s., 2H), 4.38 (d, J=11.0 Hz, 1H), 3.23 (dd, J=2.9, 11.5 Hz, 1H), 3.00-2.86 (m, 2H), 2.50-2.36 (m, 2H), 2.16-2.06 (m, 1H), 2.04-1.91 (m, 1H), 1.66 (dd, J=2.9, 13.1 Hz, 1H), 1.38-1.26 (m, 1H), 0.78-0.58 (m, 3H), 0.51 (dd, J=4.9, 9.2 Hz, 1H) ppm.

Intermediate 19

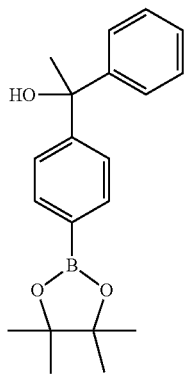 [SMILES: CC(O)(c1ccccc1)c1ccc(B2OC(C)(C)C(C)(C)O2)cc1]

1-phenyl-1-(4-(4,4,5,5-tetramethyl-1,3,2-dioxaborolan-2-yl)phenyl)ethanol

Step 1: 1-(4-bromophenyl)-1-phenyl)ethanol

To a solution of (4-bromophenyl)(phenyl)methanone (2 g, 7.66 mmol) in anhydrous THF (20 mL) was added MeMgBr (3.8 mL, 11.49 mmol) (3M) slowly at −78° C. under N₂ atmosphere, and stirred for 2 hrs. Then the mixture was stirred at 0° C. for 3 hrs. The mixture was poured into sat. NH₄Cl (100 mL) (aq), which was extracted with EtOAc (20 mL×3). The organic layer was washed with brine (20 mL), dried over Na₂SO₄, and evaporated to get the crude product, which was then purified by flash chromatography (PE/EA=100-80%) to get the 1-(4-bromophenyl)-1-phenylethanol. ¹H NMR (400 MHz, CDCl₃)=7.46-7.37 (m, 4H), 7.36-7.23 (m, 5H), 2.22 (s, 1H), 1.93 (s, 3H) ppm.

Step 2: 1-phenyl-1-(4-(4,4,5,5-tetramethyl-1,3,2-dioxaborolan-2-yl)phenyl)ethanol A degassed mixture of 1-(4-bromophenyl)-1-phenylethanol (0.5 g, 1.8 mmol), Bispinacolatodiboron (688 mg, 2.7 mmol), KOAc (530 mg, 5.4 mmol), X-Phos (85 mg, 0.18 mmol), and Pd₂(dba)₃ (165 mg, 0.18 mmol) in 10 mL of 1,4-dioxane was stirred at 80-90° C. for 12 hours under N₂. TLC showed that the reaction completed, and then the mixture was cooled to room temperature. Water (10 mL) was added into the reaction mixture, which was extracted with ethyl acetate (10 mL×3). The organic layers were washed with brine (10 mL), dried over Na₂SO₄, and concentrated in vacuo to give crude product, which was purified by flash chromatography (PE:EA=100-80%) to give 1-phenyl-1-(4-(4,4,5,5-tetramethyl-1,3,2-dioxaborolan-2-yl)phenyl)ethanol. 1H NMR (400 MHz, CDCl₃) δ=7.77 (d, J=8.3 Hz, 2H), 7.46-7.37 (m, 4H), 7.34-7.28 (m, 2H), 7.26-7.20 (m, 1H), 2.19 (s, 1H), 1.95 (s, 3H), 1.33 (s, 12H) ppm.

Intermediate 20

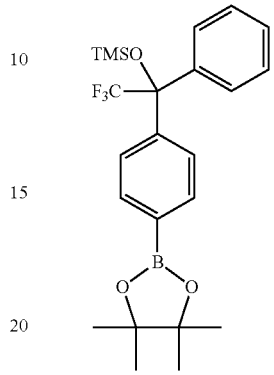

Trimethyl(2,2,2-trifluoro-1-phenyl-1-(4-(4,4,5,5-tetramethyl-1,3,2-dioxaborolan-2-yl)phenyl)ethoxy)silane Step 1 (1-(4-bromophenyl)-2,2,2-trifluoro-1-phenylethoxy)trimethylsilane To a solution of compound (4-bromophenyl)(phenyl)methanone (1 g, 3.8 mmol) in anhydrous THF (10 mL) was added TMSCF₃ (815 mg, 5.7 mmol), and followed by a solution of TBAF (10 mg, 0.038 mmol) in 0.1 mL of THF at 0° C., and stirred for 50 min at 0° C. under N₂. TLC showed that the reaction was finished, and then 1M of HCl (5 mL) was added, and stirred for 30 min. Then the mixture was basified with aq. NaHCO₃ (10 mL), and extracted with EtOAc (10 mL×3). The organic layer was washed with brine (10 mL), dried over Na₂SO₄, evaporated to get the crude product, which was then purified by flash chromatography (PE/EA=100~95%) to give (1-(4-bromophenyl)-2,2,2-trifluoro-1-phenylethoxy)trimethylsilane. ¹H NMR (400 MHz, DMSO-d6)=7.64-7.58 (m, 2H), 7.44-7.37 (m, 3H), 7.32 (d, J=7.8 Hz, 2H), 7.26 (d, J=8.5 Hz, 2H), −0.08--0.12 (m, 9H) ppm.

Step 2: trimethyl(2,2,2-trifluoro-1-phenyl-1-(4-(4,4,5,5-tetramethyl-1,3,2-dioxaborolan-2-yl)phenyl)ethoxy)silane A degassed mixture of (1-(4-bromophenyl)-2,2,2-trifluoro-1-phenylethoxy)trimethylsilane (0.5 g, 1.23 mmol), Bispinacolatodiboron (468 mg, 1.8 mmol), KOAc (361.6 mg, 3.69 mmol), X-Phos (47.7 mg, 0.1 mmol), and Pd₂(dba)₃ (91.5 mg, 0.1 mmol) in 1,4-dioxane (10 mL) was stirred at 80-90° C. for 12 hrs under N₂, then the mixture was cooled to room temperature, to which H₂O (10 mL) was added, and the mixture was extracted with ethyl acetate (10 mL×3). The organic layers were washed with brine (10 mL), dried over Na₂SO₄, and concentrated in vacuo to give crude product, which was purified by flash chromatography (PE:EA=100-80%) to give trimethyl(2,2,2-trifluoro-1-phenyl-1-(4-(4,4,5,5-tetramethyl-1,3,2-dioxaborolan-2-yl)phenyl)

ethoxy)silane. ¹H NMR (400 MHz, CDCl₃)=7.76 (d, J=8.5 Hz, 2H), 7.43-7.35 (m, 4H), 7.33-7.28 (m, 3H), 1.34 (s, 12H), −0.06 (s, 9H) ppm.

Intermediate 21 E1

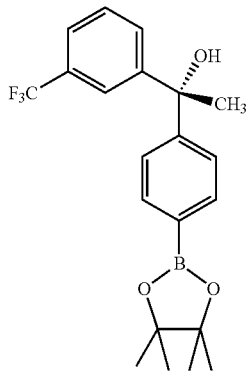 [SMILES: CC1(C)OB(c2ccc([C@@](C)(O)c3cccc(C(F)(F)F)c3)cc2)OC1(C)C]

(R)-1-(4-(4,4,5,5-tetramethyl-1,3,2-dioxaborolan-2-yl)phenyl)-1-(3-(trifluoromethyl)phenyl)ethanol Step 1: 1-(4-chlorophenyl)-1-(3-(trifluoromethyl)phenyl)ethanol To a solution of 1-(3-(trifluoromethyl)phenyl)ethanone (188 mg, 0.999 mmol) in Toluene (10 ml) was added (4-chlorophenyl)magnesium bromide (1.199 ml, 1.199 mmol) under N₂ protection and stirred for 10 minutes. The mixture was poured into water (5 mL) and filtered. The filtrate was extracted with EtOAc (10 mL). The organic layer was washed with brine, dried over Na₂SO₄ and concentrated in vacuo to give crude product, which was purified by chromatography over silica gel (4 g) (Per. Ether:THF=20:1) to give 1-(4-chlorophenyl)-1-(3-(trifluoromethyl)phenyl) ethanol. ¹H NMR (400 MHz, CDCl₃) δ 7.74 (s, 1H), 7.52 (d, J=7.43 Hz, 2H), 7.39-7.46 (m, 1H), 7.27-7.37 (m, 4H), 2.30 (s, 1H), 1.95 (s, 3H) ppm.

Step 2: (R)-1-(4-chlorophenyl)-1-(3-(trifluoromethyl)phenyl)ethanol

The compound (R)-1-(4-chlorophenyl)-1-(3-(trifluoromethyl)phenyl)ethanol and (S)-1-(4-chlorophenyl)-1-(3-(trifluoromethyl)phenyl)ethanol was obtained after resolved by SFC. SFC method: AD (250*30, 10 mm). MeOH: CO₂=15:85, 0.1% NH₃.

Step 3: (R)-1-(4-(4,4,5,5-tetramethyl-1,3,2-dioxaborolan-2-yl)phenyl)-1-(3-(trifluoromethyl)phenyl) ethanol A solution of (BPin)₂ (209 mg, 0.823 mmol), (R)-1-(4-chlorophenyl)-1-(3-(trifluoromethyl)phenyl)ethanol (165 mg, 0.549 mmol), KOAc (162 mg, 1.646 mmol), X-Phos (26.2 mg, 0.055 mmol) and Pd₂(dba)₃ (25.1 mg, 0.027 mmol) in 1,4-Dioxane (5 ml) was stirred at 120° C. for 1 hour heated by microwave. The solution was concentrated in vacuo and purified by chromatography over silica gel (4 g) (THF: pet. Ether=10:90) to give (R)-1-(4-(4,4,5,5-tetramethyl-1,3,2-dioxaborolan-2-yl)phenyl)-1-(3-(trifluoromethyl)phenyl)ethanol. ¹H NMR (400 MHz, CDCl₃) δ=1.34 (s, 12H), 1.97 (s, 3H), 7.39-7.44 (m, 3H), 7.52 (d, J=7.78 Hz, 1H), 7.49 (d, J=7.53 Hz, 1H), 7.72-7.83 (m, 3H) ppm.

Intermediate 21 E2

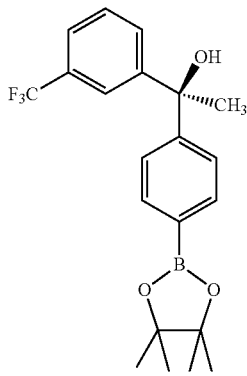 [SMILES: CC1(C)OB(c2ccc([C@](C)(O)c3cccc(C(F)(F)F)c3)cc2)OC1(C)C]

(S)-1-(4-(4,4,5,5-tetramethyl-1,3,2-dioxaborolan-2-yl)phenyl)-1-(3-(trifluoromethyl)phenyl)ethanol The title compound was obtained as another enantiomer described on the intermediate 21E2. ¹H NMR (400 MHz, CDCl₃) δ ppm 1.34 (s, 12H), 1.97 (s, 3H), 7.39-7.44 (m, 3H), 7.52 (d, J=7.78 Hz, 1H), 7.49 (d, J=7.53 Hz, 1H), 7.72-7.83 (m, 3H) ppm.

Intermediate 22

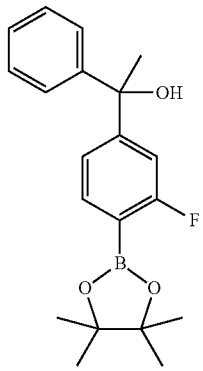 [SMILES: CC(O)(c1ccccc1)c1ccc(B2OC(C)(C)C(C)(C)O2)c(F)c1]

1-(3-fluoro-4-(4,4,5,5-tetramethyl-1,3,2-dioxaborolan-2-yl)phenyl)-1-phenylethanol Step 1: 4-bromo-3-fluoro-N-methoxy-N-methylbenzamide To a solution of 4-bromo-3-fluorobenzoic acid (3 g, 13.6 mmol) in DCM (50 mL) was added HATU (7.6 g, 20 mmol), and the mixture was stirred at 25° C. for 0.5 hour. Then N,O-dimethylhydroxylamine (2 g, 20 mmol) and triethylamine (4.12 g, 40 mmol) was added to the mixture. The reaction mixture was stirred at 25° C. for 16 hour. The mixture was added to saturate aq. NaHCO₃ (50 mL) and extracted with DCM (50 mL×3). The combine organic layer was washed with H₂O (30 mL), brine (30 mL), dried over anhydrous Na₂SO₄, and concentrated to afford the crude product which was purified on silica gel chromatography to give 4-bromo-3-fluoro-N-methoxy-N-methylbenzamide. MS: 262 (M+1).

Step 2:
(4-bromo-3-fluorophenyl)(phenyl)methanone

To a solution of 4-bromo-3-fluoro-N-methoxy-N-methyl-benzamide (Ig, 3.38 mmol) in THF (10 mL) was added phenylmagnesium bromide (Ig, 5.74 mmol) at 0° C. under N₂ atmosphere, and the mixture was stirred at 25° C. for 16 hours. Saturated aq.NH₄Cl solution (30 mL) was added to the mixture, and the mixture was extracted with ethyl acetate (50 mL×3). The combined organic layer was washed with H₂O (30 mL), brine (30 mL), and concentrated to afford the crude product which was purified on silica gel chromatography to give (4-bromo-3-fluorophenyl)(phenyl)methanone. ¹H NMR (400 MHz, DMSO-d₆) δ=7.90 (t, J=7.7 Hz, 1H), 7.75 (d, J=7.3 Hz, 2H), 7.72-7.64 (m, 2H), 7.59-7.54 (m, 2H), 7.47 (dd, J=1.5, 8.0 Hz, 1H), 3.34 (s, 3H) ppm.

Step 3:
1-(4-bromo-3-fluorophenyl)-1-phenylethanolylate

To a solution of (4-bromo-3-fluorophenyl)(phenyl)methanone (580 mg, 2.1 mmol) in THF (6 mL) was added 1M bromomethane magnesium in THF (4.2 mL, 4.2 mmol) at 0° C. under N₂ atmosphere, and the mixture was stirred at 0° C. for 3 hours. Saturated aq.NH₄Cl (20 mL) was added to the mixture, and the mixture was extracted with ethyl acetate (30 mL×3). The combine organic layer was washed with H₂O (30 mL), brine (30 mL), and concentrated to afford the crude product which was purified on silica gel chromatography with the eluent of ethyl acetate/pet.ether (0%~30%) to give 1-(4-bromo-3-fluorophenyl)-1-phenylethanol. ¹H NMR (400 MHz, DMSO-d₆) δ=7.57 (t, J=7.9 Hz, 1H), 7.44-7.37 (m, 3H), 7.28 (t, J=7.7 Hz, 2H), 7.20-7.14 (m, 2H), 5.94 (s, 1H), 1.97 (s, 4H) ppm.

Step 4: 1-(3-fluoro-4-(4,4,5,5-tetramethyl-1,3,2-dioxaborolan-2-yl)phenyl)-1-phenylethanol To a solution of 1-(4-bromo-3-fluorophenyl)-1-phenylethanol (300 mg, 1.02 mmol), 4,4,4',4',5,5,5',5'-octamethyl-2,2'-bi(1,3,2-dioxaborolane) (388 mg, 1.53 mmol) and KOAc (300 mg, 3.06 mmol) in dioxane was added Pd₂(dba)₃ (10 mg) and x-phos (10 mg) at 20° C. under N₂ atmosphere, and the mixture was stirred at 80° C. for 16 hours. Saturated aq.NH₄Cl solution (20 mL) was added to the mixture at 0° C., which was extracted with ethyl acetate (50 mL×3). The combined organic layer was washed with H₂O (30 mL), brine (30 mL) and concentrated to afford the crude product which was purified on silica gel chromatography with the eluent of ethyl acetate/pet.ether (0%~50%) to give 1-(3-fluoro-4-(4,4,5,5-tetramethyl-1,3,2-dioxaborolan-2-yl)phenyl)-1-phenylethanol. MS: 342 (M+1). ¹H NMR (400 MHz, CDCl₃) δ=7.68 (t, J=7.0 Hz, 1H), 7.40-7.38 (m, 2H), 7.31 (t, J=7.4 Hz, 2H), 7.27-7.24 (m, 1H), 7.18-7.11 (m, 2H), 1.35 (s, 12H) ppm.

Intermediate 23

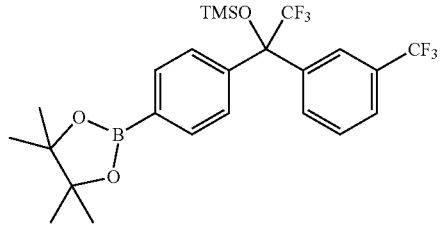

trimethyl(2,2,2-trifluoro-1-(4-(4,4,5,5-tetramethyl-1,3,2-dioxaborolan-2-yl)phen)-1-(3-(trifluoromethyl)phenyl)ethoxy)silane Step 1: (4-bromophenyl)(3-(trifluoromethyl)phenyl)methanone To a solution of 1-bromo-3-(trifluoromethyl)benzene (800 mg, 3.56 mmol) in 10 mL of THF was added Mg (129.6 mg, 5.33 mmol) under nitrogen protection and stirred at 80° C. for 2 h. Then the mixture was added to a solution of 4-bromo-N-methoxy-N-methylbenzamide (433.9 mg, 1.78 mmol) in THF (6 mL) at 0° C. under nitrogen protection and stirred at 20° C. for 12 h. The mixture was poured into aq.NH₄Cl (150 mL) and extracted with ethyl acetate (120 mL×3). The organic layer was dried over Na₂SO₄ and concentrated in vacuo to give the residue, which was purified with pre_HPLC to give (4-bromophenyl)(3-(trifluoromethyl)phenyl)methanone. ¹HNMR (400 MHz, CDCl₃): δ=8.04 (s, 1H), 7.95 (d, J=7.8 Hz, 1H), 7.87 (d, J=8.0 Hz, 1H), 7.67 (s, 4H), 7.66-7.62 (m, 1H) ppm.

Step 2: (1-(4-bromophenyl)-2,2,2-trifluoro-1-(3-(trifluoromethyl)phenyl)ethoxy)trimethylsilane To a solution of (4-bromophenyl)(3-(trifluoromethyl)phenyl)methanone (400 mg, 1.22 mmol) in 10 mL of THF was added TMSCF₃ (864.1 mg, 6.08 mmol) and followed by a solution of TBAF (31.8 mg, 0.12 mmol) under nitrogen protection at 0° C. Then the mixture was stirred at 20° C. for 4 h. The mixture was quenched with aq. NH₄Cl (50 mL) and extracted with ethyl acetate (60 mL×3). The organic layer was dried with Na₂SO₄, concentrated in vacuo and purified with flash column (ethyl acetate/pet.ether=0%~10%) to give (1-(4-bromophenyl)-2,2,2-trifluoro-1-(3-(trifluoromethyl)phenyl)ethoxy)trimethylsilane. ¹HNMR (400 MHz, CDCl₃): δ=7.62-7.57 (m, 2H), 7.54-7.50 (m, 2H), 7.49-7.46 (m, 2H), 7.24 (d, J=8.3 Hz, 2H), −0.03 (s, 9H) ppm.

Step 3: trimethyl(2,2,2-trifluoro-1-(4-(4,4,5,5-tetramethyl-1,32-dioxaborolan-2-yl)phenyl)-1-(3-(trifluoromethyl)phenyl)ethoxy)silane To a solution of (1-(4-bromophenyl)-2,2,2-trifluoro-1-(3-(trifluoromethyl)phenyl)ethoxy)trimethylsilane (0.2 g, 0.42 mmol) in dioxane (6 mL) was added 4,4,4',4',5,5,5',5'-octamethyl-2,2'-bi(1,3,2-dioxaborolane) (0.16 g, 0.64 mmol), KOAc (0.39 g, 3.95 mmol), Xphos (catalytic amount, 10 mg) and pd(dba)3 (catalytic amount, 10 mg) under N₂ atmosphere. The mixture was heated at 90° C. for 2 hours. Saturate aq.NH₄Cl (20 mL) was added to the mixture, and extracted with DCM (60 mL×3). The combined organic layer was dried over Na₂SO₄ and concentrated in vacuo to give crude product, which was purified by silica gel chromatography with the eluent of ethyl acetate/pet. ether=0%~10% give the trimethyl(2,2,2-trifluoro-1-(4-(4,4,5,5-tetramethyl-1,3,2-dioxaborolan-2-yl)phenyl)-1-(3-(trifluoromethyl)phenyl)ethoxy)silane. ¹HNMR (400 MHz, CDCl₃): δ=7.78 (d, J=8.3 Hz, 2H), 7.71 (s, 1H), 7.59 (d, J=7.5 Hz, 1H), 7.54-7.49 (m, 1H), 7.43 (d, J=7.8 Hz, 1H), 7.37 (d, J=7.8 Hz, 2H), 1.35 (s, 12H), −0.05 (s, 9H) ppm.

In the same procedure as intermediate 23, the following two intermediates were prepared using the corresponding starting material.

| Intermediate | Structure | Chemical name | NMR | MS |
|---|---|---|---|---|
| 24 | 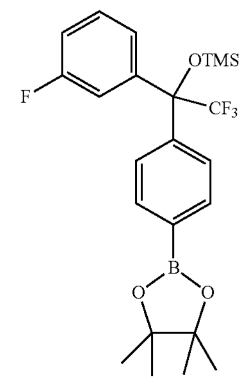 | trimethyl(2,2,2-trifluoro-1-(3-fluorophenyl)-1-(4-(4,4,5,5-tetramethyl-1,3,2-dioxaborolan-2-yl)phenyl)ethoxy)silane | ¹H NMR (400 MHz, CD₃OD) δ = 7.74 (d, J = 8.3 Hz, 2H), 7.48 (d, J = 7.8 Hz, 2H), 7.39-7.30 (m, 1H), 7.23 (d, J = 8.0 Hz, 2H), 7.11-7.02 (m, 1H), 1.37-1.29 (m, 12H). | |
| 25 | 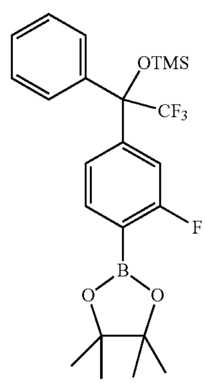 | trimethyl(2,2,2-trifluoro-1-(3-fluoro-4-(4,4,5,5-tetramethyl-1,3,2-dioxaborolan-2-yl)phenyl)-1-phenylethoxy)silane | ¹H NMR (400 MHz, CDCl₃): δ = 7.78 (d, J = 8.3 Hz, 2H), 7.71 (s, 1H), 7.59 (d, J = 7.5 Hz, 1H), 7.54-7.49 (m, 1H), 7.43 (d, J =7.8 Hz, 1H), 7.37 (d, J = 7.8 Hz, 2H), 1.35 (s, 12H), −0.05 (s, 9H). | |
| 26 | 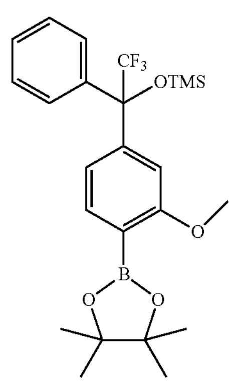 | trimethyl(2,2,2-trifluoro-1-(3-methoxy-4-(4,4,5,5-tetramethyl-1,3,2-dioxaborolan-2-yl)phenyl)-1-phenylethoxy)silane | | MS: 481.2 (M + 1) |

Intermediate 27

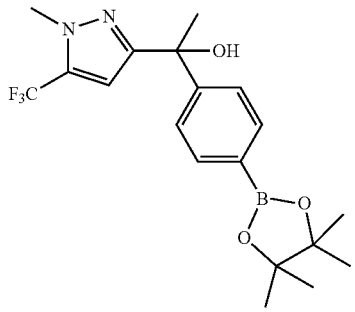

1-(1-methyl-5-(trifluoromethyl)-1H-pyrazol-3-yl)-1-(4-(4,4,5,5-tetramethyl-1,3,2-dioxaborolan-2-yl)phenyl)ethanol

Step 1: N-methoxy-N,1-dimethyl-5-(trifluoromethyl)-1H-pyrazole-3-carboxamide To a solution of 1-methyl-5-(trifluoromethyl)-1H-pyrazole-3-carboxylic acid (575 mg, 2.96 mmol) in anhydrous THF (20 mL) was added HATU (1239 mg, 3.26 mmol) and DIEA (1.15 g, 8.89 mmol) at room temperature. The solution was kept stirring for 30 min. Then the N,O-dimethylhydroxylamine (316 mg, 3.26 mmol) was added and the result solution was stirred for 3 hours. The reaction mixture was diluted with water (30 mL), extracted with EtOAc (50 mL), and the organic layer was dried over anhydrous $MgSO_4$, filtered through Celite™ (diatomaceous earth), and the filtrate was concentrated under reduced pressure. The residue was purified by silica gel column chromatography (PE/EA=3/1) to give the pure product N-methoxy-N,1-dimethyl-5-(trifluoromethyl)-1H-pyrazole-3-carboxamide. MS: 238.0 (M+1)+.

Step 2: (4-chlorophenyl)(1-methyl-5-(trifluoromethyl)-1H-pyrazol-3-yl)methanone To a solution of N-methoxy-N,1-dimethyl-5-(trifluoromethyl)-1H-pyrazole-3-carboxamide (600 mg, 2.53 mmol) in anhygrous THF (10 mL) was added (4-chlorophenyl)magnesium bromide (3.80 mL, 3.80 mmol) at 0° C. And the reaction solution was stirred for 1 hour at 0° C. The mixture was diluted with water (40 mL), extracted with EtOAc (60 mL), and the organic layer was dried over anhydrous $MgSO_4$, filtered through Celite™ (diatomaceous earth), and the filtrate was concentrated under reduced pressure. The residue was purified by silica gel column chromatography (PE/EA=30/1) to give the pure product (4-chlorophenyl)(1-methyl-5-(trifluoromethyl)-1H-pyrazol-3-yl)methanone.

Step 3: 1-(4-chlorophenyl)-1-(1-methyl-5-(trifluoromethyl)-1H-pyrazol-3-yl)ethanol To a solution of (4-chlorophenyl)(1-methyl-5-(trifluoromethyl)-1H-pyrazol-3-yl)methanone (630 mg, 2.18 mmol) in THF (10 mL) was added methylmagnesium bromide (1.1 mL, 3.27 mmol) at 0° C. And the reaction solution was stirred for 1 h at 0° C. The mixture was diluted with water (20 mL), extracted with EtOAc (30 mL), and the organic layer was dried over anhydrous $MgSO_4$, filtered. The filtrate was concentrated under reduced pressure. The crude product was purified by Pre-TLC (PE/EA=5/1) to give the pure 1-(4-chlorophenyl)-1-(1-methyl-5-(trifluoromethyl)-1H-pyrazol-3-yl)ethanol. $^1$H NMR (400 MHz, CDCl$_3$) δ=7.37-7.43 (m, 2H), 7.25-7.31 (m, 2H), 6.47 (s, 1H), 3.94 (s, 3H), 3.37 (brs, 1H), 1.88 (s, 3H) ppm.

Step 4: 1-(1-methyl-5-(trifluoromethyl)-1H-pyrazol-3-yl)-1-(4-(4,4,5,5-tetramethyl-1,3,2-dioxaborolan-2-yl)phenyl)ethanol 1-(4-chlorophenyl)-1-(1-methyl-5-(trifluoromethyl)-1H-pyrazol-3-yl)ethanol (100 mg, 0.33 mmol), Pd$_2$(dba)$_3$ (19 mg, 0.03 mmol), TCP (9 mg, 0.03 mmol), AcOK (96 mg, 0.98 mmol), (BPin)$_2$ (250 mg, 0.98 mmol) and dioxane (2 mL) were mixed and degassed with N$_2$ atmosphere. After stirred at 90° C. for 24 hours, the mixture was diluted with water (20 mL), extracted with EtOAc (30 mL), and the organic layer was dried over anhydrous $MgSO_4$, filtered. The filtrate was concentrated under reduced pressure. The crude product was purified by Pre-TLC (PE/EA=6/1) to give 1-(1-methyl-5-(trifluoromethyl)-1H-pyrazol-3-yl)-1-(4-(4,4,5,5-tetramethyl-1,3,2-dioxaborolan-2-yl)phenyl)ethanol. MS: 379.2 (M-17)

Intermediate 28

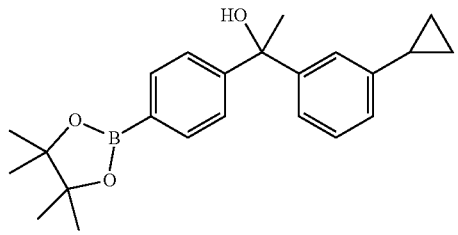 [SMILES: CC(O)(c1ccc(B2OC(C)(C)C(C)(C)O2)cc1)c1cccc(C2CC2)c1]

1-(3-cyclopropylphenyl)-1-(4-(4,4,5,5-tetramethyl-1,3,2-dioxaborolan-2-yl)phenyl)ethanol

Step 1: 1-(3-cyclopropylphenyl)-1-(4-(4,4,5,5-tetramethyl-1,3,2-dioxaborolan-2-yl)phenyl)ethanol A bottom flask was charged with magnesium (148 mg, 6.09 mmol) and anhydrous THF (0.5 mL), to the stirred mixture was added isopropylmagnesium chloride solution (catalytic amount), then a solution of 1-bromo-3-cyclopropylbenzene (1 g, 5.07 mmol) in THF (4.5 mL) was added slowly with an injection syringe under nitrogen to keep the temperature containing 50° C.~60° C. The resulted mixture was stirred at 70° C. for another 30 mins and then was allowed to cool to 20° C. The resulting Grignard reagent was added to a solution of 1-(4-(4,4,5,5-tetramethyl-1,3,2-dioxaborolan-2-yl)phenyl)ethanone (600 mg, 2.54 mmol) in THF (5 mL) drop-wise at 0° C., the mixture was stirred at 0° C. to 25° C. for 2 hours before quenched by ice-water (10 mL) slowly. The mixture was extracted with ethyl acetate (20 mL×3), and the combined organic layers were washed with brine (20 mL), dried over sodium sulfate, filtered and concentrated to afford the crude product, which was purified on silica gel column chromatography (ethyl acetate/pet. ether=0%~20%) to give 1-(3-cyclopropylphenyl)-1-(4-(4,4,5,5-tetramethyl-1,3,2-dioxaborolan-2-yl)phenyl)ethanol. $^1$H NMR (400 MHz, CDCl$_3$) d=7.77 (d, J=8.3 Hz, 2H), 7.43 (d, J=8.3 Hz, 2H), 7.22-7.06 (m, 3H), 6.93-6.86 (m, 1H), 1.94 (s, 3H), 1.90-1.81 (m, 1H), 1.34 (s, 12H), 0.97-0.90 (m, 2H), 0.73-0.61 (m, 2H) ppm.

In the same procedure as intermediate 28, the following intermediates were prepared with the corresponding starting material.

| Int. | Structure | Chemical name | NMR | MS |
|---|---|---|---|---|
| 29 | 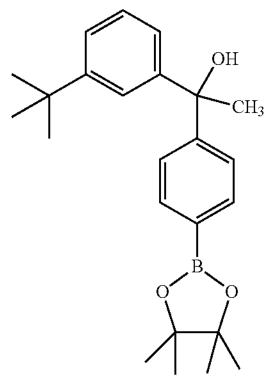 [SMILES: CC(C)(C)c1cccc(C(C)(O)c2ccc(B3OC(C)(C)C(C)(C)O3)cc2)c1] | 1-(3-(tert-butyl)phenyl)-1-(4-(4,4,5,5-tetramethyl-1,3,2-dioxaborolan-2-yl)phenyl)ethanol | $^1$H NMR(400 MHz, CDCl$_3$) δ = 7.77 (d, J = 8.3 Hz, 2H), 7.50 (t, J = 1.6 Hz, 1H), 7.43 (d, J = 8.3 Hz, 2H), 7.26 (s, 1H), 7.25-7.20 (m, 1H), 7.17-7.13 (m, 1H), 1.95 (s, 3H), 1.34 (s, 12H), 1.29 (s, 9H) | |
| 30 | 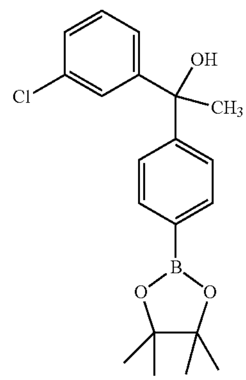 [SMILES: CC(O)(c1ccc(B2OC(C)(C)C(C)(C)O2)cc1)c1cccc(Cl)c1] | 1-(3-chlorophenyl)-1-(4-(4,4,5,5-tetramethyl-1,3,2-dioxaborolan-2-yl)phenyl)ethanol | $^1$H NMR(400 MHz, CD$_3$OD) δ = 7.69 (d, J = 8.3 Hz, 2H), 7.45-7.39 (m, 3H), 7.28 (t, J = 1.6 Hz, 1H), 7.27-7.22 (m, 1H), 7.21-7.18 (m, 1H), 1.89 (s, 3H), 1.33 (s, 13H). | |
| 31 | 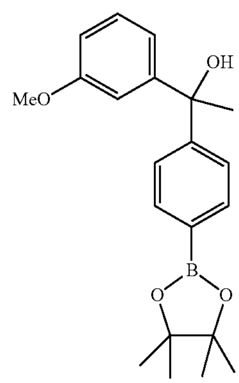 [SMILES: COc1cccc(C(C)(O)c2ccc(B3OC(C)(C)C(C)(C)O3)cc2)c1] | 1-(3-methoxyphenyl)-1-(4-(4,4,5,5-tetramethyl-1,3,2-dioxaborolan-2-yl)phenyl)ethanol | $^1$H NMR (400 MHz, CDCl$_3$) d = 7.77 (d, J = 8.28 Hz, 2H), 7.43 (d, J = 8.28 Hz, 2H), 7.22 (t, J = 8.03 Hz, 1 H), 7.02-6.97 (m, 1 H), 6.94 (d, J = 7.53 Hz, 1 H), 6.78 (dd, J = 2.26, 7.78 Hz, 1 H), 3.77 (s, 3H), 1.94 (s, 3H), 1.33 (s, 12 H). | |
| 32 | 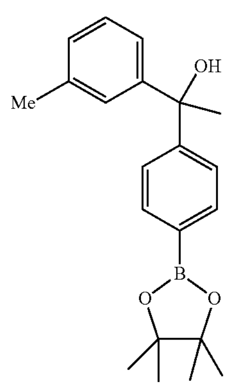 [SMILES: Cc1cccc(C(C)(O)c2ccc(B3OC(C)(C)C(C)(C)O3)cc2)c1] | 1-(4-(4,4,5,5-tetramethyl-1,3,2-dioxaborolan-2-yl)phenyl)-1-(m-tolyl)ethanol | $^1$H NMR (400 MHz, CDCl$_3$) d = 7.77 (d, J = 8.28 Hz, 2H), 7.43 (d, J = 8.28 Hz, 2H), 7.23-7.16 (m, 3 H), 7.05 (d, J = 5.52 Hz, 1 H), 2.32 (s, 3H), 1.94 (s, 3H), 1.33 (s, 12 H). | |

| Int. | Structure | Chemical name | NMR | MS |
|---|---|---|---|---|
| 33 | 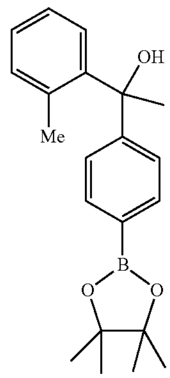 [SMILES: Cc1ccccc1C(C)(O)c1ccc(B2OC(C)(C)C(C)(C)O2)cc1] | 1-(4-(4,4,5,5-tetramethyl-1,3,2-dioxaborolan-2-yl)phenyl)-1-(o-tolyl)ethanol | $^1$H NMR (400 MHz, CDCl$_3$) δ = 7.73 (d, J = 8.0 Hz, 2H), 7.70-7.65 (m, 1H), 7.31 (d, J = 8.0 Hz, 2H), 7.28-7.21 (m, 2H), 7.14-7.07 (m, 1H), 1.98 (s, 3H), 1.92 (s, 3H), 1.34 (s, 12H). | |
| 34 | 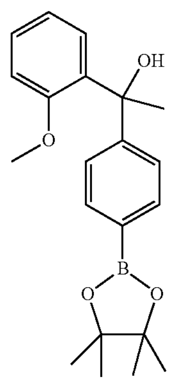 [SMILES: COc1ccccc1C(C)(O)c1ccc(B2OC(C)(C)C(C)(C)O2)cc1] | 1-(2-methoxyphenyl)-1-(4-(4,4,5,5-tetramethyl-1,3,2-dioxaborolan-2-yl)phenyl)ethanol | $^1$H NMR (400 MHz, CDCl$_3$) δ = 7.70 (d, J = 8.3 Hz, 2H), 7.46 (dd, J = 1.6, 7.7 Hz, 1H), 7.33-7.27 (m, 3H), 7.03 (dt, J = 1.0, 7.5 Hz, 1H), 6.87 (d, J = 8.3 Hz, 1H), 4.62 (d, J = 0.8 Hz, 1H), 3.57 (s, 3H), 1.82 (s, 3H), 1.33 (s, 12H) | |
| 35 | 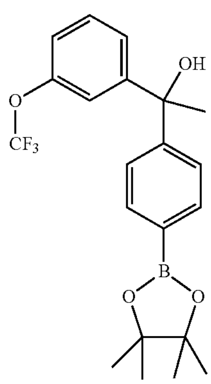 [SMILES: CC(O)(c1ccc(B2OC(C)(C)C(C)(C)O2)cc1)c1cccc(OC(F)(F)F)c1] | 1-(4-(4,4,5,5-tetramethyl-1,3,2-dioxaborolan-2-yl)phenyl)-1-(3-(trifluoromethoxy)phenyl)ethanol | $^1$H NMR 1H NMR (400 MHz, CDCl$_3$) δ = 7.76 (d, J = 8.2 Hz, 2H, 7.39 (d, J = 8.2 Hz, 2H), 7.29 (d, J = 6.7 Hz, 1H), 7.26-7.22 (m, 2H), 7.06 (d, J = 7.4 Hz, 1H), 1.93 (s, 3H), 1.31 (s, 12H). | |
| 36 | 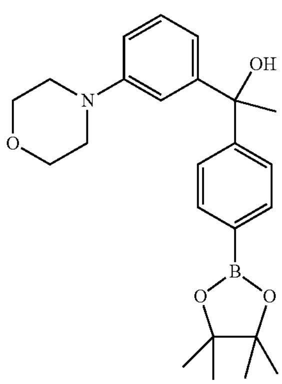 [SMILES: CC(O)(c1ccc(B2OC(C)(C)C(C)(C)O2)cc1)c1cccc(N2CCOCC2)c1] | 1-(3-morpholinophenyl)-1-(4-(4,4,5,5-tetramethyl-1,3,2-dioxaborolan-2-yl)phenyl)ethanol | $^1$H NMR (400 MHz, CDCl$_3$) δ = 7.72 (d, J = 7.8 Hz, 2H), 7.39 (d, J = 7.8 Hz, 2H), 7.16 (t, J = 8.0 Hz, 1H), 7.00 (br. s., 1H), 6.82 (d, J = 7.8 Hz, 1H), 6.74 (d, J = 6.7 Hz, 1H), 3.82-3.75 (m, 4H), 3.11-3.04 (m, 4H), 1.88 (s, 3H), 1.30 (s, 12H), 1.19 (s, 16H) | |

| Int. | Structure | Chemical name | NMR | MS |
|---|---|---|---|---|
| 37 | 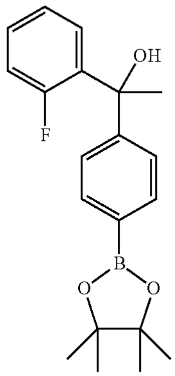 [SMILES: CC(O)(c1ccc(B2OC(C)(C)C(C)(C)O2)cc1)c1ccccc1F] | 1-(2-fluorophenyl)-1-(4-(4,4,5,5-tetramethyl-1,3,2-dioxaborolan-2-yl)phenyl)ethanol | $^1$H NMR (400 MHz, DMSO-d6) δ = 7.93 (d, J = 7.8 Hz, 2H), 7.78 (d, J = 7.8 Hz, 2H), 7.73 (d, J = 5.9 Hz, 1H), 7.20 (d, J = 7.4 Hz, 1H), 7.02-6.94 (m, 2H), 5.83 (s, 1H), 1.37 (s, 3H), 1.29 (s, 12H). | |
| 38 | 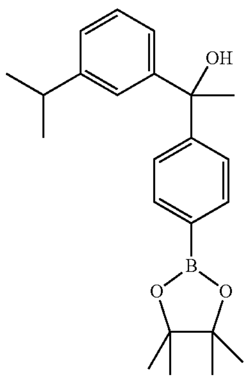 [SMILES: CC(C)c1cccc(C(C)(O)c2ccc(B3OC(C)(C)C(C)(C)O3)cc2)c1] | 1-(3-isopropylphenyl)-1-(4-(4,4,5,5-tetramethyl-1,3,2-dioxaborolan-2-yl)phenyl)ethanol | $^1$H NMR (400 MHz, DMSO-d6) δ = 7.56 (d, J = 8.2 Hz, 2H), 7.42 (d, J = 7.8 Hz, 2H), 7.30 (s, 1H), 7.15 (d, J = 3.9 Hz, 2H), 7.03 (br. s., 1H), 5.67 (s, 1H), 2.81 (td, J = 6.7, 13.9 Hz, 1H), 1.79 (s, 3H), 1.27-1.23 (m, 12H), 1.14 (d, J = 7.0 Hz, 6H). | |
| 39 | 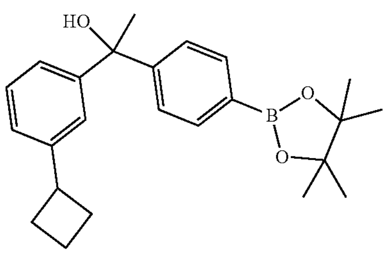 [SMILES: CC(O)(c1ccc(B2OC(C)(C)C(C)(C)O2)cc1)c1cccc(C2CCC2)c1] | 1-(3-cyclobutylphenyl)-1-(4-(4,4,5,5-tetramethyl-1,3,2-dioxaborolan-2-yl)phenyl)ethanol | $^1$H NMR (400 MHz, DMSO-d6) δ = 7.61 (d, J = 8.2 Hz, 2H), 7.46 (d, J = 8.2 Hz, 2H), 7.32 (s, 1H), 7.24-7.17 (m, 2H), 7.08 (d, J = 6.7 Hz, 1H), 5.74 (s, 1H), 2.28 (q, J = 7.8 Hz, 2H), 2.13-1.92 (m, 4H), 1.84 (s, 3H), 1.80 (d, J = 3.5 Hz, 1H), 1.30 (s, 12H). | |
| 40 | 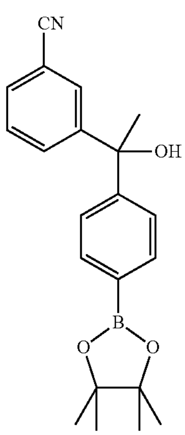 [SMILES: CC(O)(c1ccc(B2OC(C)(C)C(C)(C)O2)cc1)c1cccc(C#N)c1] | 3-(1-hydroxy-1-(4-(4,4,5,5-tetramethyl-1,3,2-dioxaborolan-2-yl)phenyl)ethyl)benzonitrile | $^1$H NMR (400 MHz, CD$_3$OD) δ = 7.90-7.81 (m, 3H), 7.72-7.64 (m, 4H), 7.61 (d, J = 7.4 Hz, 1H), 7.56-7.49 (m, 1H), 7.01 (d, J = 5.9 Hz, 1H), 4.29 (dd, J = 3.1, 12.9 Hz, 1H), 3.70 (d, J = 6.7 Hz, 1H), 3.30-3.27 (m, 1H), 3.21-3.12 (m, 1H), 2.50-2.43 (m, 2H), 2.35 (dt, J = 7.4, 13.3 Hz, 1H), 2.19 (d, J = 12.9 Hz, 1H), 2.10 (dd, J = 3.1, 12.9 Hz, 1H), 2.06-1.94 (m, 4H), 1.80-1.68 (m, 1H), 1.59-1.46 (m, 1H). | |

| Int. | Structure | Chemical name | NMR | MS |
|---|---|---|---|---|
| 41 | 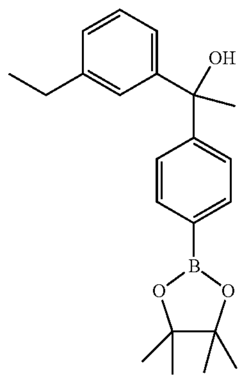 [SMILES: CCc1cccc(C(C)(O)c2ccc(B3OC(C)(C)C(C)(C)O3)cc2)c1] | 1-(3-ethylphenyl)-1-(4-(4,4,5,5-tetramethyl-1,3,2-dioxaborolan-2-yl)phenyl)ethanol | $^1$H NMR (400 MHz, CD$_3$OD) δ = 7.73-7.64 (m, 2H), 7.46-7.40 (m, 2H), 7.26 (s, 1H), 7.20 (d, J = 4.3 Hz, 2H), 7.06 (br. s., 1H), 2.63-2.59 (m, 2H), 1.90 (s, 3H), 1.36-1.33 (m, 12H), 1.23-1.15 (m, 3H) | |
| 42 | 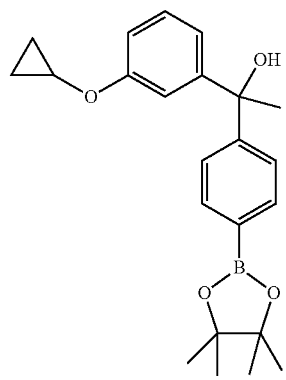 [SMILES: CC(O)(c1ccc(B2OC(C)(C)C(C)(C)O2)cc1)c1cccc(OC2CC2)c1] | 1-(3-cyclopropoxyphenyl)-1-(4-(4,4,5,5-tetramethyl-1,3,2-dioxaborolan-2-yl)phenyl)ethanol | 1HNMR (400 MHz, CDCl$_3$) δ = 7.20 (s, 1H), 7.15-7.03 (m, 2H), 6.93 (d, J = 7.4 Hz, 1H), 3.73-3.65 (m, 1H), 0.80-0.70 (m, 4H). | |
| 43 | 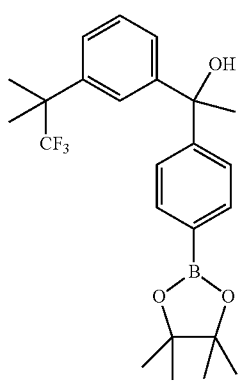 [SMILES: CC(O)(c1ccc(B2OC(C)(C)C(C)(C)O2)cc1)c1cccc(C(C)(C)C(F)(F)F)c1] | 1-(4-(4,4,5,5-tetramethyl-1,3,2-dioxaborolan-2-yl)phenyl)-1-(3-(1,1,1-trifluoro-2-methylpropan-2-yl)phenyl)ethanol | $^1$H NMR (400 MHz, DMSO-d6) δ = 7.97 (d, J = 7.8 Hz, 1H), 7.83 (d, J = 7.4 Hz, 1H), 7.66 (br. s., 1H), 7.61 (d, J = 7.4 Hz, 2H), 7.46 (d, J = 7.4 Hz, 2H), 7.33 (dd, J = 7.8, 14.1 Hz, 4H), 5.85 (br. s., 1H), 1.85 (br. s., 3H), 1.53 (br. s., 6H), 1.34-1.28 (m, 12H). | |
| 44 | 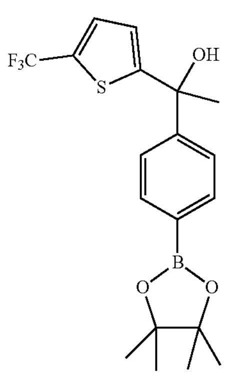 [SMILES: CC(O)(c1ccc(B2OC(C)(C)C(C)(C)O2)cc1)c1ccc(C(F)(F)F)s1] | 1-(4-(4,4,5,5-tetramethyl-1,3,2-dioxaborolan-2-yl)phenyl)-1-(5-(trifluoromethyl)thiophen-2-yl)ethanol | | MS: 381 (M—H$_2$O) |

| Int. | Structure | Chemical name | NMR | MS |
|---|---|---|---|---|
| 45 | 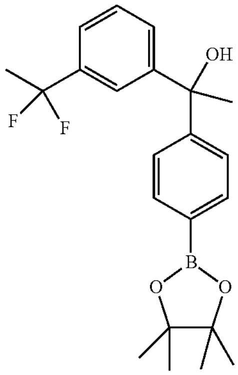 [SMILES: CC(F)(F)c1cccc(C(C)(O)c2ccc(B3OC(C)(C)C(C)(C)O3)cc2)c1] | 1-(3-(1,1-difluoroethyl)phenyl)-1-(4-(4,4,5,5-tetramethyl-1,3,2-dioxaborolan-2-yl)phenyl)ethanol | $^1$H NMR (400 MHz, CDCl$_3$) δ = 7.75 (d, J = 7.8 Hz, 2H), 7.60 (s, 1H), 7.43-7.28 (m, 5H), 2.18 (s, 1H), 1.97-1.81 (m, 6H), 1.31 (s, 12H) | |
| 46 | 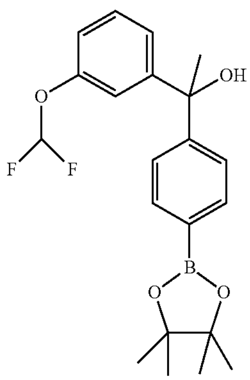 [SMILES: CC(O)(c1ccc(B2OC(C)(C)C(C)(C)O2)cc1)c1cccc(OC(F)F)c1] | 1(3-(difluoromethoxy)phenyl)-1-(4-(4,4,5,5-tetramethyl-1,3,2-dioxaborolan-2-yl)phenyl)ethanol | NA | MS: 373.1 (M—H$_2$O) |
| 47 | 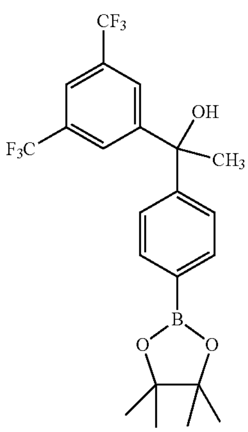 [SMILES: CC(O)(c1ccc(B2OC(C)(C)C(C)(C)O2)cc1)c1cc(C(F)(F)F)cc(C(F)(F)F)c1] | 1-(3,5-bis(trifluoromethyl)phenyl)-1-(4-(4,4,5,5-tetramethyl-1,3,2-dioxaborolan-2-yl)phenyl)ethanol | $^1$H NMR (400 MHz, CDCl$_3$) δ = 7.85 (s, 2H), 7.78 (d, J = 7.8 Hz, 2H), 7.72 (s, 1H), 7.39 (d, J = 8.2 Hz, 2H), 2.32 (s, 1H), 1.97 (s, 3H), 1.32 (s, 12H). | NA |
| 48 | 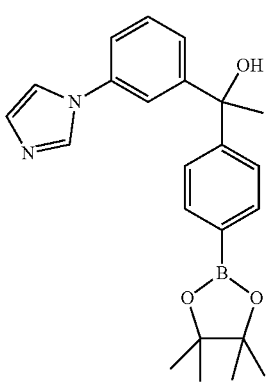 [SMILES: CC(O)(c1ccc(B2OC(C)(C)C(C)(C)O2)cc1)c1cccc(-n2ccnc2)c1] | 1-(3-(1H-imidazol-1-yl)phenyl)-1-(4-(4,4,5,5-tetramethyl-1,3,2-dioxaborolan-2-yl)phenyl)ethanol | NA | MS: 392.1 (M + 1)+ |

| Int. | Structure | Chemical name | NMR | MS |
|---|---|---|---|---|
| 49 | 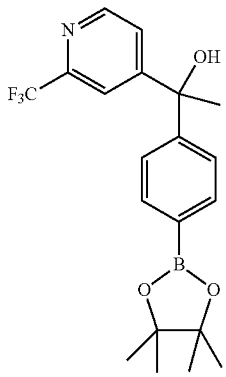 [SMILES: CC(O)(c1ccc(B2OC(C)(C)C(C)(C)O2)cc1)c1ccnc(C(F)(F)F)c1] | 1-(4-(4,4,5,5-tetramethyl-1,3,2-dioxaborolan-2-yl)phenyl)-1-(2-(trifluoromethyl)pyridin-4-yl)ethanol | $^1$H NMR (400 MHz, CDCl$_3$) δ = 8.63 (d, J = 4.7 Hz, 1H), 7.79 (d, J = 7.8 Hz, 2H), 7.39 (d, J = 7.8 Hz, 2H), 7.32 (s, 3H), 1.95 (br. s., 3H), 1.32 (s, 12H). | |
| 50 | 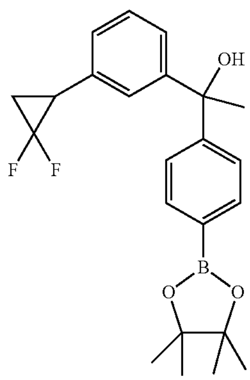 [SMILES: CC(O)(c1ccc(B2OC(C)(C)C(C)(C)O2)cc1)c1cccc(C2CC2(F)F)c1] | 1-(3-(2,2-difluorocyclopropyl)phenyl)-1-(4-(4,4,5,5-tetramethyl-1,3,2-dioxaborolan-2-yl)phenyl)ethanol | | MS: 401 (M + 1)+ |
| 51 | 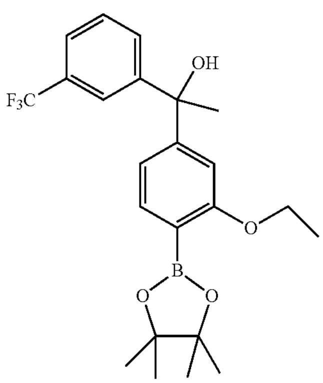 [SMILES: CCOc1cc(C(C)(O)c2cccc(C(F)(F)F)c2)ccc1B1OC(C)(C)C(C)(C)O1] | 1-(3-ethoxy-4-(4,4,5,5-tetramethyl-1,3,2-dioxaborolan-2-yl)phenyl)-1-(3-(trifluoromethyl)phenyl)ethanol | | MS: 437.2 (M + H)+ |
| 52 | 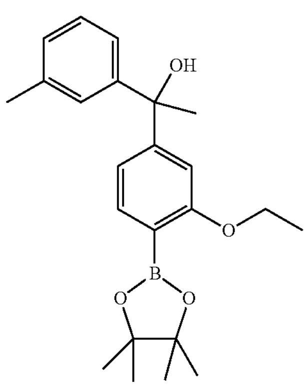 [SMILES: CCOc1cc(C(C)(O)c2cccc(C)c2)ccc1B1OC(C)(C)C(C)(C)O1] | 1-(3-ethoxy-4-(4,4,5,5-tetramethyl-1,3,2-dioxaborolan-2-yl)phenyl)-1-(m-tolyl)ethanol | | MS: 365 (M + H)$^+$. |

-continued

| Int. | Structure | Chemical name | NMR | MS |
|---|---|---|---|---|
| 53 | 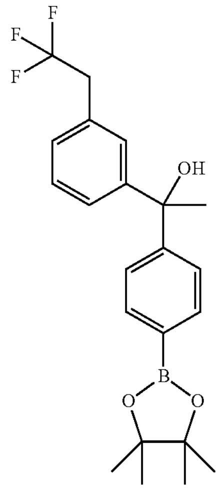 [SMILES: CC(O)(c1ccc(B2OC(C)(C)C(C)(C)O2)cc1)c1cccc(CC(F)(F)F)c1] | 1-(4-(4,4,5,5-tetramethyl-1,3,2-dioxaborolan-2-yl)phenyl)-1-(3-(2,2,2-trifluoroethyl)phenyl)ethanol | $^1$H NMR (400 MHz, CDCl$_3$) δ = 7.75 (d, J = 8.2 Hz, 2H), 7.39 (d, J = 7.8 Hz, 2H), 7.36-7.30 (m, 2H), 7.29-7.25 (m, 1H), 7.15 (d, J = 7.0 Hz, 1H), 3.31 (q, J = 11.0 Hz, 2H), 2.26-2.09 (m, 1H), 1.93 (s, 3H), 1.33-1.30 (m, 12H). | |

Intermediate 54

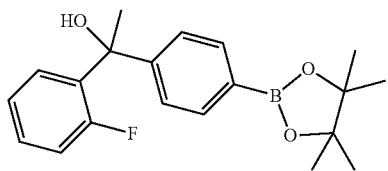 [SMILES: CC(O)(c1ccc(B2OC(C)(C)C(C)(C)O2)cc1)c1ccccc1F]

1-(2-fluorophenyl)-1-(4-(4,4,5,5-tetramethyl-1,3,2-dioxaborolan-2-yl)phenyl)ethanol To a solution of 1-bromo-2-fluorobenzene (200 mg, 1.14 mmol) in dry THF (2 mL) was added n-BuLi (0.68 mL, 1.71 mmol) at −78° C. dropwise under N$_2$ protection, then the mixture was stirred at −78° C. for 0.5 h, to which a solution of 1-(4-(4,4,5,5-tetramethyl-1,3,2-dioxaborolan-2-yl)phenyl)ethanone (224 mg, 0.91 mmol) in dry THF (2 mL) was added. The mixture was stirred −78° C. for 3 h. Then the reaction mixture was added to saturated aqueous NH$_4$Cl (20 mL), extracted with EtOAc (20 mL×2). The organic layer was washed with brine (40 mL), dried over Na$_2$SO$_4$, concentrated in vacuo, and the residue was purified by silica gel column chromatography (PE/EA=10/1) to give 1-(2-fluorophenyl)-1-(4-(4,4,5,5-tetramethyl-1,3,2-dioxaborolan-2-yl)phenyl)ethanol $^1$H NMR (400 MHz, DMSO-d$_6$) δ=7.93 (d, J=7.8 Hz, 2H), 7.78 (d, J=7.8 Hz, 2H), 7.73 (d, J=5.9 Hz, 1H), 7.20 (d, J=7.4 Hz, 1H), 7.02-6.94 (m, 2H), 5.83 (s, 1H), 1.37 (s, 3H), 1.29 (s, 12H) ppm.

Intermediate 55

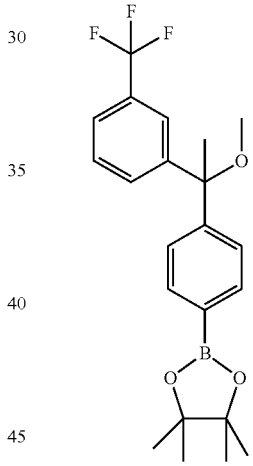

2-(4-(1-methoxy-1-(3-(trifluoromethyl)phenyl)ethyl)phenyl)-4,4,5,5-tetramethyl-1,3,2-dioxaborolane Step 1: 1-(4-bromophenyl)-1-(3-(trifluoromethyl)phenyl)ethanol To a mixture of 1-bromo-3-(trifluoromethyl)benzene (2.73 g, 12.15 mmol) in THF (15 mL) was added n-BuLi (5.2 mL, 12.15 mmol) at −78° C. dropwise. The resulting mixture was stirred at −78° C. for 2 hours under N$_2$ protection, then another solution of 1-(4-bromophenyl)ethanone (1.30 g, 6.08 mmol) in 15 mL of THF was added into. After addition, the reaction mixture was allowed to warm to ambient temperature and stirred for 20 hours. The mixture was quenched with saturate NH$_4$Cl aqueous solution (20 mL) and extracted with EtOAc (20 mL×3). The organic layers were separated and washed with brine (10 mL), dried over anhydrous Na$_2$SO$_4$. After removed the solvent in vacuum, the residue was purified by column chromatography (PE/THF=10/1) to afford 1-(4-bromophenyl)-1-(3-(trifluoromethyl)phenyl)ethanol. MS: 327 (M-17).

Step 2: 1-(1-(4-bromophenyl)-1-methoxyethyl)-3-(trifluoromethyl)benzene

To a mixture of 1-(4-bromophenyl)-1-(3-(trifluoromethyl)phenyl)ethanol (1.0 g, 2.91 mmol) in 20 mL of DMSO was added NaH (210 mg, 60% on mineral oil, 5.25 mmol) under $N_2$ protection. The mixture was stirred for 10 min, then $CH_3I$ (3.16 g, 21.80 mmol) was added. The reaction mixture was stirred at ambient temperature for 2 hours. The reaction mixture was poured into ice-water, and extracted with EtOAc (10 mL) twice. The combined organic layer was washed with brine (10 mL), dried over anhydrous $Na_2SO_4$. After removal of the solvent in vacuum, the residue was purified by column chromatography (PE/EA=20/1) to afford 1-(1-(4-bromophenyl)-1-methoxyethyl)-3-(trifluoromethyl)benzene. $^1$H NMR (400 MHz, $CDCl_3$) δ=7.66 (s, 1H) ppm 1.83 (s, 3H), 7.34-7.50 (m, 5H), 7.19 (d, J=8.61 Hz, 2H), 3.13 (s, 3H) ppm.

Step 3: 2-(4-(1-methoxy-1-(3-(trifluoromethyl)phenyl)ethyl)phenyl)-4,4,5,5-tetramethyl-1,312-dioxaborolane A mixture of 1-(1-(4-bromophenyl)-1-methoxyethyl)-3-(trifluoromethyl)benzene (100 mg, 0.28 mmol), $B(Pin)_2$ (86 mg, 0.34 mmol), AcOK (83 mg, 0.84 mmol) and Pd(dppf)$Cl_2$-DCM (5 mg) and dioxane (5 mL) was stirred at 90° C. for 6 hours under $N_2$ protection. The solvent was removed in vacuum and the residue was purified by column chromatography (PE/THF=10/1) directly to afford 2-(4-(1-methoxy-1-(3-(trifluoromethyl)phenyl)ethyl)phenyl)-4,4,5,5-tetramethyl-1,3,2-dioxaborolane. MS: 375.2 (M-17).

Intermediate 56

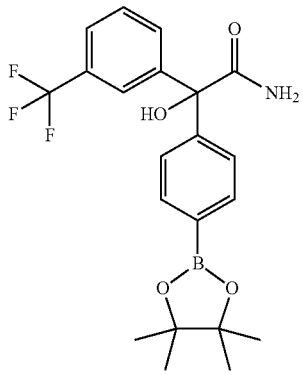 [SMILES: CC1(C)OB(c2ccc(C(O)(C(N)=O)c3cccc(C(F)(F)F)c3)cc2)OC1(C)C]

2-hydroxy-2-(4-(4,4,5,5-tetramethyl-1,3,2-dioxaborolan-2-yl)phenyl)-2-(3-(trifluoromethyl)phenyl)acetamide Step 1: 2-(4-bromophenyl)-2-(3-(trifluoromethyl)phenyl)-2-((trimethylsilyl)oxy)acetonitrile To the solution of (4-bromophenyl)(3-(trifluoromethyl)phenyl)methanone (500 mg, 1.5 mmol) and $ZnI_2$ (24 mg, 0.075 mmol) in DCM (20 mL) was added TMSCN (594 mg, 6 mmol) dropwise at 0° C. over 10 min. Then the reaction was stirred at 50° C. overnight. The reaction mixture was quenched with water (30 mL), extracted with DCM (30 mL×2). The combined organic phases were dried over $Na_2SO_4$, and the solvent was removed under reduced pressure. The resulting mixture was purified by column chromatography on silica gel (Pet. ether/EtOAc=20:1) to afford the title compound. $^1$H NMR (400 MHz, $CDCl_3$) δ: 7.59 (s, 1H), 7.47 (dd, J=7.8, 13.3 Hz, 2H), 7.38-7.32 (m, 3H), 7.20 (d, J=8.5 Hz, 2H), 0.00 (s, 9H) ppm.

Step 2: 2-(4-bromophenyl)-2-(3-(trifluoromethyl)phenyl)-2-((trimethylsilyl)oxy)acetamide To a solution of 2-(4-bromophenyl)-2-(3-(trifluoromethyl)phenyl)-2-((trimethylsilyl)oxy)acetonitrile (320 mg, 0.75 mmol) in THF (10 mL) and $H_2O$ (5 mL) was added a catalyst (CAS: 173416-05-2) (32 mg, 0.075 mmol). The mixture was refluxed overnight. The mixture was washed with water and extracted with DCM (20 mL×2). The organic layers were washed with brine, dried over anhydrous sodium sulfate and concentrated in vacuo to give 2-(4-bromophenyl)-2-(3-(trifluoromethyl)phenyl)-2-((trimethylsilyl)oxy)acetamide. MS: 446 (M+1).

Step 3: 2-hydroxy-2-(4-(4,4,5,5-tetramethyl-1,3,2-dioxaborolan-2-yl)phenyl)-2-(3-(trifluoromethyl)phenyl)acetamide The solution of 2-(4-bromophenyl)-2-(3-(trifluoromethyl)phenyl)-2-((trimethylsilyl)oxy)acetamide (170 mg, 0.38 mmol), bis(pinacolato)diboron (117 mg, 0.46 mmol), KOAc (93 mg, 0.95 mmol) and Pd(dppf)$Cl_2$ (14 mg, 0.02 mmol) in dioxane (15 mL) was stirred at 100° C. for 2 h under $N_2$. The reaction was cooled and concentrated in vacuo. The residue was purified by column chromatography on silica gel to give 2-hydroxy-2-(4-(4,4,5,5-tetramethyl-1,3,2-dioxaborolan-2-yl)phenyl)-2-(3-(trifluoromethyl)phenyl)acetamide. MS: 404 (M+1).

Intermediate 57

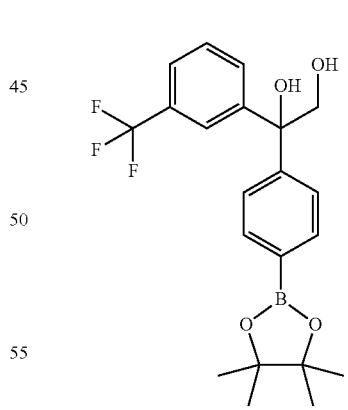

1-(4-(4,4,5,5-tetramethyl-1,3,2-dioxaborolan-2-yl)phenyl)-1-(3-(trifluoromethyl)phenyl)ethane-1,2-diol Step 1: 1-(1-(4-bromophenyl)vinyl)-3-(trifluoromethyl)benzene $InBr_3$ (50 mg, 0.15 mmol) was added to the solution of 1-(4-Bromophenyl)-1-(3-(trifluoromethyl)phenyl)ethanol (500 mg, 1.45 mmol) in DCM (10 mL). The mixture was stirred at room temperature for 2 h. The mixture was purified with silica gel column chromatography (25 g, Pet. Ether) to give 1-(1-(4-bromophenyl)vinyl)-3-(trifluoromethyl)benzene.

Step 2: 1-(4-bromophenyl)-1-(3-(trifluoromethyl)phenyl)ethane-1,2-diol

To a mixture of AD-mix-β (2.24 g), and MeSO₂NH₂ (155 mg, 1.63 mmol) in t-BuOH/H₂O (1:1, 16 mL) was stirred at room temperature for 5 min. 1-(1-(4-bromophenyl)vinyl)-3-(trifluoromethyl)benzene (532 mg, 1.63 mmol) was added at once. Then the mixture was stirred at room temperature overnight. The reaction was quenched by the addition of Na₂SO₃ (2.5 g) and stirred for 30 min. The mixture was extracted with DCM, dried over Na₂SO₄, purified by silica gel column chromatography (25 g, Pet. Ether:EtOAc=10:1 to 3:1) to give 1-(4-bromophenyl)-1-(3-(trifluoromethyl)phenyl)ethane-1,2-diol. ¹H NMR (400 MHz, CDCl₃) δ: 7.76 (s, 1H), 7.60-7.53 (m, 2H), 7.52-7.43 (m, 3H), 7.32 (d, J=8.6 Hz, 2H), 4.16 (d, J=2.3 Hz, 2H), 3.36 (br. s., 2H) ppm.

Step 3: 1-(4-(4,4,5,5-tetramethyl-1,3,2-dioxaborolan-2-yl)phenyl)-1-(3-(trifluoromethyl)phenyl)ethane-1,2-diol To a solution of 1-(4-bromophenyl)-1-(3-(trifluoromethyl)phenyl)ethane-1,2-diol (520 g, 1.44 mmol) in 1, 4-dioxane (20 mL) was added bis pinacol borate (439 mg, 1.73 mmol) and Pd(dppf)Cl₂ (63 mg, 0.086 mmol) and KOAc (423 mg, 4.32 mmol). The reaction mixture was stirred at 110° C. overnight under N₂. Then the solvent was removed under vacuum, and the residue was purified by column chromatography with silica gel (Pet. Ether/EtOAc=3:1) to afford 1-(4-(4,4,5,5-tetramethyl-1,3,2-dioxaborolan-2-yl)phenyl)-1-(3-(trifluoromethyl)phenyl)ethane-1,2-diol. ¹H NMR (400 MHz, CDCl₃) δ: 7.82 (d, J=8.2 Hz, 2H), 7.77 (br. s., 1H), 7.57 (d, J=7.8 Hz, 1H), 7.53 (d, J=7.0 Hz, 1H), 7.49-7.42 (m, 3H), 4.27-4.21 (m, 1H), 4.16 (s, 1H), 1.34 (s, 12H) ppm.

Intermediate 58

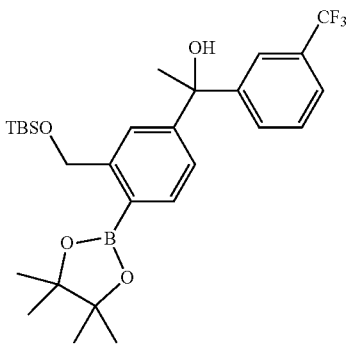 [SMILES: CC(O)(c1cccc(C(F)(F)F)c1)c1ccc(B2OC(C)(C)C(C)(C)O2)c(CO[Si](C)(C)C(C)(C)C)c1]

1-(3-(((tert-butyldimethylsilyl)oxy)methyl)-4-(4,4,5,5-tetramethyl-1,3,2-dioxaborolan-2-yl)phenyl)-1-(3-(trifluoromethyl)phenyl)ethanol Step 1: methyl 4-bromo-3-(hydroxymethyl)benzoate To a solution of methyl 4-bromo-3-formylbenzoate (1.0 g, 4.11 mmol) in anhydrous MeOH (20 mL) was added NaBH₄ (234 mg, 6.17 mmol) at 0° C. under nitrogen. The mixture was stirred at 0° C. to 25° C. for 16 h. The mixture was quenched by the addition of water (30 mL) slowly at 0° C. The mixture was then separated and the aqueous layer was extracted with DCM (50 mL×2). The combined organic layers were washed with brine (20 mL), dried over sodium sulfate, filtered and concentrated to give methyl 4-bromo-3-(hydroxymethyl)benzoate. ¹H NMR (400 MHz, CDCl₃) δ: 8.14 (s, 1H), 7.79 (dd, J=2.0, 8.2 Hz, 1H), 7.60 (d, J=8.2 Hz, 1H), 4.77 (s, 2H), 3.91 (s, 3H) ppm.

Step 2: 4-bromo-3-(hydroxymethyl)benzoic acid

To a solution of methyl 4-bromo-3-(hydroxymethyl)benzoate (1.0 g, 4.08 mmoL) in MeOH/H₂O (3:1, 21 mL) was added NaOH (245 mg, 6.12 mmol). The mixture was stirred at 25° C. for 10 h. Organic solvent was removed and the mixture was diluted with water (20 mL) and EtOAc (20 mL). The organic layer was separated and the aqueous layer was adjust acid to pH=1 with 1M HCl. The white solid was collected via filtration and the solid was dried to give 4-bromo-3-(hydroxymethyl)benzoic acid. ¹H NMR (400 MHz, DMSO-d₆) δ: 8.07 (s, 1H), 7.73-7.61 (m, 2H), 5.56 (br. s., 1H), 4.50 (br. s., 2H) ppm.

Step 3: 4-bromo-3-(hydroxymethyl)-N-methoxy-N-methylbenzamide

A mixture of 4-bromo-3-(hydroxymethyl)benzoic acid (740 mg, 3.20 mmol), N,O-dimethylhydroxylamine hydrochloride (469 mg, 4.80 mmol), HATU (1.46 g, 3.84 mmol) and TEA (1.13 g, 11.13 mol) in DCM (20 mL) was stirred at room temperature for 12 h. The mixture was washed with HCl (1M), dried over sodium sulfate, filtered and concentrated in vacuo. The residue was purified by silica gel column chromatography (EtOAc/Pet. ether=0~35%) to give 4-bromo-3-(hydroxymethyl)-N-methoxy-N-methylbenzamide. ¹H NMR (400 MHz, CDCl₃) δ: 7.80 (s, 1H), 7.57 (d, J=7.8 Hz, 1H), 7.46 (d, J=7.0 Hz, 1H), 4.74 (s, 2H), 3.54 (s, 3H), 3.35 (s, 3H), 2.43 (br. s., 1H) ppm.

Step 4: 1-(4-bromo-3-(hydroxymethyl)phenyl)ethanone

To a solution of 4-bromo-3-(hydroxymethyl)-N-methoxy-N-methylbenzamide (1.5 g, 5.47 mmol) in anhydrous THF (10 mL) at −78° C. under nitrogen, MeMgBr (3M in ether, 7.3 mL, 21.9 mmol) was added dropwise. The reaction mixture was stirred at −78° C.~30° C. for 15 h. The reaction was quenched by saturated ammonium chloride (20 mL). Then the mixture was extracted with EtOAc (50 mL×3), the combined organic layers were washed with brine (30 mL), dried over sodium sulfate, filtered and concentrated to afford the crude product, which was purified on silica gel column chromatography (EtOAc/Pet. ether=10% 60%) to give 1-(4-bromo-3-(hydroxymethyl)phenyl)ethanone. ¹H NMR (400 MHz, CDCl₃) δ: 8.08 (s, 1H), 7.74 (d, J=8.2 Hz, 1H), 7.65 (d, J=8.2 Hz, 1H), 4.81 (s, 2H), 2.61 (s, 3H) ppm.

Step 5: 1-(4-bromo-3-(((tert-butyldimethylsilyl)oxy)methyl)phenyl)ethanone

To a solution of 1-(4-bromo-3-(hydroxymethyl)phenyl)ethanone (1.0 g, 4.37 mmoL) in DMF (8 mL) was added imidazole (890 mg, 13.11 mmol) and TBSCl (910 mg, 5.67 mmol). The mixture was stirred at 25° C. for 10 h. The mixture was diluted with water (10 mL) and EtOAc (30 mL). The organic layer was separated and the aqueous layer was extracted with EtOAc (50 mL×2). The combined organic layers were washed with brine (30 mL), dried over sodium sulfate, filtered and concentrated to afford the crude product, which was purified on silica gel column chromatography (EtOAc/Pet. ether=0%~10%) to give 1-(4-bromo-3-(((tert-butyldimethylsilyl)oxy)methyl)phenyl)ethanone. $^1$H NMR (400 MHz, CDCl$_3$) δ: 8.16-8.12 (m, 1H), 7.72 (dd, J=2.3, 8.3 Hz, 1H), 7.59 (d, J=8.3 Hz, 1H), 4.76 (s, 2H), 2.60 (s, 3H), 1.00-0.98 (m, 9H), 0.16-0.14 (m, 6H) ppm.

Step 6: 1-(4-bromo-3-(((tert-butyldimethylsilyl)oxy)methyl)-1-(3-(trifluoromethyl)phenyl)ethanol To a solution of 1-bromo-3-(trifluoromethyl)benzene (491 mg, 2.18 mmol) in anhydrous THF (5 mL) under nitrogen, n-BuLi (0.93 mL, 2.33 mmol) was added at −78° C. drop-wise. The mixture was stirred at −78° C. for 30 mins. Then a solution of 1-(4-bromo-3-(((tert-butyldimethylsilyl)oxy)methyl)phenyl)ethanone (500 mg, 1.46 mmol) in anhydrous THF (5 mL) was added at −78° C. drop-wise and the mixture was stirred at this temperature for 3 h. The mixture was quenched by sat.NH$_4$Cl aqueous (10 mL) slowly at −78° C.~0° C. The mixture was extracted with ethyl acetate (30 mL×3). The combined organic layers were washed with brine (20 mL), dried over sodium sulfate, filtered and concentrated to afford the crude product, which was purified on silica gel column chromatography (THF/Pet. ether=0~15%) to give 1-(4-bromo-3-(((tert-butyldimethylsilyl)oxy)methyl)phenyl)-1-(3-(trifluoromethyl)phenyl)ethanol. $^1$H NMR (400 MHz, CDCl$_3$) δ: 7.75 (s, 1H), 7.56-7.48 (m, 3H), 7.46 (d, J=8.3 Hz, 1H), 7.44-7.39 (m, 1H), 7.26-7.23 (m, 1H), 4.69 (s, 2H), 2.21 (br. s., 1H), 1.96 (s, 3H), 0.88 (s, 10H), 0.04 (s, 6H) ppm.

Step 7: 1-(3-(((tert-butyldimethylsilyl)oxy)methyl)-4-(4,4,5,5-tetramethyl-1,3,2-dioxaborolan-2-yl)phenyl)-1-(3-(trifluoromethyl)phenyl)ethanol To a solution of 1-(4-bromo-3-(((tert-butyldimethylsilyl)oxy)methyl)phenyl)-1-(3-(trifluoromethyl)phenyl)ethanol (680 mg, 1.39 mmol), KOAc (341 mg, 3.47 mmol) and 4-(4,4,5,5-tetramethyl-1,3,2-dioxaborolan-2-yl)benzamide (423 mg, 1.67 mmol) in dioxane (15 mL) was added Pd(dppf)Cl$_2$ (catalytic amount) under nitrogen protection. Then the mixture was heated to 100° C. stirred for 3 h. After cooled to room temperature, the mixture was filtered and the filtrate was concentrated in vacuo and purified on silica gel chromatography (EtOAc/Pet. ether=0%~10%) to give 1-(3-(((tert-butyldimethylsilyl)oxy)methyl)-4-(4,4,5,5-tetramethyl-1,3,2-dioxaborolan-2-yl)phenyl)-1-(3-(trifluoromethyl)phenyl)ethanol. $^1$H NMR (400 MHz, CDCl$_3$) δ: 7.80-7.72 (m, 2H), 7.58 (s, 1H), 7.53 (d, J=7.4 Hz, 1H), 7.47 (d, J=7.4 Hz, 1H), 7.37 (dd, J=7.6, 19.4 Hz, 2H), 4.98 (s, 2H), 1.96 (s, 3H), 1.32 (s, 12H), 0.87 (s, 9H), 0.00 (s, 6H) ppm.

The following intermediates in Table 2 were prepared using the same procedure as in intermediate 58 using the corresponding aromatic halide in step 1 and/or different aromatic halide for the Grignard addition.

TABLE 2

| Intermediate | Structure | Chemical name | NMR | MS |
|---|---|---|---|---|
| 59 | 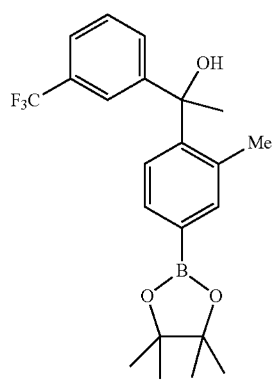 [SMILES: Cc1cc(B2OC(C)(C)C(C)(C)O2)ccc1C(C)(O)c1cccc(C(F)(F)F)c1] | 1-(2-methyl-4-(4,4,5,5-tetramethyl-1,3,2-dioxaborolan-2-yl)phenyl)-1-(3-(trifluoromethyl)phenyl)ethanol | | MS: 389 (M + 1)$^+$ |
| 60 | 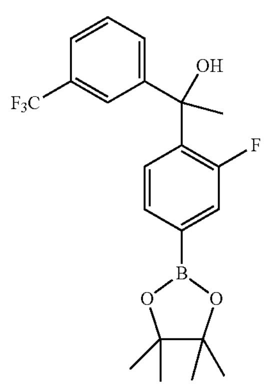 [SMILES: CC(O)(c1cccc(C(F)(F)F)c1)c1ccc(B2OC(C)(C)C(C)(C)O2)cc1F] | 1-(2-fluoro-4-(4,4,5,5-tetramethyl-1,3,2-dioxaborolan-2-yl)phenyl)-1-(3-(trifluoromethyl)phenyl)ethanol | $^1$H NMR (CDCl3 400 MHz): δ = 7.68 (br. s., 1H), 7.66-7.61 (m, 2H), 7.54-7.46 (m, 2H), 7.45-7.36 (m, 2H), 1.97 (s, 3H), 1.27 (s, 12H) | MS: 411 (M + 1)+ |

TABLE 2-continued

| Intermediate | Structure | Chemical name | NMR | MS |
|---|---|---|---|---|
| 61 | 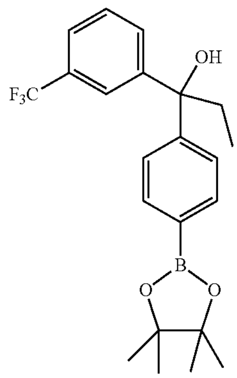 [SMILES: CCC(O)(c1ccc(B2OC(C)(C)C(C)(C)O2)cc1)c1cccc(C(F)(F)F)c1] | 1-(4-(4,4,5,5-tetramethyl-1,3,2-dioxaborolan-2-yl)phenyl)-1-(3-(trifluoromethyl)phenyl)propan-1-ol | | MS: 389 (M-17) |
| 62 | | 1-([1,1'-biphenyl]-3-yl)-1-(4-(4,4,5,5-tetramethyl-1,3,2-dioxaborolan-2-yl)phenyl)ethanol | $^1$H NMR (400 MHz, CDCl$_3$) δ = 7.76 (d, J = 8.2 Hz, 2H), 7.63 (s, 1H), 7.53 (d, J = 7.4 Hz, 2H), 7.48-7.32 (m, 8H), 1.98 (s, 3H), 1.31 (s, 12H). | |
| 62 | | 1-(3-cyclopropyl-4-(4,4,5,5-tetramethyl-1,3,2-dioxaborolan-2-yl)phenyl)-1-(3-(trifluoromethyl)phenyl)ethanol | $^1$H NMR (400 MHz, CDCl$_3$) δ = 7.72-7.63 (m, 2H), 7.46 (d, J = 7.4 Hz, 2H), 7.39-7.31 (m, 1H), 7.13-7.07 (m, 1H), 6.90 (s, 1H), 2.68-2.56 (m, 1H), 1.90 (s, 3H), 1.32 (s, 12H), 0.96-0.88 (m., 2H), 0.59 (d, J = 3.9 Hz, 2H). | |
| 63 | 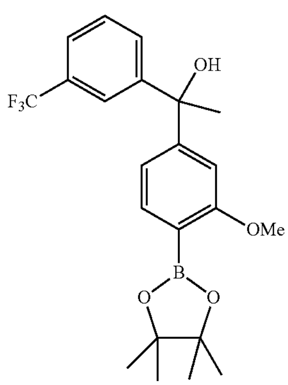 [SMILES: COc1cc(C(C)(O)c2cccc(C(F)(F)F)c2)ccc1B1OC(C)(C)C(C)(C)O1] | 1-(3-methoxy-4-(4,4,5,5-tetramethyl-1,3,2-dioxaborolan-2-yl)phenyl)-1-(3-(trifluoromethyl)phenyl)ethanol | $^1$H NMR (400 MHz, CDCl$_3$) ppm 1.30 (s, 12 H) 1.90 (s, 3 H) 3.73 (s, 3 H) 6.87-6.90 (m, 1 H) 6.93 (s, 1 H) 7.35 (d, J = 7.83 Hz, 1 H) 7.48 (d, J = 7.83 Hz, 1 H) 7.45 (d, J = 8.22 Hz, 1 H) 7.58 (d, J = 7.83 Hz, 1 H) 7.71 (s, 1 H) | |

TABLE 2-continued

| Intermediate | Structure | Chemical name | NMR | MS |
|---|---|---|---|---|
| 64 | 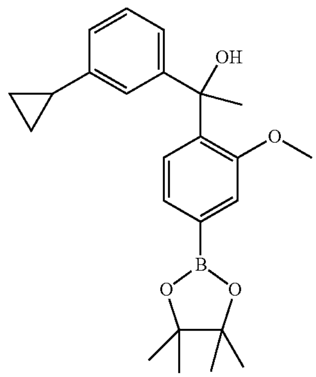 [SMILES: COc1cc(B2OC(C)(C)C(C)(C)O2)ccc1C(C)(O)c1cccc(C2CC2)c1] | 1-(3-cyclopropylphenyl)-1-(2-methoxy-4-(4,4,5,5-tetramethyl-1,3,2-dioxaborolan-2-yl)phenyl)ethanol | ¹H NMR (400 MHz, CDCl₃) δ ppm 7.51-7.40 (m, 2H), 7.29 (s, 1H), 7.14-7.05 (m, 2H), 6.96 (d, J = 7.4 Hz, 1H), 6.84 (d, J = 7.4 Hz, 1H), 4.69 (br. s., 1H), 3.64 (s, 3H), 1.82 (s, 3H), 1.35 (s, 11H), 1.29-1.18 (m, 1H), 0.90 (d, J = 7.0 Hz, 2H), 0.64 (d, J = 4.3 Hz, 2H). | |
| 65 | 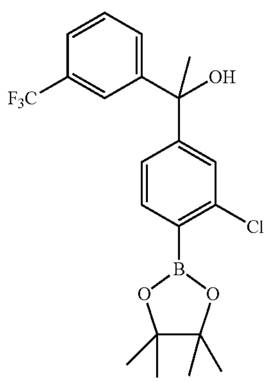 [SMILES: CC(O)(c1cccc(C(F)(F)F)c1)c1ccc(B2OC(C)(C)C(C)(C)O2)c(Cl)c1] | 1-(3-chloro-4-(4,4,5,5-tetramethyl-1,3,2-dioxaborolan-2-yl)phenyl)-1-(3-(trifluoromethyl)phenyl)ethanol | | MS: 409 (M-17) |
| 66 | 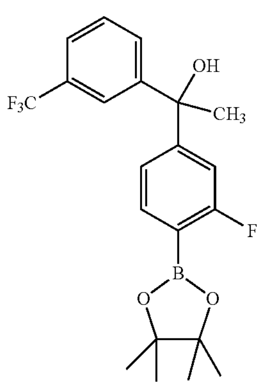 [SMILES: CC(O)(c1cccc(C(F)(F)F)c1)c1ccc(B2OC(C)(C)C(C)(C)O2)c(F)c1] | 1-(3-fluoro-4-(4,4,5,5-tetramethyl-1,3,2-dioxaborolan-2-yl)phenyl)-1-(3-(trifluoromethyl)phenyl)ethanol | | MS: 393 (M-17) |

TABLE 2-continued

| Intermediate | Structure | Chemical name | NMR | MS |
|---|---|---|---|---|
| 68 | 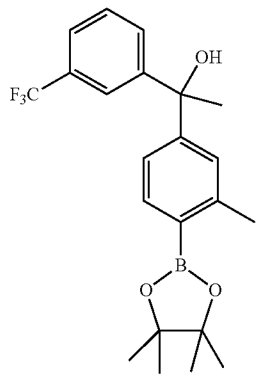 [SMILES: Cc1cc(C(C)(O)c2cccc(C(F)(F)F)c2)ccc1B1OC(C)(C)C(C)(C)O1] | 1-(3-methyl-4-(4,4,5,5-tetramethyl-1,3,2-dioxaborolan-2-yl)phenyl)-1-(3-(trifluoromethyl)phenyl)ethanol | $^1$H NMR (400 MHz, CDCl$_3$) δ ppm 7.69-7.76 (m, 2 H), 7.48 (t, J = 9.39 Hz, 2 H), 7.33-7.41 (m, 1 H), 7.14-7.22 (m, 2 H), 2.50 (s, 3 H), 1.91-1.94 (m, 3 H), 1.31 (s, 12 H). | |
| 69 | 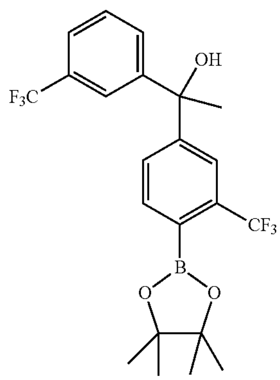 [SMILES: CC(O)(c1cccc(C(F)(F)F)c1)c1ccc(B2OC(C)(C)C(C)(C)O2)c(C(F)(F)F)c1] | 1-(4-(4,4,5,5-tetramethyl-1,3,2-dioxaborolan-2-yl)-3-(trifluoromethyl)phenyl)-1-(3-(trifluoromethyl)phenyl)ethanol | | MS: 443 (M-17) |

Intermediate 70

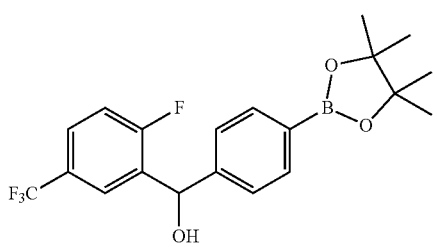 [SMILES: CC1(C)OB(c2ccc(C(O)c3cc(C(F)(F)F)ccc3F)cc2)OC1(C)C]

(2-fluoro-5-(trifluoromethyl)phenyl)(4-(4,4,5,5-tetramethyl-1,3,2-dioxaborolan-2-yl)phenyl)methanol

Step 1: (4-bromophenyl)(2-fluoro-5-(trifluoromethyl)phenyl)methanol

To the solution of n_BuLi (0.72 mL, 1.8 mmol) and t-BuOK (1.8 mL, 1.8 mmol) in THF (10 mL) at −78° C. was added 1-fluoro-4-(trifluoromethyl)benzene (300 mg, 1.8 mmol). The reaction was stirred at −78° C. for 0.5 h. Then a solution of 4-bromobenzaldehyde (370 mg, 2 mmol) in THF (10 mL) was added dropwise to the reaction. The reaction was stirred for another 5 min and then removed from the cooling bath to warm to room temperature for 2 h. The reaction mixture was quenched with NH$_4$Cl (sat. aq.), extracted with EtOAc, the combined organic phases were dried over Na$_2$SO$_4$, and the solvent was removed under reduced pressure. The residue was purified by column chromatography on silica gel (Pet. Ether:EtOAc=10:1) to afford (4-bromophenyl)(2-fluoro-5-(trifluoromethyl)phenyl)methanol. $^1$H NMR (400 MHz, CDCl$_3$) δ: 7.87 (d, J=5.9 Hz, 1H), 7.53 (br. s., 1H), 7.46 (d, J=7.8 Hz, 2H), 7.25 (d, J=8.6 Hz, 2H), 7.10 (t, J=9.0 Hz, 1H), 6.09 (s, 1H), 2.38 (br. s., 1H) ppm.

Step 2: (2-fluoro-5-(trifluoromethyl)phenyl)(4-(4,4,5,5-tetramethyl-1,3,2-dioxaborolan-2-yl)phenyl)methanol The solution of (4-bromophenyl)(2-fluoro-5-(trifluoromethyl)phenyl)methanol (210 mg, 0.6 mmol), bis(pinacolato)diboron (184 mg, 0.72 mmol), KOAc (147 mg, 1.5 mmol) and Pd(dppf)Cl$_2$ (22 mg, 0.03 mmol) in dioxane (15 mL) was stirred at 100° C. under N$_2$ for 2 h. The reaction mixture was cooled and concentrated in vacuo, and the residue was purified by chromatography on silica gel (Pet. Ether:EtOAc=10:1) to afford the title compound. $^1$H NMR (400 MHz, CDCl$_3$) δ: 7.88 (d, J=5.5 Hz, 1H), 7.78 (d, J=7.8 Hz, 2H), 7.50 (br. s., 1H), 7.38 (d, J=7.8 Hz, 2H), 7.08 (t, J=9.2 Hz, 1H), 6.14 (br. s., 1H), 1.31 (s, 12H) ppm.

The following intermediates were prepared in the same procedure as intermediate 21E1, using different ketones or aromatic halides.

| Intermediate | Structure | Chemical name | NMR | MS |
|---|---|---|---|---|
| 71 | 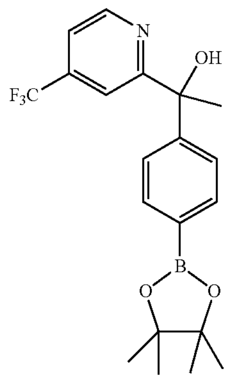 [SMILES: CC(O)(c1ccc(B2OC(C)(C)C(C)(C)O2)cc1)c1cc(C(F)(F)F)ccn1] | 1-(4-(4,4,5,5-tetramethyl-1,3,2-dioxaborolan-2-yl)phenyl)-1-(4-(trifluoromethyl)pyridin-2-yl)ethanol | | MS: 376.2 (M-17) |
| 72 | 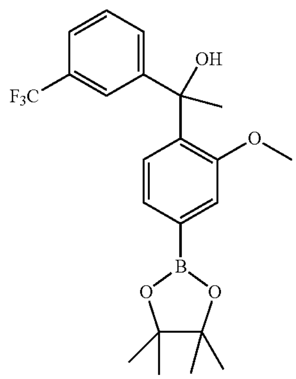 [SMILES: COc1cc(B2OC(C)(C)C(C)(C)O2)ccc1C(C)(O)c1cccc(C(F)(F)F)c1] | 1-(2-methoxy-4-(4,4,5,5-tetramethyl-1,3,2-dioxaborolan-2-yl)phenyl)-1-(3-(trifluoromethyl)phenyl)ethanol | | MS: 405 (M-17)+ |
| 73 | 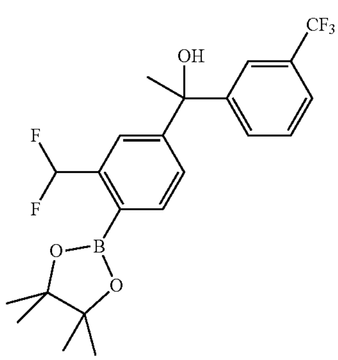 [SMILES: CC(O)(c1cccc(C(F)(F)F)c1)c1ccc(B2OC(C)(C)C(C)(C)O2)c(C(F)F)c1] | 1-(3-(difluoromethyl)-4-(4,4,5,5-tetramethyl-1,3,2-dioxaborolan-2-yl)phenyl)-1-(3-(trifluoromethyl)phenyl)ethanol | $^1$H NMR (400 MHz, CDCl$_3$) d = 7.76 (br. s., 1H), 7.61 (br. s., 1H), 7.56-7.38 (m, 5H), 6.77 (s, 0.25H), 6.63 (s, 0.5H), 6.49 (s, 0.25H), 2.00 (s, 3H), 1.26 (s, 12H). | |

Intermediate 74

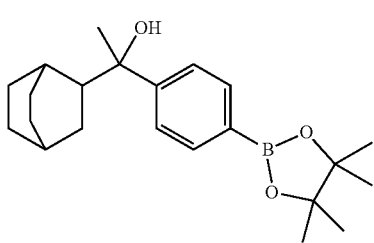 [SMILES: CC(O)(c1ccc(B2OC(C)(C)C(C)(C)O2)cc1)C1CC2CCC1CC2]

1-(bicyclo[2.2.2]octan-2-yl)-1-(4-(4,4,5,5-tetramethyl-1,3,2-dioxaborolan-2-yl)phenyl)ethanol Step 1: 1-(bicyclo[2.2.2]oct-5-en-2-yl)ethanone To the solution of cyclohexa-1,3-diene (2.6 g, 32.5 mmol) and but-3-en-2-one (12.56 g, 179 mmol) in DCM (50 mL) was cooled to 0° C. SnCl$_4$ (8.45 g, 32.5 mmol) was added slowly, and then the mixture was stirred at 0° C. for 90 min. Then the reaction was quenched with saturated NaHCO$_3$ aqueous to pH=9. The mixture was extracted with DCM, dried over Na$_2$SO$_4$, concentrated to give 1-(bicyclo[2.2.2]oct-5-en-2-yl)ethanone. $^1$H NMR (400 MHz, CDCl$_3$) δ: 6.30-6.24 (m, 1H), 6.13-6.07 (m, 1H), 2.92-2.87 (m, 1H), 2.66 (dt, J=2.0, 7.7 Hz, 1H), 2.63-2.57 (m, 1H), 2.11 (s, 3H), 1.65-1.56 (m, 2H), 1.54-1.46 (m, 1H), 1.38-1.22 (m, 3H) ppm.

Step 2: 1-(bicyclo[2.2.2]octan-2-yl)ethanone

To a solution of 1-(bicyclo[2.2.2]oct-5-en-2-yl)ethanone (2.7 g, 1.79 mmol) in EtOAc (30 mL) was added Pd—C (50%, 200 mg) under $N_2$. The suspension was degassed under vacuum and purged with $H_2$ several times. The mixture was stirred under $H_2$ balloon at room temperature for 4 h. The mixture was filtered and concentrated to give 1-(bicyclo[2.2.2]octan-2-yl)ethanone. $^1$H NMR (400 MHz, $CDCl_3$) δ: 2.68-2.60 (m, 1H), 2.14 (s, 3H), 2.08-2.00 (m, 1H), 1.95 (br. s., 1H), 1.65 (d, J=2.0 Hz, 3H), 1.57-1.35 (m, 7H) ppm.

Step 3: 1-(bicyclo[2.2.2]octan-2-yl)-1-(4-chlorophenyl)ethanol (4-Chlorophenyl)magnesium bromide (9.7 mL, 9.7 mmol) was added dropwise to a stirred solution of 1-(bicyclo[2.2.2]octan-2-yl)ethanone (744 mg, 4.86 mmol) in THF (15 mL) at 0° C. Then the mixture was allowed to warm to room temperature overnight. The mixture was added aq. $NH_4Cl$ (30 mL), stirred for 5 minutes. The mixture was extracted with EtOAc (2×50 mL). The organic layers were combined and dried over sodium sulfate, purified with silica gel column chromatography (Pet. Ether→Pet. Ether/EtOAc: =95:5) to give 1-(bicyclo[2.2.2]octan-2-yl)-1-(4-chlorophenyl)ethanol.

Step 4: 1-(bicyclo[2.2.2]octan-2-yl)-1-(4-(4,4,5,5-tetramethyl-1,3,2-dioxaborolan-2-yl)phenyl)ethanol To a solution of 1-(bicyclo[2.2.2]octan-2-yl)-1-(4-chlorophenyl)ethanol (1.28 g, 4.38 mmol) in 1,4-dioxane (20 mL) was added 4,4,4',4',5,5,5',5'-octamethyl-2,2'-bi(1,3,2-dioxaborolane) (1.350 g, 5.32 mmol) and $Pd_2(dba)_3$ (0.266 g, 0.290 mmol) and X-phos (0.277 g, 0.580 mmol) and KOAc (1.423 g, 14.50 mmol). The reaction mixture was stirred at 120° C. under $N_2$ overnight. After that, the solvent was removed under vacuum, and the residue was purified by column chromatography with silica gel (Pet. Ether: EtOAc=95:5) to afford the title compound. MS: 339.3 (M-17).

The following intermediates were prepared in the same procedure as intermediate 27 using corresponding aromatic acid in step 1 and aromatic halides in step 2.

| Int. | Structure | Chemical name | NMR | MS |
|---|---|---|---|---|
| 75 | 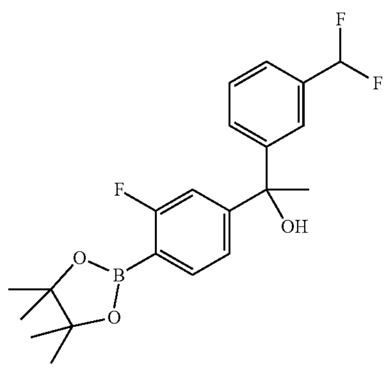 [SMILES: CC(O)(c1cccc(C(F)F)c1)c1ccc(B2OC(C)(C)C(C)(C)O2)c(F)c1] | 1-(3-(difluoromethyl)phenyl)-1-(3-fluoro-4-(4,4,5,5-tetramethyl-1,3,2-dioxaborolan-2-yl)phenyl)ethanol | | MS: 375 (M-17). |
| 76 | 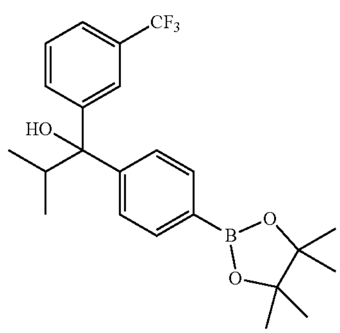 [SMILES: CC(C)C(O)(c1ccc(B2OC(C)(C)C(C)(C)O2)cc1)c1cccc(C(F)(F)F)c1] | 2-methyl-1-(4-(4,4,5,5-tetramethyl-1,3,2-dioxaborolan-2-yl)phenyl)-1-(3-(trifluoromethyl)phenyl)propan-1-ol | | MS: 403 (M-17) |

| Int. | Structure | Chemical name | NMR | MS |
|---|---|---|---|---|
| 77 | 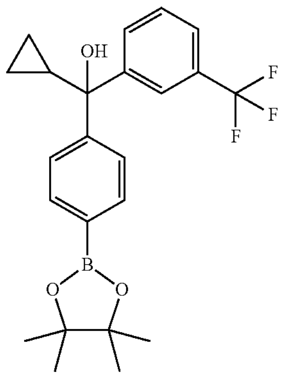 [SMILES: CC1(C)OB(c2ccc(C(O)(c3cccc(C(F)(F)F)c3)C3CC3)cc2)OC1(C)C] | cyclopropyl(4-(4,4,5,5-tetramethyl-1,3,2-dioxaborolan-2-yl)phenyl)(3-(trifluoromethyl)phenyl)methanol | | MS: 401 (M-17) |
| 78 | 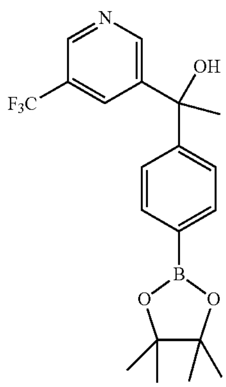 [SMILES: CC(O)(c1ccc(B2OC(C)(C)C(C)(C)O2)cc1)c1cncc(C(F)(F)F)c1] | 1-(4-(4,4,5,5-tetramethyl-1,3,2-dioxaborolan-2-yl)phenyl)-1-(5-(trifluoromethyl)pyridin-3-yl)ethanol | $^1$H NMR (400 MHz, CDCl$_3$) δ = 8.77 (d, J = 16.4 Hz, 1H), 8.04 (br. s., 1H), 7.82 (d, J = 7.8 Hz, 2H), 7.44 (d, J = 8.2 Hz, 2H), 2.02 (s, 3H), 1.35 (s, 11H). | NA |
| 79 | 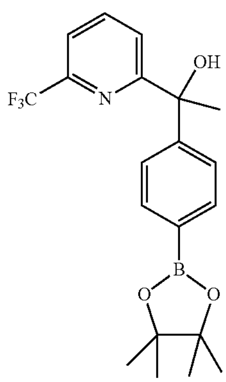 [SMILES: CC(O)(c1ccc(B2OC(C)(C)C(C)(C)O2)cc1)c1cccc(C(F)(F)F)n1] | 1-(4-(4,4,5,5-tetramethyl-1,3,2-dioxaborolan-2-yl)phenyl)-1-(6-(trifluoromethyl)pyridin-2-yl)ethanol | $^1$H NMR (400 MHz, CDCl$_3$) δ = 7.82-7.71 (m, 3H), 7.54 (d, J = 7.8 Hz, 1H), 7.51-7.41 (m, 3H), 1.94 (s, 3H), 1.30 (s, 13H). | NA |

Intermediate 80

1-(3-ethoxy-4-(4,4,5,5-tetramethyl-1,3,2-dioxaborolan-2-yl)phenyl)-2,2,2-trifluoro-1-(3-(trifluoromethyl)phenyl)ethanol Step 1: methyl 4-bromo-3-ethoxybenzoate

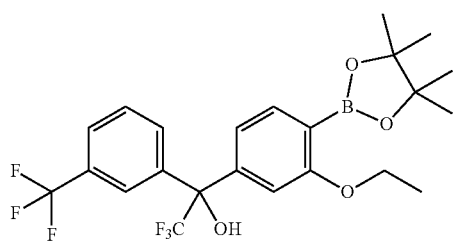 [SMILES: CCOc1cc(C(O)(c2cccc(C(F)(F)F)c2)C(F)(F)F)ccc1B1OC(C)(C)C(C)(C)O1]

To a mixture of methyl 4-bromo-3-hydroxybenzoate (4 g, 17.31 mmol) and K$_2$CO$_3$ (5.98 g, 43.3 mmol) in DMF (30 mL) was added iodoethane (6.75 g, 43.3 mmol) dropwise. The reaction mixture was stirred at 10° C. for 8 h. The reaction was complete detected by TLC (Petroleum ether/EtOAc=10:1). The reaction was quenched with 1N HCl (100 mL), and extracted with ethyl acetate (100 mL×2). The organic layers were washed with brine, dried over anhydrous sodium sulfate, concentrated to afford methyl 4-bromo-3-ethoxybenzoate.

Step 2: 4-bromo-3-ethoxybenzoic acid

To a solution of methyl 4-bromo-3-ethoxybenzoate (4.1 g, 15.82 mmol) in THF (20 mL) and MeOH (20.00 mL) was added LiOH (1.137 g, 47.5 mmol) and water (20 mL). The mixture was stirred at 12° C. for 3 h. The reaction was quenched with 1N HCl to pH=2 and extracted with EtOAc (100 mL×2). The combined organic layers were dried over anhydrous sodium sulfate, concentrated in vacuum to give 4-bromo-3-ethoxybenzoic acid.

Step 3: 4-bromo-3-ethoxy-N-methoxy-N-methylbenzamide

A mixture of 4-bromo-3-ethoxybenzoic acid (3.9 g, 15.91 mmol), N,O-dimethylhydroxylamine·HCl (1.863 g, 19.10 mmol), HATU (6.05 g, 15.91 mmol) and DIEA (8.34 mL, 47.7 mmol) in THF (30 mL) was stirred at 10° C. for 2 h. TLC detected the reaction was complete. The reaction mixture was quenched with sat. NH$_4$Cl aqueous (100 mL), extracted with EtOAc (80 mL×2). The organic layer was dried over sodium sulfate, concentrated to give the crude product, which was purified by column chromatography on silica gel (Pet. ether/EtOAc=3:1) to give 4-bromo-3-ethoxy-N-methoxy-N-methylbenzamide. H NMR (400 MHz, CDCl$_3$) δ: 7.55 (d, J=8.2 Hz, 1H), 7.22 (s, 1H), 7.18-7.13 (m, 1H), 4.13 (q, J=6.9 Hz, 2H), 3.54 (s, 3H), 3.35 (s, 3H), 1.47 (t, J=7.0 Hz, 3H) ppm.

Step 4: (4-bromo-3-ethoxyphenyl)(3-(trifluoromethyl)phenyl)methanone

To a mixture of magnesium (0.127 g, 5.21 mmol) and isopropylmagnesium chloride (0.347 mL, 0.694 mmol) in THF (2 mL) was added a solution of 1-bromo-3-(trifluoromethyl)benzene (0.937 g, 4.16 mmol) in THF (5 mL) dropwise at 80° C. under N$_2$. The solution was added to a solution of 4-bromo-3-ethoxy-N-methoxy-N-methylbenzamide (1 g, 3.47 mmol) in THF (10 mL) and the reaction was stirred at 15° C. for 2 h. TLC detected the reaction was complete. The reaction mixture was quenched with sat. NH$_4$Cl aqueous (50 mL), extracted with EtOAc (50 mL×2). The combined organic phases were dried over Na$_2$SO$_4$, and concentrated to give (4-bromo-3-ethoxyphenyl)(3-(trifluoromethyl)phenyl)methanone.

Step 5: 1-(4-bromo-3-ethoxyphenyl)-2,2,2-trifluoro-1-(3-(trifluoromethyl)phenyl)ethanol To a solution of (4-bromo-3-ethoxyphenyl)(3-(trifluoromethyl)phenyl)methanone (1.3 g, 3.48 mmol) in THF (25 mL) were added trimethyl(trifluoromethyl)silane (0.743 g, 5.23 mmol) and tetrabutylammonium difluorotriphenylsilicate (0.940 g, 1.742 mmol) at 0° C. The reaction was stirred for 12 h at 14° C. under N$_2$. The reaction was quenched with 1M HCl (20 mL). 30 min later, the mixture was basified with aq. NaHCO$_3$ (30 mL), extracted with EtOAc (20 mL×3). The organic layer was washed with brine (30 mL), dried over Na$_2$SO$_4$, evaporated to give the crude product, which was purified by flash chromatography (Pet.ether/EtOAc=10:1) to give 1-(4-bromo-3-ethoxyphenyl)-2,2,2-trifluoro-1-(3-(trifluoromethyl)phenyl)ethanol. $^1$H NMR (400 MHz, CDCl$_3$) δ: 7.82 (br. s., 1H), 7.62 (t, J=7.2 Hz, 2H), 7.57-7.46 (m, 2H), 7.03 (s, 1H), 6.89 (d, J=8.2 Hz, 1H), 4.09-3.99 (m, 2H), 3.08 (s, 1H), 1.44 (t, J=7.0 Hz, 3H) ppm.

Step 6: 1-(3-ethoxy-4-(4,4,5,5-tetramethyl-1,3,2-dioxaborolan-2-yl)phenyl)-2,2,2-trifluoro-1-(3-(trifluoromethyl)phenyl)ethanol The solution of 1-(4-bromo-3-ethoxyphenyl)-2,2,2-trifluoro-1-(3-(trifluoromethyl)phenyl)ethanol (800 mg, 1.805 mmol),4,4,4',4',5,5,5',5'-octamethyl-2,2'-bi(1,3,2-dioxaborolane) (550 mg, 2.166 mmol), potassium acetate (531 mg, 5.42 mmol) and PdCl$_2$(dppf) (66.0 mg, 0.090 mmol) in 1,4-dioxane (15 mL) was stirred at 110° C. for 4 h under N$_2$. The unit was cooled and concentrated in vacuo. The residue was purified by chromatography on silica gel (Pet.ether:EtOAc=10:1) to give 1-(3-ethoxy-4-(4,4,5,5-tetramethyl-1,3,2-dioxaborolan-2-yl)phenyl)-2,2,2-trifluoro-1-(3-(trifluoromethyl)phenyl)ethanol. $^1$H NMR (400 MHz, CDCl$_3$) δ: 7.80 (s, 1H), 7.61-7.55 (m, 2H), 7.46-7.40 (m, 2H), 7.03 (d, J=7.8 Hz, 1H), 6.94 (s, 1H), 3.96 (td, J=6.6, 12.7 Hz, 2H), 3.02 (s, 1H), 1.40-1.33 (m, 15H) ppm.

Intermediate 81

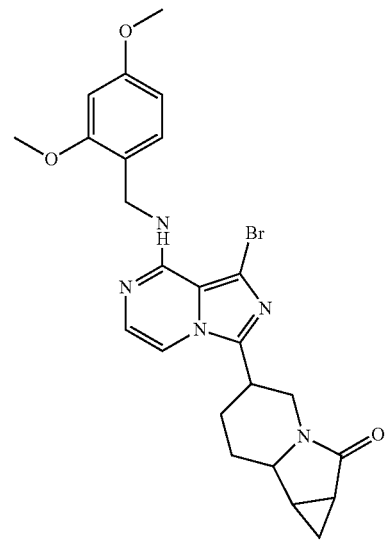 [SMILES: COc1ccc(CNc2nccn3c(C4CCC5C6CC6C(=O)N5C4)nc(Br)c23)c(OC)c1]

Trans-4-(8-amino-3-(2-oxooctahydro-1H-cyclopropa[a]indolizin-5-yl)imidazo[1,5-a]pyrazin-1-yl)-3-ethoxy-N-(4-(trifluoromethyl)pyridin-2-yl)benzamide

Step 1: methyl 6-vinylnicotinate

To a solution of methyl 6-bromonicotinate (10 g, 46.3 mmol) in Me2CHOH (200 mL) was added C2H3BF4K+ (14.16 g, 93 mmol), Et$_3$N (19.36 mL, 139 mmol), Pd(dppf)Cl2 (0.2 g). The mixture was stirred at 100° C. for 12 hours under N$_2$ atmosphere. The mixture was concentrated and the residue was purified by column chromatography on silica gel (Pet.ether:EtOAc=15:1) to give methyl 6-vinylnicotinate. MS: 164.2 (M+1). Acq DRt=0.824 min).

Step 2: methyl 6-(2-(ethoxycarbonyl)cyclopropyl)nicotinate

Ethyl diazoacetate (381 mg, 3.31 mmol) was added to a solution of methyl 6-vinylnicotinate (450 mg, 2.76 mmol) in dimethylbenzene (20 mL). The mixture was heated to 130° C. to reflux for 2 hours, then cooled to 25° C. and stirred for another 12 hours. The reaction solution was concentrated in vacuo and purified with column chromatography on silica gel ($CH_2Cl_2$/MeOH=100%~10%) to give methyl 6-(2-(ethoxycarbonyl)cyclopropyl)nicotinate. MS: 250.2 (M+1). Acq Method DRt=0.995 min). $^1$H NMR (400 MHz, $CD_3OD$): δ=8.94 (s, 1H), 8.23 (d, J=6.0 Hz, 1H), 7.45 (d, J=8.0 Hz, 1H), 4.13 (q, J=6.8 Hz, 2H), 3.90 (s, 3H), 2.68-2.66 (m, 1H), 2.27-2.24 (m, 1H), 1.64-1.59 (m, 2H), 1.23 (t, J=7.2 Hz, 3H) ppm.

Step 3: methyl 6-(2-(ethoxycarbonyl)cyclopropyl)piperidine-3-carboxylate

To a solution of methyl 6-(2-(ethoxycarbonyl)cyclopropyl)nicotinate (250 mg, 1.003 mmol) in acetonitrile (50 mL) was added $NaBH_3CN$ (63.0 mg, 1.003 mmol) at 0° C. The mixture was stirred at 15° C. for 12 h. The reaction solution was quenched with water (20 mL) and extracted with EtOAc (20 mL×2). The organic layer was concentrated to give crude product and purified with prep-HPLC (TFA) to give methyl 6-(2-(ethoxycarbonyl)cyclopropyl)piperidine-3-carboxylate. MS: 256.2 (M+1). Acq Method D (Rt=0.918 min). $^1$H NMR (400 MHz, $CDCl_3$)=4.21-4.09 (m, 2H), 3.36-3.39 (m, 4H), 2.91 (s, 2H), 2.31-1.55 (m, 6H), 3.90 (s, 3H), 1.28-0.93 (m, 5H) ppm.

Step 4: methyl 2-oxooctahydro-1H-cyclopropa[a]indolizine-5-carboxylate

A solution of methyl 6-(2-(ethoxycarbonyl)cyclopropyl)piperidine-3-carboxylate (200 mg, 0.783 mmol) in toluene (100 mL) was heated to 80° C. and stirred for 12 hours. The reaction solution was concentrated and purified with prep-HPLC (TFA) to give methyl 6-(2-(ethoxycarbonyl)cyclopropyl)piperidine-3-carboxylate. MS: 210.2 (M+1). (Method D, Rt=0.678 min). $^1$H NMR (400 MHz, $CDCl_3$) δ=4.38 (d, J=6.8 Hz, 1H), 3.67 (s, 3H), 3.60 (s, 1H), 2.77-2.73 (m, 1H), 2.64 (s, 1H), 2.25 (d, J=6.8 Hz, 1H), 1.95-1.92 (m, 2H), 1.84-1.80 (m, 5H), 1.63-1.62 (m, 1H), 1.50-1.47 (m, 1H), 0.96-0.92 (m, 1H), 0.59 (d, J=3.6 Hz, 1H) ppm.

Step 5: 2-oxooctahydro-1H-cyclopropa[a]indolizine-5-carboxylic acid

To a solution of methyl 6-(2-(ethoxycarbonyl)cyclopropyl)piperidine-3-carboxylate (5 g, 23.90 mmol) in THF/$H_2O$ (1:1, 80 mL) was added lithium hydroxide (1.431 g, 59.7 mmol). The mixture was stirred at 8° C. for 13 hours. The reaction was acidified to pH=3-5 with 2M aq.HCl and concentrated to give crude product 2-oxooctahydro-1H-cyclopropa[a]indolizine-5-carboxylic acid. MS: 196.2 (M+1). (Method D, Rt=0.418 min).

Step 6: N-((3-chloropyrazin-2-yl)methyl)-2-oxooctahydro-1H-cyclopropa[a]indolizine-5-carboxamide To the solution of 2-oxooctahydro-1H-cyclopropa[a]indolizine-5-carboxylic acid (3.5 g, 10.76 mmol) in $CH_2Cl_2$ (150 mL) and DMF (20 mL) was added EDC (3.09 g, 16.14 mmol) and DMAP (1.971 g, 16.14 mmol) under $N_2$, followed by (3-chloropyrazin-2-yl)methanamine hydrochloride (2.324 g, 12.91 mmol). The resulting mixture was stirred at 15° C. for 3 h. TLC (DCM:MeOH=10:1) and LCMS showed the starting material was consumed completely. The mixture was diluted with $H_2O$ (350 mL), extracted with DCM (80 mL×2). The combined organic layers were dried over anhydrous sodium sulfate, filtered and concentrated under vacuum to give crude product which was purified by combi flash (DCM:THF=100-20%) to give N-((3-chloropyrazin-2-yl)methyl)-2-oxooctahydro-1H-cyclopropa[a]indolizine-5-carboxamide. MS (ESI): 321.0 (M+1). Acq Method DRt=1.078 min). $^1$H NMR (400 MHz, $CDCl_3$)=8.45 (br. s., 1H), 8.37-8.30 (m, 1H), 7.72 (br. s., 1H), 4.75-4.60 (m, 2H), 4.24-4.13 (m, 1H), 3.79-3.64 (m, 1H), 2.89-2.78 (m, 1H), 2.15-2.03 (m, 3H), 1.99-1.87 (m, 1H), 1.85-1.72 (m, 1H), 1.36-1.22 (m, 2H), 1.19-1.01 (m, 1H), 0.79-0.61 (m, 1H).

Step 7: 5-(8-chloroimidazo[1,5-a]pyrazin-3-yl)hexahydro-1H-cyclopropa[a]indolizin-2(1aH)-one To a solution of N-((3-chloropyrazin-2-yl)methyl)-2-oxooctahydro-1H-cyclopropa[a]indolizine-5-carboxamide (2.0 g, 6.23 mmol) in acetonitrile (80 mL) was added $PCl_5$ (3.90 g, 18.70 mmol) in portions at 0° C. After addition, the mixture was allowed to warm to room temperature (20° C.) and stirred for 12 hrs under $N_2$ atmosphere. Then the mixture was poured into ice aq. $NaHCO_3$ (100 mL) slowly, and stirred for 20 min. The mixture was then extracted with DCM (20 mL×3). The organic layer was washed with brine (20 mL), dried over $Na_2SO_4$, and concentrated in vacuo to give the residue, which was then purified with prep_HPLC to give 5-(8-chloroimidazo[1,5-a]pyrazin-3-yl)hexahydro-1H-cyclopropa[a]indolizin-2(1aH)-one. MS (ESI): 303.0 (M+1). Acq Method DRt=1.178 min). $^1$H NMR (400 MHz, $CD_3OD$) δ=8.27-8.22 (m, 1H), 7.96 (s, 1H), 7.47-7.40 (m, 1H), 4.18-4.07 (m, 1H), 3.89-3.79 (m, 1H), 3.25-3.14 (m, 1H), 3.07-2.95 (m, 1H), 2.15 (d, J=9.0 Hz, 2H), 2.04-1.85 (m, 3H), 1.63-1.47 (m, 1H), 1.13-1.05 (m, 1H), 0.82 (d, J=3.5 Hz, 1H) ppm.

Step 8: 5-(1-bromo-8-chloroimidazo[1,5-a]pyrazin-3-yl)hexahydro-1H-cyclopropa[a]indolizin-2(1aH)-one NBS was added in one portion to the solution of 5-(8-chloroimidazo[1,5-a]pyrazin-3-yl)hexahydro-1H-cyclopropa[a]indolizin-2(1aH)-one (900 mg, 2.97 mmol) in DMF (12 mL) and the mixture was stirred at room temperature (20° C.) for 2 h. The mixture was then pouted into aq. $NaHCO_3$ (30 mL). The mixture was extracted with EtOAc (35 mL×3), washed with water (10 mL×2) and dried over $Na_2SO_4$. The organic layer was concentrated in vacuo, and purified with silica gel (methyl/dichloromethane 0%~15%) to give the crude product of 5-(1-bromo-8-chloroimidazo[1,5-a]pyrazin-3-yl)hexahydro-1H-cyclopropa[a]indolizin-2(1aH)-one. $^1$H NMR (400 MHz, $CD_3OD$)=8.20 (dt, J=5.1, 16.3 Hz, 1H), 7.39-7.32 (m, 1H), 4.15-4.06 (m, 2H), 3.88-3.79 (m, 1H), 3.63 (d, J=13.3 Hz, 1H), 3.17-3.08 (m, 1H), 2.19-2.11 (m, 3H), 2.00-1.88 (m, 3H), 1.58-1.47 (m, 1H) ppm. MS (ESI): 381/383 (M+1). Acq Method DRt=1.014 min).

Step 9: 5-(1-bromo-8-chloroimidazo[1,5-a]pyrazin-3-yl)hexahydro-1H-cyclopropa[a]indolizin-2(1aH)-one To the solution of 5-(1-bromo-8-chloroimidazo[1,5-a]pyrazin-3-yl)hexahydro-1H-cyclopropa[a]indolizin-2(1aH)-one (850 mg, 2.227 mmol)) in DMF (15 mL) was added $K_2CO_3$ (923 mg, 6.68 mmol) and (2,4-dimethoxyphenyl)

methanamine (447 mg, 2.67 mmol) and the mixture was stirred at 80° C. for 2 hours under $N_2$. The mixture was partitioned between water (50 mL) and ethyl acetate (150 mL), the organic layer was concentrated in vacuo. The residue was purified with preparative HPLC on Gilson 281 instrument fitted with a Waters XSELECT C18 150*30 mm*5 um using water and acetonitrile as the eluents. Mobile phase A: water (containing 0.1% TFA, v/v), mobile phase B: acetonitrile. Gradient: 19-35% B, 0-13.0 min; 100% B, 13.2-15.2 min; 10% B, 15.4-17 minFlowRate: 25 ml/min to give 5-(1-bromo-8-((2,4-dimethoxybenzyl)amino)imidazo [1,5-a]pyrazin-3-yl)hexahydro-1H-cyclopropa[a]indolizin-2(1aH)-one (isomer 1) (the faster eluting) $^1$H NMR (400 MHz, $CDCl_3$) δ=7.11-7.06 (m, 1H), 7.05-7.01 (m, 1H), 6.74 (br. s., 1H), 6.47 (d, J=2.0 Hz, 1H), 6.42 (dd, J=2.2, 8.0 Hz, 1H), 4.65 (d, J=5.5 Hz, 2H), 4.13 (dd, J=3.7, 13.5 Hz, 1H), 3.86 (s, 3H), 3.78 (s, 3H), 3.71-3.64 (m, 1H), 2.87 (t, J=12.3 Hz, 1H), 2.71-2.61 (m, 1H), 2.12-2.02 (m, 2H), 1.97 (d, J=7.8 Hz, 2H), 1.40-1.30 (m, 1H), 1.28-1.20 (m, 1H), 1.04-0.96 (m, 1H), 0.71 (d, J=3.9 Hz, 1H). HPLC METHOD C: (Rt=3.11 min). And 5-(1-bromo-8-((2,4-dimethoxybenzyl)amino)imidazo[1,5-a]pyrazin-3-yl)hexahydro-1H-cyclopropa[a]indolizin-2(1aH)-one (isomer 2) (the slower eluting). $^1$H NMR (400 MHz, $CDCl_3$) δ=7.14-7.07 (m, 2H), 6.72 (br. s., 1H), 6.47 (d, J=2.0 Hz, 1H), 6.42 (dd, J=2.3, 8.2 Hz, 1H), 4.65 (d, J=5.5 Hz, 2H), 4.19 (dd, J=3.5, 13.3 Hz, 1H), 3.86 (s, 3H), 3.78 (s, 3H), 3.74-3.67 (m, 1H), 3.46 (d, J=10.6 Hz, 1H), 2.98-2.89 (m, 1H), 2.84-2.75 (m, 1H), 2.10 (d, J=6.3 Hz, 2H), 1.97 (dd, J=3.1, 12.9 Hz, 1H), 1.90 (br. s., 1H), 1.74-1.68 (m, 1H), 1.51-1.40 (m, 1H), 1.12-1.05 (m, 1H). HPLC METHODC:Rt=3.21 min).

Step 10: 5-(1-bromo-8-chloroimidazo[1,5-a]pyrazin-3-yl)hexahydro-1H-cyclopropa[a]indolizin-2(1aH)-one (isomer 1A), 5-(1-bromo-8-chloroimidazo[1,5-a]pyrazin-3-yl)hexahydro-1H-cyclopropa[a] indolizin-2(1aH)-one (isomer 1B), 5-(1-bromo-8-chloroimidazo[1,5-a]pyrazin-3-yl)hexahydro-1H-cyclopropa[a]indolizin-2(1aH)-one (isomer 2A), and 5-(1-bromo-8-chloroimidazo[1,5-a]pyrazin-3-yl) hexahydro-1H-cyclopropa[a]indolizin-2(1aH)-one (isomer 2B)

5-(1-bromo-8-((2,4-dimethoxybenzyl)amino)imidazo[1,5-a]pyrazin-3-yl)hexahydro-1H-cyclopropa[a]indolizin-2 (1aH)-one (isomer 1) (300 mg, 0.585 mmol) was purified with chiral HPLC [SFC condition: Instrument: SFC-80; Column: AS 250×30 mm I.D., 20 um; Mobile phase: A: Supercritical $CO_2$, B: MeOH (0.1% $NH_3H_2O$), A:B=60:40 at 70 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.] to get trans-5-(1-bromo-8-((2,4-dimethoxybenzyl)amino)imidazo[1,5-a]pyrazin-3-yl)hexahydro-1H-cyclopropa[a]indolizin-2 (1aH)-one (isomer 1A)(faster eluting): $^1$H NMR (400 MHz, $CDCl_3$) δ=7.24 (d, J=8.6 Hz, 1H), 7.10-7.06 (m, 1H), 7.06-7.01 (m, 1H), 6.73 (t, J=5.3 Hz, 1H), 6.47 (s, 1H), 6.42 (dd, J=2.0, 8.2 Hz, 1H), 4.65 (d, J=5.5 Hz, 2H), 4.13 (dd, J=3.3, 13.1 Hz, 1H), 3.86 (s, 3H), 3.78 (s, 3H), 3.67 (d, J=9.4 Hz, 1H), 2.87 (t, J=12.3 Hz, 1H), 2.72-2.62 (m, 1H), 2.12-2.03 (m, 2H), 2.00-1.93 (m, 3H), 1.40-1.27 (m, 1H), 1.03-0.97 (m, 1H), 0.71 (d, J=3.9 Hz, 1H). Acq Method AS-H_S_3_5_40_3ML_8MIN_15CM.M (Rt=4.848 min, 100% Area). 5-(1-bromo-8-((2,4-dimethoxybenzyl)amino) imidazo[1,5-a]pyrazin-3-yl)hexahydro-1H-cyclopropa[a]indolizin-2(1aH)-one (isomer 1B) (slower eluting). $^1$H NMR (400 MHz, $CDCl_3$) δ=7.25 (d, J=8.2 Hz, 1H), 7.10-7.07 (m, 1H), 7.06-7.02 (m, 1H), 6.74 (t, J=5.3 Hz, 1H), 6.48 (s, 1H), 6.43 (dd, J=1.6, 8.2 Hz, 1H), 4.65 (d, J=5.5 Hz, 2H), 4.14 (dd, J=3.7, 13.1 Hz, 1H), 3.87 (s, 3H), 3.78 (s, 3H), 3.68 (d, J=12.1 Hz, 1H), 2.87 (t, J=12.3 Hz, 1H), 2.71-2.63 (m, 1H), 2.12-2.04 (m, 2H), 2.01-1.92 (m, 3H), 1.39-1.30 (m, 1H), 1.04-0.96 (m, 1H), 0.71 (d, J=3.9 Hz, 1H). Acq Method AS-H_S_3_5_40_3ML_8MIN_15CM.M (Rt=4.977 min, 99.6% Area). 5-(1-bromo-8-((2,4-dimethoxybenzyl)amino) imidazo[1,5-a]pyrazin-3-yl)hexahydro-1H-cyclopropa[a]indolizin-2(1aH)-one (isomer 2) (150 mg, 0.293 mmol) was purified with chiral HPLC [SFC condition: Instrument: SFC-80; Column: AS 250×30 mm I.D., 10 um; Mobile phase: A: Supercritical $CO_2$, B: MeOH (0.1°% $NH_3H_2O$), A:B=50:50 at 80 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.] to get Peak 1 5-(1-bromo-8-((2,4-dimethoxybenzyl)amino)imidazo[1,5-a]pyrazin-3-yl)hexahydro-1H-cyclopropa[a]indolizin-2(1aH)-one (isomer 2A): $^1$H NMR (400 MHz, $CDCl_3$) δ=7.29-7.22 (m, 1H), 7.15-7.06 (m, 2H), 6.73 (t, J=5.1 Hz, 1H), 6.48 (s, 1H), 6.43 (dd, J=2.0, 8.2 Hz, 1H), 4.66 (d, J=5.5 Hz, 2H), 4.19 (dd, J=3.7, 13.1 Hz, 1H), 3.87 (s, 3H), 3.79 (s, 3H), 3.47 (d, J=10.6 Hz, 1H), 3.00-2.89 (m, 1H), 2.84-2.75 (m, 1H), 2.10 (d, J=6.3 Hz, 1H), 1.98 (dd, J=2.7, 12.9 Hz, 1H), 1.91 (br. s., 1H), 1.76-1.67 (m, 1H), 1.51-1.41 (m, 1H), 1.27-1.20 (m, 1H), 1.13-1.06 (m, 1H), 0.72 (d, J=3.5 Hz, 1H). Acq Method AS-H_S_3_5_40_3ML_8MIN_15CM.M (Rt=4.030 min, 90.1% Area). 5-(1-bromo-8-((2,4-dimethoxybenzyl)amino) imidazo[1,5-a]pyrazin-3-yl)hexahydro-1H-cyclopropa[a]indolizin-2(1aH)-one (isomer 2B): $^1$H NMR (400 MHz, $CDCl_3$) δ=7.29-7.22 (m, 1H), 7.16-7.06 (m, 2H), 6.73 (t, J=5.1 Hz, 1H), 6.48 (s, 1H), 6.43 (dd, J=2.0, 8.2 Hz, 1H), 4.66 (d, J=5.5 Hz, 2H), 4.19 (dd, J=3.5, 12.9 Hz, 1H), 3.87 (s, 3H), 3.79 (s, 3H), 3.71 (q, J=6.8 Hz, 1H), 3.47 (d, J=9.4 Hz, 1H), 2.99-2.90 (m, 1H), 2.85-2.76 (m, 1H), 2.10 (d, J=6.3 Hz, 1H), 1.98 (dd, J=2.7, 12.9 Hz, 1H), 1.90 (br. s., 1H), 1.75-1.68 (m, 1H), 1.46 (dq, J=5.3, 12.1 Hz, 1H), 1.26-1.20 (m, 1H), 1.13-1.05 (m, 1H). Acq Method AS-H_S_3_5_40_3ML_8MIN_15CM.M (Rt=4.597 min, 95.97% Area).

Example 1

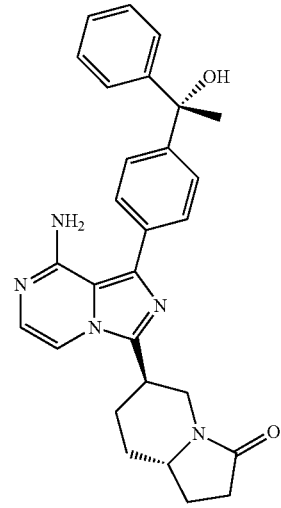 [SMILES: C[C@](O)(c1ccccc1)c1ccc(-c2nc([C@@H]3CC[C@H]4CCC(=O)N4C3)n3ccnc(N)c23)cc1]

(6R,8aS)-6-(8-amino-1-(4-((S)-1-hydroxy-1-phenyl-ethyl)phenyl)imidazo[1,5-a]pyrazin-3-yl)hexahydroindolizin-3(2H)-one

Step 1: (6R,8aS)-6-(8-amino-1-(4-(1-hydroxy-1-phenylethyl)phenyl)imidazo[1,5-a]pyrazin-3-yl)hexahydroindolizin-3(2H)-one To a solution of (6R,8aS)-6-(8-amino-1-bromoimidazo[1,5-a]pyrazin-3-yl)hexahydroindolizin-3(2H)-one (50 mg, 0.143 mmol), 1-phenyl-1-(4-(4,4,5,5-tetramethyl-1,3,2-dioxaborolan-2-yl)phenyl)ethanol (60.2 mg, 0.185 mmol) and $K_2CO_3$ (60 mg, 0.43 mmol) in dioxane/$H_2O$ (2 mL, 3:1) was added Pd(dppf) Cl2 (10.5 mg, 0.014 mmol) under $N_2$ atmosphere, and stirred at 90° C. for 60 min. LCMS showed that the reaction was complete, then the mixture was cooled to room temperature, $H_2O$ (5 mL) was added, and the mixture was extracted with EtOAc (10 mL×3). The organic layer was evaporated to get the crude product, which was then separated by prep-HPLC to afford the compound (6R,8aS)-6-(8-amino-1-(4-(1-hydroxy-1-phenylethyl)phenyl)imidazo[1,5-a]pyrazin-3-yl)hexahydroindolizin-3(2H)-one. $^1$H NMR (400 MHz, $CD_3OD$) δ=7.88 (d, J=6.0 Hz, 1H), 7.71-7.60 (m, 4H), 7.53-7.49 (m, 2H), 7.37-7.30 (m, 2H), 7.27-7.21 (m, 1H), 7.02 (d, J=6.0 Hz, 1H), 4.29 (dd, J=2.6, 12.9 Hz, 1H), 3.70 (dtd, J=3.6, 7.1, 10.9 Hz, 1H), 3.38-3.34 (m, 1H), 3.32-3.28 (m, 1H), 3.22-3.13 (m, 1H), 2.51-2.44 (m, 2H), 2.41-2.30 (m, 1H), 2.20 (d, J=12.8 Hz, 1H), 2.14-2.07 (m, 1H), 2.06-1.95 (m, 4H), 1.81-1.69 (m, 1H), 1.59-1.47 (m, 1H) ppm. MS: 468.4 (M+1).

Step 2: (6R,8aS)-6-(8-amino-1-(4-((S)-1-hydroxy-1-phenylethyl)phenyl)imidazo[1,5-a]pyrazin-3-yl)hexahydroindolizin-3(2H)-one The compound (6R,8aS)-6-(8-amino-1-(4-(1-hydroxy-1-phenylethyl)phenyl)imidazo[1,5-a]pyrazin-3-yl)hexahydroindolizin-3(2H)-one (150 mg, 0.32 mmol) was separated by SFC to get the crude product, which was then purified by prep-HPLC to get the compound (6R,8aS)-6-(8-amino-1-(4-((S)-1-hydroxy-1-phenylethyl)phenyl)imidazo[1,5-a]pyrazin-3-yl)hexahydroindolizin-3(2H)-one (34.92 mg) as a white solid. SFC method: Instrument: Thar 80 Column:AD 250 mm*30 mm, 10 um Mobile phase: A: Supercritical $CO_2$, B: EtOH (0.05% $NH_3H_2O$, A:B=45:55 at 80 ml/min Column Temp: 38° C. Nozzle Pressure: 100 Bar Nozzle Temp: 60° C. Evaporator Temp: 20° C. Trimmer Temp: 25° C. Wavelength: 220 nm. $^1$H NMR (400 MHz, $CD_3OD$) δ=7.88 (d, J=6.0 Hz, 1H), 7.70-7.63 (m, 4H), 7.54-7.49 (m, 2H), 7.36-7.30 (m, 2H), 7.27-7.21 (m, 1H), 7.02 (d, J=5.8 Hz, 1H), 4.29 (dd, J=2.6, 12.9 Hz, 1H), 3.75-3.65 (m, 1H), 3.36 (d, J=2.8 Hz, 1H), 3.31-3.28 (m, 1H), 3.23-3.13 (m, 1H), 2.51-2.44 (m, 2H), 2.41-2.30 (m, 1H), 2.20 (d, J=13.6 Hz, 1H), 2.14-2.07 (m, 1H), 2.07-1.94 (m, 4H), 1.81-1.69 (m, 1H), 1.59-1.47 (m, 1H) ppm. MS: 468.4 (M+1).

Example 2

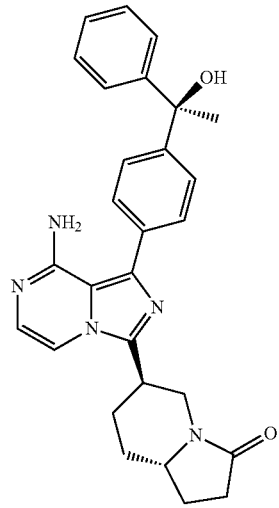 [SMILES: C[C@@](O)(c1ccccc1)c1ccc(-c2nc([C@@H]3CC[C@H]4CCC(=O)N4C3)n3ccnc(N)c23)cc1]

(6R,8aS)-6-(8-amino-1-(4-((R)-1-hydroxy-1-phenylethyl)phenyl)imidazo[1,5-a]pyrazin-3-yl)hexahydroindolizin-3(2H)-one The compound (6R,8aS)-6-(8-amino-1-(4-(1-hydroxy-1-phenylethyl)phenyl)imidazo[1,5-a]pyrazin-3-yl)hexahydroindolizin-3(2H)-one (150 mg, 0.32 mmol) was separated by SFC to get the crude product, which was then purified by prep-HPLC to get the compound (6R,8aS)-6-(8-amino-1-(4-((R)-1-hydroxy-1-phenylethyl)phenyl)imidazo[1,5-a]pyrazin-3-yl)hexahydroindolizin-3(2H)-one (34.92 mg) as a solid. SFC method: Instrument: Thar 80 Column: AD 250 mm*30 mm, 10 um Mobile phase: A: Supercritical $CO_2$, B: EtOH (0.05% $NH_3H_2O$, A:B=45:55 at 80 ml/min Column Temp: 38° C. Nozzle Pressure: 100 Bar Nozzle Temp: 60° C. Evaporator Temp: 20° C. Trimmer Temp: 25° C. Wavelength: 220 nm. $^1$H NMR (400 MHz, $CD_3OD$) δ=7.88 (d, J=6.0 Hz, 1H), 7.70-7.62 (m, 4H), 7.53-7.48 (m, 2H), 7.36-7.30 (m, 2H), 7.27-7.21 (m, 1H), 7.02 (d, J=6.0 Hz, 1H), 4.33-4.25 (m, 1H), 3.70 (dtd, J=3.6, 7.2, 10.9 Hz, 1H), 3.38-3.34 (m, 1H), 3.31-3.28 (m, 1H), 3.22-3.13 (m, 1H), 2.51-2.44 (m, 2H), 2.41-2.30 (m, 1H), 2.24-2.16 (m, 1H), 2.14-2.07 (m, 1H), 2.06-1.94 (m, 4H), 1.81-1.69 (m, 1H), 1.59-1.46 (m, 1H) ppm. MS: 468.4 (M+1).

Example 3

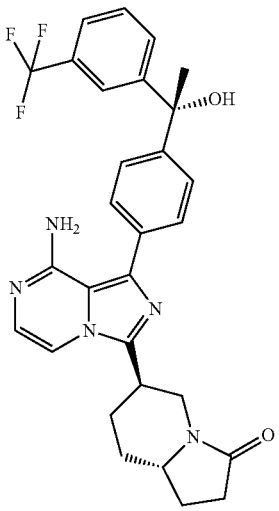 [SMILES: C[C@@](O)(c1ccc(-c2nc([C@@H]3CC[C@H]4CCC(=O)N4C3)n3ccnc(N)c23)cc1)c1cccc(C(F)(F)F)c1]

(6R,8aS)-6-(8-amino-1-(4-((R)-1-hydroxy-1-(3-(trifluoromethyl)phenyl)ethyl)phenyl)imidazo[1,5-a]pyrazin-3-yl)hexahydroindolizin-3(2H)-one Step 1: (6R,8aS)-6-(1-(4-acetylphenyl)-8-aminoimidazo[1,5-a]pyrazin-3-yl)hexahydroindolizin-3(2H)-one To a solution of (6R,8aS)-6-(8-amino-1-bromoimidazo[1,5-a]pyrazin-3-yl)hexahydroindolizin-3(2H)-one (500 mg, 1.32 mmol) and (4-acetylphenyl)boronic acid (0.78 g, 1.98 mmol) in 5 mL of dioxane/H$_2$O (4:1) was added K$_2$CO$_3$ (0.55 g, 3.97 mmol) and Pd(dppf) Cl2 (catalytic amount, 10 mg) under nitrogen protection. Then the mixture was heated to 80° C. for 4 hour. Then the mixture was poured into water (50 mL) and extracted with EtOAc (80 mL×3). The organic layer was dried and concentrated in vacuo and purified with HPLC to give (6R,8aS)-6-(1-(4-acetylphenyl)-8-aminoimidazo[1,5-a]pyrazin-3-yl)hexahydroindolizin-3(2H)-one. 1HNMR (400 MHz, CDCl$_3$) δ=8.11-8.05 (m, 2H), 7.81-7.75 (m, 2H), 7.31 (d, J=5.0 Hz, 1H), 7.15 (d, J=5.3 Hz, 1H), 5.19 (br. s., 2H), 4.47-4.39 (m, 1H), 3.65-3.56 (m, 1H), 3.16-3.00 (m, 2H), 2.66 (s, 3H), 2.50-2.43 (m, 2H), 2.31 (td, J=7.3, 13.1 Hz, 1H), 2.24-2.05 (m, 3H), 1.76-1.65 (m, 1H), 1.48-1.36 (m, 1H) ppm.

Step 2: (6R,8aS)-6-(8-amino-1-(4-(1-hydroxy-1-(3-(trifluoromethyl)phenyl)ethyl)phenyl)imidazo[1,5-a]pyrazin-3-yl)hexahydroindolizin-3(2H)-one To a solution of 1-bromo-3-(trifluoromethyl)benzene (200 mg, 0.89 mmol) in 5 mL of THF was added Mg (43.2 mg, 1.78 mmol) under nitrogen protection and stirred at 80° C. for 2 h. Then the mixture was added to a solution of (6R,8aS)-6-(1-(4-acetylphenyl)-8-aminoimidazo[1,5-a]pyrazin-3-yl)hexahydroindolizin-3(2H)-one (86.5 mg, 0.22 mmol) in THF (3 mL) at 0° C. under nitrogen protection and stirred at 20° C. for 12 h. The mixture was poured into water (50 mL) and extracted with EA (80 mL×3). The organic layer was dried and concentrated in vacuo and purified with HPLC to give (6R,8aS)-6-(8-amino-1-(4-(1-hydroxy-1-(3-(trifluoromethyl)phenyl)ethyl)phenyl)imidazo[1,5-a]pyrazin-3-yl)hexahydroindolizin-3(2H)-one. $^1$HNMR (400 MHz, CD$_3$OD) δ=7.88 (d, J=6.0 Hz, 1H), 7.85 (s, 1H), 7.77 (d, J=7.0 Hz, 1H), 7.72-7.66 (m, 4H), 7.59-7.51 (m, 2H), 7.02 (d, J=6.0 Hz, 1H), 4.29 (dd, J=2.8, 13.1 Hz, 1H), 3.75-3.66 (m, 1H), 3.39-3.34 (m, 1H), 3.23-3.13 (m, 1H), 2.51-2.44 (m, 2H), 2.41-2.31 (m, 1H), 2.24-2.16 (m, 1H), 2.11 (dd, J=3.3, 13.1 Hz, 1H), 2.03 (s, 3H), 1.99 (br. s., 1H), 1.80-1.70 (m, 1H), 1.59-1.47 (m, 1H) ppm. MS: 536.4 (M+1).

Step 3: (6R,8aS)-6-(8-amino-1-(4-((R)-1-hydroxy-1-(3-(trifluoromethyl)phenyl)ethyl)phenyl)imidazo[1,5-a]pyrazin-3-yl)hexahydroindolizin-3(2H)-one The compound (6R,8aS)-6-(8-amino-1-(4-(1-hydroxy-1-phenylethyl)phenyl)imidazo[1,5-a]pyrazin-3-yl)hexahydroindolizin-3(2H)-one (150 mg, 0.32 mmol) was separated by SFC to get the crude product, which was then purified by prep-HPLC to get the compound (6R,8aS)-6-(8-amino-1-(4-((R)-1-hydroxy-1-phenylethyl)phenyl)imidazo[1,5-a]pyrazin-3-yl)hexahydroindolizin-3(2H)-one (34.92 mg) as a solid. SFC method: Instrument: "Column: Chiralpak AD-3 50*4.6 mm I.D., 3 um Mobile phase: methanol (0.05% DEA) in CO$_2$ from 5% to 40% Flow rate: 4 mL/min Wavelength: 220 nm". $^1$H NMR (400 MHz, CD$_3$OD) δ=7.82 (s, 1H), 7.75 (d, J=7.0 Hz, 1H), 7.68-7.59 (m, 5H), 7.57-7.49 (m, 2H), 7.05 (d, J=5.0 Hz, 1H), 4.28 (dd, J=2.8, 12.8 Hz, 1H), 3.75-3.66 (m, 1H), 3.31-3.23 (m, 1H), 3.18-3.09 (m, 1H), 2.50-2.43 (m, 2H), 2.40-2.30 (m, 1H), 2.18 (d, J=13.3 Hz, 1H), 2.13-2.05 (m, 1H), 2.02 (s, 3H), 2.01-1.93 (m, 1H), 1.81-1.68 (m, 1H), 1.59-1.47 (m, 1H) ppm. LCMS Method C: retention time: 2.701 min, (M+H)+ m/z: 536.2.

Example 4

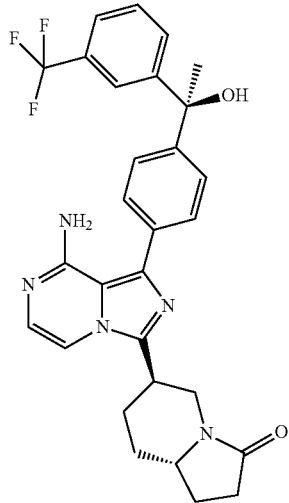 [SMILES: C[C@](O)(c1ccc(-c2nc([C@@H]3CC[C@H]4CCC(=O)N4C3)n3ccnc(N)c23)cc1)c1cccc(C(F)(F)F)c1]

(6R,8aS)-6-(8-amino-1-(4-((S)-1-hydroxy-1-(3-(trifluoromethyl)phenyl)ethyl)phenyl)imidazo[1,5-a]pyrazin-3-yl)hexahydroindolizin-3(2H)-one Step 1: (6R,8aS)-6-(8-amino-1-(4-((S)-1-hydroxy-1-(3-(trifluoromethyl)phenyl)ethyl)phenyl)imidazo[1,5-a]pyrazin-3-yl)hexahydroindolizin-3(2H)-one The compound (6R,8aS)-6-(8-amino-1-(4-(1-hydroxy-1-phenylethyl)phenyl)imidazo[1,5-a]pyrazin-3-yl)hexahydroindolizin-3(2H)-one (150 mg, 0.32 mmol) was separated by SFC to get the crude product, which was then purified by prep-HPLC to get the compound (6R,8aS)-6-(8-amino-1-(4-((R)-1-hydroxy-1-phenylethyl)phenyl)imidazo[1,5-a]pyrazin-3-yl)hexahydroindolizin-3(2H)-one (34.92 mg) as a solid. SFC method: Instrument: "Column: Chiralpak AD-3 50*4.6 mm I.D., 3 um Mobile phase: methanol (0.05% DEA) in $CO_2$ from 5% to 40% Flow rate: 4 mL/min Wavelength: 220 nm". $^1$H NMR (400 MHz, $CD_3OD$) δ=7.82 (s, 1H), 7.75 (d, J=7.3 Hz, 1H), 7.68-7.59 (m, 5H), 7.57-7.49 (m, 2H), 7.05 (d, J=5.0 Hz, 1H), 4.28 (dd, J=2.8, 12.8 Hz, 1H), 3.70 (dtd, J=3.6, 7.1, 10.7 Hz, 1H), 3.31-3.23 (m, 1H), 3.18-3.08 (m, 1H), 2.52-2.44 (m, 2H), 2.40-2.30 (m, 1H), 2.22-2.14 (m, 1H), 2.09 (dd, J=3.4, 13.2 Hz, 1H), 2.02 (s, 3H), 2.01-1.93 (m, 1H), 1.80-1.70 (m, 1H), 1.58-1.48 (m, 1H). LCMS Method D Retention time: 2.705 min, (M+H)+ m/z: 536.2.

Example 5

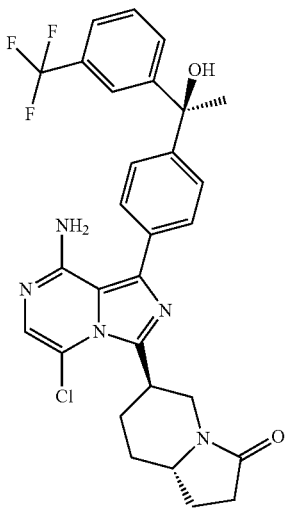 [SMILES: C[C@](O)(c1ccc(-c2nc([C@@H]3CC[C@H]4CCC(=O)N4C3)n3c(Cl)cnc(N)c23)cc1)c1cccc(C(F)(F)F)c1]

(6R,8aS)-6-(8-amino-5-chloro-1-(4-((S)-1-hydroxy-1-(3-(trifluoromethyl)phenyl)ethyl)phenyl)imidazo[1,5-a]pyrazin-3-yl)hexahydroindolizin-3(2H)-one Step 1: (6R,8aS)-6-(8-amino-5-chloro-1-(4-(1-hydroxy-1-(3-(trifluoromethyl)phenyl)ethyl)phenyl)imidazo[1,5-a]pyrazin-3-yl)hexahydroindolizin-3(2H)-one The mixture of (6R,8aS)-6-(8-amino-1-bromo-5-chloroimidazo[1,5-a]pyrazin-3-yl)hexahydroindolizin-3(2H)-one (100 mg, 0.26 mmol), 1-(4-(4,4,5,5-tetramethyl-1,3,2-dioxaborolan-2-yl)phenyl)-1-(3-(trifluoromethyl)phenyl)ethanol (205 mg, 0.52 mmol), $Na_2CO_3$ (109 mg, 0.78 mmol) and Pd(dppf) Cl2(10 mg) was added in dioxane/$H_2O$ (2 mL/0.5 mL) and stirred at 90° C. for 20 h under $N_2$. Removed the solvent in vacuum and the residue was purified by HPLC directly to afford (6R,8aS)-6-(8-amino-5-chloro-1-(4-(1-hydroxy-1-(3-(trifluoromethyl)phenyl)ethyl)phenyl)imidazo[1,5-a]pyrazin-3-yl)hexahydroindolizin-3(2H)-one.

Step 2: (6R,8aS)-6-(8-amino-5-chloro-1-(4-((S)-1-hydroxy-1-(3-(trifluoromethyl)phenyl)ethyl)phenyl)imidazo[1,5-a]pyrazin-3-yl)hexahydroindolizin-3(2H)-one The compound (6R,8aS)-6-(8-amino-5-chloro-1-(4-(1-hydroxy-1-(3-(trifluoromethyl)phenyl)ethyl)phenyl)imidazo[1,5-a]pyrazin-3-yl)hexahydroindolizin-3(2H)-one was separated by SFC to get the crude product, which was then purified by prep-HPLC to get the compound (6R,8aS)-6-(8-amino-5-chloro-1-(4-((S)-1-hydroxy-1-(3-(trifluoromethyl)phenyl)ethyl)phenyl)imidazo[1,5-a]pyrazin-3-yl)hexahydroindolizin-3(2H)-one. SFC method: Chiralpak AD-3 50*4.6 mm I.D., 3 um Mobile phase: 40% ethanol (0.05% DEA) in $CO_2$ Flow rate: 4 mL/min Wavelength: 220 nm. $^1$H NMR (400 MHz, $CD_3OD$) δ=7.81 (s, 1H) 7.72 (d, J=7.03 Hz, 1H) 7.65-7.60 (m, 2H) 7.59-7.55 (m, 2H) 7.55-7.47 (m, 2H) 6.98 (s, 1H) 4.43-4.35 (m, 1H) 4.00-3.89 (m, 1H) 3.70-3.58 (m, 1H) 3.17 (t, J=12.17 Hz, 1H) 2.48-2.38 (m, 2H) 2.37-2.23 (m, 2H) 2.09-2.02 (m, 1H) 2.00 (s, 3H) 1.98-1.92 (m, 1H) 1.77-1.65 (m, 1H) 1.45 (dd, J=11.54, 3.26 Hz, 1H) MS-ESI (m/z): 570.2 (M+1)$^+$ Acq Method D: 1.067 min)

Example 6

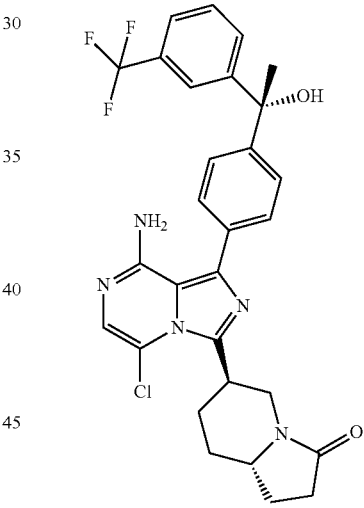

(6R,8aS)-6-(8-amino-5-chloro-1-(4-((R)-1-hydroxy-1-(3-(trifluoromethyl)phenyl)ethyl)phenyl)imidazo[1,5-a]pyrazin-3-yl)hexahydroindolizin-3(2H)-one Step 1: (6R,8aS)-6-(8-amino-5-chloro-1-(4-((R)-1-hydroxy-1-(3-(trifluoromethyl)phenyl)ethyl)phenyl)imidazo[1,5-a]pyrazin-3-yl)hexahydroindolizin-3(2H)-one The compound (6R,8aS)-6-(8-amino-5-chloro-1-(4-(1-hydroxy-1-(3-(trifluoromethyl)phenyl)ethyl)phenyl)imidazo[1,5-a]pyrazin-3-yl)hexahydroindolizin-3(2H)-one was separated by SFC to get the crude product, which was then purified by prep-HPLC to get the compound (6R,8aS)-6-(8-amino-5-chloro-1-(4-((S)-1-hydroxy-1-(3-(trifluoromethyl)phenyl)ethyl)phenyl)imidazo[1,5-a]pyrazin-3-yl)hexahydroindolizin-3(2H)-one. SFC method: Chiralpak AD-3

50*4.6 mm I.D., 3 um Mobile phase: 40% ethanol (0.05% DEA) in CO₂ Flow rate: 4 mL/min Wavelength: 220 nm. ¹H NMR (400 MHz, CD₃OD) δ=7.81 (s, 1H) 7.72 (d, J=7.03 Hz, 1H) 7.63 (m, J=8.53 Hz, 2H) 7.57 (m, J=8.53 Hz, 2H) 7.55-7.47 (m, 2H) 6.99 (s, 1H) 4.43-4.34 (m, 1H) 4.02-3.91 (m, 1H) 3.70-3.60 (m, 1H) 3.17 (t, J=12.30 Hz, 1H) 2.48-2.40 (m, 2H) 2.36-2.25 (m, 2H) 2.08-2.02 (m, 1H) 2.00 (s, 3H) 1.97 (d, J=2.76 Hz, 1H) 1.78-1.65 (m, 1H) 1.46 (dd, J=12.30, 2.76 Hz, 1H) MS-ESI (m/z): 570.2 (M+1)+Acq Method D: 1.067 min)

Example 7

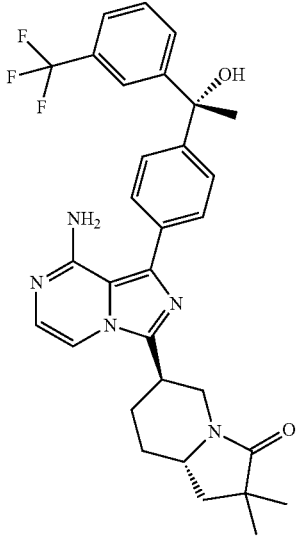 [SMILES: CC1(C)C[C@@H]2CC[C@@H](c3nc(-c4ccc([C@@](C)(O)c5cccc(C(F)(F)F)c5)cc4)c4c(N)nccn34)CN2C1=O]

(6R,8aS)-6-(8-amino-1-(4-((R)-1-hydroxy-1-(3-(trifluoromethyl)phenyl)ethyl)phenyl)imidazo[1,5-a]pyrazin-3-yl)-2,2-dimethylhexahydroindolizin-3(2H)-one Step 1: (6R,8aS)-6-(8-amino-1-(4-((R)-1-hydroxy-1-(3-(trifluoromethyl)phenyl)ethyl)phenyl)imidazo[1,5-a]pyrazin-3-yl)-2,2-dimethylhexahydroindolizin-3(2H)-one The mixture of (6R,8aS)-6-(8-amino-1-bromoimidazo[1,5-a]pyrazin-3-yl)-2,2-dimethylhexahydroindolizin-3(2H)-one (300 mg, 0.796 mmol), (R)-1-(4-(4,4,5,5-tetramethyl-1,3,2-dioxaborolan-2-yl)phenyl)-1-(3-(trifluoromethyl)phenyl)ethanol (405.61 mg, 1.034 mmol), Pd(dppf) Cl2 (58.55 mg, 0.080 mmol) and Na₂CO₃ (252.99 mg, 2.387 mmol) in dioxane/H₂O (16 mL/4 mL) was stirred at 100° C. for 24 h under nitrogen atmosphere. Remove the solvent in vacuo. The mixture was treated with ethyl acetate and water, the organic layer was separated, dried over sodium sulfate, filtered and the filtrate was concentrated. The residue was purified by preparative HPLC separation to afford the desired compound (6R,8aS)-6-(8-amino-1-(4-((R)-1-hydroxy-1-(3-(trifluoromethyl)phenyl)ethyl)phenyl)imidazo[1,5-a]pyrazin-3-yl)-2,2-dimethylhexahydroindolizin-3(2H)-one. ¹H NMR (400 MHz, CD₃OD) δ=7.88 (d, J=5.6 Hz, 1H) 7.84 (s, 1H) 7.76 (d, J=6.4 Hz, 1H) 7.72-7.62 (m, 4H) 7.58-7.48 (m, 2H) 7.01 (d, J=5.6 Hz, 1H) 4.26 (dd, J1=12.8, J2=2.4 Hz, 1H) 3.62 (d, J=8.0 Hz, 1H) 3.34 (s, 1H) 3.22-3.10 (m, 1H) 2.28-2.10 (m, 3H) 2.06-1.92 (m, 4H) 1.62 (dd, J1=12.8, J2=8.0 Hz, 1H) 1.54-1.39 (m, 1H) 1.22 (s, 3H) 1.15 (s, 3H) LCMS Method C: 2.319 min, (M+H)+ m/z: 564.2.

Example 8 and 9

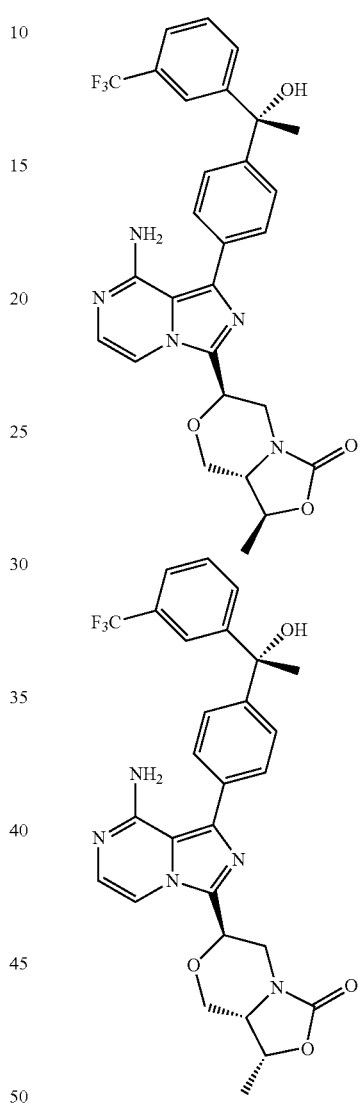

(6R,8aS)-6-(8-amino-1-(4-((R)-1-hydroxy-1-(3-(trifluoromethyl)phenyl)ethyl)phenyl)imidazo[1,5-a]pyrazin-3-yl)-1-methyltetrahydrooxazolo[4,3-c][14]oxazin-3(1H)-one (isomer 1) and (6R,8aS)-6-(8-amino-1-(4-((R)-1-hydroxy-1-(3-(trifluoromethyl)phenyl)ethyl)phenyl)imidazo[1,5-a]pyrazin-3-yl)-1-methyltetrahydrooxazolo[4,3-c][1,4]oxazin-3(1H)-one (isomer 2)

(6R,8aS)-6-(8-aminoimidazo[1,5-a]pyrazin-3-yl)-1-methyltetrahydrooxazolo[4,3-c][1,4]oxazin-3(1H)-one (100 mg, 0.346 mmol), (R)-1-(4-(4,4,5,5-tetramethyl-1,3,2-dioxaborolan-2-yl)phenyl)-1-(3-(trifluoromethyl)phenyl)ethanol (163 mg, 0.415 mmol) and K₂CO₃ (143 mg, 1.037 mmol) were added into dioxane/H₂O (1 mL/0.3 mL)

sequently. After de-gassed three times, PdCl$_2$(dppf) (12.65 mg, 0.017 mmol) was added under nitrogen protection. Then the mixture was heated to 90° C. and stirred for 2 hour. After cooled to room temperature (15° C.), the mixture was purified by prep-HPLC to get (6R,8aS)-6-(8-amino-1-(4-((R)-1-hydroxy-1-(3-(trifluoromethyl)phenyl)ethyl)phenyl) imidazo[1,5-a]pyrazin-3-yl)-1-methyltetrahydrooxazolo[4, 3-c][1,4]oxazin-3(1H)-one (isomer 1). MS: 554.1 (M+1). $^1$H NMR (400 MHz, CD$_3$OD) δ=7.91 (d, J=4.7 Hz, 1H), 7.83 (s, 1H), 7.73 (d, J=7.0 Hz, 1H), 7.65 (s, 4H), 7.55-7.47 (m, 2H), 7.00 (br. s., 1H), 5.00 (dd, J=2.7, 11.0 Hz, 1H), 4.42-4.34 (m, 1H), 4.20-4.10 (m, 2H), 3.76-3.65 (m, 3H), 1.99 (s, 3H), 1.45 (d, J=6.3 Hz, 3H) ppm; and (6R,8aS)-6-(8-amino-1-(4-((R)-1-hydroxy-1-(3-(trifluoromethyl)phenyl)ethyl)phenyl)imidazo[1,5-a]pyrazin-3-yl)-1-methyltetrahydrooxazolo[4,3-c][1,4]oxazin-3(1H)-one (isomer 2). MS: 554.1 (M+1). $^1$H NMR (400 MHz, CD$_3$OD) δ=7.91 (d, J=5.9 Hz, 1H), 7.83 (s, 1H), 7.73 (d, J=7.0 Hz, 1H), 7.65 (s, 4H), 7.54-7.47 (m, 2H), 7.00 (d, J=5.9 Hz, 1H), 4.97 (dd, J=2.7, 11.0 Hz, 1H), 4.14 (dd, J=2.7, 13.7 Hz, 1H), 4.09 (d, J=3.1 Hz, 1H), 4.06 (br. s., 1H), 4.01 (dd, J=3.5, 7.8 Hz, 1H), 3.94-3.87 (m, 1H), 3.74 (dd, J=11.2, 13.5 Hz, 1H), 1.99 (s, 3H), 1.37 (d, J=6.7 Hz, 3H) ppm.

Example 10

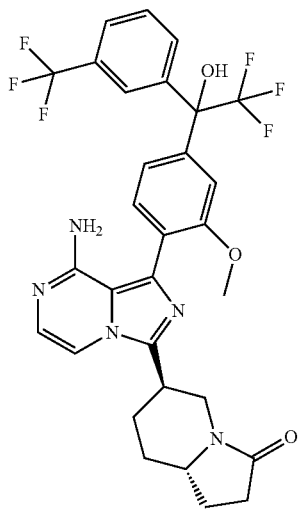 [SMILES: COc1cc(C(O)(c2cccc(C(F)(F)F)c2)C(F)(F)F)ccc1-c1nc([C@@H]2CC[C@H]3CCC(=O)N3C2)n2ccnc(N)c12]

(6R,8aS)-6-(8-amino-1-(2-methoxy-4-(2,2,2-trifluoro-1-hydroxy-1-(3-(trifluoromethyl)phenyl)ethyl) phenyl)imidazo[1,5-a]pyrazin-3-yl)hexahydroindolizin-3(2H)-one Step 1: (6R,8aS)-6-(8-amino-1-(2-methoxy-4-(2,2,2-trifluoro-1-hydroxy-1-(3-(trifluoromethyl)phenyl) ethyl)phenyl)imidazo[1,5-a]pyrazin-3-yl)hexahydroindolizin-3(2H)-one To a solution of 2,2,2-trifluoro-1-(3-methoxy-4-(4,4,5,5-tetramethyl-1,3,2-dioxaborolan-2-yl)phenyl)-1-(3-(trifluoromethyl)phenyl)ethanol (180 mg, 0.378 mmol) and (6R, 8aS)-6-(8-amino-1-bromoimidazo[1,5-a]pyrazin-3-yl) hexahydroindolizin-3(2H)-one (132 mg, 0.378 mmol) in 1,4-Dioxane (15 mL) were added PdCl2(dppf) (13.83 mg, 0.019 mmol), K$_2$CO$_3$ (131 mg, 0.945 mmol) and Water (5 mL). The reaction mixture was stirred at 80° C. for 4 hrs under N$_2$ protection. The reaction mixture was diluted with EtOAc (20 mL) and washed with water (20 mL) and brine, dried over Na$_2$SO$_4$ and concentrated in vacuo. The residue was purified by pre-HPLC to afford (6R,8aS)-6-(8-amino-1-(2-methoxy-4-(2,2,2-trifluoro-1-hydroxy-1-(3-(trifluoromethyl)phenyl)ethyl)phenyl) imidazo[1,5-a]pyrazin-3-yl) hexahydroindolizin-3(2H)-one. MS-ESI (m/z): 620 (M+1)$^+$ (Acq Method D:Rt:1.085 min).

Step 2: (6R,8aS)-6-(8-amino-1-(2-methoxy-4-(2,2,2-trifluoro-1-hydroxy-1-(3-(trifluoromethyl)phenyl) ethyl)phenyl)imidazo[1,5-a]pyrazin-3-yl)hexahydroindolizin-3(2H)-one (6R,8aS)-6-(8-amino-1-(2-methoxy-4-(2,2,2-trifluoro-1-hydroxy-1-(3-(trifluoromethyl)phenyl)ethyl)phenyl)imidazo[1,5-a]pyrazin-3-yl)hexahydroindolizin-3(2H)-one (peak 1) was obtained from (6R,8aS)-6-(8-amino-1-(2-methoxy-4-(2,2,2-trifluoro-1-hydroxy-1-(3-(trifluoromethyl)phenyl)ethyl)phenyl)imidazo[1,5-a]pyrazin-3-yl) hexahydroindolizin-3(2H)-one (85 mg, 0.137 mmol) under SFC purification. Column: Chiralcel OD-3 150×4.6 mm I.D., 3 um Mobile phase: ethanol (0.05% DEA) in CO$_2$ from 5% to 40% Flow rate: 2.5 mL/min Wavelength: 220 nm. $^1$H NMR (400 MHz, CD$_3$OD) δ=7.88 (s, 1H), 7.85-7.78 (m, 2H), 7.69 (d, J=7.4 Hz, 1H), 7.64-7.56 (m, 1H), 7.53 (d, J=8.2 Hz, 1H), 7.42 (s, 1H), 7.20 (d, J=7.8 Hz, 1H), 6.96 (d, J=5.9 Hz, 1H), 4.25 (dd, J=2.7, 12.5 Hz, 1H), 3.81 (s, 3H), 3.66 (d, J=7.0 Hz, 1H), 3.28-3.23 (m, 1H), 3.17-3.06 (m, 1H), 2.49-2.39 (m, 2H), 2.37-2.26 (m, 1H), 2.16 (d, J=12.9 Hz, 1H), 2.06 (dd, J=2.9, 13.1 Hz, 1H), 1.95 (q, J=12.7 Hz, 1H), 1.78-1.64 (m, 1H), 1.56-1.42 (m, 1H) ppm. MS-ESI (m/z): 620 (M+1)+(Acq Method D:Rt:1.085 min).

Example 11

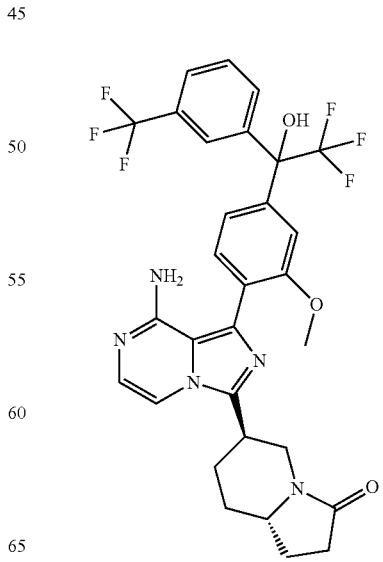

(6R,8aS)-6-(8-amino-1-(2-methoxy-4-(2,2,2-trifluoro-1-hydroxy-1-(3-(trifluoromethyl)phenyl)ethyl)phenyl)imidazo[1,5-a]pyrazin-3-yl)hexahydroindolizin-3(2H)-one Step 1: (6R,8aS)-6-(8-amino-1-(2-methoxy-4-(2,2,2-trifluoro-1-hydroxy-1-(3-(trifluoromethyl)phenyl)ethyl)phenyl)imidazo[1,5-a]pyrazin-3-yl)hexahydroindolizin-3(2H)-one (6R,8aS)-6-(8-amino-1-(2-methoxy-4-(2,2,2-trifluoro-1-hydroxy-1-(3-(trifluoromethyl)phenyl)ethyl)phenyl)imidazo[1,5-a]pyrazin-3-yl)hexahydroindolizin-3(2H)-one (peak 2) was obtained from (6R,8aS)-6-(8-amino-1-(2-methoxy-4-(2,2,2-trifluoro-1-hydroxy-1-(3-(trifluoromethyl)phenyl)ethyl)phenyl)imidazo[1,5-a]pyrazin-3-yl)hexahydroindolizin-3(2H)-one (85 mg, 0.137 mmol) under SFC purification. Column: Chiralcel OD-3 150×4.6 mm I.D., 3 um Mobile phase: ethanol (0.05% DEA) in $CO_2$ from 5% to 40% Flow rate: 2.5 mL/min Wavelength: 220 nm. $^1$H NMR (400 MHz, $CD_3OD$) δ=7.88 (s, 1H), 7.85-7.78 (m, 2H), 7.69 (d, J=7.8 Hz, 1H), 7.64-7.56 (m, 1H), 7.53 (d, J=7.8 Hz, 1H), 7.41 (s, 1H), 7.21 (d, J=8.2 Hz, 1H), 6.96 (d, J=6.3 Hz, 1H), 4.25 (dd, J=2.7, 12.9 Hz, 1H), 3.81 (s, 3H), 3.66 (d, J=7.0 Hz, 1H), 3.26 (br. s., 1H), 3.16-3.05 (m, 1H), 2.48-2.40 (m, 2H), 2.37-2.26 (m, 1H), 2.16 (d, J=13.3 Hz, 1H), 2.06 (dd, J=2.9, 13.1 Hz, 1H), 2.01-1.89 (m, 1H), 1.77-1.64 (m, 1H), 1.56-1.41 (m, 1H). MS-ESI (m/z): 620 $(M+1)^+$ (Acq Method D:Rt:1.085 min).

Example 12

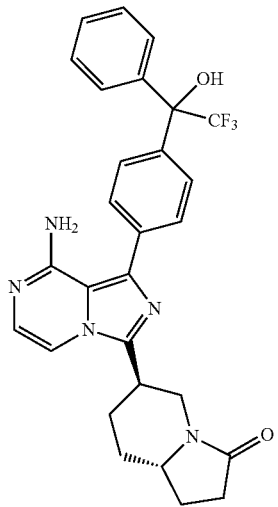 [SMILES: Nc1nccn2c([C@@H]3CC[C@H]4CCC(=O)N4C3)nc(-c3ccc(C(O)(c4ccccc4)C(F)(F)F)cc3)c12]

(6R,8aS)-6-(8-amino-1-(4-(2,2,2-trifluoro-1-hydroxy-1-phenethyl)phenyl)imidazo[1,5-a]pyrazin-3-yl)hexahydroindolizin-3(2H)-one Step 1 (6R,8aS)-6-(8-amino-1-(4-(2,2,2-trifluoro-1-phenyl-1-((trimethylsilyl)oxy)ethyl)phenyl)imidazo[1,5-a]pyrazin-3-yl)hexahydroindolizin-3(2H)-one To a solution of intermediate 1 (60 mg, 0.17 mmol), trimethyl(2,2,2-trifluoro-1-phenyl-1-(4-(4,4,5,5-tetramethyl-1,3,2-dioxaborolan-2-yl)phenyl)ethoxy)silane (99 mg, 0.22 mmol) and $K_2CO_3$ (70.5 mg, 0.51 mmol) in dioxane/$H_2O$ (2 mL, 3:1) was added Pd(dppf) Cl2 (12.4 mg, 0.017 mmol) under $N_2$ atmosphere, and stirred at 90° C. for 60 min. The mixture was cooled to room temperature. $H_2O$ (5 mL) was added into reaction, and the mixture was extracted with EtOAc (10 mL×3). The organic layer was evaporated to get the crude product, which was then separated by prep-HPLC to afford (6R,8aS)-6-(8-amino-1-(4-(2,2,2-trifluoro-1-phenyl-1-((trimethylsilyl)oxy)ethyl)phenyl)imidazo[1,5-a]pyrazin-3-yl)hexahydroindolizin-3(2H)-one. MS: 594.4 (M+1). $^1$H NMR (400 MHz, $CD_3OD$)=7.67-7.61 (m, 3H), 7.60-7.55 (m, 2H), 7.44 (br. s., 2H), 7.41-7.36 (m, 3H), 7.05 (d, J=5.3 Hz, 1H), 4.27 (dd, J=2.8, 12.8 Hz, 1H), 3.68 (dtd, J=3.5, 7.2, 10.8 Hz, 1H), 3.28-3.21 (m, 1H), 3.17-3.08 (m, 1H), 2.49-2.42 (m, 2H), 2.38-2.28 (m, 1H), 2.17 (d, J=13.3 Hz, 1H), 2.11-2.04 (m, 1H), 2.04-1.92 (m, 1H), 1.78-1.67 (m, 1H), 1.58-1.45 (m, 1H), −0.01 (s, 9H) ppm.

Step 2: (6R,8aS)-6-(8-amino-1-(4-(2,2,2-trifluoro-1-hydroxy-1-phenylethyl)phenyl)imidazo[1,5-a]pyrazin-3-yl)hexahydroindolizin-3(2H)-one A mixture of (6R,8aS)-6-(8-amino-1-(4-(2,2,2-trifluoro-1-phenyl-1-((trimethylsilyl)oxy)ethyl)phenyl)imidazo[1,5-a]pyrazin-3-yl)hexahydroindolizin-3(2H)-one (80 mg, 0.135 mmol) in 6M HCl (4 mL) was stirred at 15° C. for 30 min under $N_2$. Then the mixture was basified with sat. $NaHCO_3$ (aq.) to PH=8, which was extracted with EtOAc (10 mL×3). The organic layer was evaporated to get the crude product, which was separated to get (6R,8aS)-6-(8-amino-1-(4-(2,2,2-trifluoro-1-hydroxy-1-phenylethyl)phenyl)imidazo[1,5-a]pyrazin-3-yl)hexahydroindolizin-3(2H)-one. MS: 522.4 (M+1). $^1$H NMR (400 MHz, $CD_3OD$)=7.87 (d, J=6.0 Hz, 1H), 7.74-7.68 (m, 4H), 7.55 (d, J=6.8 Hz, 2H), 7.41-7.33 (m, 3H), 7.01 (d, J=6.0 Hz, 1H), 4.28 (dd, J=2.8, 13.1 Hz, 1H), 3.68 (dtd, J=3.6, 7.1, 10.8 Hz, 1H), 3.36-3.32 (m, 1H), 3.29-3.27 (m, 1H), 3.21-3.11 (m, 1H), 2.49-2.42 (m, 2H), 2.39-2.28 (m, 1H), 2.18 (d, J=13.3 Hz, 1H), 2.13-2.05 (m, 1H), 2.04-1.92 (m, 1H), 1.78-1.67 (m, 1H), 1.58-1.45 (m, 1H) ppm.

Example 13

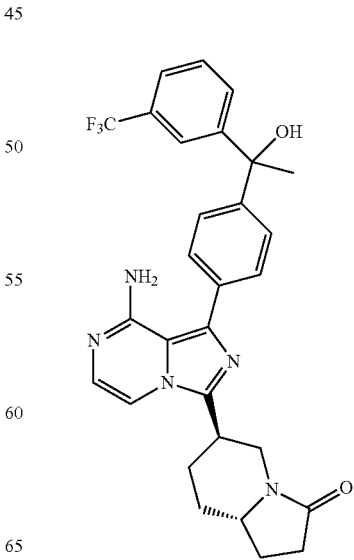

(6R,8aS)-6-(8-amino-1-(4-(1-hydroxy-1-(3-(trifluoromethyl)phenyl)ethyl)phenyl)imidazo[1,5-a]pyrazin-3-yl)hexahydroindolizin-3(2H)-one Step 1 (6R,8aS)-6-(1-(4-acetylphenyl)-8-aminoimidazo[1,5-a]pyrazin-3-yl)hexahydroindolizin-3(2H)-one To a solution of (6R,8aS)-6-(8-amino-1-bromoimidazo[1,5-a]pyrazin-3-yl)hexahydroindolizin-3(2H)-one (500 mg, 1.32 mmol) and (4-acetylphenyl)boronic acid (0.78 g, 1.98 mmol) in dioxane/H₂O (v:v=4:1) (5 mL) were added K₂CO₃ (0.55 g, 3.97 mmol) and Pd(dppf)Cl₂ (10 mg) under nitrogen protection. Then the mixture was heated to 80° C. for 4 hour. Then the mixture was poured into water (50 mL) and extracted with EtOAc (80 mL×3). The organic layer was dried and concentrated in vacuo to give the crude product, which was purified with HPLC to give (6R,8aS)-6-(1-(4-acetylphenyl)-8-aminoimidazo[1,5-a]pyrazin-3-yl)hexahydroindolizin-3(2H)-one. ¹HNMR (400 MHz, CDCl₃): δ=8.11-8.05 (m, 2H), 7.81-7.75 (m, 2H), 7.31 (d, J=5.0 Hz, 1H), 7.15 (d, J=5.3 Hz, 1H), 5.19 (br. s., 2H), 4.47-4.39 (m, 1H), 3.65-3.56 (m, 1H), 3.16-3.00 (m, 2H), 2.66 (s, 3H), 2.50-2.43 (m, 2H), 2.31 (td, J=7.3, 13.1 Hz, 1H), 2.24-2.05 (m, 3H), 1.76-1.65 (m, 1H), 1.48-1.36 (m, 1H) ppm.

Step 2: (6R,8aS)-6-(8-amino-1-(4-(1-hydroxy-1-(3-(trifluoromethyl)phenyl)ethyl)phenyl)imidazo[1,5-a]pyrazin-3-yl)hexahydroindolizin-3(2H)-one To a solution of 1-bromo-3-(trifluoromethyl)benzene (200 mg, 0.89 mmol) in 5 mL of THF was added Mg (43.2 mg, 1.78 mmol) under nitrogen protection and stirred at 80° C. for 2 h. Then the mixture was added to a solution of (6R,8aS)-6-(1-(4-acetylphenyl)-8-aminoimidazo[1,5-a]pyrazin-3-yl)hexahydroindolizin-3(2H)-one (86.5 mg, 0.22 mmol) in THF (3 mL) at 0° C. under nitrogen protection and stirred at 20° C. for 12 h. The mixture was poured into water (50 mL) and extracted with EtOAc (80 mL×3). The organic layer was dried over Na₂SO₄, concentrated in vacuo and purified with Prep-HPLC to give (6R,8aS)-6-(8-amino-1-(4-(1-hydroxy-1-(3-(trifluoromethyl)phenyl)ethyl)phenyl)imidazo[1,5-a]pyrazin-3-yl)hexahydroindolizin-3(2H)-one
¹HNMR (400 MHz, CD₃OD): δ=7.88 (d, J=6.0 Hz, 1H), 7.85 (s, 1H), 7.77 (d, J=7.0 Hz, 1H), 7.72-7.66 (m, 4H), 7.59-7.51 (m, 2H), 7.02 (d, J=6.0 Hz, 1H), 4.29 (dd, J=2.8, 13.1 Hz, 1H), 3.75-3.66 (m, 1H), 3.39-3.34 (m, 1H), 3.23-3.13 (m, 1H), 2.51-2.44 (m, 2H), 2.41-2.31 (m, 1H), 2.24-2.16 (m, 1H), 2.11 (dd, J=3.3, 13.1 Hz, 1H), 2.03 (s, 3H), 1.99 (br. s., 1H), 1.80-1.70 (m, 1H), 1.59-1.47 (m, 1H). MS: 536.4 (M+1) ppm.

The following examples in Table 2 were prepared using the same procedure as described in Example 13 with a different Grignard reagent in step 2.

TABLE 2

| Example Number | Structure | IUPAC Name | Exact Mass [M + H]+ | Retention time (min, method) |
|---|---|---|---|---|
| 14 | 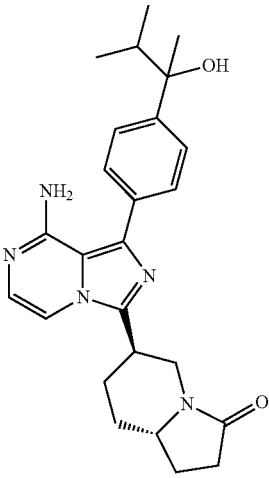 [SMILES: CC(C)C(C)(O)c1ccc(-c2nc([C@@H]3CC[C@H]4CCC(=O)N4C3)n3ccnc(N)c23)cc1] | (6R,8aS)-6-{8-amino-1-[4-(1-hydroxy-1,2-dimethylpropyl)phenyl]imidazo[1,5-a]pyrazin-3-yl}hexahydroindolizin-3(2H)-one | Calc'd 434.3, found 434.4 | 2.333(C) |

TABLE 2-continued

| Example Number | Structure | IUPAC Name | Exact Mass [M + H]+ | Retention time (min, method) |
|---|---|---|---|---|
| 15 | 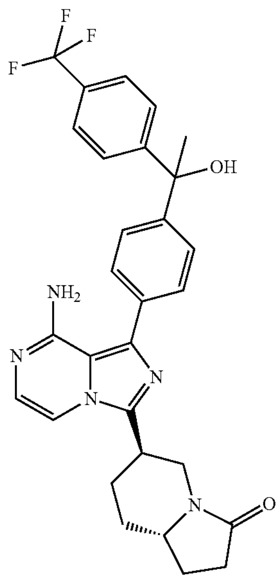 [SMILES: CC(O)(c1ccc(-c2nc([C@@H]3CC[C@H]4CCC(=O)N4C3)n3ccnc(N)c23)cc1)c1ccc(C(F)(F)F)cc1] | (6R,8aS)-6-[8-amino-1-(4-{1-hydroxy-1-[4-(trifluoromethyl)phenyl]ethyl}phenyl)imidazo[1,5-a]pyrazin-3-yl]hexahydroindolizin-3(2H)-one | Calc'd 536.2, found 536.4 | 2.557(C) |
| 16 | 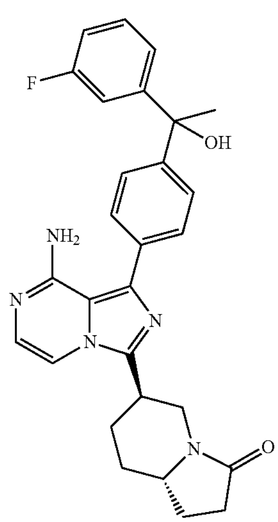 [SMILES: CC(O)(c1ccc(-c2nc([C@@H]3CC[C@H]4CCC(=O)N4C3)n3ccnc(N)c23)cc1)c1cccc(F)c1] | (6R,8aS)-6-(8-amino-1-{4-[1-(3-fluorophenyl)-1-hydroxyethyl]phenyl}imidazo[1,5-a]pyrazin-3-yl)hexahydroindolizin-3(2H)-one | Calc'd 486.2, found 486.4 | 2.391(C) |

TABLE 2-continued

| Example Number | Structure | IUPAC Name | Exact Mass [M + H]+ | Retention time (min, method) |
|---|---|---|---|---|
| 17 | 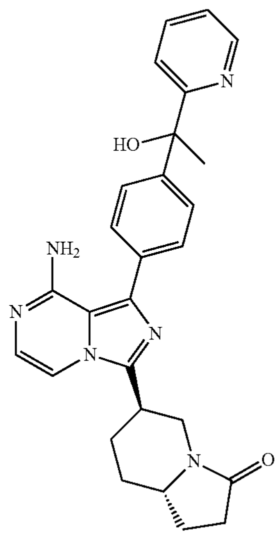 [SMILES: CC(O)(c1ccc(-c2nc([C@@H]3CC[C@H]4CCC(=O)N4C3)n3ccnc(N)c23)cc1)c1ccccn1] | (6R,8aS)-6-{8-amino-1-[4-(1-hydroxy-1-pyridin-2-ylethyl)phenyl]imidazo[1,5-a]pyrazin-3-yl}hexahydroindolizin-3(2H)-one | Calc'd 469.2, found 469.4 | 1.958(C) |
| 18 | 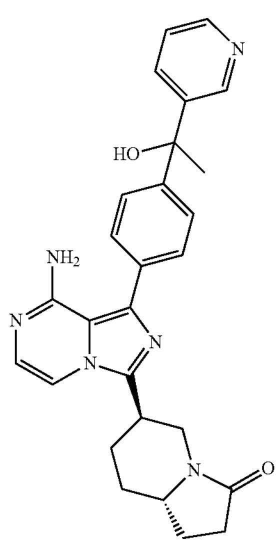 [SMILES: CC(O)(c1ccc(-c2nc([C@@H]3CC[C@H]4CCC(=O)N4C3)n3ccnc(N)c23)cc1)c1cccnc1] | (6R,8aS)-6-{8-amino-1-[4-(1-hydroxy-1-pyridin-3-ylethyl)phenyl]imidazo[1,5-a]pyrazin-3-yl}hexahydroindolizin-3(2H)-one | Calc'd 469.2, found 469.4 | 1.929(C) |

TABLE 2-continued

| Example Number | Structure | IUPAC Name | Exact Mass [M + H]+ | Retention time (min, method) |
|---|---|---|---|---|
| 19 | 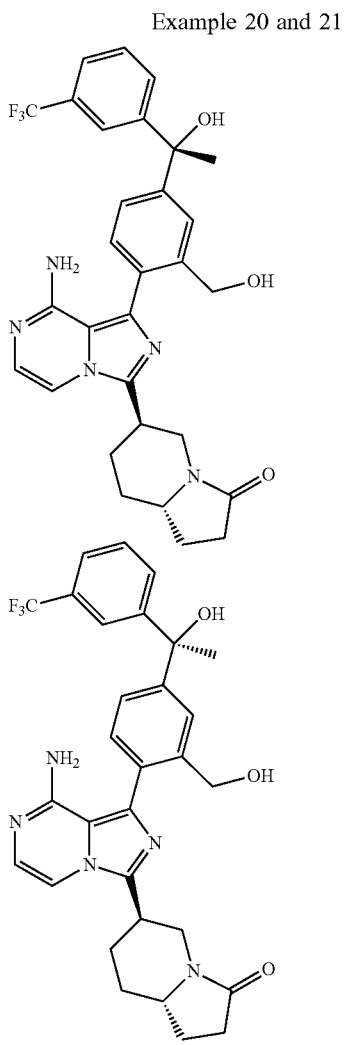 | (6R,8aS)-6-(8-amino-1-{4-(1-(4-fluorophenyl)-1-hydroxyethyl]phenyl}imidazo[1,5-a]pyrazin-3-yl)hexahydroindolizin-3(2H)-one | Calc'd 486.2, found 486.4 | 2.395(C) |

Example 20 and 21

(6R,8aS)-6-(8-amino-1-(4-((R)-1-hydroxy-1-(3-(trifluoromethyl)phenyl)ethyl)-2-(hydroxymethyl)phenyl)imidazo[1,5-a]pyrazin-3-yl)hexahydroindolizin-3(2H)-one (isomer 1) and (6R,8aS)-6-(8-amino-1-(4-((S)-1-hydroxy-1-(3-(trifluoromethyl)phenyl)ethyl)-2-(hydroxymethyl)phenyl)imidazo[1,5-a]pyrazin-3-yl)hexahydroindolizin-3(2H)-one (isomer 2)

Step 1: (6R,8aS)-6-(8-amino-1-(2-(((tert-butyldimethylsilyl)oxy)methyl)-4-(1-hydroxy-1-(3-(trifluoromethyl)phenyl)ethyl)phenyl)imidazo[1,5-a]pyrazin-3-yl)hexahydroindolizin-3(2H)-one To a solution of 1-(3-(((tert-butyldimethylsilyl)oxy)methyl)-4-(4,4,5,5-tetramethyl-1,3,2-dioxaborolan-2-yl)phenyl)-1-(3-(trifluoromethyl)phenyl)ethanol (275 mg, 0.513 mmol) and (6R,8aS)-6-(8-amino-1-bromoimidazo[1,5-a]pyrazin-3-yl)hexahydroindolizin-3(2H)-one (150 mg, 0.428 mmol) in dioxane (4.5 mL) and water (1.5 mL) was added $K_2CO_3$ (177 mg, 1.28 mmol). After degassed with nitrogen for several times, Pd(dppf)Cl$_2$ (cat. amount) was added and the reaction was degassed with nitrogen for several times again, the mixture was heated to 90° C. and stirred under nitrogen for one hour. It was cooled to 20° C., diluted generously with water (5 mL) and ethyl acetate (10 mL), filtered through a celite to remove palladium. Separated and the aqueous layer was extracted with ethyl acetate (30 mL×3), and the combined organic layers were washed with brine (10 mL), dried over sodium sulfate, filtered and concentrated to afford the crude product, which was purified on silica gel column chromatography (MeOH/DCM=0~10%) to give (6R,8aS)-6-(8-amino-1-(2-(((tert-butyldimethylsilyl)oxy)methyl)-4-(1-hydroxy-1-(3-(trifluoromethyl)phenyl)ethyl)phenyl)imidazo[1,5-a]pyrazin-3-yl)hexahydroindolizin-3(2H)-one. MS: 680.3 (M+H)$^+$ Step 2: (6R,8aS)-6-(8-amino-1-(4-(1-hydroxy-1-(3-(trifluoromethyl)phenyl)ethyl)-2-(hydroxymethyl)phenyl)imidazo[1,5-a]pyrazin-3-yl)hexahydroindolizin-3(2H)-one (isomer 1) and (6R,8aS)-6-(8-amino-1-(4-(1-hydroxy-1-(3-(trifluoromethyl)phenyl)ethyl)-2-(hydroxymethyl)phenyl)imidazo[1,5-a]pyrazin-3-yl)hexahydroindolizin-3(2H)-one (isomer 2)

To a solution of (6R,8aS)-6-(8-amino-1-(2-(((tert-butyldimethylsilyl)oxy)methyl)-4-(1-hydroxy-1-(3-(trifluoromethyl)phenyl)ethyl)phenyl)imidazo[1,5-a]pyrazin-3-yl)hexahydroindolizin-3(2H)-one (160 mg, 0.235 mmol) in anhydrous THF (5 mL), TBAF (0.47 mL, 0.47 mmol) was added. The reaction mixture was stirred at 15° C. for 3 hours. The reaction was quenched by water (3 mL), extracted with EtOAc (15 mL). The organic layer was concentrated to afford the crude product, which was purified on silica gel column chromatography (MeOH/DCM=0% 10%) to give (6R,8aS)-6-(8-amino-1-(4-(1-hydroxy-1-(3-(trifluoromethyl)phenyl)ethyl)-2-(hydroxymethyl)phenyl)imidazo[1,5-a]pyrazin-3-yl)hexahydroindolizin-3(2H)-one, which was resolved by SFC separation. SFC method: Column: Chiralpak AD-3 150×4.6 mm I.D., 3 um Mobile phase: methanol (0.05% DEA) in $CO_2$ from 5% to 40% Flow rate: 2.5 mL/min Wavelength: 220 nm". Two isomers were obtained. (6R,8aS)-6-(8-amino-1-(4-(1-hydroxy-1-(3-(trifluoromethyl)phenyl)ethyl)-2-(hydroxymethyl)phenyl)imidazo[1,5-a]pyrazin-3-yl)hexahydroindolizin-3(2H)-one (isomer 1) $^1$H NMR (400 MHz, $CD_3OD$) δ ppm 7.89 (d, J=5.9 Hz, 1H), 7.84 (d, J=17.6 Hz, 2H), 7.77 (d, J=6.7 Hz, 1H), 7.65-7.49 (m, 3H), 7.43 (d, J=8.2 Hz, 1H), 7.02 (d, J=5.9 Hz, 1H), 4.57 (s, 2H), 4.31 (dd, J=2.7, 12.9 Hz, 1H), 3.68 (d, J=7.0 Hz, 1H), 3.37 (br. s., 1H), 3.15-3.06 (m, 1H), 2.51-2.43 (m, 2H), 2.39-2.31 (m, 1H), 2.21 (d, J=12.9 Hz, 1H), 2.10 (dd, J=2.7, 13.3 Hz, 1H), 2.07-1.89 (m, 4H), 1.79-1.70 (m, 1H), 1.58-1.47 (m, 1H) ppm;

(6R,8aS)-6-(8-amino-1-(4-(1-hydroxy-1-(3-(trifluoromethyl)phenyl)ethyl)-2-(hydroxymethyl)phenyl)imidazo[1,5-a]pyrazin-3-yl)hexahydroindolizin-3(2H)-one (isomer 2)

$^1$H NMR (400 MHz, $CD_3OD$) δ ppm 7.90 (d, J=6.3 Hz, 1H), 7.86 (s, 1H), 7.82 (s, 1H), 7.77 (d, J=6.7 Hz, 1H), 7.60 (d, J=7.8 Hz, 1H), 7.58-7.49 (m, 2H), 7.44 (d, J=8.2 Hz, 1H), 7.02 (d, J=5.9 Hz, 1H), 4.57 (s, 2H), 4.34-4.28 (m, 1H), 3.68 (d, J=7.0 Hz, 1H), 3.37 (br. s., 1H), 3.15-3.07 (m, 1H), 2.50-2.42 (m, 2H), 2.35 (dt, J=7.6, 13.4 Hz, 1H), 2.21 (d, J=12.9 Hz, 1H), 2.13-1.91 (m, 5H), 1.79-1.70 (m, 1H), 1.58-1.48 (m, 1H) ppm.

Example 22

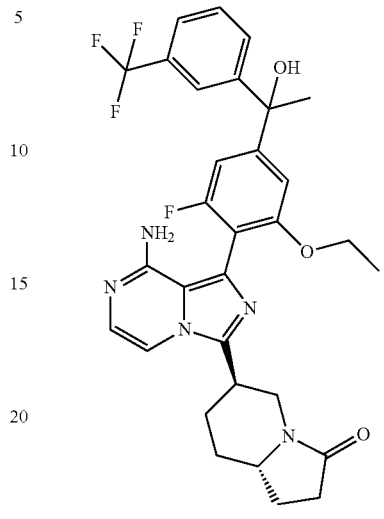

(6R,8aS)-6-(8-amino-1-(2-ethoxy-6-fluoro-4-(1-hydroxy-1-(3-(trifluoromethyl)phenyl)ethyl)phenyl)imidazo[1,5-a]pyrazin-3-yl)hexahydroindolizin-3(2H)-one Step 1: 3-ethoxy-5-fluoro-N-methoxy-N-methyl-4-(4,4,5,5-tetramethyl-1,32-dioxaborolan-2-yl)benzamide To a solution of 3-ethoxy-5-fluoro-4-(4,4,5,5-tetramethyl-1,3,2-dioxaborolan-2-yl)benzoic acid (2 g, 6.45 mmol) and isopropyl carbonochloridate (0.4 g, 3.3 mmol) in DCM (10 mL). The solution was stirred at 0° C. for 1 h, then to the mixture was added N,O-dimethylhydroxylamine-HCl (0.944 g, 9.67 mmol) and $Et_3N$ (0.94 g, 6.6 mmol) in DCM (10 mL). The solution was stirred at 0° C. for 2 h. Then the reaction mixture was filtered, the organic phase was washed with water (20 mL), brine (20 mL), dried over $Na_2SO_4$, concentrated in vacuo, the residue was purified by silica gel column chromatography (25 g, Pet. Ether:EtOAc=2:1) to give 3-ethoxy-5-fluoro-N-methoxy-N-methyl-4-(4,4,5,5-tetramethyl-1,3,2-dioxaborolan-2-yl)benzamide. $^1$H NMR (400 MHz, $CDCl_3$) δ: 6.95 (d, J=8.6 Hz, 1H), 6.91 (s, 1H), 4.03 (q, J=6.8 Hz, 2H), 3.51 (s, 3H), 3.33 (s, 3H), 1.42-1.38 (m, 15H) ppm.

Step 2: 4-(8-amino-3-((6R,8aS)-3-oxooctahydroindolizin-6-yl)imidazo[1,5-a]pyrazin-1-yl)-3-ethoxy-5-fluoro-N-methoxy-N-methylbenzamide To a mixture of (6R,8aS)-6-(8-amino-1-bromoimidazo[1,5-a]pyrazin-3-yl)hexahydroindolizin-3(2H)-one (2 g, 5.71 mmol) and 3-ethoxy-5-fluoro-N-methoxy-N-methyl-4-(4,4,5,5-tetramethyl-1,3,2-dioxaborolan-2-yl)benzamide (3.03 g, 8.57 mmol) in THF (20 mL) was added $K_2CO_3$ (17.13 mL, 17.13 mmol), then 1,1'-BIS(DI-TERT-BUTYLPHOSPHINO)FERROCENE PALLADIUM DICHLORIDE (0.372 g, 0.571 mmol) was added to the reaction mixture under $N_2$. The reaction was stirred at 100° C. for 1.5 h under microwave. The reaction mixture was quenched with water (50 mL), extracted with EtOAc (2×50 mL). The combined organic phase was washed with brine (100 mL), dried over Na₂SO₄, concentrated in vacuo, purification by silica gel column chromatography (DCM:THF=1:4) to give 4-(8-amino-3-((6R,8aS)-3-oxooctahydroindolizin-6-yl)imidazo[1,5-a]pyrazin-1-yl)-3-ethoxy-5-fluoro-N-methoxy-N-methylbenzamide. MS: 497.2 [M+1]. ¹H NMR (400 MHz, MeOD-d4) δ:7.62 (d, J=5.1 Hz, 1H), 7.20 (s, 1H), 7.16 (d, J=8.6 Hz, 1H), 7.02 (d, J=4.7 Hz, 1H), 4.26 (d, J=12.5 Hz, 1H), 4.15-4.05 (m, 2H), 3.73-3.68 (m, 1H), 3.65 (s, 3H), 3.38 (s, 3H), 3.13-3.01 (m, 1H), 2.47-2.40 (m, 2H), 2.31 (dd, J=6.3, 12.9 Hz, 1H), 2.18 (d, J=13.7 Hz, 1H), 2.06 (dd, J=2.9, 13.1 Hz, 1H), 1.85 (br. s., 2H), 1.71 (dd, J=6.7, 12.5 Hz, 1H), 1.55-1.47 (m, 1H), 1.27-1.19 (m, 3H) ppm.

Step 3: (6R,8aS)-6-(8-amino-1-(2-ethoxy-6-fluoro-4-(3-(trifluoromethyl)benzoyl)phenyl)imidazo[1,5-a]pyrazin-3-yl)hexahydroindolizin-3(2H)-one
0351909-126-2

To a suspension of magnesium (196 mg, 8.06 mmol) in THF (2 mL) was added dropwise a solution of 1-bromo-3-(trifluoromethyl)benzene (1813 mg, 8.06 mmol) in THF (6 mL). Then the mixture was heated to 80° C. and stirred for 1 h. After the mixture was cooled to 15° C. 4-(8-Amino-3-((6R,8aS)-3-oxooctahydroindolizin-6-yl)imidazo[1,5-a]pyrazin-1-yl)-3-ethoxy-5-fluoro-N-methoxy-N-methylbenzamide (800 mg, 1.611 mmol) in THF (10 mL) was added dropwise to the former mixture at 0° C. Then the mixture was stirred at 0° C. to 15° C. for 18 h. TLC showed the starting material was consumed completely, the reaction was quenched with sat. NH₄Cl aqueous (40 mL), extracted with EtOAc (2×40 mL). The combined organic phase was washed with brine (80 mL), dried over Na₂SO₄, concentrated in vacuo, purified by silica gel column chromatography (40 g, DCM:THF=1:4) to give (6R,8aS)-6-(8-amino-1-(2-ethoxy-6-fluoro-4-(3-(trifluoromethyl)benzoyl)phenyl)imidazo[1,5-a]pyrazin-3-yl)hexahydroindolizin-3(2H)-one. MS: 582.3 [M+1]. ¹H NMR (400 MHz, MeOD-d4) δ:8.16-8.08 (m, 2H), 7.98 (d, J=7.8 Hz, 1H), 7.78 (t, J=7.6 Hz, 1H), 7.63 (d, J=4.7 Hz, 1H), 7.33 (s, 1H), 7.23 (d, J=8.6 Hz, 1H), 7.04 (d, J=5.1 Hz, 1H), 4.28 (d, J=12.9 Hz, 1H), 4.15-4.04 (m, 2H), 3.69 (dd, J=6.8, 10.4 Hz, 1H), 3.15-3.02 (m, 1H), 2.48-2.39 (m, 2H), 2.32 (dd, J=6.3, 12.9 Hz, 1H), 2.20 (br. s., 1H), 2.11-2.05 (m, 1H), 2.00-1.91 (m, 1H), 1.87-1.67 (m, 2H), 1.57-1.45 (m, 1H), 1.31-1.19 (m, 3H) ppm.

Step 4: (6R,8aS)-6-(8-amino-1-(2-ethoxy-6-fluoro-4-(1-hydroxy-1-(3-(trifluoromethyl)phenyl)ethyl)phenyl)imidazo[1,5-a]pyrazin-3-yl)hexahydroindolizin-3(2H)-one To a solution of (6R,8aS)-6-(8-amino-1-(2-ethoxy-6-fluoro-4-(3-(trifluoromethyl)benzoyl)phenyl)imidazo[1,5-a]pyrazin-3-yl)hexahydroindolizin-3(2H)-one (430 mg, 0.739 mmol) in THF (10 mL) was added methylmagnesium bromide (3.70 ml, 3.70 mmol) at 0° C. The solution was stirred at 0° C. for 2 h. LCMS showed the material was consumed half and the by-product was found. Then the reaction was quenched with sat. NH₄Cl aqueous (10 mL), extracted with EtOAc (2×10 mL). The organic phase was washed with water (20 mL), brine (20 mL), dried over Na₂SO₄, concentrated in vacuo to give the residue, which was purified by prep-HPLC (ACN/water with 0.1% TFA modifier) to give the title compound. MS: 598.2 [M+1]. ¹H NMR (400 MHz, CD₃OD) δ: 7.84 (d, J=6.3 Hz, 2H), 7.77 (br. s., 1H), 7.57-7.50 (m, 2H), 7.09 (d, J=9.0 Hz, 1H), 6.97 (d, J=5.5 Hz, 2H), 4.25 (d, J=12.9 Hz, 1H), 4.11-4.00 (m, 2H), 3.65 (d, J=7.0 Hz, 1H), 3.13-3.04 (m, 1H), 2.49-2.40 (m, 2H), 2.36-2.28 (m, 1H), 2.16 (d, J=12.9 Hz, 1H), 2.06 (d, J=10.6 Hz, 1H), 1.98 (s, 3H), 1.92 (d, J=9.4 Hz, 1H), 1.75-1.66 (m, 1H), 1.57-1.35 (m, 2H), 1.20 (t, J=6.5 Hz, 3H) ppm.

The following examples in Table 3 were prepared using the procedure described above using the appropriate intermediates.

TABLE 3

| Example number | Structure | IUPAC Name | Exact Mass [M + H]+ | LC-MS retention time (min, method) |
|---|---|---|---|---|
| 23 | 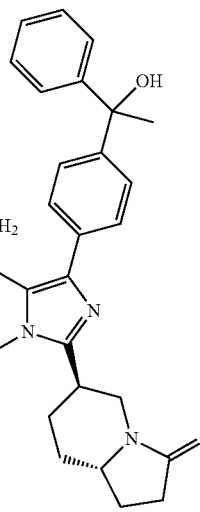 | (6R,8aS)-6-{8-amino-1-[4-(1-hydroxy-1-phenylethyl)phenyl]imidazol[1,5-a]pyrazin-3-yl}hexahydroindolizin-3(2H)-one | Calc'd 468.2, found 468.4 | 2.359(C) |

TABLE 3-continued

| Example number | Structure | IUPAC Name | Exact Mass [M + H]+ | LC-MS retention time (min, method) |
|---|---|---|---|---|
| 24 | 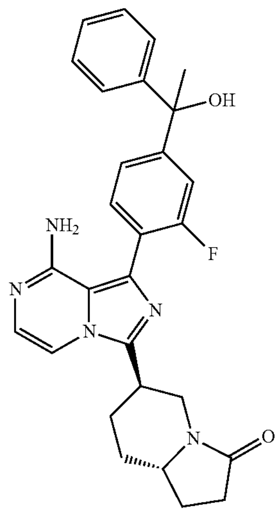 [SMILES: CC(O)(c1ccccc1)c1ccc(-c2nc([C@@H]3CC[C@H]4CCC(=O)N4C3)n3ccnc(N)c23)c(F)c1] | (6R,8aS)-6-{8-amino-1-[2-fluoro-4-(1-hydroxy-1-phenylethyl)phenyl imidazo[1,5-a]pyrazin-3-yl}hexahydroindolizin-3(2H)-one | Calc'd 486.2, found 486.3 | 2.380(C) |
| 25 | 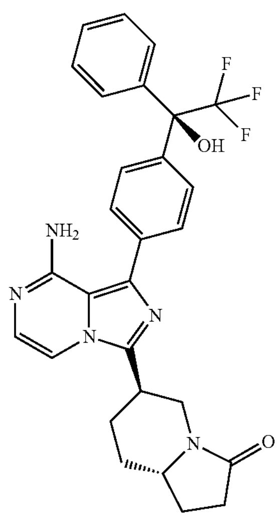 [SMILES: Nc1nccn2c([C@@H]3CC[C@H]4CCC(=O)N4C3)nc(-c3ccc([C@](O)(c4ccccc4)C(F)(F)F)cc3)c12] | (6R,8aS)-6-(8-amino-1-{4-[(1R)-2,2,2-trifluoro-1-hydroxy-1-phenylethyl]phenyl}imidazo[1,5-a]pyrazin-3-yl)hexahydroindolizin-3(2H)-one | Calc'd 522.2, found 522.4 | 2.497(C) |
| 26 | 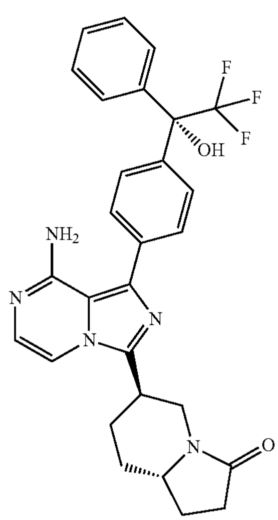 [SMILES: Nc1nccn2c([C@@H]3CC[C@H]4CCC(=O)N4C3)nc(-c3ccc([C@@](O)(c4ccccc4)C(F)(F)F)cc3)c12] | (6R,8aS)-6-(8-amino-1-{4-[(1S)-2,2,2-trifluoro-1-hydroxy-1-phenylethyl]phenyl}imidazo[1,5-a]pyrazin-3-yl)hexahydroindolizin-3(2H)-one | Calc'd 522.2, found 522.4 | 2.502(C) |

TABLE 3-continued

| Example number | Structure | IUPAC Name | Exact Mass [M + H]+ | LC-MS retention time (min, method) |
|---|---|---|---|---|
| 27 | 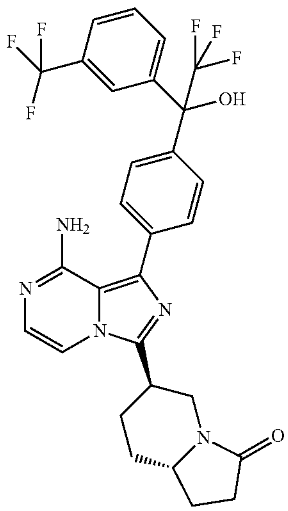 [SMILES: Nc1nccn2c([C@@H]3CC[C@H]4CCC(=O)N4C3)nc(-c3ccc(C(O)(c4cccc(C(F)(F)F)c4)C(F)(F)F)cc3)c12] | (6R,8aS)-6-[8-amino-1-(4-{2,2,2-trifluoro-1-hydroxy-1-[3-(trifluoromethyl)phenyl]ethyl}phenyl)imidazo[1,5-a]pyrazin-3-yl]hexahydroindolizin-3(2H)-one | Calc'd 590.2, found 590.3 | 2.650(C) |
| 28 | 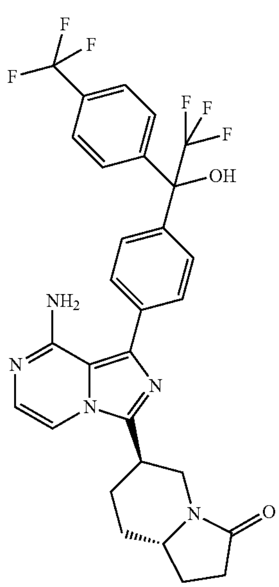 [SMILES: Nc1nccn2c([C@@H]3CC[C@H]4CCC(=O)N4C3)nc(-c3ccc(C(O)(c4ccc(C(F)(F)F)cc4)C(F)(F)F)cc3)c12] | (6R,8aS)-6-[8-amino-1-(4-{2,2,2-trifluoro-1-hydroxy-1-[4-(trifluoromethyl)phenyl]ethyl}phenyl)imidazo[1,5-a]pyrazin-3-yl]hexahydroindolizin-3(2H)-one | Calc'd 590.2, found 590.3 | 2.675(C) |

TABLE 3-continued

| Example number | Structure | IUPAC Name | Exact Mass [M + H]+ | LC-MS retention time (min, method) |
| --- | --- | --- | --- | --- |
| 29 | 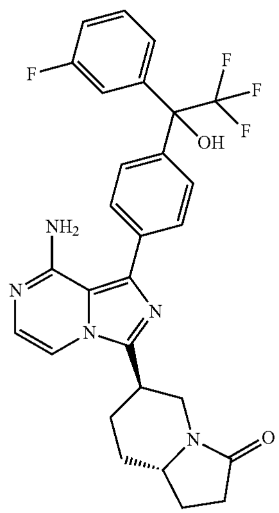 [SMILES: Nc1nccn2c([C@@H]3CC[C@H]4CCC(=O)N4C3)nc(-c3ccc(C(O)(c4cccc(F)c4)C(F)(F)F)cc3)c12] | (6R,8aS)-6-(8-amino-1-{4-[2,2,2-trifluoro-1-(3-fluorophenyl)-1-hydroxyethyl]phenyl}imidazo[1,5-a]pyrazin-3-yl)hexahydroindolizin-3(2H)-one | Calc'd 540.2, found 540.3 | 2.258(C) |
| 30 | 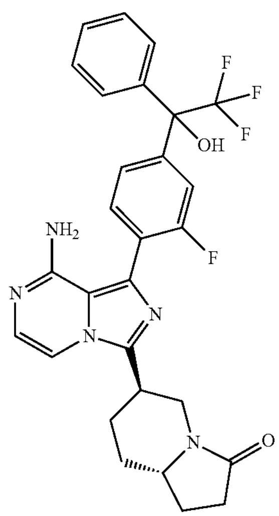 [SMILES: Nc1nccn2c([C@@H]3CC[C@H]4CCC(=O)N4C3)nc(-c3ccc(C(O)(c4ccccc4)C(F)(F)F)cc3F)c12] | (6R,8aS)-6-{8-amino-1-[2-fluoro-4-(2,2,2-trifluoro-1-hydroxy-1-phenylethyl)phenyl]imidazo[1,5-a]pyrazin-3-yl}hexahydroindolizin-3(2H)-one | Calc'd 540.2, found 540.3 | 2.502(C) |
| 31 | 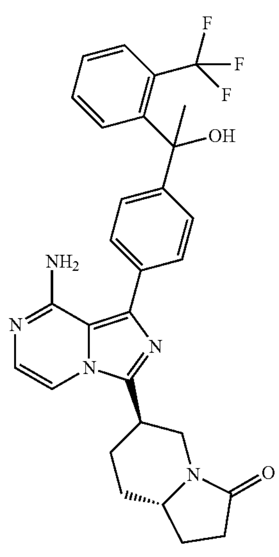 [SMILES: CC(O)(c1ccc(-c2nc([C@@H]3CC[C@H]4CCC(=O)N4C3)n3ccnc(N)c23)cc1)c1ccccc1C(F)(F)F] | (6R,8aS)-6-[8-amino-1-(4-{1-hydroxy-1-[2-(trifluoromethyl)phenyl]ethyl}phenyl)imidazo[1,5-a]pyrazin-3-yl]hexahydroindolizin-3(2H)-one | Calc'd 536.2, found 536.4 | 2.498(C) |

TABLE 3-continued
| Example number | Structure | IUPAC Name | Exact Mass [M + H]+ | LC-MS retention time (min, method) |
|---|---|---|---|---|
| 32 | 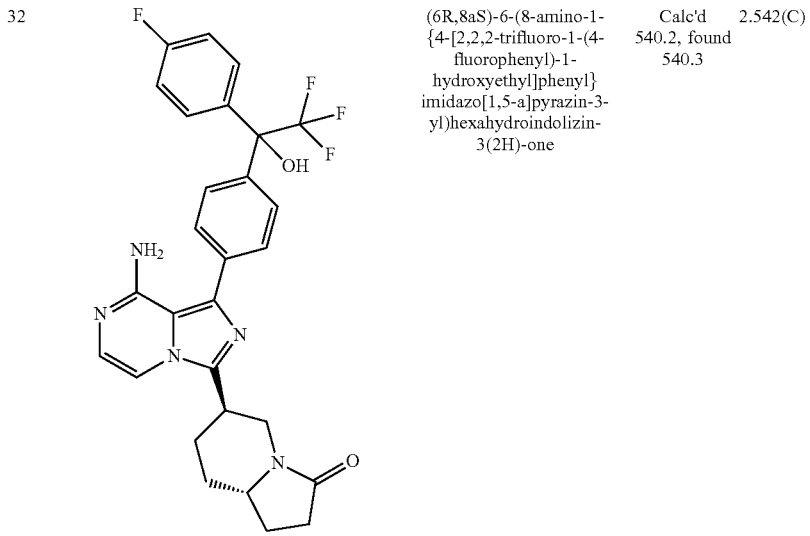 | (6R,8aS)-6-(8-amino-1-{4-[2,2,2-trifluoro-1-(4-fluorophenyl)-1-hydroxyethyl]phenyl}imidazo[1,5-a]pyrazin-3-yl)hexahydroindolizin-3(2H)-one | Calc'd 540.2, found 540.3 | 2.542(C) |
| 33 | 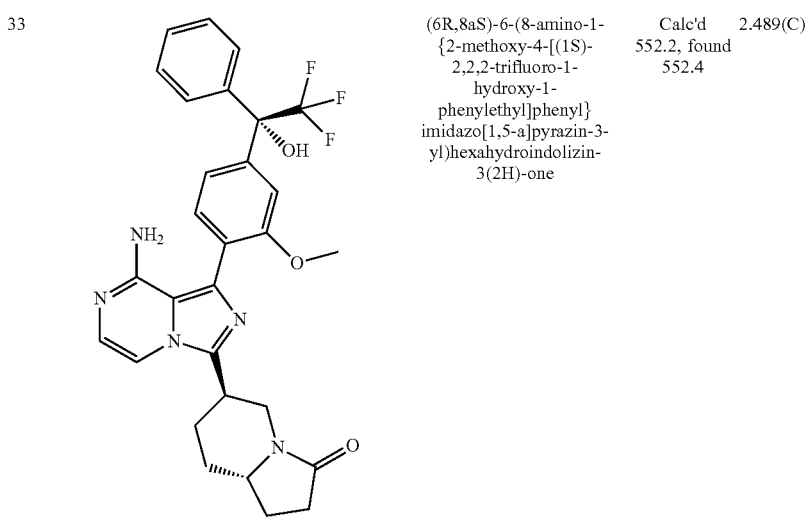 | (6R,8aS)-6-(8-amino-1-{2-methoxy-4-[(1S)-2,2,2-trifluoro-1-hydroxy-1-phenylethyl]phenyl}imidazo[1,5-a]pyrazin-3-yl)hexahydroindolizin-3(2H)-one | Calc'd 552.2, found 552.4 | 2.489(C) |

TABLE 3-continued

| Example number | Structure | IUPAC Name | Exact Mass [M + H]+ | LC-MS retention time (min, method) |
|---|---|---|---|---|
| 34 | 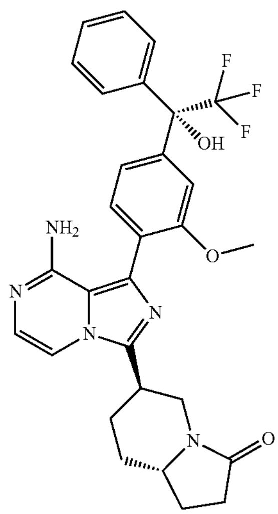 [SMILES: COc1cc([C@](O)(c2ccccc2)C(F)(F)F)ccc1-c1nc([C@@H]2CC[C@H]3CCC(=O)N3C2)n2ccnc(N)c12] | (6R,8aS)-6-(8-amino-1-{2-methoxy-4-[(1S)-2,2,2-trifluoro-1-hydroxy-1-phenylethyl]phenyl}imidazo[1,5-a]pyrazin-3-yl)hexahydroindolizin-3(2H)-one | Calc'd 552.2, found 552.4 | 2.495(C) |
| 35 | 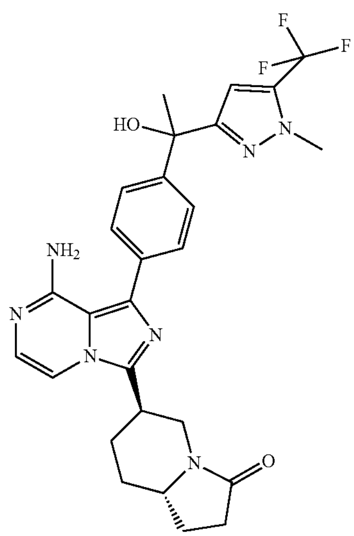 [SMILES: Cn1nc(C(C)(O)c2ccc(-c3nc([C@@H]4CC[C@H]5CCC(=O)N5C4)n4ccnc(N)c34)cc2)cc1C(F)(F)F] | (6R,8aS)-6-[8-amino-1-(4-{1-hydroxy-1-[1-methyl-5-(trifluoromethyl)-1H-pyrazol-3-yl]ethyl}phenyl)imidazo[1,5-a]pyrazin-3-yl]hexahydroindolizin-3(2H)-one | Calc'd 540.2, found 540.2 | 2.180(C) |
| 36 | 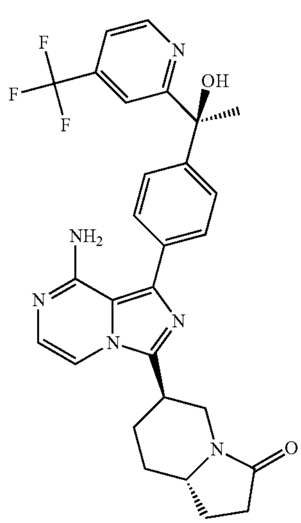 [SMILES: C[C@](O)(c1ccc(-c2nc([C@@H]3CC[C@H]4CCC(=O)N4C3)n3ccnc(N)c23)cc1)c1cc(C(F)(F)F)ccn1] | (6R,8aS)-6-8-amino-1-(4-{(1S)-1-hydroxy-1-[4-(trifluoromethyl)pyridin-2-yl]ethyl}phenyl)imidazo[1,5-a]pyrazin-3-yl]hexahydroindolizin-3(2H)-one | Calc'd 537.2, found 537.1 | 2.356(C) |

TABLE 3-continued

| Example number | Structure | IUPAC Name | Exact Mass [M + H]+ | LC-MS retention time (min, method) |
| --- | --- | --- | --- | --- |
| 37 | 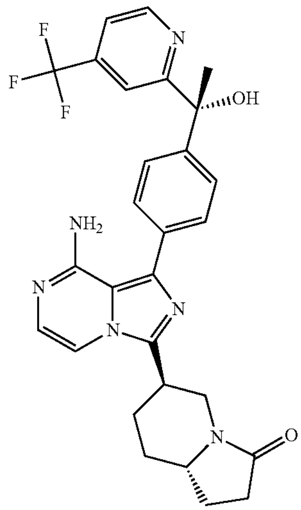 [SMILES: C[C@@](O)(c1ccc(-c2nc([C@@H]3CC[C@H]4CCC(=O)N4C3)n3ccnc(N)c23)cc1)c1cc(C(F)(F)F)ccn1] | (6R,8aS)-6-[8-amino-1-(4-{(1R)-1-hydroxy-1-[4-(trifluoromethyl)pyridin-2-yl]ethyl}phenyl)imidazo[1,5-a]pyrazin-3-yl]hexahydroindolizin-3(2H)-one | Calc'd 537.2, found 537.1 | 2.356(C) |
| 38 | 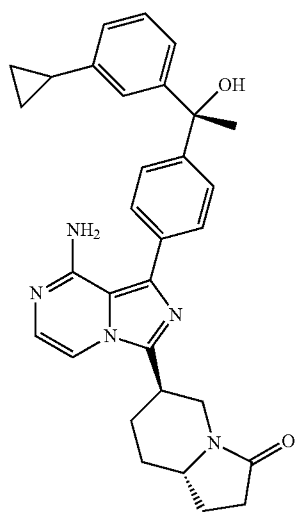 [SMILES: C[C@@](O)(c1ccc(-c2nc([C@@H]3CC[C@H]4CCC(=O)N4C3)n3ccnc(N)c23)cc1)c1cccc(C2CC2)c1] | (6R,8aS)-6-(8-amino-1-{4-[(1R)-1-(3-cyclopropylphenyl)-1-hydroxyethyl]phenyl}imidazo[1,5-a]pyrazin-3-yl)hexahydroindolizin-3(2H)-one | Calc'd 508.3, found 508.1 | 2.483(C) |
| 39 | 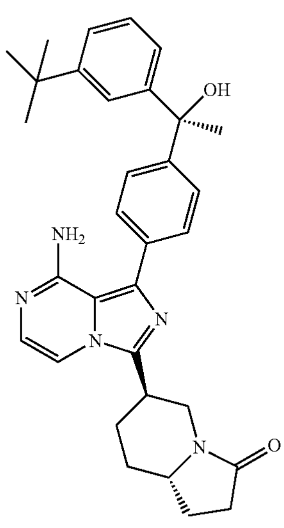 [SMILES: CC(C)(C)c1cccc([C@@](C)(O)c2ccc(-c3nc([C@@H]4CC[C@H]5CCC(=O)N5C4)n4ccnc(N)c34)cc2)c1] | (6R,8aS)-6-(8-amino-1-{4-[(1S)-1-(3-tert-butylphenyl)-1-hydroxyethyl]phenyl}imidazo[1,5-a]pyrazin-3-yl)hexahydroindolizin-3(2H)-one | Calc'd 524.3, found 524.1 | 2.305(C) |

TABLE 3-continued

| Example number | Structure | IUPAC Name | Exact Mass [M + H]+ | LC-MS retention time (min, method) |
|---|---|---|---|---|
| 40 | 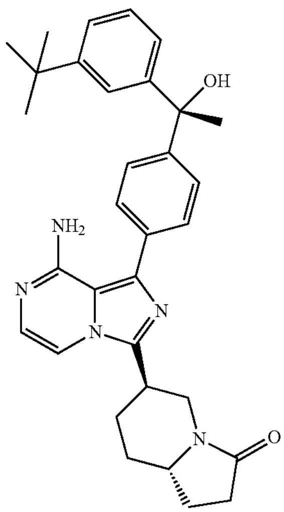 [SMILES: CC(C)(C)c1cccc([C@](C)(O)c2ccc(-c3nc([C@@H]4CC[C@H]5CCC(=O)N5C4)n4ccnc(N)c34)cc2)c1] | (6R,8aS)-6-(8-amino-1-{4-[(1R)-1-(3-tert-butylphenyl)-1-hydroxyethyl]phenyl}imidazo[1,5-a]pyrazin-3-yl)hexahydroindolizin-3(2H)-one | Calc'd 524.3, found 524.1 | 2.312(C) |
| 41 | 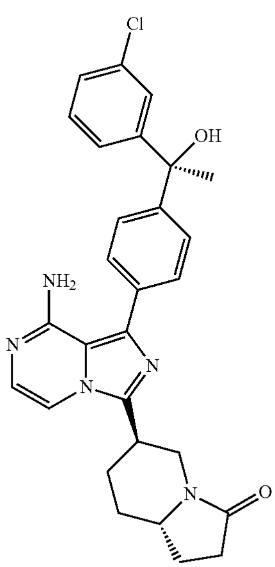 [SMILES: C[C@](O)(c1ccc(-c2nc([C@@H]3CC[C@H]4CCC(=O)N4C3)n3ccnc(N)c23)cc1)c1cccc(Cl)c1] | (6R,8aS)-6-(8-amino-1-{4-[(1S)-1-(3-chlorophenyl)-1-hydroxyethyl]phenyl}imidazo[1,5-a]pyrazin-3-yl)hexahydroindolizin-3(2H)-one | Calc'd 502.2, found 502.0 | 2.421(C) |

TABLE 3-continued

| Example number | Structure | IUPAC Name | Exact Mass [M + H]+ | LC-MS retention time (min, method) |
|---|---|---|---|---|
| 42 | 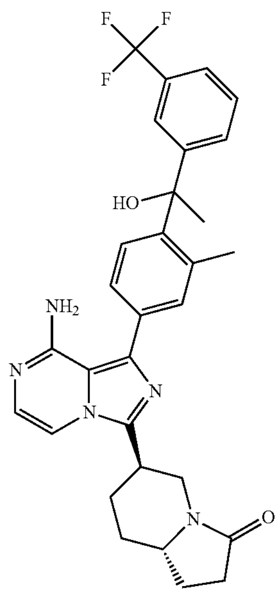 [SMILES: Cc1cc(-c2nc([C@@H]3CC[C@H]4CCC(=O)N4C3)n3ccnc(N)c23)ccc1C(C)(O)c1cccc(C(F)(F)F)c1] | (6R,8aS)-6-[8-amino-1-(4-{1-hydroxy-1-[3-(trifluoromethyl)phenyl]ethyl}-3-methylphenyl)imidazo[1,5-a]pyrazin-3-yl]hexahydroindolizin-3(2H)-one | Calc'd 550.2, found 550.2 | 2.324(C) |
| 43 | 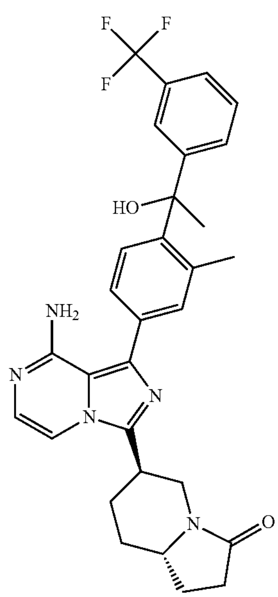 [SMILES: Cc1cc(-c2nc([C@@H]3CC[C@H]4CCC(=O)N4C3)n3ccnc(N)c23)ccc1C(C)(O)c1cccc(C(F)(F)F)c1] | (6R,8aS)-6-[8-amino-1-(4-{1-hydroxy-1-[3-(trifluoromethyl)phenyl]ethyl}-3-methylphenyl)imidazo[1,5-a]pyrazin-3-yl]hexahydroindolizin-3(2H)-one | Calc'd 550.2, found 550.2 | 2.325(C) |

TABLE 3-continued

| Example number | Structure | IUPAC Name | Exact Mass [M + H]+ | LC-MS retention time (min, method) |
|---|---|---|---|---|
| 44 | 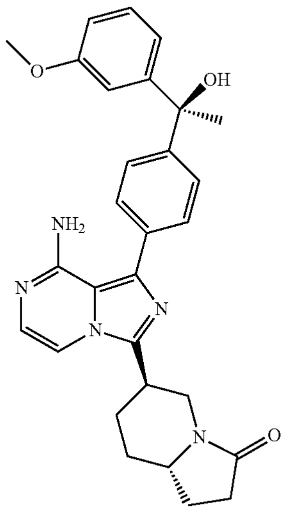 [SMILES: COc1cccc([C@@](C)(O)c2ccc(-c3nc([C@@H]4CC[C@H]5CCC(=O)N5C4)n4ccnc(N)c34)cc2)c1] | (6R,8aS)-6-(8-amino-1-{4-[(1S)-1-hydroxy-1-(3-methoxyphenyl)ethyl]phenyl}imidazo[1,5-a]pyrazin-3-yl)hexahydroindolizin-3(2H)-one | Calc'd 498.3, found 498.1 | 2.778(C) |
| 45 | 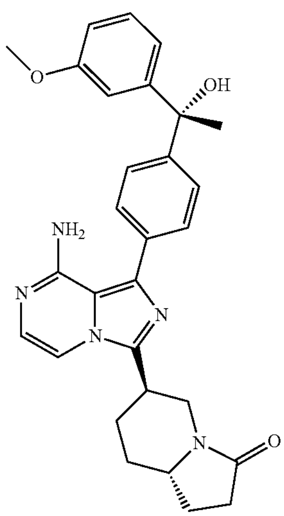 [SMILES: COc1cccc([C@](C)(O)c2ccc(-c3nc([C@@H]4CC[C@H]5CCC(=O)N5C4)n4ccnc(N)c34)cc2)c1] | (6R,8aS)-6-(8-amino-1-{4-[(1R)-1-hydroxy-1-(3-methoxyphenyl)ethyl]phenyl}imidazo[1,5-a]pyrazin-3-yl)hexahydroindolizin-3(2H)-one | Calc'd 498.3, found 498.2 | 2.774(C) |
| 46 | 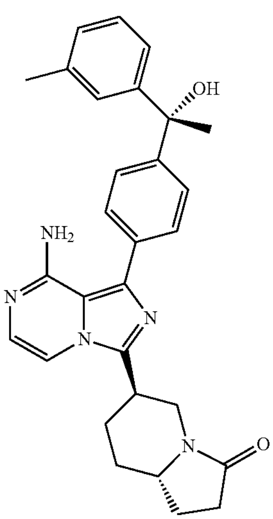 [SMILES: Cc1cccc([C@](C)(O)c2ccc(-c3nc([C@@H]4CC[C@H]5CCC(=O)N5C4)n4ccnc(N)c34)cc2)c1] | (6R,8aS)-6-(8-amino-1-(4-[(1R)-1-hydroxy-1-(3-methylphenyl)ethyl]phenyl}imidazo[1,5-a]pyrazin-3-yl)hexahydroindolizin-3(2H)-one | Calc'd 482.3, found 482.2 | 2.397(C) |

TABLE 3-continued

| Example number | Structure | IUPAC Name | Exact Mass [M + H]+ | LC-MS retention time (min, method) |
|---|---|---|---|---|
| 47 | 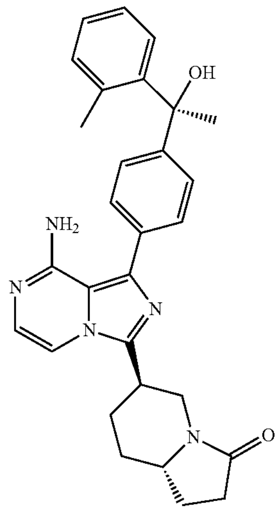 [SMILES: Cc1ccccc1[C@@](C)(O)c1ccc(-c2nc([C@@H]3CC[C@H]4CCC(=O)N4C3)n3ccnc(N)c23)cc1] | (6R,8aS)-6-(8-amino-1-{4-[(1S)-1-hydroxy-1-(2-methylphenyl)ethyl]phenyl}imidazo[1,5-a]pyrazin-3-yl)hexahydroindolizin-3(2H)-one | Calc'd 482.3, found 482.2 | 2.405(C) |
| 48 | 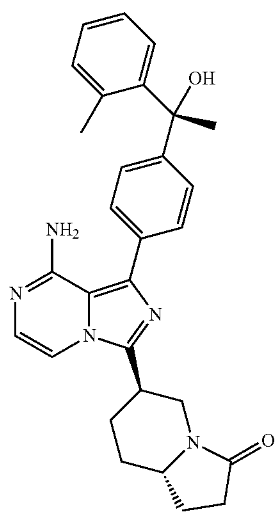 [SMILES: Cc1ccccc1[C@](C)(O)c1ccc(-c2nc([C@@H]3CC[C@H]4CCC(=O)N4C3)n3ccnc(N)c23)cc1] | (6R,8aS)-6-(8-amino-1-{4-[(1R)-1-hydroxy-1-(2-methylphenyl)ethyl]phenyl}imidazo[1,5-a]pyrazin-3-yl)hexahydroindolizin-3(2H)-one | Calc'd 482.3, found 482.2 | 2.398(C) |
| 49 | 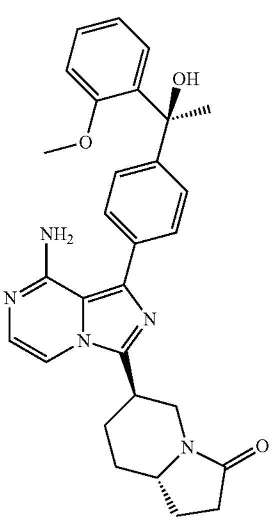 [SMILES: COc1ccccc1[C@@](C)(O)c1ccc(-c2nc([C@@H]3CC[C@H]4CCC(=O)N4C3)n3ccnc(N)c23)cc1] | (6R,8aS)-6-(8-amino-1-{4-[(1S)-1-hydroxy-1-(2-methoxyphenyl)ethyl]phenyl}imidazo[1,5-a]pyrazin-3-yl)hexahydroindolizin-3(2H)-one | Calc'd 498.3, found 498.2 | 2.816(C) |

TABLE 3-continued

| Example number | Structure | IUPAC Name | Exact Mass [M + H]+ | LC-MS retention time (min, method) |
|---|---|---|---|---|
| 50 | 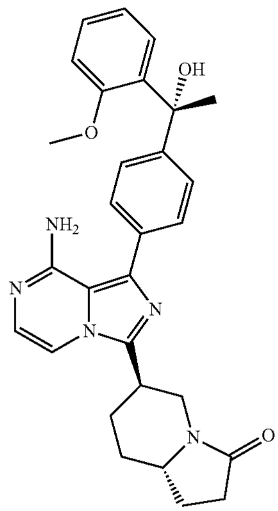 [SMILES: COc1ccccc1[C@](C)(O)c1ccc(-c2nc([C@@H]3CC[C@H]4CCC(=O)N4C3)n3ccnc(N)c23)cc1] | (6R,8aS)-6-(8-amino-1-{4-[(1R)-1-hydroxy-1-(2-methoxyphenyl)ethyl]phenyl}imidazo[1,5-a]pyrazin-3-yl)hexahydroindolizin-3(2H)-one | Calc'd 498.3, found 498.2 | 2.822(C) |
| 51 | 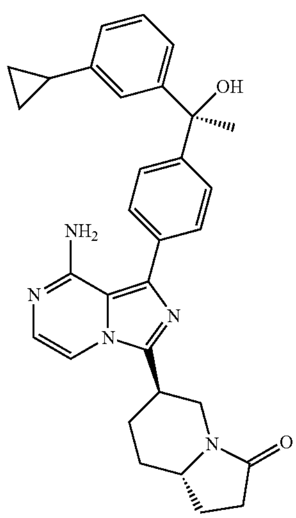 [SMILES: C[C@](O)(c1ccc(-c2nc([C@@H]3CC[C@H]4CCC(=O)N4C3)n3ccnc(N)c23)cc1)c1cccc(C2CC2)c1] | (6R,8aS)-6-(8-amino-1-{4-[(1S)-1-(3-cyclopropylphenyl)-1-hydroxyethyl]phenyl}imidazo[1,5-a]pyrazin-3-yl)hexahydroindolizin-3(2H)-one | Calc'd 508.3, found 508.2 | 2.493(C) |

TABLE 3-continued
| Example number | Structure | IUPAC Name | Exact Mass [M + H]+ | LC-MS retention time (min, method) |
|---|---|---|---|---|
| 52 | 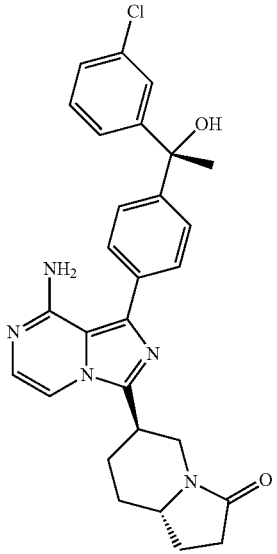 [SMILES: C[C@@](O)(c1ccc(-c2nc([C@@H]3CC[C@H]4CCC(=O)N4C3)n3ccnc(N)c23)cc1)c1cccc(Cl)c1] | (6R,8aS)-6-(8-amino-1-{4-[(1R)-1-(3-chlorophenyl)-1-hydroxyethyl]phenyl}imidazo[1,5-a]pyrazin-3-yl)hexahydroindolizin-3(2H)-one | Calc'd 502.2, found 502.1 | 2.442(C) |
| 53 | 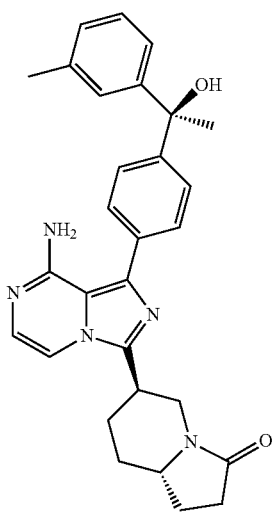 [SMILES: Cc1cccc([C@@](C)(O)c2ccc(-c3nc([C@@H]4CC[C@H]5CCC(=O)N5C4)n4ccnc(N)c34)cc2)c1] | (6R,8aS)-6-(8-amino-1-{4-[(1S)-1-hydroxy-1-(3-methylphenyl)ethyl]phenyl}imidazo[1,5-a]pyrazin-3-yl)hexahydroindolizin-3(2H)-one | Calc'd 482.3, found 482.2 | 2.387(C) |

TABLE 3-continued

| Example number | Structure | IUPAC Name | Exact Mass [M + H]+ | LC-MS retention time (min, method) |
|---|---|---|---|---|
| 54 | 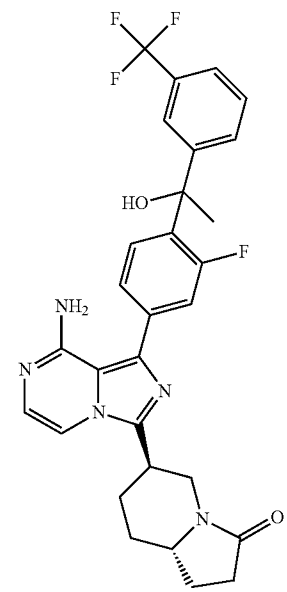 [SMILES: CC(O)(c1cccc(C(F)(F)F)c1)c1ccc(-c2nc([C@@H]3CC[C@H]4CCC(=O)N4C3)n3ccnc(N)c23)cc1F] | (6R,8aS)-6-[8-amino-1-(3-fluoro-4-{1-hydroxy-1-[3-(trifluoromethyl)phenyl]ethyl}phenyl)imidazo[1,5-a]pyrazin-3-yl]hexahydroindolizin-3(2H)-one | Calc'd 554.2, found 554.1 | 2.580(C) |
| 55 | 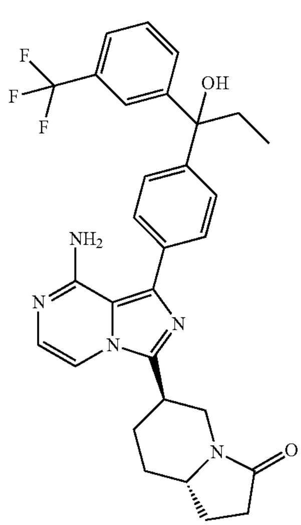 [SMILES: CCC(O)(c1ccc(-c2nc([C@@H]3CC[C@H]4CCC(=O)N4C3)n3ccnc(N)c23)cc1)c1cccc(C(F)(F)F)c1] | (6R,8aS)-6-[8-amino-1-(4-{1-hydroxy-1-[3-(trifluoromethyl)phenyl]propyl}phenyl)imidazo[1,5-a]pyrazin-3-yl]hexahydroindolizin-3(2H)-one | Calc'd 550.2, found 550.2 | 2.300(C) |

TABLE 3-continued
| Example number | Structure | IUPAC Name | Exact Mass [M + H]+ | LC-MS retention time (min, method) |
|---|---|---|---|---|
| 56 | 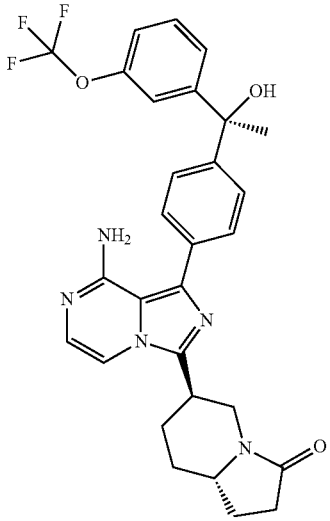 [SMILES: C[C@](O)(c1ccc(-c2nc([C@@H]3CC[C@H]4CCC(=O)N4C3)n3ccnc(N)c23)cc1)c1cccc(OC(F)(F)F)c1] | (6R,8aS)-6-[8-amino-1-(4-{(1S)-1-hydroxy-1-[3-(trifluoromethoxy)phenyl]ethyl}phenyl)imidazo[1,5-a]pyrazin-3-yl]hexahydroindolizin-3(2H)-one | Calc'd 552.2, found 552.2 | 2.555(C) |
| 57 | 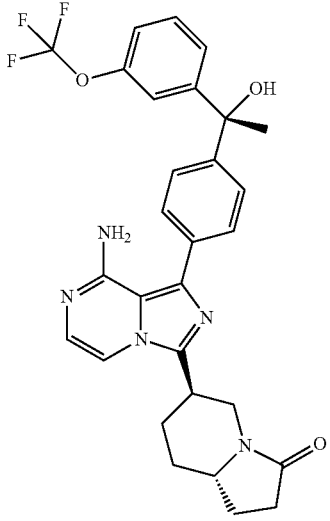 [SMILES: C[C@@](O)(c1ccc(-c2nc([C@@H]3CC[C@H]4CCC(=O)N4C3)n3ccnc(N)c23)cc1)c1cccc(OC(F)(F)F)c1] | (6R,8aS)-6-[8-amino-1-(4-{(1R)-1-hydroxy-1-[3-(trifluoromethoxy)phenyl]ethyl}phenyl)imidazo[1,5-a]pyrazin-3-yl]hexahydroindolizin-3(2H)-one | Calc'd 552.2, found 552.2 | 2.554(C) |

TABLE 3-continued

| Example number | Structure | IUPAC Name | Exact Mass [M + H]+ | LC-MS retention time (min, method) |
|---|---|---|---|---|
| 58 | 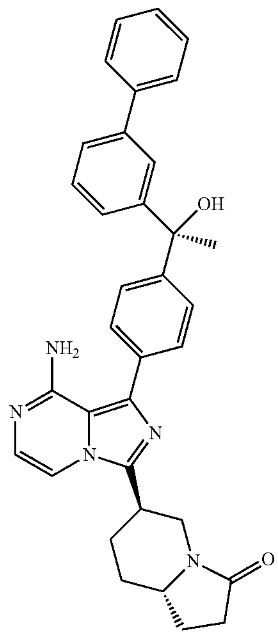 [SMILES: C[C@](O)(c1ccc(-c2nc([C@@H]3CC[C@H]4CCC(=O)N4C3)n3ccnc(N)c23)cc1)c1cccc(-c2ccccc2)c1] | (6R,8aS)-6-(8-amino-1-{4-[(1S)-1-biphenyl-3-yl-1-hydroxyethyl]phenyl}imidazo[1,5-a]pyrazin-3-yl)hexahydroindolizin-3(2H)-one | Calc'd 544.3, found 544.2 | 2.293(C) |
| 59 | 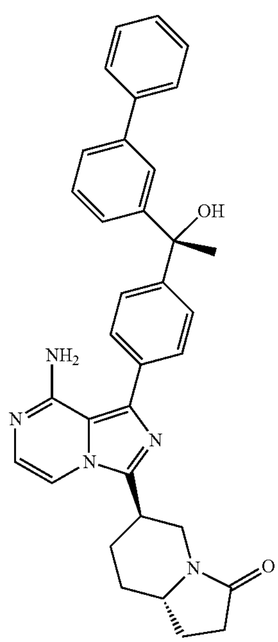 [SMILES: C[C@@](O)(c1ccc(-c2nc([C@@H]3CC[C@H]4CCC(=O)N4C3)n3ccnc(N)c23)cc1)c1cccc(-c2ccccc2)c1] | (6R,8aS)-6-(8-amino-1-{4-[(1R)-1-biphenyl-3-yl-1-hydroxyethyl]phenyl}imidazo[1,5-a]pyrazin-3-yl)hexahydroindolizin-3(2H)-one | Calc'd 544.3, found 544.2 | 2.293(C) |

TABLE 3-continued

| Example number | Structure | IUPAC Name | Exact Mass [M + H]+ | LC-MS retention time (min, method) |
|---|---|---|---|---|
| 60 | 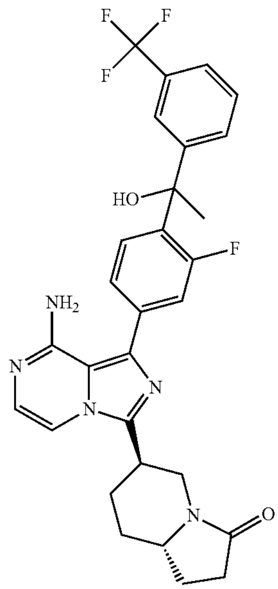 [SMILES: CC(O)(c1cccc(C(F)(F)F)c1)c1ccc(-c2nc([C@@H]3CC[C@H]4CCC(=O)N4C3)n3ccnc(N)c23)cc1F] | (6R,8aS)-6-[8-amino-1-(3-fluoro-4-{1-hydroxy-1-[3-(trifluoromethyl)phenyl]ethyl}phenyl)imidazo[1,5-a]pyrazin-3-yl]hexahydroindolizin-3(2H)-one | Calc'd 554.2, found 554.1 | 2.578(C) |
| 61 | 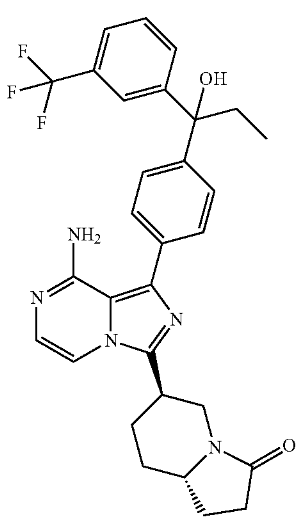 [SMILES: CCC(O)(c1ccc(-c2nc([C@@H]3CC[C@H]4CCC(=O)N4C3)n3ccnc(N)c23)cc1)c1cccc(C(F)(F)F)c1] | (6R,8aS)-6-[8-amino-1-(4-{1-hydroxy-1-[3-(trifluoromethyl)phenyl]propyl}phenyl)imidazo[1,5-a]pyrazin-3-yl]hexahydroindolizin-3(2H)-one | Calc'd 550.2, found 550.2 | 2.302(C) |

TABLE 3-continued
| Example number | Structure | IUPAC Name | Exact Mass [M + H]+ | LC-MS retention time (min, method) |
|---|---|---|---|---|
| 62 | 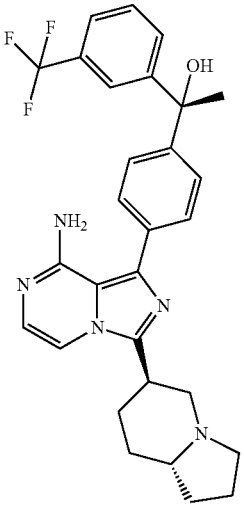 [SMILES: C[C@@](O)(c1ccc(-c2nc([C@@H]3CC[C@H]4CCCN4C3)n3ccnc(N)c23)cc1)c1cccc(C(F)(F)F)c1] | (1R)-1-(4-{8-amino-3-[(6R,8aS)-octahydroindolizin-6-yl]imidazo[1,5-a]pyrazin-1-yl}phenyl)-1-[3-(trifluoromethyl)phenyl]ethanol | Calc'd 522.2, found 522.2 | 1.924(C) |
| 63 | 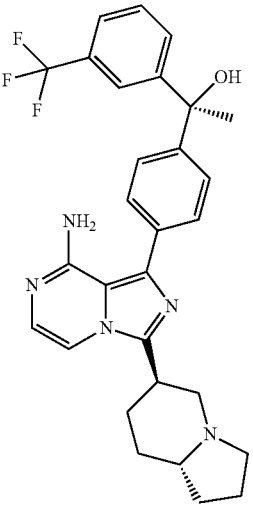 [SMILES: C[C@](O)(c1ccc(-c2nc([C@@H]3CC[C@H]4CCCN4C3)n3ccnc(N)c23)cc1)c1cccc(C(F)(F)F)c1] | (1S)-1-(4-{8-amino-3-[(6R,8aS)-octahydroindolizin-6-yl]imidazo[1,5-a]pyrazin-1-yl}phenyl)-1-[3-(trifluoromethyl)phenyl]ethanol | Calc'd 522.2, found 522.2 | 1.919(C) |

TABLE 3-continued
| Example number | Structure | IUPAC Name | Exact Mass [M + H]+ | LC-MS retention time (min, method) |
|---|---|---|---|---|
| 64 | 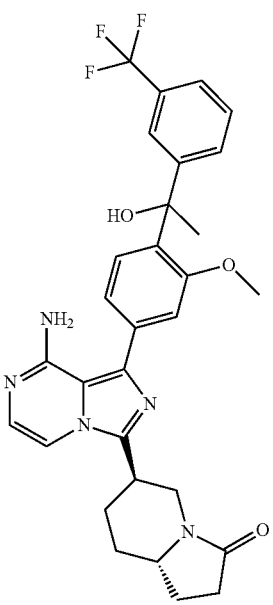 [SMILES: COc1cc(-c2nc([C@@H]3CC[C@H]4CCC(=O)N4C3)n3ccnc(N)c23)ccc1C(C)(O)c1cccc(C(F)(F)F)c1] | (6R,8aS)-6-[8-amino-1-(4-{1-hydroxy-1-[3-(trifluoromethyl)phenyl]ethyl}-3-methoxyphenyl)imidao[1,5-a]pyrazin-3-yl]hexahydroindolizin-3(2H)-one | Calc'd 566.2, found 566.2 | 2.587(C) |
| 65 | 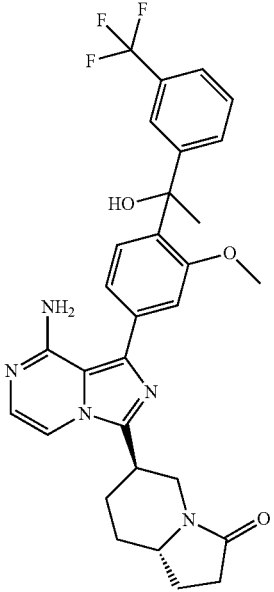 [SMILES: COc1cc(-c2nc([C@@H]3CC[C@H]4CCC(=O)N4C3)n3ccnc(N)c23)ccc1C(C)(O)c1cccc(C(F)(F)F)c1] | (6R,8aS)-6-[8-amino-1-(4-{1-hydroxy-1-[3-(trifluoromethyl)phenyl]ethyl}-3-methoxyphenyl)imidazo[1,5-a]pyrazin-3-yl]hexahydroindolizin-3(2H)-one | Calc'd 566.2, found 566.2 | 2.580(C) |

TABLE 3-continued

| Example number | Structure | IUPAC Name | Exact Mass [M + H]+ | LC-MS retention time (min, method) |
|---|---|---|---|---|
| 66 | 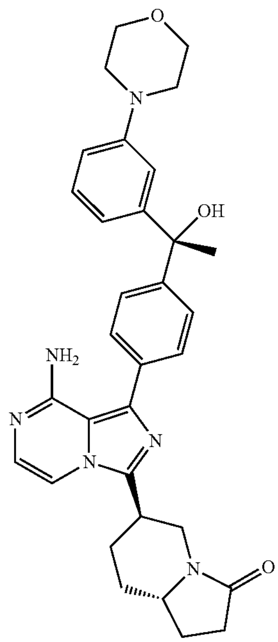 [SMILES: C[C@@](O)(c1ccc(-c2nc([C@@H]3CC[C@H]4CCC(=O)N4C3)n3ccnc(N)c23)cc1)c1cccc(N2CCOCC2)c1] | (6R,8aS)-6-(8-amino-1-{4-[(1R)-1-hydroxy-1-(3-morpholin-4-ylphenyl)ethyl]phenyl}imidazo[1,5-a]pyrazin-3-yl)hexahydroindolizin-3(2H)-one | Calc'd 553.3, found 553.2 | 2.161(C) |
| 67 | 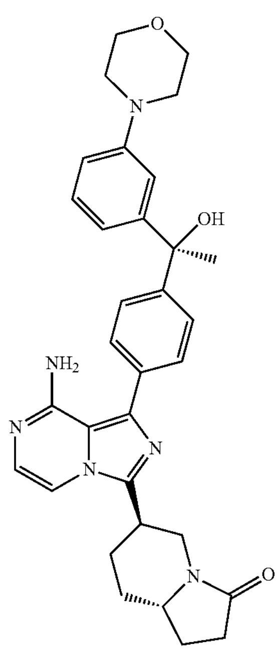 [SMILES: C[C@](O)(c1ccc(-c2nc([C@@H]3CC[C@H]4CCC(=O)N4C3)n3ccnc(N)c23)cc1)c1cccc(N2CCOCC2)c1] | (6R,8aS)-6-(8-amino-1-{4-[(1S)-1-hydroxy-1-(3-morpholin-4-ylphenyl)ethyl]phenyl}imidazo[1,5-a]pyrazin-3-yl)hexahydroindolizin-3(2H)-one | Calc'd 553.3, found 553.2 | 2.158(C) |

TABLE 3-continued

| Example number | Structure | IUPAC Name | Exact Mass [M + H]+ | LC-MS retention time (min, method) |
|---|---|---|---|---|
| 68 | 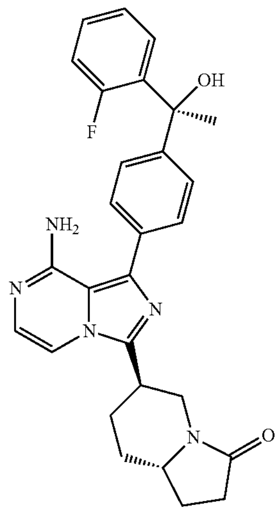 [SMILES: C[C@](O)(c1ccc(-c2nc([C@@H]3CC[C@H]4CCC(=O)N4C3)n3ccnc(N)c23)cc1)c1ccccc1F] | (6R,8aS)-6-(8-amino-1-{4-[(1S)-1-(2-fluorophenyl)-1-hydroxyethyl]phenyl}imidazo[1,5-a]pyrazin-3-yl)hexahydroindolizin-3(2H)-one | Calc'd 486.2, found 486.1 | 2.326(C) |
| 69 | 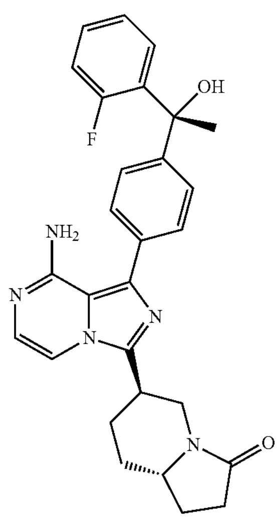 [SMILES: C[C@@](O)(c1ccc(-c2nc([C@@H]3CC[C@H]4CCC(=O)N4C3)n3ccnc(N)c23)cc1)c1ccccc1F] | (6R,8aS)-6-(8-amino-1-{4-[(1R)-1-(2-fluorophenyl)-1-hydroxyethyl]phenyl}imidazo[1,5-a]pyrazin-3-yl)hexahydroindolizin-3(2H)-one | Calc'd 486.2, found 486.1 | 2.326(C) |

TABLE 3-continued

| Example number | Structure | IUPAC Name | Exact Mass [M + H]+ | LC-MS retention time (min, method) |
|---|---|---|---|---|
| 70 | 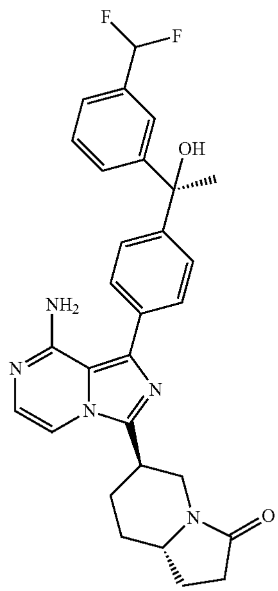 [SMILES: C[C@](O)(c1ccc(-c2nc([C@@H]3CC[C@H]4CCC(=O)N4C3)n3ccnc(N)c23)cc1)c1cccc(C(F)F)c1] | (6R,8aS)-6-[8-amino-1-(4-{(1S)-1-[3-(difluoromethyl)phenyl]-1-hydroxyethyl}phenyl)imidazo[1,5-a]pyrazin-3-yl]hexahydroindolizin-3(2H)-one | Calc'd 518.2, found 518.2 | 2.383(C) |
| 71 | 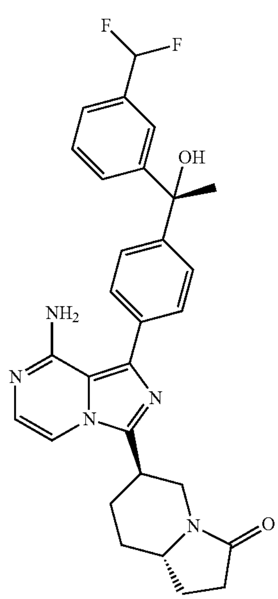 [SMILES: C[C@@](O)(c1ccc(-c2nc([C@@H]3CC[C@H]4CCC(=O)N4C3)n3ccnc(N)c23)cc1)c1cccc(C(F)F)c1] | (6R,8aS)-6-[8-amino-1-(4-{(1R)-1-[3-(difluoromethyl)phenyl]-1-hydroxyethyl}phenyl)imidazo[1,5-a]pyrazin-3-yl]hexahydroindolizin-3(2H)-one | Calc'd 518.2, found 518.2 | 2.383(C) |

TABLE 3-continued

| Example number | Structure | IUPAC Name | Exact Mass [M + H]+ | LC-MS retention time (min, method) |
| --- | --- | --- | --- | --- |
| 72 | 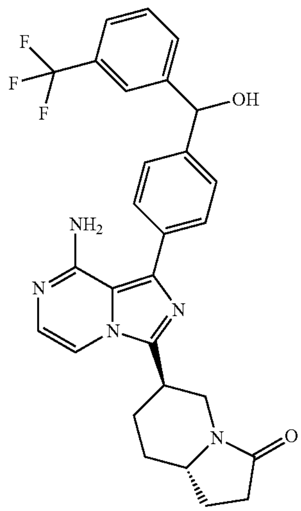 [SMILES: Nc1nccn2c([C@@H]3CC[C@H]4CCC(=O)N4C3)nc(-c3ccc(C(O)c4cccc(C(F)(F)F)c4)cc3)c12] | (6R,8aS)-6-[8-amino-1-(4-{hydroxy[3-(trifluoromethyl)phenyl]methyl}phenyl)imidazo[1,5-a]pyrazin-3-yl]hexahydroindolizin-3(2H)-one | Calc'd 522.2, found 522.2 | 2.428(C) |
| 73 | 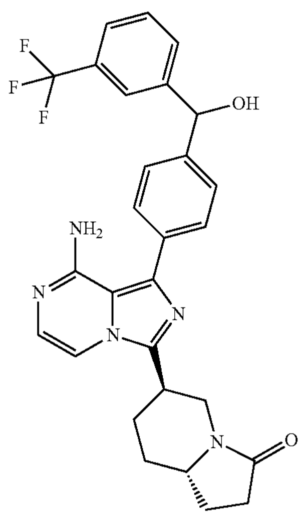 [SMILES: Nc1nccn2c([C@@H]3CC[C@H]4CCC(=O)N4C3)nc(-c3ccc(C(O)c4cccc(C(F)(F)F)c4)cc3)c12] | (6R,8aS)-6-[8-amino-1-(4-{hydroxy[3-(trifluoromethyl)phenyl]methyl}phenyl)imidazo[1,5-a]pyrazin-3-yl]hexahydroindolizin-3(2H)-one | Calc'd 522.2, found 522.2 | 2.434(C) |
| 74 | 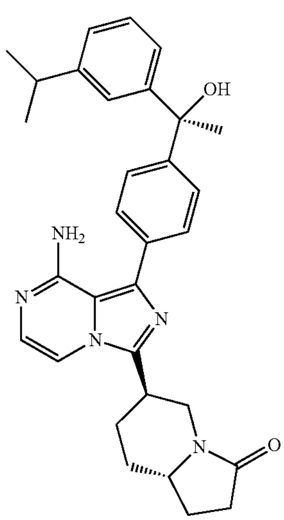 [SMILES: CC(C)c1cccc([C@@](C)(O)c2ccc(-c3nc([C@@H]4CC[C@H]5CCC(=O)N5C4)n4ccnc(N)c34)cc2)c1] | (6R,8aS)-6-[8-amino-1-(4-{(1S)-1-hydroxy-1-[3-(1-methylethyl)phenyl]ethyl}phenyl)imidazo[1,5-a]pyrazin-3-yl]hexahydroindolizin-3(2H)-one | Calc'd 510.3, found 510.2 | 2.236(C) |

TABLE 3-continued

| Example number | Structure | IUPAC Name | Exact Mass [M + H]+ | LC-MS retention time (min, method) |
| --- | --- | --- | --- | --- |
| 75 | 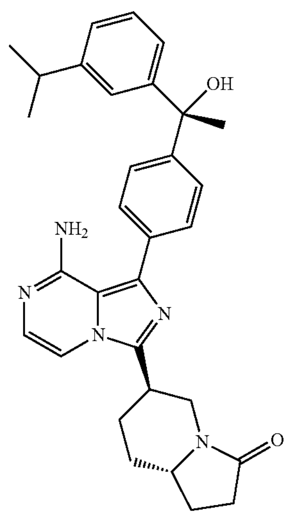 [SMILES: CC(C)c1cccc([C@](C)(O)c2ccc(-c3nc([C@@H]4CC[C@H]5CCC(=O)N5C4)n4ccnc(N)c34)cc2)c1] | (6R,8aS)-6-[8-amino-1-(4-{(1R)-1-hydroxy-1-[3(1-methylethyl)phenyl]ethyl}phenyl)imidazo[1,5-a]pyrazin-3-yl]hexahydroindolizin-3(2H)-one | Calc'd 510.3, found 510.2 | 2.241(C) |
| 76 | 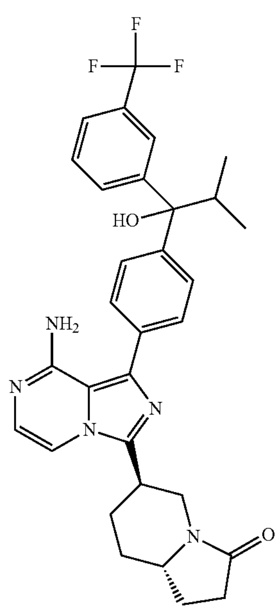 [SMILES: CC(C)C(O)(c1ccc(-c2nc([C@@H]3CC[C@H]4CCC(=O)N4C3)n3ccnc(N)c23)cc1)c1cccc(C(F)(F)F)c1] | (6R,8aS)-6-[8-amino-1-(4-{1-hydroxy-2-methyl-1-[3-(trifluoromethyl)phenyl]propyl}phenyl)imidazo[1,5-a]pyrazin-3-yl]hexahydroindolizin-3(2H)-one | Calc'd 564.3, found 564.2 | 2.379(C) |

TABLE 3-continued

| Example number | Structure | IUPAC Name | Exact Mass [M + H]+ | LC-MS retention time (min, method) |
|---|---|---|---|---|
| 77 | 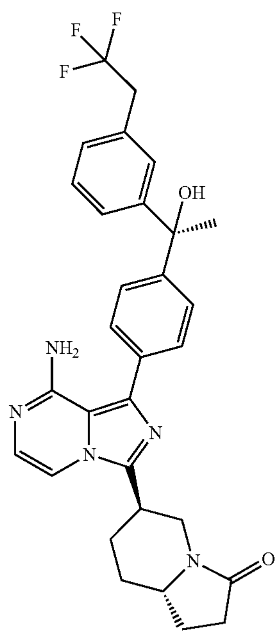 [SMILES: C[C@](O)(c1ccc(-c2nc([C@@H]3CC[C@H]4CCC(=O)N4C3)n3ccnc(N)c23)cc1)c1cccc(CC(F)(F)F)c1] | (6R,8aS)-6-[8-amino-1-(4-{(1S)-1-hydroxy-1-[3-(2,2,2-trifluoroethyl)phenyl]ethyl}phenyl)imidazo[1,5-a]pyrazin-3-yl]hexahydroindolizin-3(2H)-one | Calc'd 550.2, found 550.2 | 2.469(C) |
| 78 | 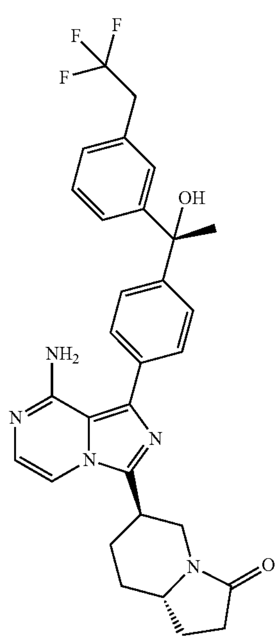 [SMILES: C[C@@](O)(c1ccc(-c2nc([C@@H]3CC[C@H]4CCC(=O)N4C3)n3ccnc(N)c23)cc1)c1cccc(CC(F)(F)F)c1] | (6R,8aS)-6-[8-amino-1-(4-{(1R)-1-hydroxy-1-[3-(2,2,2-trifluoroethyl)phenyl]ethyl}phenyl)imidazo[1,5-a]pyrazin-3-yl]hexahydroindolizin-3(2H)-one | Calc'd 550.2, found 550.2 | 2.477(C) |

TABLE 3-continued

| Example number | Structure | IUPAC Name | Exact Mass [M + H]+ | LC-MS retention time (min, method) |
|---|---|---|---|---|
| 79 | 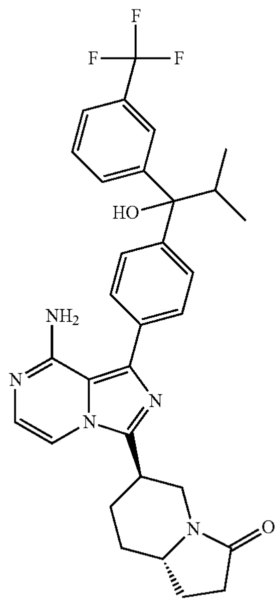 [SMILES: CC(C)C(O)(c1ccc(-c2nc([C@@H]3CC[C@H]4CCC(=O)N4C3)n3ccnc(N)c23)cc1)c1cccc(C(F)(F)F)c1] | (6R,8aS)-6-[8-amino-1-(4-{1-hydroxy-2-methyl-1-[3-(trifluoromethyl)phenyl]propyl}phenyl)imidazo[1,5-a]pyrazin-3-yl]hexahydroindolizin-3(2H)-one | Calc'd 564.3, found 564.2 | 2.371(C) |
| 80 | 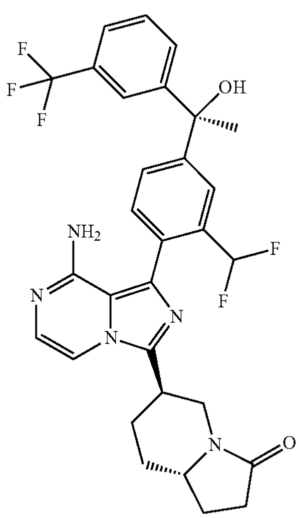 [SMILES: C[C@@](O)(c1cccc(C(F)(F)F)c1)c1ccc(-c2nc([C@@H]3CC[C@H]4CCC(=O)N4C3)n3ccnc(N)c23)c(C(F)F)c1] | (6R,8aS)-6-{8-amino-1-[2-(difluoromethyl)-4-{(1S)-1-hydroxy-1-[3-(trifluoromethyl)phenyl]ethyl}phenyl]imidazo[1,5-a]pyrazin-3-yl}-hexahydroindolizin-3(2H)-one | Calc'd 586.2, found 586.1 | 2.631(C) |

TABLE 3-continued

| Example number | Structure | IUPAC Name | Exact Mass [M + H]+ | LC-MS retention time (min, method) |
|---|---|---|---|---|
| 81 | 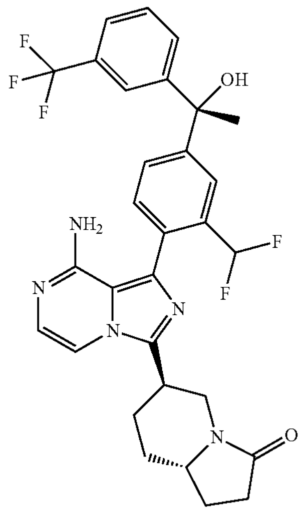 [SMILES: C[C@](O)(c1cccc(C(F)(F)F)c1)c1ccc(-c2nc([C@@H]3CC[C@H]4CCC(=O)N4C3)n3ccnc(N)c23)c(C(F)F)c1] | (6R,8aS)-6-{8-amino-1-[2-(difluoromethyl)-4-{(1R)-1-hydroxy-1-[3-(trifluoromethyl)phenyl]ethyl}phenyl]imidazo[1,5-a]pyrazin-3-yl}hexahydroindolizin-3(2H)-one | Calc'd 586.2, found 586.1 | 2.635(C) |
| 82 | 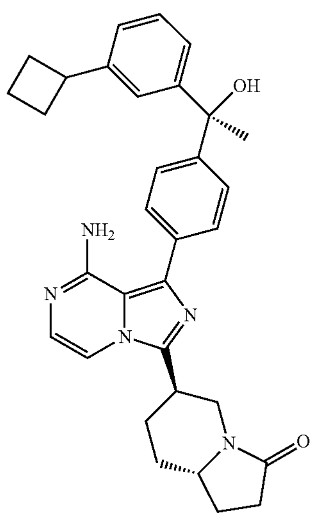 [SMILES: C[C@](O)(c1ccc(-c2nc([C@@H]3CC[C@H]4CCC(=O)N4C3)n3ccnc(N)c23)cc1)c1cccc(C2CCC2)c1] | (6R,8aS)-6-(8-amino-1-{4-[(1S)-1-(3-cyclobutylphenyl)-1-hydroxyethyl]phenyl}imidazo[1,5-a]pyrazin-3-yl)hexahydroindolizin-3(2H)-one | Calc'd 522.3, found 522.2 | 2.303(C) |
| 83 | 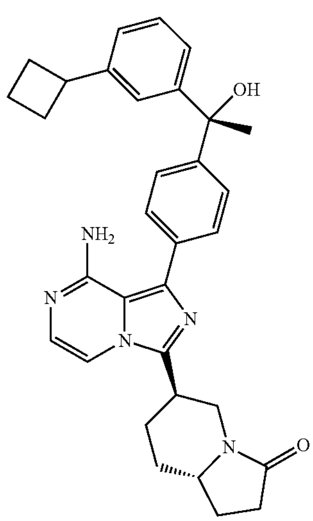 [SMILES: C[C@@](O)(c1ccc(-c2nc([C@@H]3CC[C@H]4CCC(=O)N4C3)n3ccnc(N)c23)cc1)c1cccc(C2CCC2)c1] | (6R,8aS)-6-(8-amino-1-{4-[(1R)-1-(3-cyclobutylphenyl)-1-hydroxyethyl]phenyl}imidazo[1,5-a]pyrazin-3-yl)hexahydroindolizin-3(2H)-one | Calc'd 522.3, found 522.2 | 2.303(C) |

TABLE 3-continued

| Example number | Structure | IUPAC Name | Exact Mass [M + H]+ | LC-MS retention time (min, method) |
|---|---|---|---|---|
| 84 | 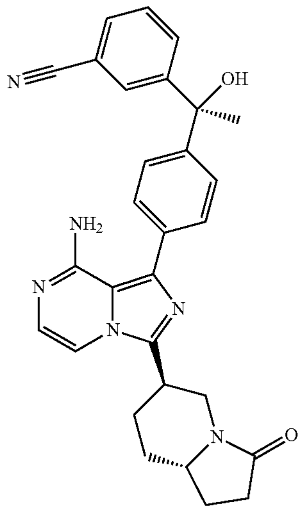 [SMILES: C[C@](O)(c1ccc(-c2nc([C@@H]3CC[C@H]4CCC(=O)N4C3)n3ccnc(N)c23)cc1)c1cccc(C#N)c1] | 3-[(1S)-1-(4-{8-amino-3-[(6R,8aS)-3-oxooctahydroindolizin-6-yl]imidazo[1,5-a]pyrazin-1-yl}phenyl)-1-hydroxyethyl]benzonitrile | Calc'd 493.2, found 493.2 | 2.248(C) |
| 85 | 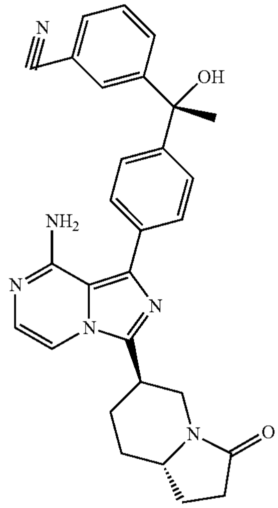 [SMILES: C[C@@](O)(c1ccc(-c2nc([C@@H]3CC[C@H]4CCC(=O)N4C3)n3ccnc(N)c23)cc1)c1cccc(C#N)c1] | 3-[(1R)-1-(4-{8-amino-3-[(6R,8aS)-3-oxooctahydroindolizin-6-yl]imidazo[1,5-a]pyrazin-1-yl}phenyl)-1-hydroxyethyl]benzonitrile | Calc'd 493.2, found 493.2 | 2.249(C) |
| 86 | 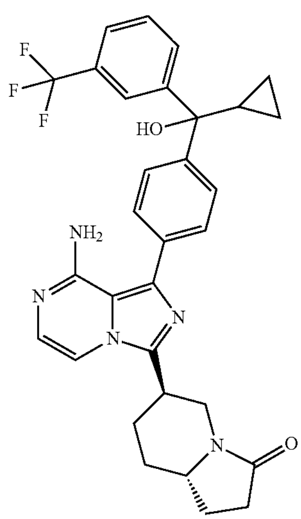 [SMILES: Nc1nccn2c([C@@H]3CC[C@H]4CCC(=O)N4C3)nc(-c3ccc(C(O)(c4cccc(C(F)(F)F)c4)C4CC4)cc3)c12] | (6R,8aS)-6-[8-amino-1-(4-{cyclopropyl(hydroxy)[3-(trifluoromethyl)phenyl]methyl}phenyl)imidazo[1,5-a]pyrazin-3-yl]hexahydroindolizin-3(2H)-one | Calc'd 562.2, found 562.2 | 2.326(C) |

TABLE 3-continued

| Example number | Structure | IUPAC Name | Exact Mass [M + H]+ | LC-MS retention time (min, method) |
|---|---|---|---|---|
| 87 | 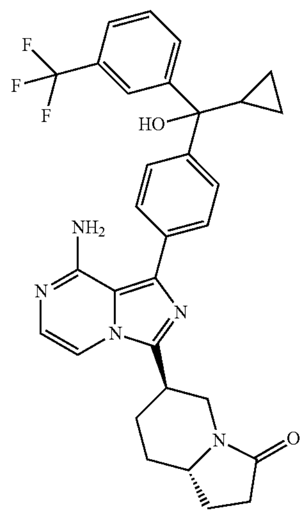 [SMILES: Nc1nccn2c([C@@H]3CC[C@H]4CCC(=O)N4C3)nc(-c3ccc(C(O)(c4cccc(C(F)(F)F)c4)C4CC4)cc3)c12] | (6R,8aS)-6-[8-amino-1-(4-{cyclopropyl(hydroxy)[3-(trifluoromethyl)phenyl]methyl}phenyl)imidazo[1,5-a]pyrazin-3-yl]hexahydroindolizin-3(2H)-one | Calc'd 562.2, found 562.2 | 2.332(C) |
| 88 | 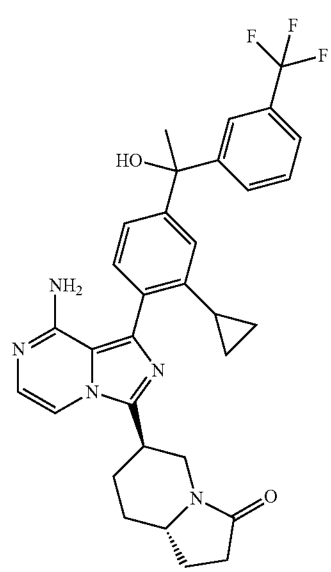 [SMILES: CC(O)(c1cccc(C(F)(F)F)c1)c1ccc(-c2nc([C@@H]3CC[C@H]4CCC(=O)N4C3)n3ccnc(N)c23)c(C2CC2)c1] | (6R,8aS)-6-[8-amino-1-(2-cyclopropyl-4-{1-hydroxy-1-[3-(trifluoromethyl)phenyl]ethyl}phenyl)imidazo[1,5-a]pyrazin-3-yl]hexahydroindolizin-3(2H)-one | Calc'd 576.3, found 576.2 | 2.279(C) |

TABLE 3-continued

| Example number | Structure | IUPAC Name | Exact Mass [M + H]+ | LC-MS retention time (min, method) |
|---|---|---|---|---|
| 89 | 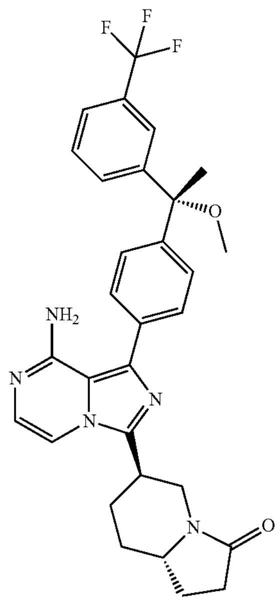 [SMILES: CO[C@](C)(c1ccc(-c2nc([C@@H]3CC[C@H]4CCC(=O)N4C3)n3ccnc(N)c23)cc1)c1cccc(C(F)(F)F)c1] | (6R,8aS)-6-[8-amino-1-(4-{(1R)-1-methoxy-1-[3-(trifluoromethyl)phenyl]ethyl}phenyl)imidazo[1,5-a]pyrazin-3-yl]hexahydroindolizin-3(2H)-one | Calc'd 550.2, found 550.2 | 2.417(C) |
| 90 | 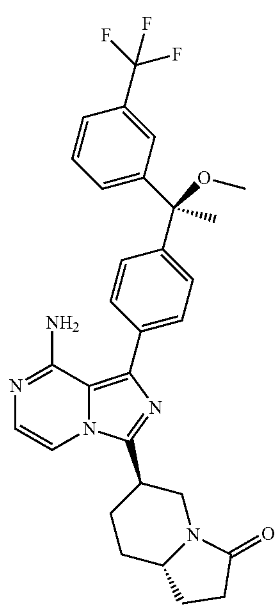 [SMILES: CO[C@@](C)(c1ccc(-c2nc([C@@H]3CC[C@H]4CCC(=O)N4C3)n3ccnc(N)c23)cc1)c1cccc(C(F)(F)F)c1] | (6R,8aS)-6-[8-amino-1-(4-{(1S)-1-methoxy-1-[3-(trifluoromethyl)phenyl]ethyl}phenyl)imidazo[1,5-a]pyrazin-3-yl]hexahydroindolizin-3(2H)-one | Calc'd 550.2, found 550.2 | 2.422(C) |

TABLE 3-continued

| Example number | Structure | IUPAC Name | Exact Mass [M + H]+ | LC-MS retention time (min, method) |
|---|---|---|---|---|
| 91 | 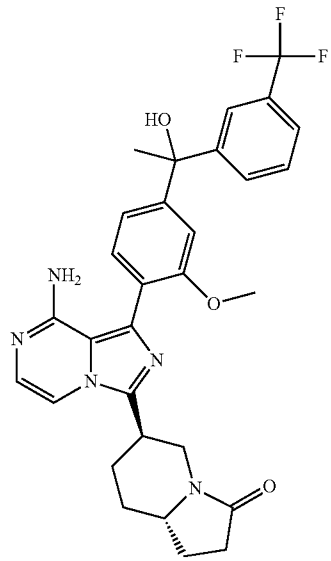 [SMILES: COc1cc(C(C)(O)c2cccc(C(F)(F)F)c2)ccc1-c1nc([C@@H]2CC[C@H]3CCC(=O)N3C2)n2ccnc(N)c12] | (6R,8aS)-6-[8-amino-1-(4-{1-hydroxy-1-[3-(trifluoromethyl)phenyl]ethyl}-2-methoxyphenyl)imidazo[1,5-a]pyrazin-3-yl]hexahydroindolizin-3(2H)-one | Calc'd 566.2, found | |
| 92 | 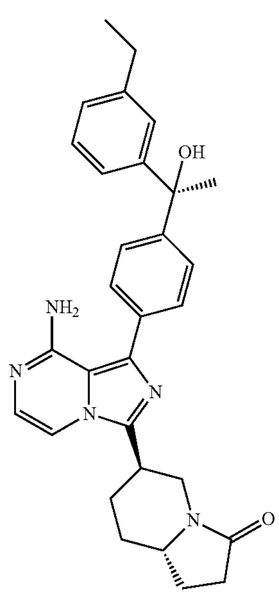 [SMILES: CCc1cccc([C@@](C)(O)c2ccc(-c3nc([C@@H]4CC[C@H]5CCC(=O)N5C4)n4ccnc(N)c34)cc2)c1] | (6R,8aS)-6-(8-amino-1-{4-[(1S)-1-(3-ethylphenyl)-1-hydroxyethyl]phenyl}imidazo[1,5-a]pyrazin-3-yl)hexahydroindolizin-3(2H)-one | Calc'd 496.3, found 496.3 | 2.456(C) |

TABLE 3-continued

| Example number | Structure | IUPAC Name | Exact Mass [M + H]+ | LC-MS retention time (min, method) |
|---|---|---|---|---|
| 93 | 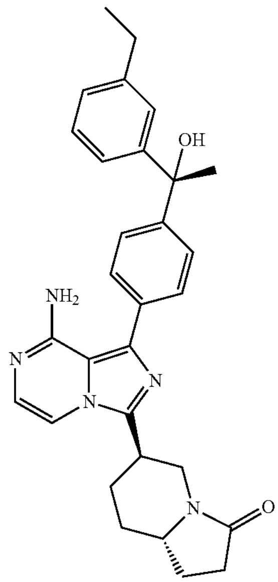 [SMILES: CCc1cccc([C@](C)(O)c2ccc(-c3nc([C@@H]4CC[C@H]5CCC(=O)N5C4)n4ccnc(N)c34)cc2)c1] | (6R,8aS)-6-(8-amino-1-(4-[(1R)-1-(3-ethylphenyl)-1-hydroxyethyl]phenyl}imidazo[1,5-a]pyrazin-3-yl)hexahydroindolizin-3(2H)-one | Calc'd 496.3, found 496.2 | 2.467(C) |
| 94 | 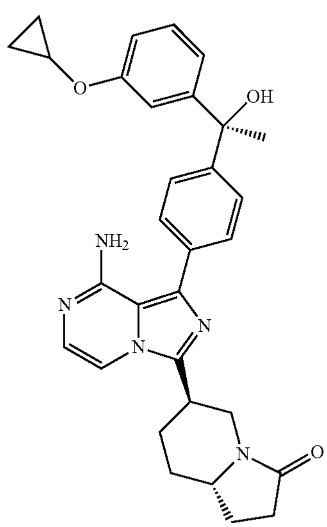 [SMILES: C[C@](O)(c1ccc(-c2nc([C@@H]3CC[C@H]4CCC(=O)N4C3)n3ccnc(N)c23)cc1)c1cccc(OC2CC2)c1] | (6R,8aS)-6-[8-amino-1-(4-{(1S)-1-[3-(cyclopropyloxy)phenyl]-1-hydroxyethyl}phenyl)imidazo[1,5-a]pyrazin-3-yl]hexahydroindolizin-3(2H)-one | Calc'd 524.3, found 524.2 | 2.429(C) |

TABLE 3-continued

| Example number | Structure | IUPAC Name | Exact Mass [M + H]+ | LC-MS retention time (min, method) |
|---|---|---|---|---|
| 95 | 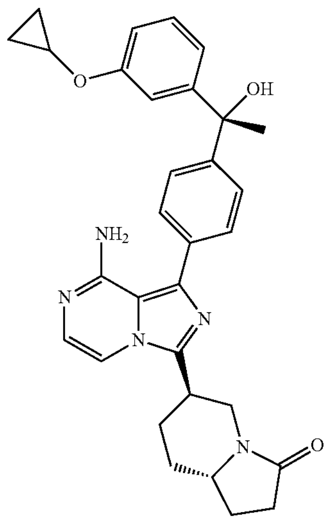 [SMILES: C[C@@](O)(c1ccc(-c2nc([C@@H]3CC[C@H]4CCC(=O)N4C3)n3ccnc(N)c23)cc1)c1cccc(OC2CC2)c1] | (6R,8aS)-6-[8-amino-1-(4-{(1R)-1-[3-(cyclopropyloxy)phenyl]-1-hydroxyethyl}phenyl)imidazo[1,5-a]pyrazin-3-yl]hexahydroindolizin-3(2H)-one | Calc'd 524.3, found 524.2 | 2.431(C) |
| 96 | 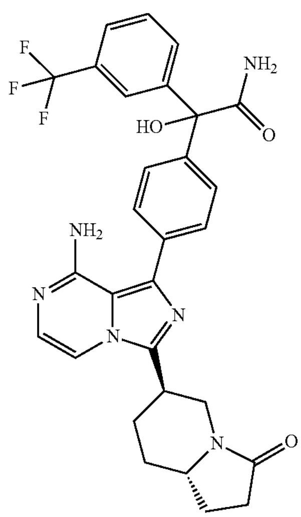 [SMILES: NC(=O)C(O)(c1ccc(-c2nc([C@@H]3CC[C@H]4CCC(=O)N4C3)n3ccnc(N)c23)cc1)c1cccc(C(F)(F)F)c1] | 2-(4-{8-amino-3-[(6R,8aS)-3-oxooctahydroindolizin-6-yl]imidazo[1,5-a]pyrazin-1-yl}phenyl)-2-hydroxy-2-[3-(trifluoromethyl)phenyl]acetamide | Calc'd 565.2, found 565.2 | 2.270(C) |
| 97 | 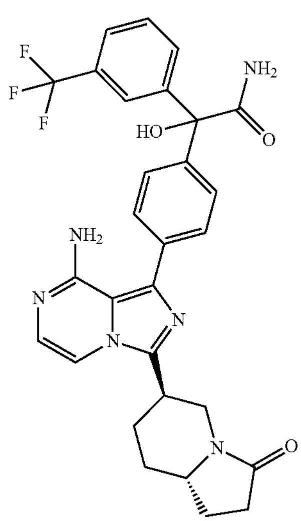 [SMILES: NC(=O)C(O)(c1ccc(-c2nc([C@@H]3CC[C@H]4CCC(=O)N4C3)n3ccnc(N)c23)cc1)c1cccc(C(F)(F)F)c1] | 2-(4-{8-amino-3-[(6R,8aS)-3-oxooctahydroindolizin-6-yl]imidazo[1,5-a]pyrazin-1-yl}phenyl)-2-hydroxy-2-[3-(trifluoromethyl)phenyl]acetamide | Calc'd 565.2, found 565.2 | 2.292(C) |

TABLE 3-continued

| Example number | Structure | IUPAC Name | Exact Mass [M + H]+ | LC-MS retention time (min, method) |
|---|---|---|---|---|
| 98 | 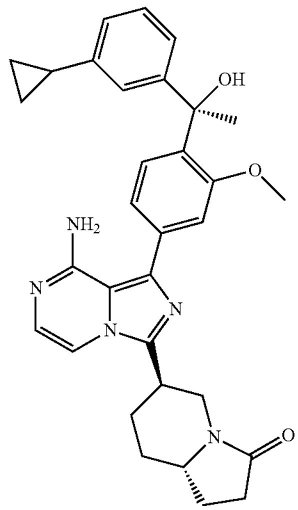 [SMILES: COc1cc(-c2nc([C@@H]3CC[C@H]4CCC(=O)N4C3)n3ccnc(N)c23)ccc1[C@](C)(O)c1cccc(C2CC2)c1] | (6R,8aS)-6-(8-amino-1-{4-[(1R)-1-(3-cyclopropylphenyl)-1-hydroxyethyl]-3-methoxyphenyl}imidazo[1,5-a]pyrazin-3-yl)hexahydroindolizin-3(2H)-one | Calc'd 538.3, found 538.3 | 2.550(C) |
| 99 | 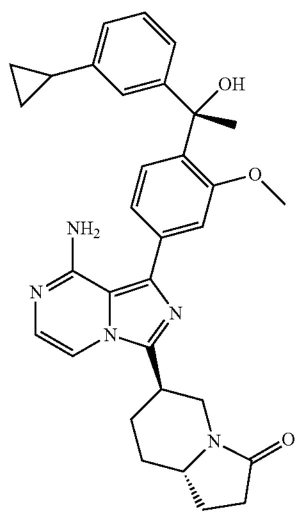 [SMILES: COc1cc(-c2nc([C@@H]3CC[C@H]4CCC(=O)N4C3)n3ccnc(N)c23)ccc1[C@@](C)(O)c1cccc(C2CC2)c1] | (6R,8aS)-6-(8-amino-1-{4-[(1S)-1-(3-cyclopropylphenyl)-1-hydroxyethyl]-3-methoxyphenyl}imidazo[1,5-a]pyrazin-3-yl)hexahydroindolizin-3(2H)-one | Calc'd 538.3, found 538.2 | 2.571(C) |
| 100 | 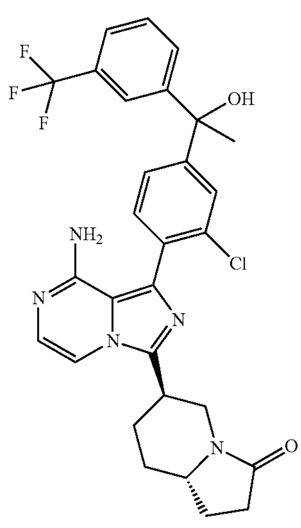 [SMILES: CC(O)(c1cccc(C(F)(F)F)c1)c1ccc(-c2nc([C@@H]3CC[C@H]4CCC(=O)N4C3)n3ccnc(N)c23)c(Cl)c1] | (6R,8aS)-6-[8-amino-1-(2-chloro-4-{1-hydroxy-1-[3-(trifluoromethyl)phenyl]ethyl}phenyl)imidazo[1,5-a]pyrazin-3-yl]hexahydroindolizin-3(2H)-one | Calc'd 570.2, found 570.1 | 2.218(C) |

TABLE 3-continued
| Example number | Structure | IUPAC Name | Exact Mass [M + H]+ | LC-MS retention time (min, method) |
|---|---|---|---|---|
| 101 | 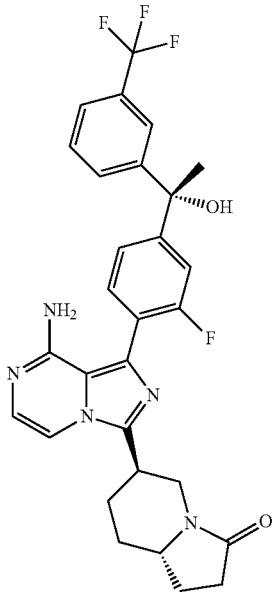 | (6R,8aS)-6-[8-amino-1-(2-fluoro-4-{(1S)-1-hydroxy-1-[3-(trifluoromethyl)phenyl]ethyl}phenyl)imidazo[1,5-a]pyrazin-3-yl]hexahydroindolizin-3(2H)-one | Calc'd 554.2, found 554.2 | 2.539(C) |
| 102 | 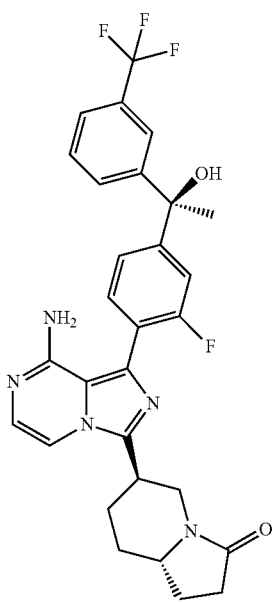 [SMILES: C[C@@](O)(c1cccc(C(F)(F)F)c1)c1ccc(-c2nc([C@@H]3CC[C@H]4CCC(=O)N4C3)n3ccnc(N)c23)c(F)c1] | (6R,8aS)-6-[8-amino-1-(2-fluoro-4-{(1R)-1-hydroxy-1-[3-(trifluoromethyl)phenyl]ethyl}phenyl)imidazo[1,5-a]pyrazin-3-yl]hexahydroindolizin-3(2H)-one | Calc'd 554.2, found 554.1 | 2.538(C) |

| Example number | Structure | IUPAC Name | Exact Mass [M + H]+ | LC-MS retention time (min, method) |
|---|---|---|---|---|
| 103 | 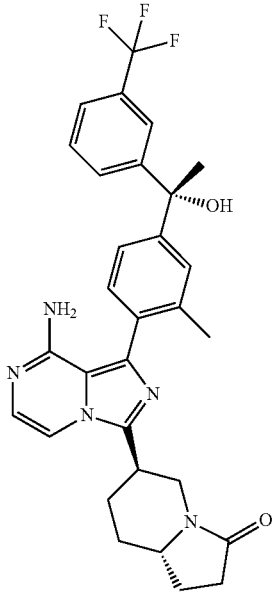 [SMILES: Cc1cc([C@@](C)(O)c2cccc(C(F)(F)F)c2)ccc1-c1nc([C@@H]2CC[C@H]3CCC(=O)N3C2)n2ccnc(N)c12] | (6R,8aS)-6-[8-amino-1-(4-{(1R)-1-hydroxy-1-[3-(trifluoromethyl)phenyl]-ethyl}-2-methylphenyl)imidazo[1,5-a]pyrazin-3-yl]hexahydroindolizin-3(2H)-one | Calc'd 550.2, found 550.1 | 2.413(C) |
| 104 | 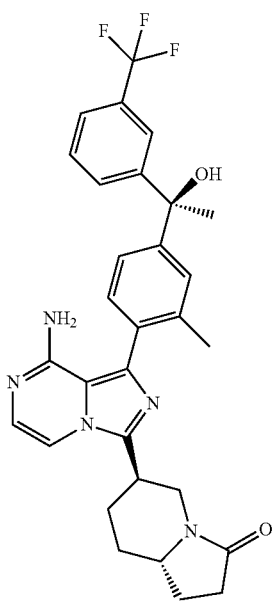 [SMILES: Cc1cc([C@](C)(O)c2cccc(C(F)(F)F)c2)ccc1-c1nc([C@@H]2CC[C@H]3CCC(=O)N3C2)n2ccnc(N)c12] | (6R,8aS)-6-[8-amino-1-(4-{(1S)-1-hydroxy-1-[3-(trifluoromethyl)phenyl]ethyl}-2-methylphenyl)imidazo[1,5-a]pyrazin-3-yl]hexahydroindolizin-3(2H)-one | Calc'd 550.2, found 550.2 | 2.501(C) |

TABLE 3-continued

| Example number | Structure | IUPAC Name | Exact Mass [M + H]+ | LC-MS retention time (min, method) |
|---|---|---|---|---|
| 105 | 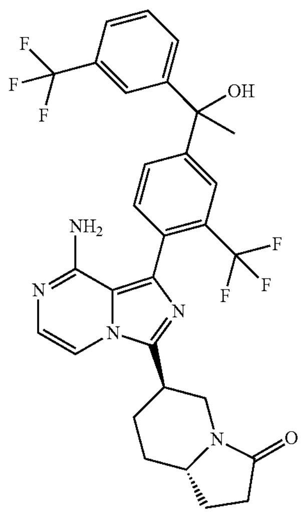 [SMILES: CC(O)(c1cccc(C(F)(F)F)c1)c1ccc(-c2nc([C@@H]3CC[C@H]4CCC(=O)N4C3)n3ccnc(N)c23)c(C(F)(F)F)c1] | (6R,8aS)-6-{8-amino-1-[4-{1-hydroxy-1-[3-(trifluoromethyl)phenyl]ethyl}-2-(trifluoromethyl)phenyl]imidazo[1,5-a]pyrazin-3-yl}hexahydroindolizin-3(2H)-one | Calc'd 604.2, found 604.1 | 2.322(C) |
| 106 | 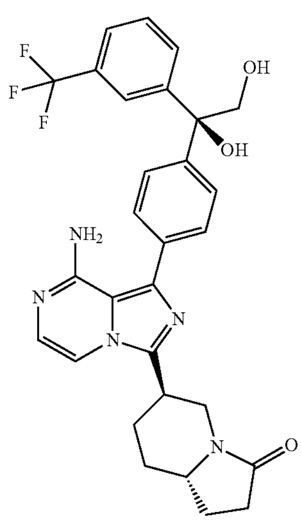 [SMILES: Nc1nccn2c([C@@H]3CC[C@H]4CCC(=O)N4C3)nc(-c3ccc([C@@](O)(CO)c4cccc(C(F)(F)F)c4)cc3)c12] | (6R,8aS)-6-[8-amino-1-(4-{(1S)-1,2-dihydroxy-1-[3-(trifluoromethyl)phenyl]ethyl}phenyl)imidazo[1,5-a]pyrazin-3-yl]hexahydroindolizin-3(2H)-one | Calc'd 552.2, found 552.2 | 2.668(C) |

TABLE 3-continued
| Example number | Structure | IUPAC Name | Exact Mass [M + H]+ | LC-MS retention time (min, method) |
|---|---|---|---|---|
| 107 | 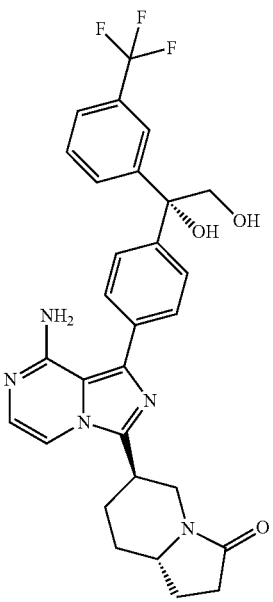 [SMILES: Nc1nccn2c([C@@H]3CC[C@H]4CCC(=O)N4C3)nc(-c3ccc([C@](O)(CO)c4cccc(C(F)(F)F)c4)cc3)c12] | (6R,8aS)-6-[8-amino-1-(4-{(1R)-1,2-dihydroxy-1-[3-(trifluoromethyl)phenyl]ethyl}phenyl)imidazo[1,5-a]pyrazin-3-yl]hexahydroindolizin-3(2H)-one | Calc'd 552.2, found 552.2 | 2.678(C) |
| 108 | 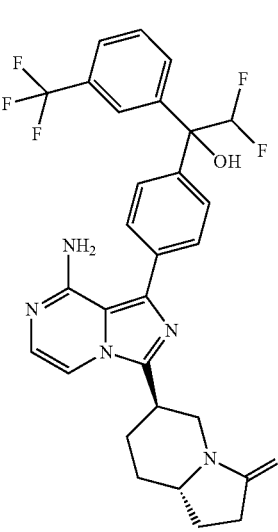 | (6R,8aS)-6-[8-amino-1-(4-{2,2-difluoro-1-hydroxy-1-[3-(trifluoromethyl)phenyl]ethyl}phenyl)imidazo[1,5-a]pyrazin-3-yl]hexahydroindolizin-3(2H)-one | Calc'd 572.2, found 272.2 | 2.378(C) |

TABLE 3-continued

| Example number | Structure | IUPAC Name | Exact Mass [M + H]+ | LC-MS retention time (min, method) |
|---|---|---|---|---|
| 109 | 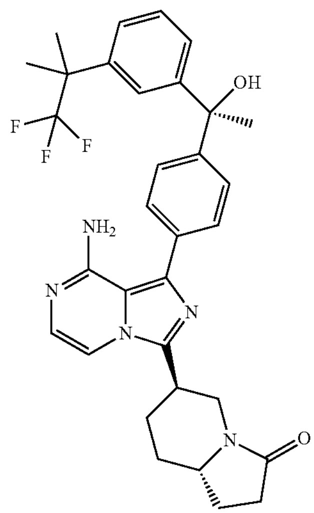 [SMILES: CC(C)(c1cccc([C@@](C)(O)c2ccc(-c3nc([C@@H]4CC[C@H]5CCC(=O)N5C4)n4ccnc(N)c34)cc2)c1)C(F)(F)F] | (6R,8aS)-6-[8-amino-1-(4-{(1S)-1-hydroxy-1-[3-(2,2,2-trifluoro-1,1-dimethylethyl)phenyl]ethyl}phenyl)imidazo[1,5-a]pyrazin-3-yl]hexahydroindolizin-3(2H)-one | Calc'd 578.3, found 578.2 | 2.322(C) |
| 110 | 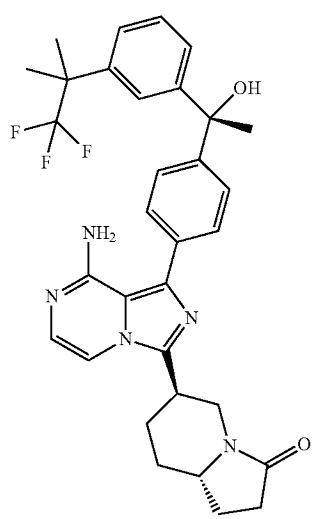 [SMILES: CC(C)(c1cccc([C@](C)(O)c2ccc(-c3nc([C@@H]4CC[C@H]5CCC(=O)N5C4)n4ccnc(N)c34)cc2)c1)C(F)(F)F] | (6R,8aS)-6-[8-amino-1-(4-{(1R)-1-hydroxy-1-[3-(2,2,2-trifluoro-1,1-dimethylethyl)phenyl]ethyl}phenyl)imidazo[1,5-a]pyrazin-3-yl]hexahydroindolizin-3(2H)-one | Calc'd 578.3, found 578.2 | 2.322(C) |
| 111 | 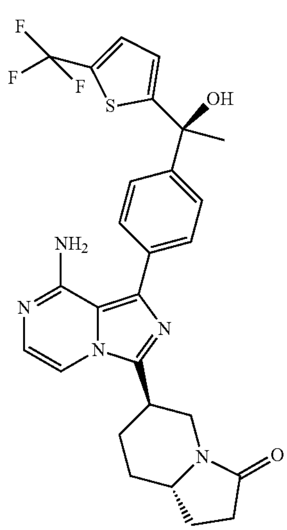 [SMILES: C[C@](O)(c1ccc(-c2nc([C@@H]3CC[C@H]4CCC(=O)N4C3)n3ccnc(N)c23)cc1)c1ccc(C(F)(F)F)s1] | (6R,8aS)-6-[8-amino-1-(4-{(1S)-1-hydroxy-1-[5-(trifluoromethyl)thiophen-2-yl]ethyl}phenyl)imidazo[1,5-a]pyrazin-3-yl]hexahydroindolizin-3(2H)-one | Calc'd 542.2, found 542.2 | 2.318(C) |

TABLE 3-continued

| Example number | Structure | IUPAC Name | Exact Mass [M + H]+ | LC-MS retention time (min, method) |
|---|---|---|---|---|
| 112 | 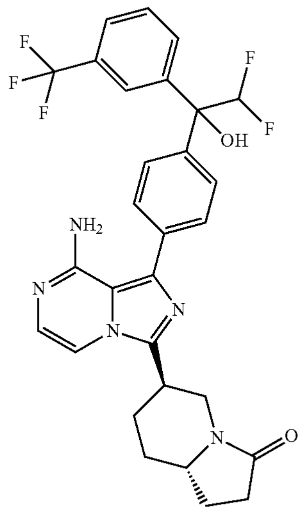 [SMILES: Nc1nccn2c([C@@H]3CC[C@H]4CCC(=O)N4C3)nc(-c3ccc(C(O)(c4cccc(C(F)(F)F)c4)C(F)F)cc3)c12] | (6R,8aS)-6-[8-amino-1-(4-{2,2-difluoro-1-hydroxy-1-[3-(trifluoromethyl)phenyl]ethyl}phenyl)imidazo[1,5-a]pyrazin-3-yl]hexahydroindolizin-3(2H)-one | Calc'd 572.2, found 572.2 | 2.359(C) |
| 113 | 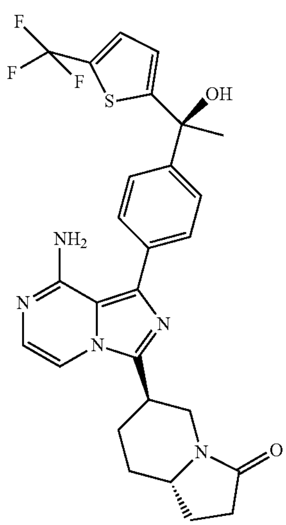 [SMILES: C[C@](O)(c1ccc(-c2nc([C@@H]3CC[C@H]4CCC(=O)N4C3)n3ccnc(N)c23)cc1)c1ccc(C(F)(F)F)s1] | (6R,8aS)-6-[8-amino-1-(4-{(1S)-1-hydroxy-1-[5-(trifluoromethyl)thiophen-2-yl]ethyl}phenyl)imidazo[1,5-a]pyrazin-3-yl]hexahydroindolizin-3(2H)-one | Calc'd 542.2, found 542.1 | 2.350(C) |

TABLE 3-continued

| Example number | Structure | IUPAC Name | Exact Mass [M + H]+ | LC-MS retention time (min, method) |
|---|---|---|---|---|
| 114 | 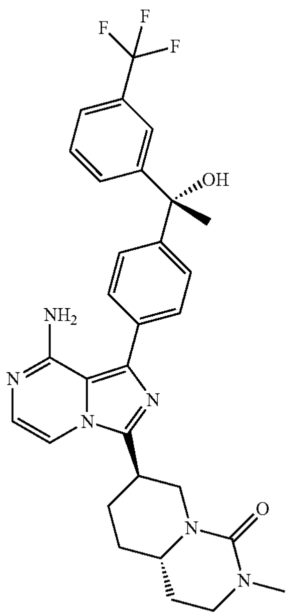 [SMILES: CN1CC[C@@H]2CC[C@@H](c3nc(-c4ccc([C@@](C)(O)c5cccc(C(F)(F)F)c5)cc4)c4c(N)nccn34)CN2C1=O] | (4aS,7R)-7-[8-amino-1-(4-{(1R)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one | Calc'd 565.3, found 565.2 | 2.292(C) |
| 115 | 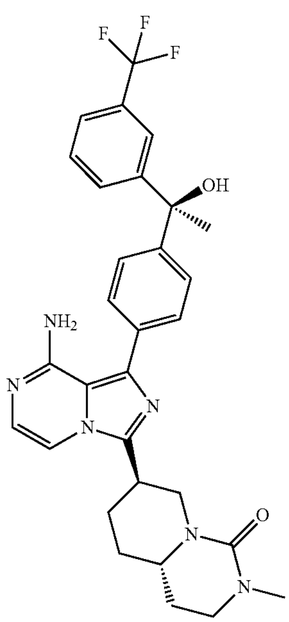 [SMILES: CN1CC[C@@H]2CC[C@@H](c3nc(-c4ccc([C@](C)(O)c5cccc(C(F)(F)F)c5)cc4)c4c(N)nccn34)CN2C1=O] | (4aS,7R)-7-[8-amino-1-(4-{(1S)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one | Calc'd 565.3, found 565.2 | 2.292(C) |

TABLE 3-continued

| Example number | Structure | IUPAC Name | Exact Mass [M + H]+ | LC-MS retention time (min, method) |
|---|---|---|---|---|
| 116 | 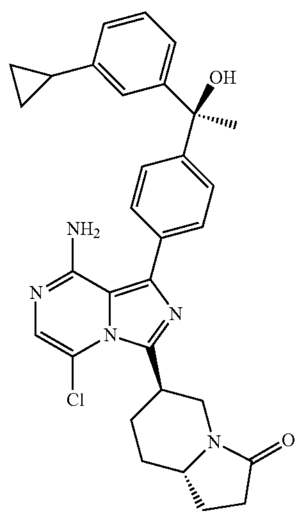 [SMILES: C[C@](O)(c1ccc(-c2nc([C@@H]3CC[C@H]4CCC(=O)N4C3)n3c(Cl)cnc(N)c23)cc1)c1cccc(C2CC2)c1] | (6R,8aS)-6-(8-amino-5-chloro-1-{4-[(1S)-1-(3-cyclopropylphenyl)-1-hydroxyethyl]phenyl}imidazo[1,5-a]pyrazin-3-yl)hexahydroindolizin-3(2H)-one | Calc'd 542.2, found 542.2 | 2.283(C) |
| 117 | 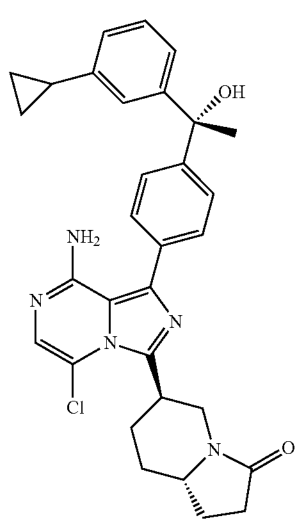 [SMILES: C[C@@](O)(c1ccc(-c2nc([C@@H]3CC[C@H]4CCC(=O)N4C3)n3c(Cl)cnc(N)c23)cc1)c1cccc(C2CC2)c1] | (6R,8aS)-6-(8-amino-5-chloro-1-{4-[(1R)-1-(3-cyclopropylphenyl)-1-hydroxyethyl]phenyl}imidazo[1,5-a]pyrazin-3-yl)hexahydroindolizin-3(2H)-one | Calc'd 542.2, found 542.2 | 2.284(C) |

TABLE 3-continued

| Example number | Structure | IUPAC Name | Exact Mass [M + H]+ | LC-MS retention time (min, method) |
|---|---|---|---|---|
| 118 | 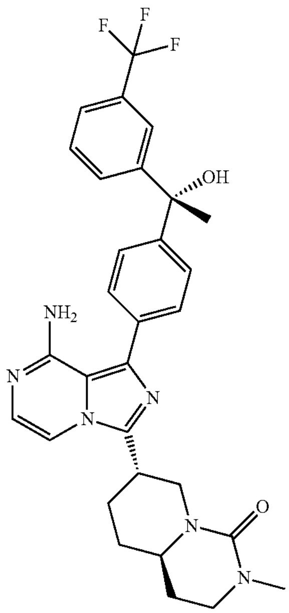 [SMILES: CN1CC[C@H]2CC[C@H](c3nc(-c4ccc([C@@](C)(O)c5cccc(C(F)(F)F)c5)cc4)c4c(N)nccn34)CN2C1=O] | (4aR,7S)-7-[8-amino-1-(4-{(1R)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one | Calc'd 565.3, found 565.2 | 2.296(C) |
| 119 | 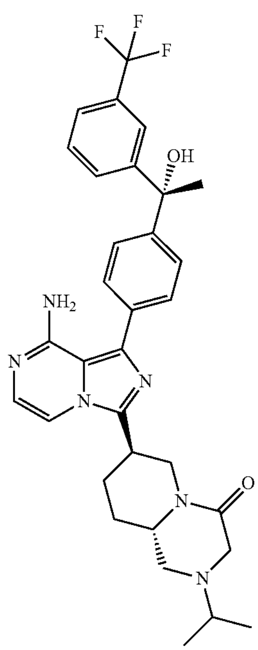 [SMILES: CC(C)N1CC(=O)N2C[C@H](c3nc(-c4ccc([C@@](C)(O)c5cccc(C(F)(F)F)c5)cc4)c4c(N)nccn34)CC[C@H]2C1] | (7R,9aS)-7-(8-amino-1-(4-{(1R)-1-hydroxy-1-[3-(trifluoromethyl)phenyl]ethyl}phenyl)imidazo[1,5-a]pyrazin-3-yl]-2-(1-methylethyl)octahydro-4H-pyrido[1,2-a]pyrazin-4-one | Calc'd 593.3, found 593.3 | 1.888(C) |

TABLE 3-continued

| Example number | Structure | IUPAC Name | Exact Mass [M + H]+ | LC-MS retention time (min, method) |
|---|---|---|---|---|
| 120 | 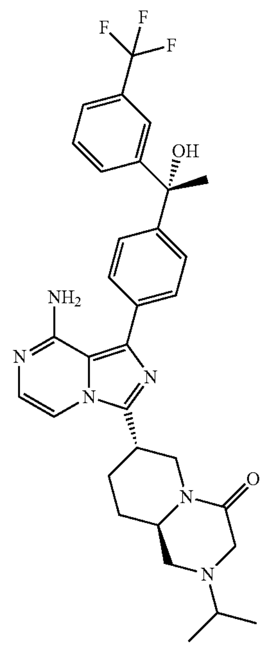 [SMILES: CC(C)N1CC(=O)N2C[C@@H](c3nc(-c4ccc([C@@](C)(O)c5cccc(C(F)(F)F)c5)cc4)c4c(N)nccn34)CC[C@@H]2C1] | (7S,9aR)-7-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)octahydro-4H-pyrido[1,2-a]pyrazin-4-one | Calc'd 593.3, found 593.2 | 1.894(C) |
| 121 | 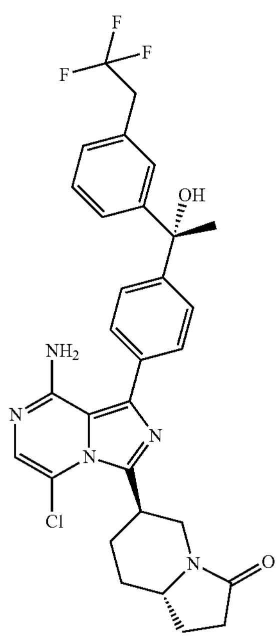 [SMILES: C[C@@](O)(c1ccc(-c2nc([C@@H]3CC[C@H]4CCC(=O)N4C3)n3c(Cl)cnc(N)c23)cc1)c1cccc(CC(F)(F)F)c1] | (6R,8aS)-6-[8-amino-5-chloro-1-(4-{(1R)-1-hydroxy-1-[3-(2,2,2-trifluoroethyl)phenyl]ethyl}phenyl)imidazo[1,5-a]pyrazin-3-yl]hexahydroindolizin-3(2H)-one | Calc'd 584.2, found 584.2 | 2.282(C) |

TABLE 3-continued

| Example number | Structure | IUPAC Name | Exact Mass [M + H]+ | LC-MS retention time (min, method) |
|---|---|---|---|---|
| 122 | 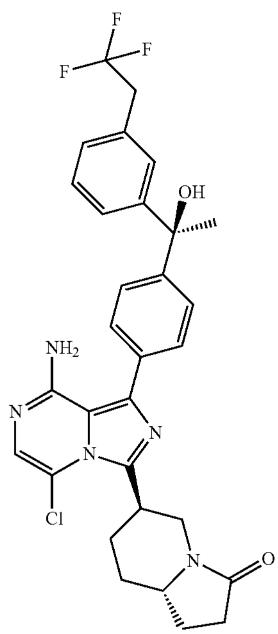 [SMILES: C[C@](O)(c1ccc(-c2nc([C@@H]3CC[C@H]4CCC(=O)N4C3)n3c(Cl)cnc(N)c23)cc1)c1cccc(CC(F)(F)F)c1] | (6R,8aS)-6-[8-amino-5-chloro-1-(4-{(1S)-1-hydroxy-1-(3-(2,2,2-trifluoroethyl)phenyl]ethyl}phenyl)imidazo[1,5-a]pyrazin-3-yl]hexahydroindolizin-3(2H)-one | Calc'd 584.2, found 584.2 | 2.285(C) |
| 123 | 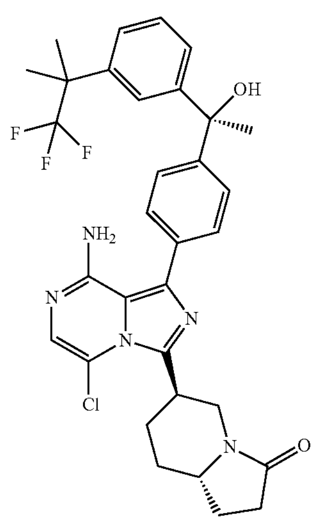 [SMILES: CC(C)(c1cccc([C@@](C)(O)c2ccc(-c3nc([C@@H]4CC[C@H]5CCC(=O)N5C4)n4c(Cl)cnc(N)c34)cc2)c1)C(F)(F)F] | (6R,8aS)-6-[8-amino-5-chloro-1-(4-{(1S)-1-hydroxy-1-[3-(2,2,2-trifluoro-1,1-dimethylethyl)phenyl]ethyl}phenyl)imidazo[1,5-a]pyrazin-3-yl]hexahydroindolizin-3(2H)-one | Calc'd 612.2, found 612.2 | 2.441(C) |

TABLE 3-continued

| Example number | Structure | IUPAC Name | Exact Mass [M + H]+ | LC-MS retention time (min, method) |
|---|---|---|---|---|
| 124 | 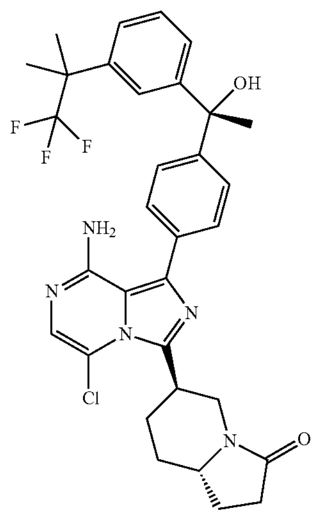 [SMILES: CC(C)(c1cccc([C@](C)(O)c2ccc(-c3nc([C@@H]4CC[C@H]5CCC(=O)N5C4)n4c(Cl)cnc(N)c34)cc2)c1)C(F)(F)F] | (6R,8aS)-6-[8-amino-5-chloro-1-(4-{(1R)-1-hydroxy-1-[3-(2,2,2-trifluoro-1,1-dimethylethyl)phenyl]ethyl}phenyl)imidazo[1,5-a]pyrazin-3-yl]hexahydroindolizin-3(2H)-one | Calc'd 612.2, found 612.2 | 2.440(C) |
| 125 | 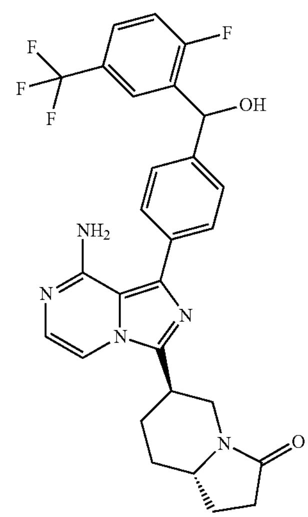 [SMILES: Nc1nccn2c([C@@H]3CC[C@H]4CCC(=O)N4C3)nc(-c3ccc(C(O)c4cc(C(F)(F)F)ccc4F)cc3)c12] | (6R,8aS)-6-(8-amino-1-(4-{[2-fluoro-5-(trifluoromethyl)phenyl](hydroxy)methyl}phenyl)imidazo[1,5-a]pyrazin-3-yl]hexahydroindolizin-3(2H)-one | Calc'd 540.2, found 540.1 | 2.465(C) |
| 126 | 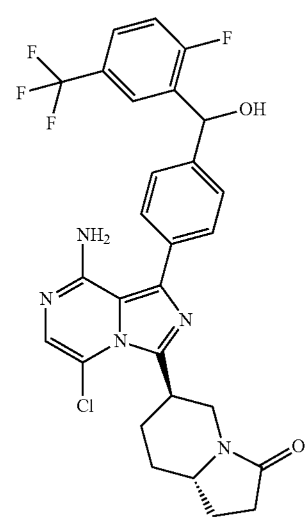 [SMILES: Nc1ncc(Cl)n2c([C@@H]3CC[C@H]4CCC(=O)N4C3)nc(-c3ccc(C(O)c4cc(C(F)(F)F)ccc4F)cc3)c12] | (6R,8aS)-6-[8-amino-5-chloro-1-(4-{[2-fluoro-5-(trifluoromethyl)phenyl]hydroxy)methyl}phenyl)imidazo[1,5-a]pyrazin-3-yl]hexahydroindolizin-3(2H)-one | Calc'd 574.2, found 574.0 | 2.280(C) |

TABLE 3-continued

| Example number | Structure | IUPAC Name | Exact Mass [M + H]+ | LC-MS retention time (min, method) |
|---|---|---|---|---|
| 127 | 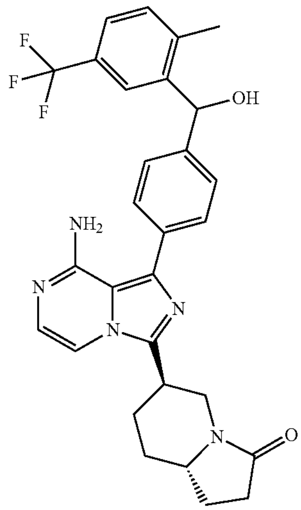 [SMILES: Cc1ccc(C(F)(F)F)cc1C(O)c1ccc(-c2nc([C@@H]3CC[C@H]4CCC(=O)N4C3)n3ccnc(N)c23)cc1] | (6R,8aS)-6-[8-amino-1-(4-{hydroxy[2-methyl-5-(trifluoromethyl)phenyl]methyl}phenyl)imidazo[1,5-a]pyrazin-3-yl]hexahydroindolizin-3(2H)-one | Calc'd 536.2, found 536.2 | 2.538(C) |
| 128 | 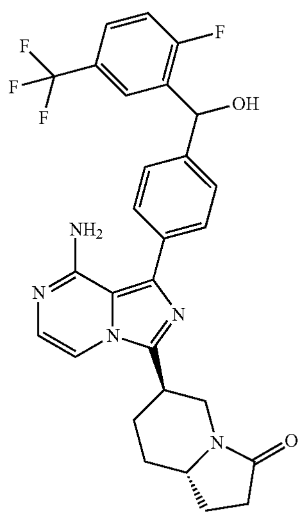 [SMILES: Nc1nccn2c([C@@H]3CC[C@H]4CCC(=O)N4C3)nc(-c3ccc(C(O)c4cc(C(F)(F)F)ccc4F)cc3)c12] | (6R,8aS)-6-(8-amino-1-(4-{[2-fluoro-5-(trifluoromethyl)phenyl](hydroxy)methyl}phenyl)imidazo[1,5-a]pyrazin-3-yl]hexahydroindolizin-3(2H)-one | Calc'd 540.2, found 540.1 | 2.489(C) |
| 129 | 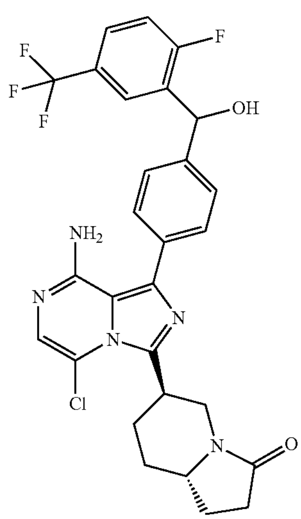 [SMILES: Nc1ncc(Cl)n2c([C@@H]3CC[C@H]4CCC(=O)N4C3)nc(-c3ccc(C(O)c4cc(C(F)(F)F)ccc4F)cc3)c12] | (6R,8aS)-6-[8-amino-5-chloro-1-(4-{[2-fluoro-5-(trifluoromethyl)phenyl](hydroxy)methyl}phenyl)imidazo[1,5-a]pyrazin-3-yl]hexahydroindolizin-3(2H)-one | Calc'd 574.2, found 574.1 | 2.274(C) |

TABLE 3-continued

| Example number | Structure | IUPAC Name | Exact Mass [M + H]+ | LC-MS retention time (min, method) |
|---|---|---|---|---|
| 130 | 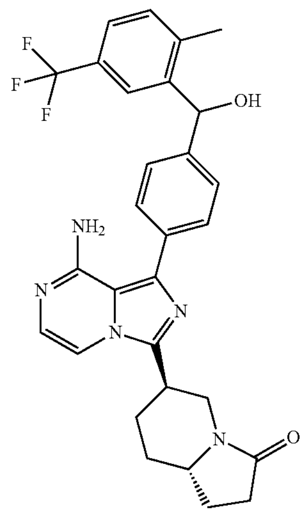 [SMILES: Cc1ccc(C(F)(F)F)cc1C(O)c1ccc(-c2nc([C@@H]3CC[C@H]4CCC(=O)N4C3)n3ccnc(N)c23)cc1] | (6R,8aS)-6-[8-amino-1-(4-{hydroxy[2-methyl-5-(trifluoromethyl)phenyl]methyl}phenyl)imidazo[1,5-a]pyrazin-3-yl]hexahydroindolizin-3(2H)-one | Calc'd 536.2, found 536.2 | 2.536(C) |
| 131 | 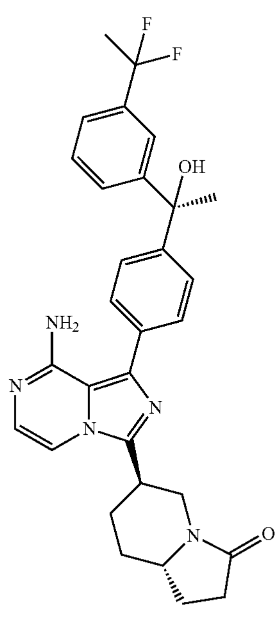 [SMILES: CC(F)(F)c1cccc([C@@](C)(O)c2ccc(-c3nc([C@@H]4CC[C@H]5CCC(=O)N5C4)n4ccnc(N)c34)cc2)c1] | (6R,8aS)-6-[8-amino-1-(4-{(1S)-1-[3-(1,1-difluoroethyl)phenyl]-1-hydroxyethyl}phenyl)imidazo[1,5-a]pyrazin-3-yl]hexahydroindolizin-3(2H)-one | Calc'd 532.3, found 532.2 | 2.599(C) |

TABLE 3-continued
| Example number | Structure | IUPAC Name | Exact Mass [M + H]+ | LC-MS retention time (min, method) |
|---|---|---|---|---|
| 132 | 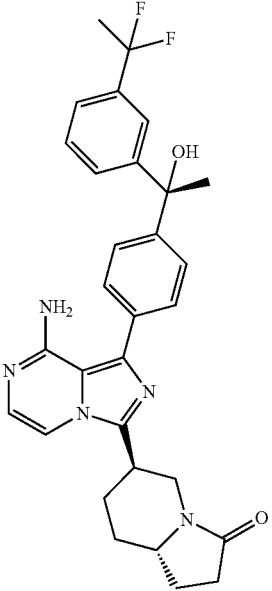 [SMILES: CC(F)(F)c1cccc([C@](C)(O)c2ccc(-c3nc([C@@H]4CC[C@H]5CCC(=O)N5C4)n4ccnc(N)c34)cc2)c1] | (6R,8aS)-6-[8-amino-1-(4-{(1R)-1-[3-(1,1-difluoroethyl)phenyl]-1-hydroxyethyl}phenyl)imidazo[1,5-a]pyrazin-3-yl]hexahydroindolizin-3(2H)-one | Calc'd 532.3, found 532.3 | 2.661(C) |
| 133 | 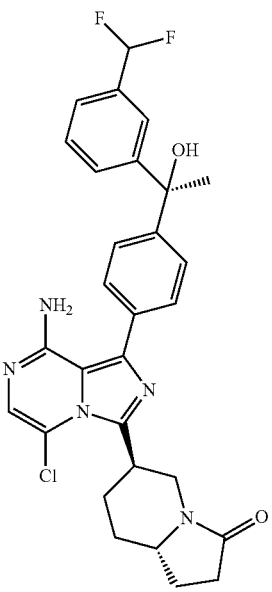 [SMILES: C[C@](O)(c1ccc(-c2nc([C@@H]3CC[C@H]4CCC(=O)N4C3)n3c(Cl)cnc(N)c23)cc1)c1cccc(C(F)F)c1] | (6R,8aS)-6-[8-amino-5-chloro-1-(4-{(1S)-1-[3-(difluoromethyl)phenyl]-1-hydroxyethyl}phenyl)imidazo[1,5-a]pyrazin-3-yl]hexahydroindolizin-3(2H)-one | Calc'd 552.2, found 552.2 | 2.689(C) |

TABLE 3-continued

| Example number | Structure | IUPAC Name | Exact Mass [M + H]+ | LC-MS retention time (min, method) |
|---|---|---|---|---|
| 134 | 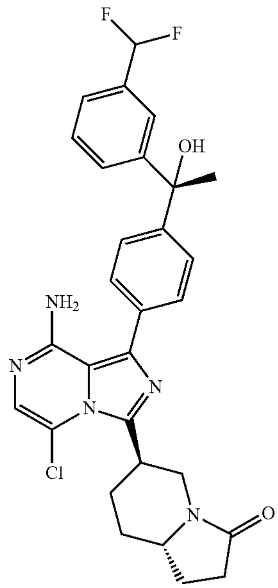 [SMILES: C[C@@](O)(c1ccc(-c2nc([C@@H]3CC[C@H]4CCC(=O)N4C3)n3c(Cl)cnc(N)c23)cc1)c1cccc(C(F)F)c1] | (6R,8aS)-6-[8-amino-5-chloro-1-(4-{(1R)-1-[3-(difluoromethyl)phenyl]-1-hydroxyethyl}phenyl)imidazo[1,5-a]pyrazin-3-yl]hexahydroindolizin-3(2H)-one | Calc'd 552.2, found 552.2 | 2.688(C) |
| 135 | 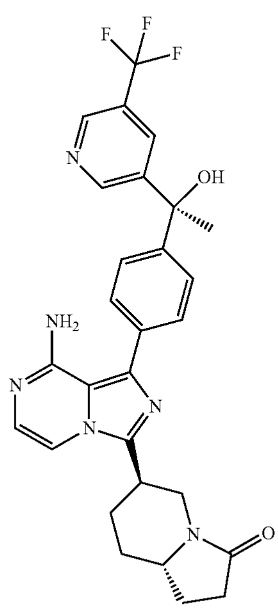 [SMILES: C[C@](O)(c1ccc(-c2nc([C@@H]3CC[C@H]4CCC(=O)N4C3)n3ccnc(N)c23)cc1)c1cncc(C(F)(F)F)c1] | (6R,8aS)-6-[8-amino-1-(4-{(1S)-1-hydroxy-1-[5-(trifluoromethyl)pyridin-3-yl]ethyl}phenyl)imidazo[1,5-a]pyrazin-3-yl]hexahydroindolizin-3(2H)-one | Calc'd 537.2, found 537.1 | 2.284(C) |

TABLE 3-continued
| Example number | Structure | IUPAC Name | Exact Mass [M + H]+ | LC-MS retention time (min, method) |
|---|---|---|---|---|
| 136 | 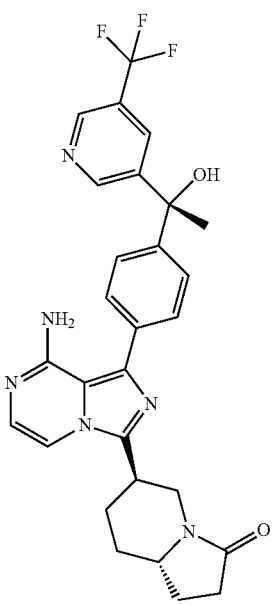 [SMILES: C[C@@](O)(c1ccc(-c2nc([C@@H]3CC[C@H]4CCC(=O)N4C3)n3ccnc(N)c23)cc1)c1cncc(C(F)(F)F)c1] | (6R,8aS)-6-[8-amino-1-(4-{(1R)-1-hydroxy-1-[5-(trifluoromethyl)pyridin-3-yl]ethyl}phenyl)imidazo[1,5-a]pyrazin-3-yl]hexahydroindolizin-3(2H)-one | Calc'd 537.2, found 537.2 | 2.285(C) |
| 137 | 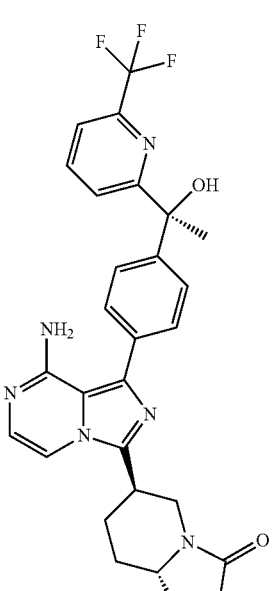 | (6R,8aS)-6-[8-amino-1-(4-{(1S)-1-hydroxy-1-[6-(trifluoromethyl)pyridin-2-yl]ethyl}phenyl)imidazo[1,5-a]pyrazin-3-yl]hexahydroindolizin-3(2H)-one | Calc'd 537.2, found 537.2 | 2.448(C) |

TABLE 3-continued
| Example number | Structure | IUPAC Name | Exact Mass [M + H]+ | LC-MS retention time (min, method) |
|---|---|---|---|---|
| 138 | 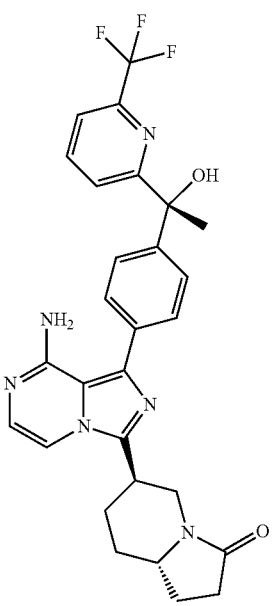 | (6R,8aS)-6-[8-amino-1-(4-{(1R)-1-hydroxy-1-[6-(trifluoromethyl)pyridin-2-yl]ethyl}phenyl)imidazo[1,5-a]pyrazin-3-yl]hexahydroindolizin-3(2H)-one | Calc'd 537.2, found 537.2 | 2.449(C) |
| 139 | 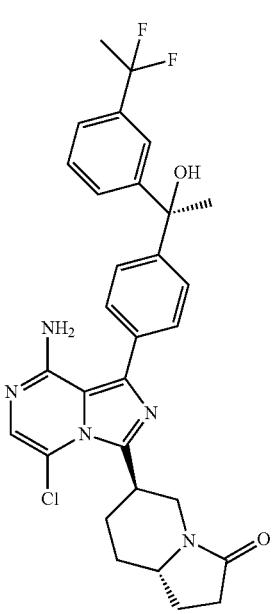 [SMILES: CC(F)(F)c1cccc([C@@](C)(O)c2ccc(-c3nc([C@@H]4CC[C@H]5CCC(=O)N5C4)n4c(Cl)cnc(N)c34)cc2)c1] | (6R,8aS)-6-[8-amino-5-chloro-1-(4-{(1S)-1-[3-(1,1-difluoroethyl)phenyl]-1-hydroxyethyl}phenyl)imidazo[1,5-a]pyrazin-3-yl]hexahydroindolizin-3(2H)-one | Calc'd 566.2, found 566.1 | 2.253(C) |

TABLE 3-continued
| Example number | Structure | IUPAC Name | Exact Mass [M + H]+ | LC-MS retention time (min, method) |
|---|---|---|---|---|
| 140 | 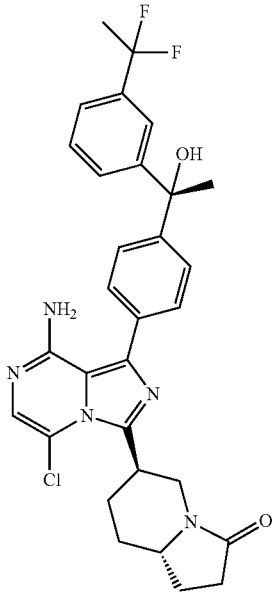 [SMILES: CC(F)(F)c1cccc([C@](C)(O)c2ccc(-c3nc([C@@H]4CC[C@H]5CCC(=O)N5C4)n4c(Cl)cnc(N)c34)cc2)c1] | (6R,8aS)-6-[8-amino-5-chloro-1-(4-{(1R)-1-[3-(1,1-difluoroethyl)phenyl)-1-hydroxyethyl}(phenyl)imidazo[1,5-a]pyrazin-3-yl)hexahydroindolizin-3(2H)-one | Calc'd 566.2, found 566.1 | 2.251(C) |
| 141 | 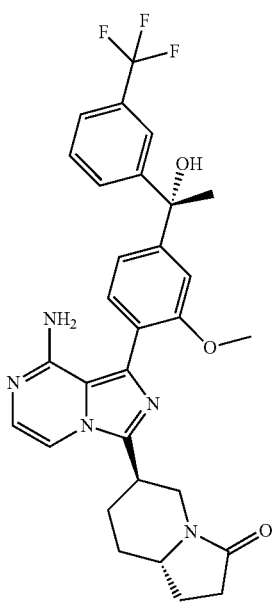 [SMILES: COc1cc([C@@](C)(O)c2cccc(C(F)(F)F)c2)ccc1-c1nc([C@@H]2CC[C@H]3CCC(=O)N3C2)n2ccnc(N)c12] | (6R,8aS)-6-[8-amino-1-(4-{(1S)-1-hydroxy-1-[3-(trifluoromethyl)phenyl]ethyl}-2-methoxyphenyl)imidazo[1,5-a]pyrazin-3-yl]hexahydroindolizin-3(2H)-one | Calc'd 566.2, found | |

TABLE 3-continued
| Example number | Structure | IUPAC Name | Exact Mass [M + H]+ | LC-MS retention time (min, method) |
|---|---|---|---|---|
| 142 | 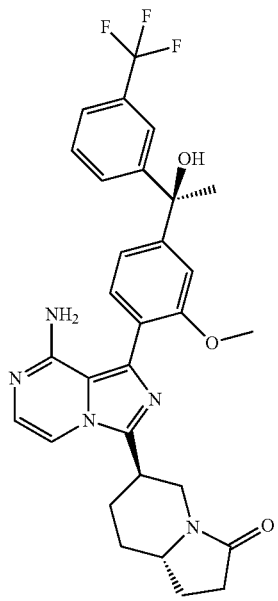 [SMILES: COc1cc([C@](C)(O)c2cccc(C(F)(F)F)c2)ccc1-c1nc([C@@H]2CC[C@H]3CCC(=O)N3C2)n2ccnc(N)c12] | (6R,8aS)-6-[8-amino-1-(4-{(1R)-1-hydroxy-1-[3-(trifluoromethyl)phenyl]ethyl}-2-methoxyphenyl)imidazo[1,5-a]pyrazin-3-yl]hexahydroindolizin-3(2H)-one | Calc'd 566.2, found | |
| 143 | 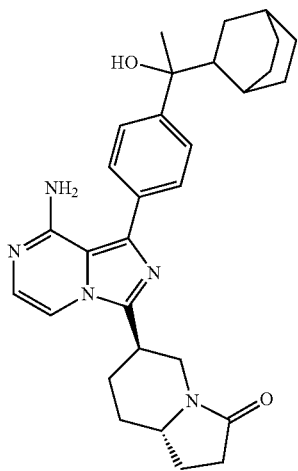 | (6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3(2H)-one | Calc'd 500.3, found 500.2 | 2.343(C) |

TABLE 3-continued
| Example number | Structure | IUPAC Name | Exact Mass [M + H]+ | LC-MS retention time (min, method) |
|---|---|---|---|---|
| 144 | 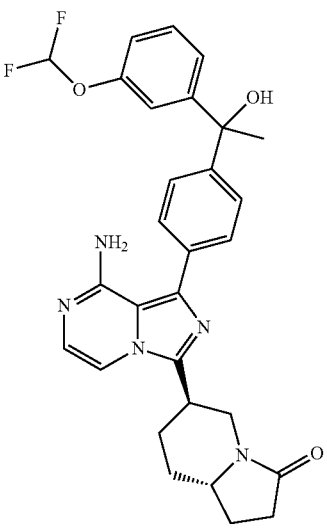 [SMILES: CC(O)(c1ccc(-c2nc([C@@H]3CC[C@H]4CCC(=O)N4C3)n3ccnc(N)c23)cc1)c1cccc(OC(F)F)c1] | (6R,8aS)-6-[8-amino-1-(4-{1-[3-(difluoromethoxy)phenyl]-1-hydroxyethyl}phenyl)imidazo[1,5-a]pyrazin-3-yl]hexahydroindolizin-3(2H)-one | Calc'd 534.2, found 534.2 | 2.422(C) |
| 145 | 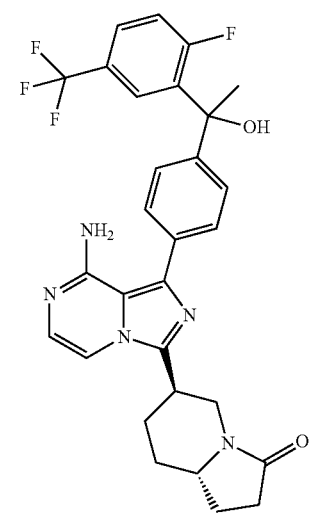 [SMILES: CC(O)(c1ccc(-c2nc([C@@H]3CC[C@H]4CCC(=O)N4C3)n3ccnc(N)c23)cc1)c1cc(C(F)(F)F)ccc1F] | (6R,8aS)-6-[8-amino-1-(4-{1-[2-fluoro-5-(trifluoromethyl)phenyl]-1-hydroxyethyl}phenyl)imidazo[1,5-a]pyrazin-3-yl]hexahydroindolizin-3(2H)-one | Calc'd 554.2, found 554.1 | 2.540(C) |

TABLE 3-continued
| Example number | Structure | IUPAC Name | Exact Mass [M + H]+ | LC-MS retention time (min, method) |
|---|---|---|---|---|
| 146 | 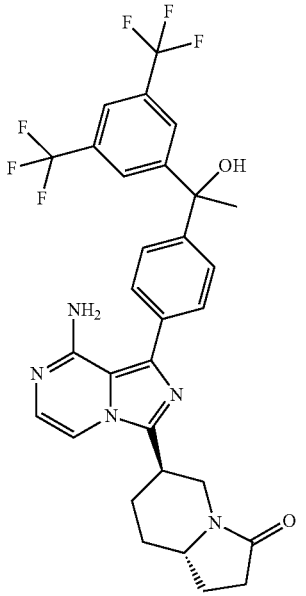 [SMILES: CC(O)(c1ccc(-c2nc([C@@H]3CC[C@H]4CCC(=O)N4C3)n3ccnc(N)c23)cc1)c1cc(C(F)(F)F)cc(C(F)(F)F)c1] | (6R,8aS)-6-[8-amino-1-(4-{1-[3,5-bis(trifluoromethyl)phenyl]-1-hydroxyethyl}phenyl)imidazo[1,5-a]pyrazin-3-yl]hexahydroindolizin-3(2H)-one | Calc'd 604.2, found 604.2 | 2.552(C) |
| 147 | 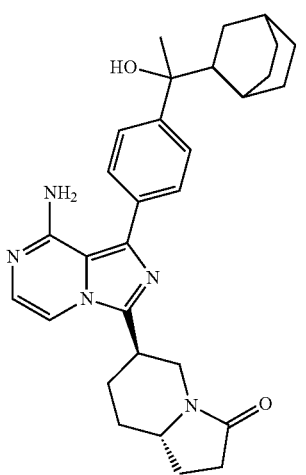 [SMILES: CC(O)(c1ccc(-c2nc([C@@H]3CC[C@H]4CCC(=O)N4C3)n3ccnc(N)c23)cc1)C1CC2CCC1CC2] | (6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3(2H)-one | Calc'd 500.3, found 500.2 | 2.352(C) |

TABLE 3-continued

| Example number | Structure | IUPAC Name | Exact Mass [M + H]+ | LC-MS retention time (min, method) |
|---|---|---|---|---|
| 148 | 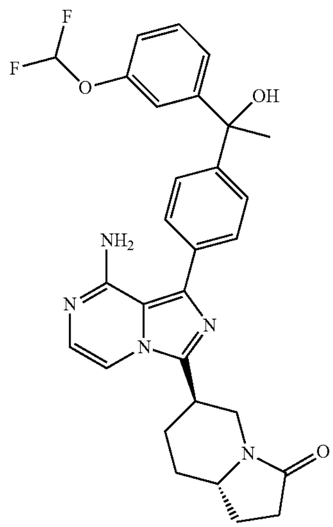 [SMILES: CC(O)(c1ccc(-c2nc([C@@H]3CC[C@H]4CCC(=O)N4C3)n3ccnc(N)c23)cc1)c1cccc(OC(F)F)c1] | (6R,8aS)-6-[8-amino-1-(4-{1-[3-(difluoromethoxy)phenyl]-1-hydroxyethyl}phenyl)imidazo[1,5-a]pyrazin-3-yl]hexahydroindolizin-3(2H)-one | Calc'd 534.2, found 534.2 | 2.421(C) |
| 149 | 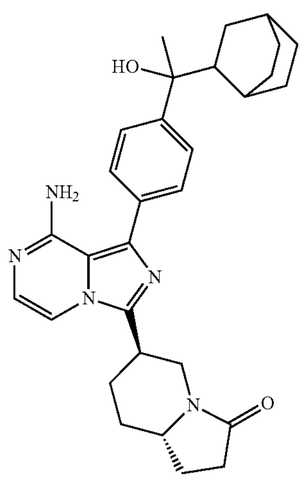 [SMILES: CC(O)(c1ccc(-c2nc([C@@H]3CC[C@H]4CCC(=O)N4C3)n3ccnc(N)c23)cc1)C1CC2CCC1CC2] | (6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3(2H)-one | Calc'd 500.3, found 500.2 | 2.292(C) |
| 150 | 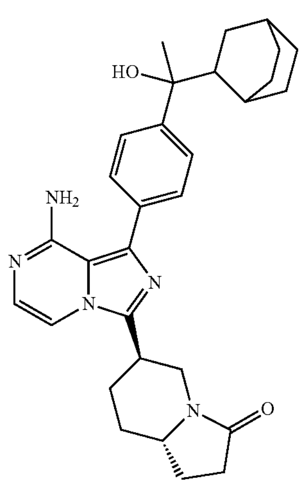 [SMILES: CC(O)(c1ccc(-c2nc([C@@H]3CC[C@H]4CCC(=O)N4C3)n3ccnc(N)c23)cc1)C1CC2CCC1CC2] | (6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3(2H)-one | Calc'd 500.3, found 500.2 | 2.299(C) |

TABLE 3-continued

| Example number | Structure | IUPAC Name | Exact Mass [M + H]+ | LC-MS retention time (min, method) |
| --- | --- | --- | --- | --- |
| 151 | 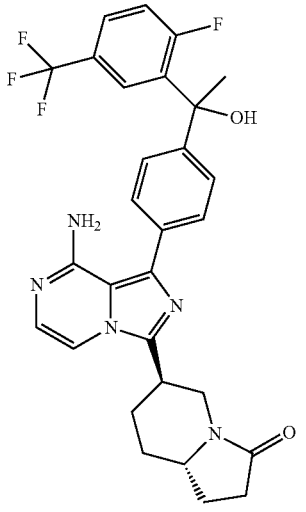 [SMILES: CC(O)(c1ccc(-c2nc([C@@H]3CC[C@H]4CCC(=O)N4C3)n3ccnc(N)c23)cc1)c1cc(C(F)(F)F)ccc1F] | (6R,8aS)-6-[8-amino-1-(4-{1-[2-fluoro-5-(trifluoromethyl)pheny]-1-hydroxyethyl}phenyl)imidazo[1,5-a]pyrazin-3-yl]hexahydroindolizin-3(2H)-one | Calc'd 554.2, found 554.2 | 2.538(C) |
| 152 | 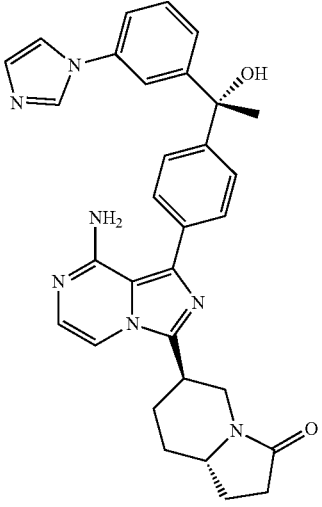 [SMILES: C[C@@](O)(c1ccc(-c2nc([C@@H]3CC[C@H]4CCC(=O)N4C3)n3ccnc(N)c23)cc1)c1cccc(-n2ccnc2)c1] | (6R,8aS)-6-[8-amino-1-(4-{(1R)-1-hydroxy-1-[3-(1H-imidazol-1-yl)phenyl]ethyl}phenyl)imidazo[1,5-a]pyrazin-3-yl]hexahydroindolizin-3(2H)-one | Calc'd 534.3, found 534.3 | 3.257(C) |
| 153 | 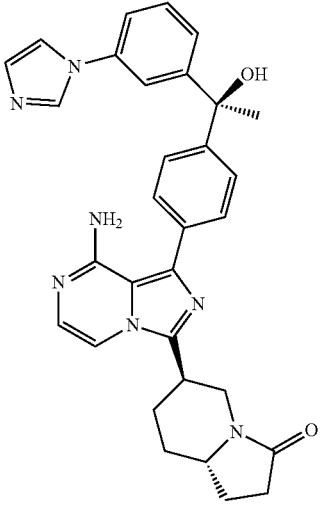 [SMILES: C[C@](O)(c1ccc(-c2nc([C@@H]3CC[C@H]4CCC(=O)N4C3)n3ccnc(N)c23)cc1)c1cccc(-n2ccnc2)c1] | (6R,8aS)-6-[8-amino-1-(4-{(1S)-1-hydroxy-1-[3-(1H-imidazol-1-yl)phenyl]ethyl}phenyl)imidazo[1,5-a]pyrazin-3-yl]hexahydroindolizin-3(2H)-one | Calc'd 534.3, found 534.2 | 2.387(C) |

TABLE 3-continued
| Example number | Structure | IUPAC Name | Exact Mass [M + H]+ | LC-MS retention time (min, method) |
|---|---|---|---|---|
| 154 | 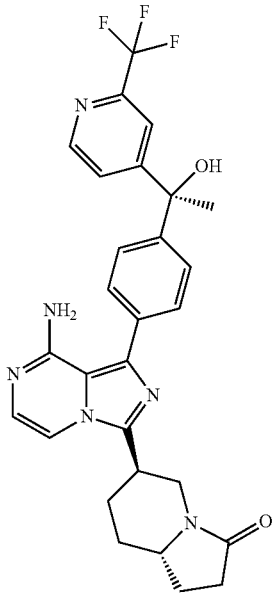 [SMILES: C[C@](O)(c1ccc(-c2nc([C@@H]3CC[C@H]4CCC(=O)N4C3)n3ccnc(N)c23)cc1)c1ccnc(C(F)(F)F)c1] | (6R,8aS)-6-[8-amino-1-(4-{(1S)-1-hydroxy-1-[2-(trifluoromethyl)pyridin-4-yl]ethyl}phenyl)imidazo[1,5-a]pyrazin-3-yl]hexahydroindolizin-3(2H)-one | Calc'd 537.2, found 537.2 | 2.288(C) |
| 155 | 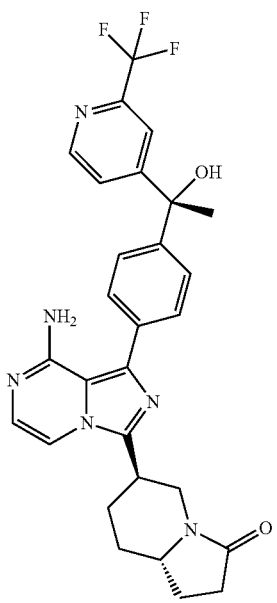 [SMILES: C[C@@](O)(c1ccc(-c2nc([C@@H]3CC[C@H]4CCC(=O)N4C3)n3ccnc(N)c23)cc1)c1ccnc(C(F)(F)F)c1] | (6R,8aS)-6-[8-amino-1-(4-{(1R)-1-hydroxy-1-[2-(trifluoromethyl)pyridin-4-yl]ethyl}phenyl)imidazo[1,5-a]pyrazin-3-yl]hexahydroindolizin-3(2H)-one | Calc'd 537.2, found 537.2 | 2.291(C) |

TABLE 3-continued
| Example number | Structure | IUPAC Name | Exact Mass [M + H]+ | LC-MS retention time (min, method) |
|---|---|---|---|---|
| 156 | 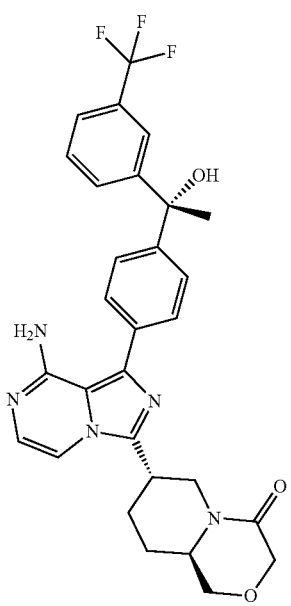 [SMILES: C[C@@](O)(c1ccc(-c2nc([C@H]3CC[C@@H]4COCC(=O)N4C3)n3ccnc(N)c23)cc1)c1cccc(C(F)(F)F)c1] | (7S,9aR)-7-(8-amino-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one | Calc'd 552.2, found 552.2 | 2.083(C) |
| 157 | 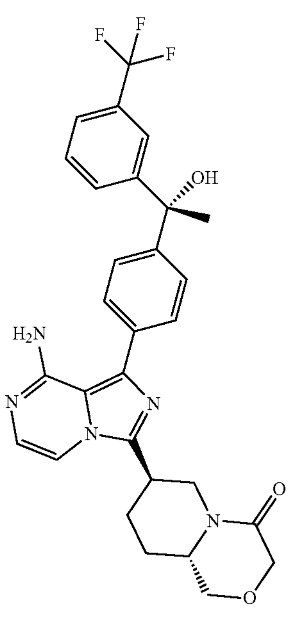 [SMILES: C[C@@](O)(c1ccc(-c2nc([C@@H]3CC[C@H]4COCC(=O)N4C3)n3ccnc(N)c23)cc1)c1cccc(C(F)(F)F)c1] | (7R,9aS)-7-[8-amino-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one | Calc'd 552.2, found 552.2 | 2.082(C) |

TABLE 3-continued

| Example number | Structure | IUPAC Name | Exact Mass [M + H]+ | LC-MS retention time (min, method) |
|---|---|---|---|---|
| 158 | 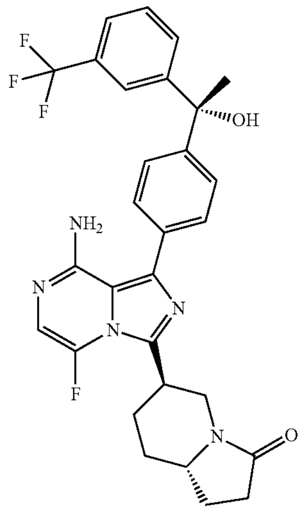 [SMILES: C[C@@](O)(c1ccc(-c2nc([C@@H]3CC[C@H]4CCC(=O)N4C3)n3c(F)cnc(N)c23)cc1)c1cccc(C(F)(F)F)c1] | (6R,8aS)-6-[8-amino-5-fluoro-1-(4-{(1R)-1-hydroxy-1-[3-(trifluoromethyl)phenyl]ethyl}phenyl)imidazo[1,5-a]pyrazin-3-yl]hexahydroindolizin-3(2H)-one | Calc'd 554.2, found 554.1 | 2.467(C) |
| 159 | 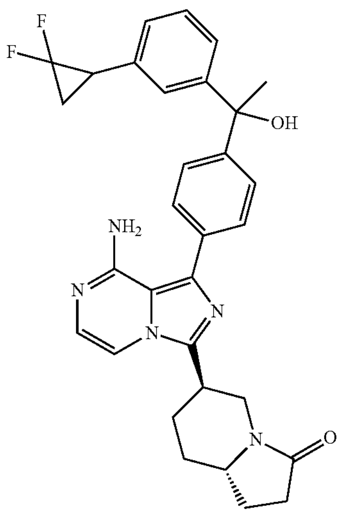 [SMILES: CC(O)(c1ccc(-c2nc([C@@H]3CC[C@H]4CCC(=O)N4C3)n3ccnc(N)c23)cc1)c1cccc(C2CC2(F)F)c1] | (6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one | Calc'd 544.3, found 544.2 | 2.531(C) |
| 160 | 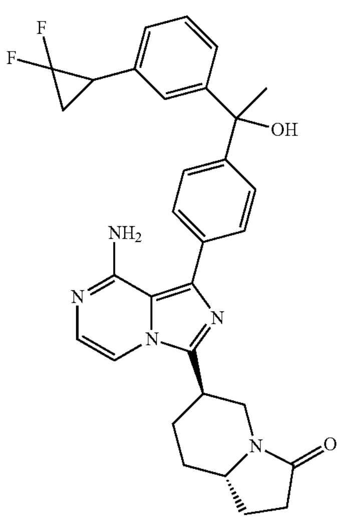 [SMILES: CC(O)(c1ccc(-c2nc([C@@H]3CC[C@H]4CCC(=O)N4C3)n3ccnc(N)c23)cc1)c1cccc(C2CC2(F)F)c1] | (6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one | Calc'd 544.3, found 544.2 | 2.526(C) |

| Example number | Structure | IUPAC Name | Exact Mass [M + H]+ | LC-MS retention time (min, method) |
|---|---|---|---|---|
| 161 | 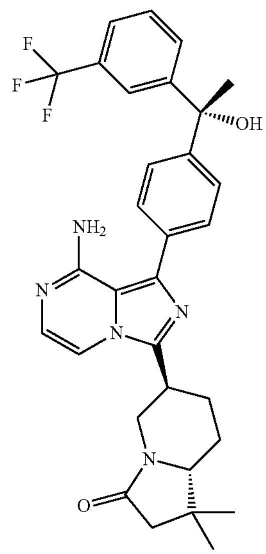 [SMILES: CC1(C)CC(=O)N2C[C@@H](c3nc(-c4ccc([C@@](C)(O)c5cccc(C(F)(F)F)c5)cc4)c4c(N)nccn34)CC[C@@H]21] | (6S,8aR)-6-[8-amino-1-(4-{(1R)-1-hydroxy-1-[3-(trifluoromethyl)phenyl]ethyl}phenyl)imidazo[1,5-a]pyrazin-3-yl]-1,1-dimethylhexahydroindolizin-3(2H)-one | Calc'd 564.3, found 564.2 | 2.213(C) |
| 162 | 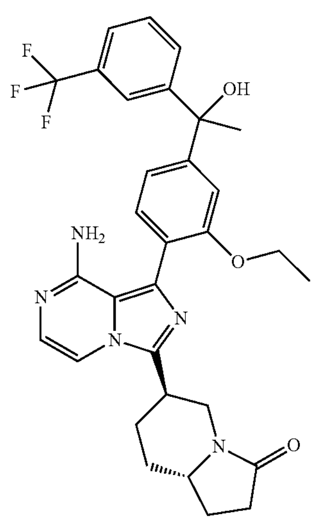 [SMILES: CCOc1cc(C(C)(O)c2cccc(C(F)(F)F)c2)ccc1-c1nc([C@@H]2CC[C@H]3CCC(=O)N3C2)n2ccnc(N)c12] | (6R,8aS)-6-[8-amino-1-(2-ethoxy-4-{1-hydroxy-1-[3-(trifluoromethyl)phenyl]ethyl}phenyl)imidazo[1,5-a]pyrazin-3-yl]hexahydroindolizin-3(2H)-one | Calc'd 580.3, found 580.2 | 2.514(C) |

TABLE 3-continued

| Example number | Structure | IUPAC Name | Exact Mass [M + H]+ | LC-MS retention time (min, method) |
|---|---|---|---|---|
| 163 | 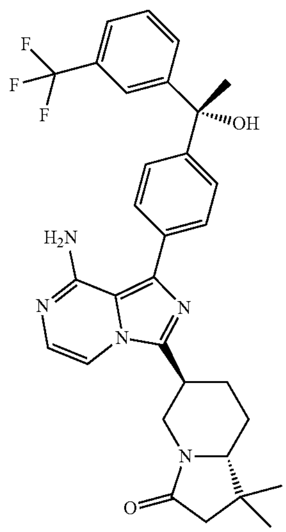 [SMILES: CC1(C)CC(=O)N2C[C@@H](c3nc(-c4ccc([C@@](C)(O)c5cccc(C(F)(F)F)c5)cc4)c4c(N)nccn34)CC[C@@H]21] | (6S,8aR)-6-[8-amino-1-(4-{(1R)-1-hydroxy-1-[3-(trifluoromethyl)phenyl]ethyl}phenyl)imidazo[1,5-a]pyrazin-3-yl]-1,1-dimethylhexahydroindolizin-3(2H)-one | Calc'd 564.3, found 564.2 | 2.249(C) |
| 164 | 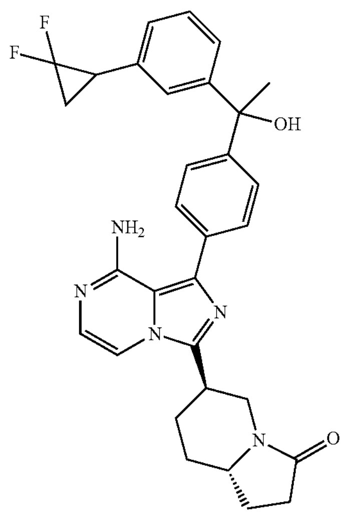 [SMILES: CC(O)(c1ccc(-c2nc([C@@H]3CC[C@H]4CCC(=O)N4C3)n3ccnc(N)c23)cc1)c1cccc(C2CC2(F)F)c1] | (6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one | Calc'd 544.3, found 544.2 | 2.358(C) |
| 165 | 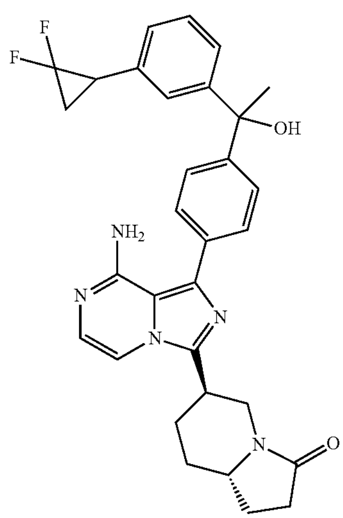 [SMILES: CC(O)(c1ccc(-c2nc([C@@H]3CC[C@H]4CCC(=O)N4C3)n3ccnc(N)c23)cc1)c1cccc(C2CC2(F)F)c1] | (6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one | Calc'd 544.3, found 544.2 | 2.356(C) |

TABLE 3-continued

| Example number | Structure | IUPAC Name | Exact Mass [M + H]+ | LC-MS retention time (min, method) |
|---|---|---|---|---|
| 166 | 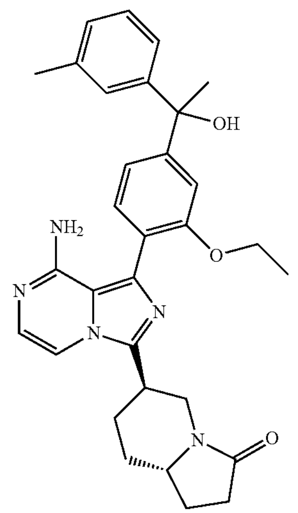 [SMILES: CCOc1cc(C(C)(O)c2cccc(C)c2)ccc1-c1nc([C@@H]2CC[C@H]3CCC(=O)N3C2)n2ccnc(N)c12] | (6R,8aS)-6-(8-amino-1-{2-ethoxy-4-[1-hydroxy-1-(3-methylphenyl)ethyl]phenyl}imidazo[1,5-a]pyrazin-3-yl)hexahydroindolizin-3(2H)-one | Calc'd 526.3, found 526.2 | 2.335(C) |
| 167 | 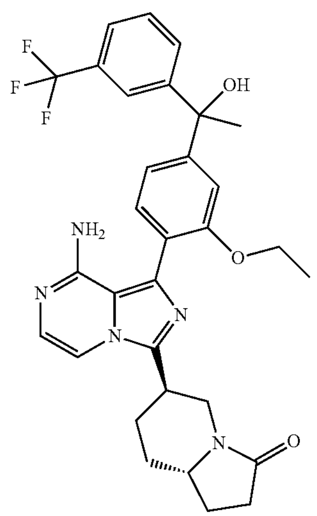 [SMILES: CCOc1cc(C(C)(O)c2cccc(C(F)(F)F)c2)ccc1-c1nc([C@@H]2CC[C@H]3CCC(=O)N3C2)n2ccnc(N)c12] | (6R,8aS)-6-[8-amino-1-(2-ethoxy-4-{1-hydroxy-1-[3-(trifluoromethyl)phenyl]ethyl}phenyl)imidazo[1,5-a]pyrazin-3-yl]hexahydroindolizin-3(2H)-one | Calc'd 580.3, found 580.2 | 2.483(C) |
| 168 | 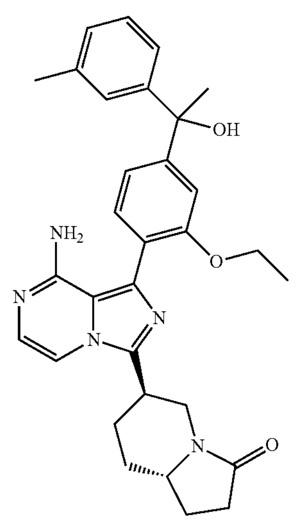 [SMILES: CCOc1cc(C(C)(O)c2cccc(C)c2)ccc1-c1nc([C@@H]2CC[C@H]3CCC(=O)N3C2)n2ccnc(N)c12] | (6R,8aS)-6-(8-amino-1-{2-ethoxy-4-[1-hydroxy-1-(3-methylphenyl)ethyl]phenyl}imidazo[1,5-a]pyrazin-3-yl)hexahydroindolizin-3(2H)-one | Calc'd 526.3, found 526.2 | 2.325(C) |

TABLE 3-continued

| Example number | Structure | IUPAC Name | Exact Mass [M + H]+ | LC-MS retention time (min, method) |
|---|---|---|---|---|
| 169 | 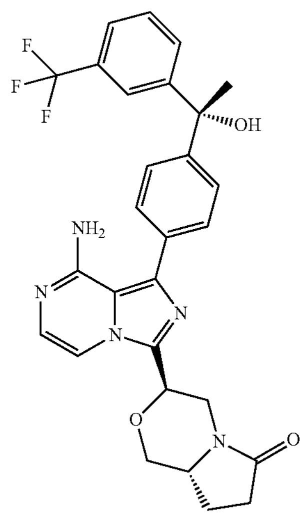 [SMILES: C[C@@](O)(c1ccc(-c2nc([C@H]3CN4C(=O)CC[C@@H]4CO3)n3ccnc(N)c23)cc1)c1cccc(C(F)(F)F)c1] | (3R,8aR)-3-[8-amino-1-(4-{(1R)-1-hydroxy-1-[3-(trifluoromethyl)phenyl]ethyl}phenyl)imidazo[1,5-a]pyrazin-3-yl]hexahydro-6H-pyrrolo[2,1-c][1,4]oxazin-6-one | Calc'd 538.2, found 538.2 | 2.855(C) |
| 170 | 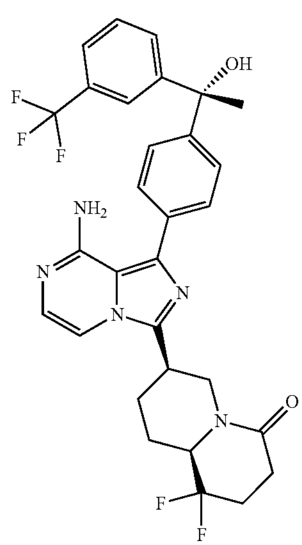 [SMILES: C[C@@](O)(c1ccc(-c2nc([C@@H]3CC[C@H]4N(C3)C(=O)CCC4(F)F)n3ccnc(N)c23)cc1)c1cccc(C(F)(F)F)c1] | (7R,9aR)-7-[8-amino-1-(4-{(1R)-1-hydroxy-1-[3-(trifluoromethyl)phenyl]ethyl}phenyl)imidazo[1,5-a]pyrazin-3-yl]-1,1-difluorooctahydro-4H-quinolizin-4-one | Calc'd 586.2, found 586.2 | 2.796(C) |

TABLE 3-continued

| Example number | Structure | IUPAC Name | Exact Mass [M + H]+ | LC-MS retention time (min, method) |
|---|---|---|---|---|
| 171 | 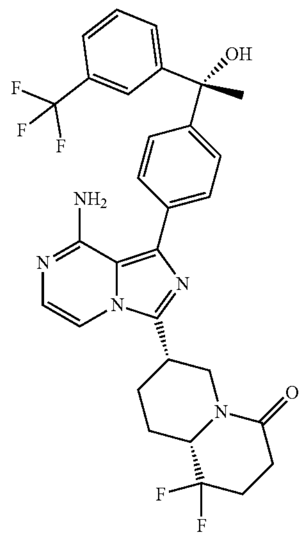 [SMILES: C[C@@](O)(c1ccc(-c2nc([C@H]3CC[C@@H]4N(C3)C(=O)CCC4(F)F)n3ccnc(N)c23)cc1)c1cccc(C(F)(F)F)c1] | (7S,9aS)-7-[8-amino-1-(4-{(1R)-1-hydroxy-1-[3-(trifluoromethyl)phenyl]ethyl}phenyl)imidazo[1,5-a]pyrazin-3-yl]-1,1-difluorooctahydro-4H-quinolizin-4-one | Calc'd 586.2, found 586.2 | 2.793(C) |
| 172 | 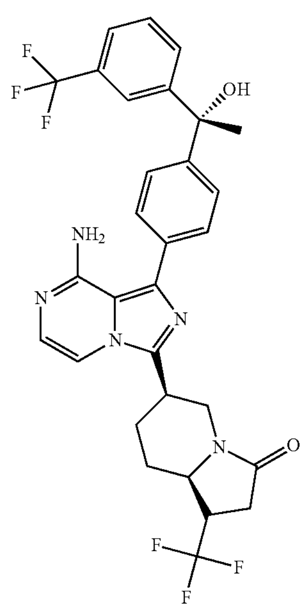 | (1S,6R,8aR)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3(2H)-one | Calc'd 604.2, found 604.1 | 2.417(C) |

TABLE 3-continued

| Example number | Structure | IUPAC Name | Exact Mass [M + H]+ | LC-MS retention time (min, method) |
|---|---|---|---|---|
| 173 | 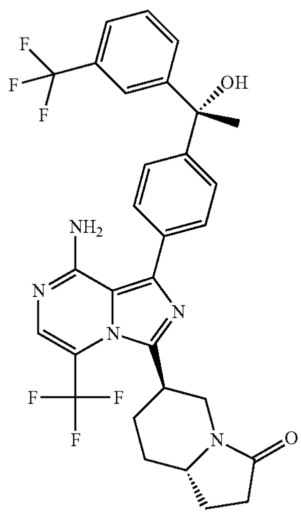 [SMILES: C[C@@](O)(c1ccc(-c2nc([C@@H]3CC[C@H]4CCC(=O)N4C3)n3c(C(F)(F)F)cnc(N)c23)cc1)c1cccc(C(F)(F)F)c1] | (6R,8aS)-6-[8-amino-1-(4-{(1R)-1-hydroxy-1-[3-(trifluoromethyl)phenyl]ethyl}phenyl)-5-(trifluoromethyl)imidazo[1,5-a]pyrazin-3-yl]hexahydroindolizin-3(2H)-one | Calc'd 604.2, found 604.2 | 2.885(C) |
| 174 | 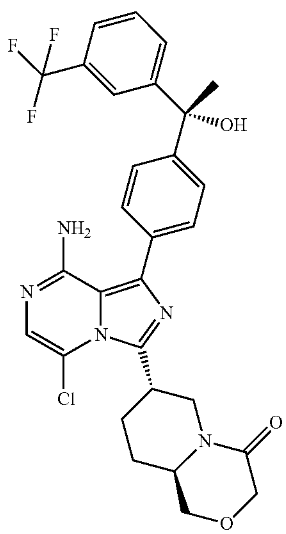 [SMILES: C[C@@](O)(c1ccc(-c2nc([C@H]3CC[C@@H]4COCC(=O)N4C3)n3c(Cl)cnc(N)c23)cc1)c1cccc(C(F)(F)F)c1] | (7S,9aR)-7-[8-amino-5-chloro-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one | Calc'd 586.2, found 586.1 | 2.722(C) |
| 175 | 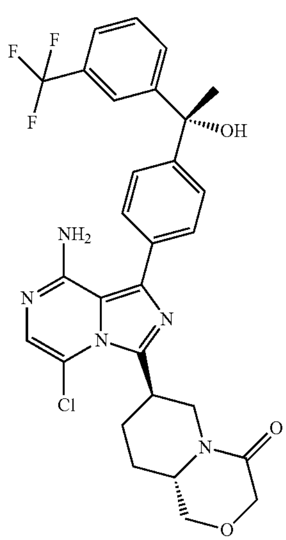 [SMILES: C[C@@](O)(c1ccc(-c2nc([C@@H]3CC[C@H]4COCC(=O)N4C3)n3c(Cl)cnc(N)c23)cc1)c1cccc(C(F)(F)F)c1] | (7R,9aS)-7-(8-amino-5-chloro-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one | Calc'd 586.2, found 586.2 | 2.719(C) |

TABLE 3-continued

| Example number | Structure | IUPAC Name | Exact Mass [M + H]+ | LC-MS retention time (min, method) |
|---|---|---|---|---|
| 176 | 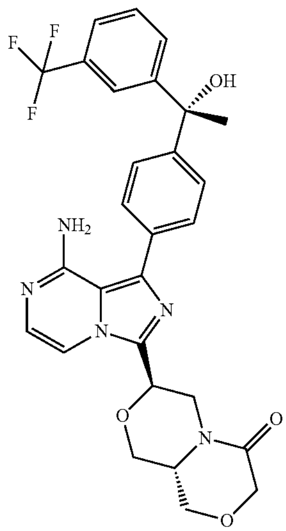 [SMILES: C[C@@](O)(c1ccc(-c2nc([C@H]3CN4C(=O)COC[C@@H]4CO3)n3ccnc(N)c23)cc1)c1cccc(C(F)(F)F)c1] | (7R,9aR)-7-[8-amino-1-(4-{(1R)-1-hydroxy-1-[3-(trifluoromethyl)phenyl]ethyl}phenyl)imidazo[1,5-a]pyrazin-3-yl]tetrahydro-1H-[1,4]oxazino[3,4-c][1,4]oxazin-4(3H)-one | Calc'd 554.2, found 554.1 | 2.848(C) |
| 177 | 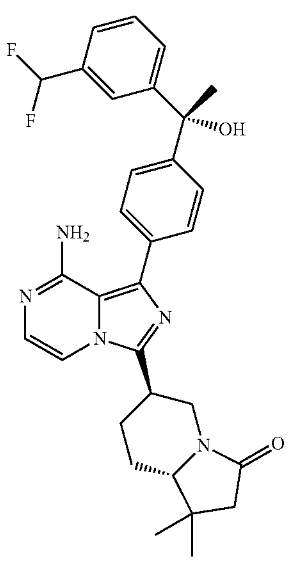 [SMILES: CC1(C)CC(=O)N2C[C@H](c3nc(-c4ccc([C@@](C)(O)c5cccc(C(F)F)c5)cc4)c4c(N)nccn34)CC[C@H]21] | (6R,8aS)-6-[8-amino-1-(4-{(1R)-1-[3-(difluoromethyl)phenyl]-1-hydroxyethyl}phenyl)imidazo[1,5-a]pyrazin-3-yl]-1,1-dimethylhexahydroindolizin-3(2H)-one | Calc'd 546.3, found 546.2 | 2.890(C) |

TABLE 3-continued

| Example number | Structure | IUPAC Name | Exact Mass [M + H]+ | LC-MS retention time (min, method) |
|---|---|---|---|---|
| 178 | 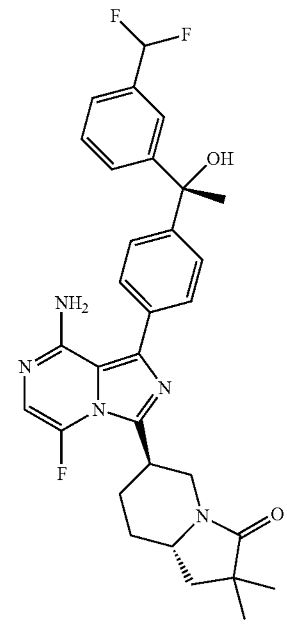 [SMILES: CC1(C)C[C@@H]2CC[C@@H](c3nc(-c4ccc([C@@](C)(O)c5cccc(C(F)F)c5)cc4)c4c(N)ncc(F)n34)CN2C1=O] | (6R,8aS)-6-[8-amino-1-(4-{(1R)-1-[3-(difluoromethyl)phenyl]-1-hydroxyethyl}phenyl)-5-fluoroimidazo[1,5-a]pyrazin-3-yl]-2,2-dimethylhexahydroindolizin-3(2H)-one | Calc'd 546.3, found 546.2 | 2.697(C) |
| 179 | 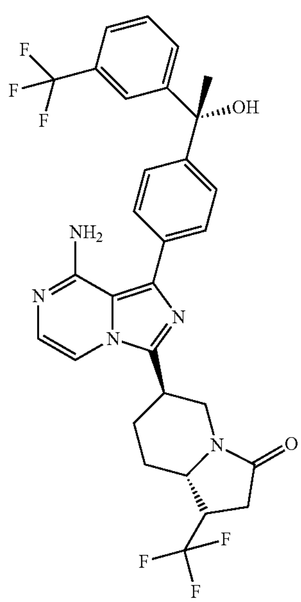 | (1R,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3(2H)-one | Calc'd 604.2, found 604.2 | 2.395(C) |

TABLE 3-continued

| Example number | Structure | IUPAC Name | Exact Mass [M + H]+ | LC-MS retention time (min, method) |
|---|---|---|---|---|
| 180 | 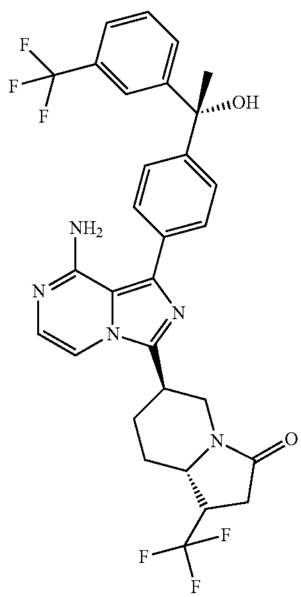 | (1R,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3(2H)-one | Calc'd 604.2, found 604.2 | 2.895(C) |
| 181 | 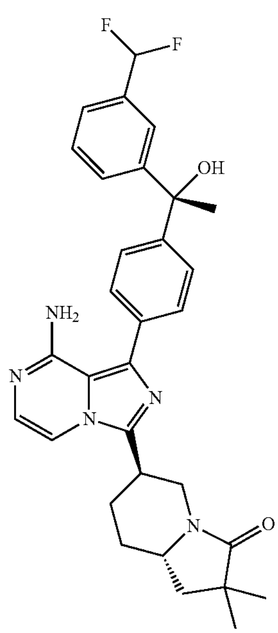 [SMILES: CC1(C)C[C@@H]2CC[C@@H](c3nc(-c4ccc([C@@](C)(O)c5cccc(C(F)F)c5)cc4)c4c(N)nccn34)CN2C1=O] | (6R,8aS)-6-[8-amino-1-(4-{(1R)-1-[3-(difluoromethyl)phenyl]-1-hydroxyethyl}phenyl)imidazo[1,5-a]pyrazin-3-yl]-2,2-dimethylhexahydroindolizin-3(2H)-one | Calc'd 546.3, found 546.2 | 2.856(C) |

TABLE 3-continued

| Example number | Structure | IUPAC Name | Exact Mass [M + H]+ | LC-MS retention time (min, method) |
|---|---|---|---|---|
| 182 | 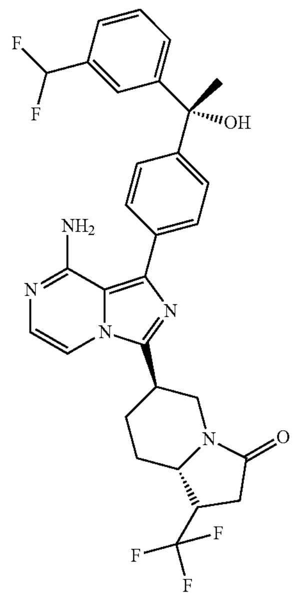 | (1R,6R,8aS)-6-[8-amino-1-(4-{(1R)-1-[3-(difluoromethyl)phenyl]-1-hydroxyethyl}phenyl)imidazo[1,5-a]pyrazin-3-yl]-1-(trifluoromethyl)hexahydroindolizin-3(2H)-one | Calc'd 586.2, found 586.2 | 2.604(C) |
| 183 | 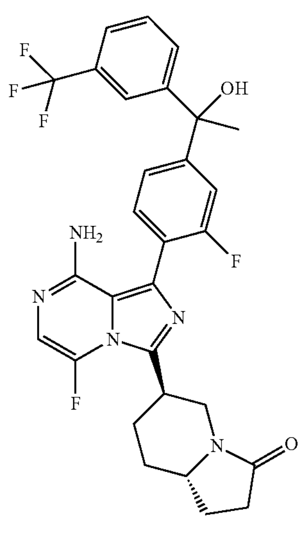 [SMILES: CC(O)(c1cccc(C(F)(F)F)c1)c1ccc(-c2nc([C@@H]3CC[C@H]4CCC(=O)N4C3)n3c(F)cnc(N)c23)c(F)c1] | (6R,8aS)-6-[8-amino-5-fluoro-1-(2-fluoro-4-{1-hydroxy-1-[3-(trifluoromethyl)phenyl]ethyl}phenyl)imidazo[1,5-a]pyrazin-3-yl]hexahydroindolizin-3(2H)-one | Calc'd 572.2, found 572.1 | 2.603(C) |

TABLE 3-continued

| Example number | Structure | IUPAC Name | Exact Mass [M + H]+ | LC-MS retention time (min, method) |
|---|---|---|---|---|
| 184 | 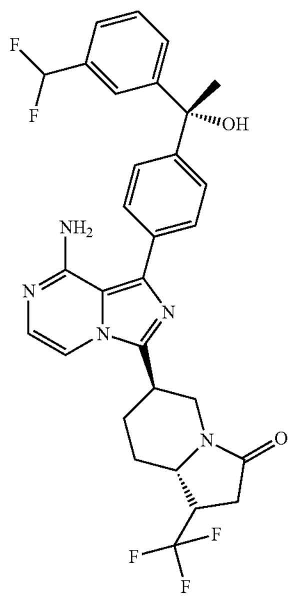 | (1R,6R,8aS)-6-[8-amino-1-(4-{(1R)-1-[3-(difluoromethyl)phenyl]-1-hydroxyethyl}phenyl)imidazo[1,5-a]pyrazin-3-yl]-1-(trifluoromethyl)hexahydroindolizin-3(2H)-one | Calc'd 586.2, found 586.2 | 2.544(C) |
| 185 | 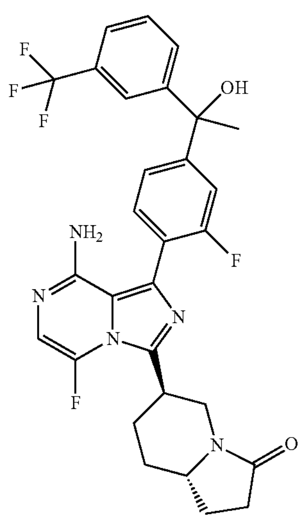 [SMILES: CC(O)(c1cccc(C(F)(F)F)c1)c1ccc(-c2nc([C@@H]3CC[C@H]4CCC(=O)N4C3)n3c(F)cnc(N)c23)c(F)c1] | (6R,8aS)-6-[8-amino-5-fluoro-1-(2-fluoro-4-{1-hydroxy-1-[3-(trifluoromethyl)phenyl]ethyl}phenyl)imidazo[1,5-a]pyrazin-3-yl]hexahydroindolizin-3(2H)-one | Calc'd 572.2, found 572.1 | 2.598(C) |

TABLE 3-continued

| Example number | Structure | IUPAC Name | Exact Mass [M + H]+ | LC-MS retention time (min, method) |
|---|---|---|---|---|
| 186 | 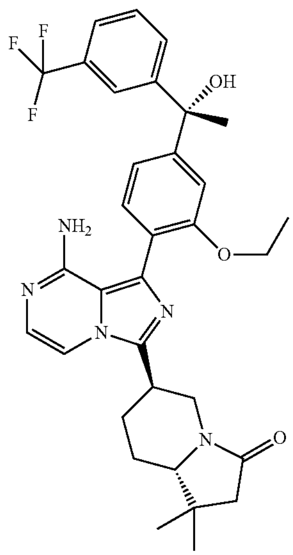 [SMILES: CCOc1cc([C@@](C)(O)c2cccc(C(F)(F)F)c2)ccc1-c1nc([C@@H]2CC[C@@H]3N(C2)C(=O)CC3(C)C)n2ccnc(N)c12] | (6R,8aS)-6-[8-amino-1-(2-ethoxy-4-{(1S)-1-hydroxy-1-[3-(trifluoromethyl)phenyl]ethyl}phenyl)imidazo[1,5-a]pyrazin-3-yl]-1,1-dimethylhexahydroindolizin-3(2H)-one | Calc'd 608.3, found 608.2 | 2.446(C) |
| 187 | 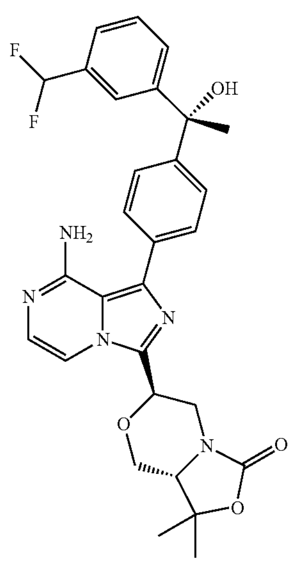 [SMILES: CC1(C)OC(=O)N2C[C@H](c3nc(-c4ccc([C@@](C)(O)c5cccc(C(F)F)c5)cc4)c4c(N)nccn34)OC[C@H]21] | (6R,8aS)-6-[8-amino-1-(4-{(1R)-1-[3-(difluoromethyl)phenyl]-1-hydroxyethyl}phenyl)imidazo[1,5-a]pyrazin-3-yl]-1,1-dimethyltetrahydro-1H-[1,3]oxazolo[4.3-c][1,4]oxazin-3-one | Calc'd 550.2, found 550.2 | 2.442(C) |

TABLE 3-continued

| Example number | Structure | IUPAC Name | Exact Mass [M + H]+ | LC-MS retention time (min, method) |
|---|---|---|---|---|
| 188 | 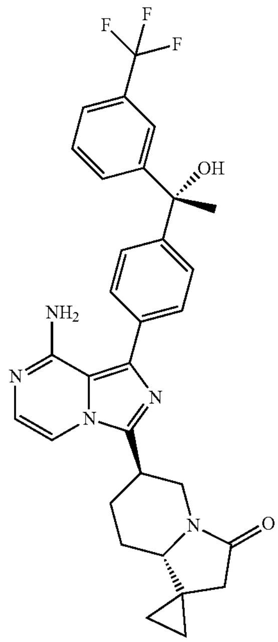 [SMILES: C[C@@](O)(c1ccc(-c2nc([C@@H]3CC[C@@H]4N(C3)C(=O)CC43CC3)n3ccnc(N)c23)cc1)c1cccc(C(F)(F)F)c1] | (6'R,8a'S)-6'-[8-amino-1-(4-{(1R)-1-hydroxy-1-[3-(trifluoromethyl)phenyl]ethyl}phenyl)imidazo[1,5-a]pyrazin-3-yl]tetrahydro-5'H-spiro[cyclopropane-1,1'-indolizin]-3'(2'H)-one | Calc'd 562.2, found 562.2 | 2.653(C) |
| 189 | 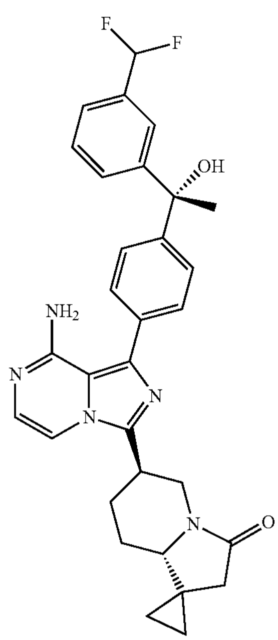 [SMILES: C[C@@](O)(c1ccc(-c2nc([C@@H]3CC[C@@H]4N(C3)C(=O)CC43CC3)n3ccnc(N)c23)cc1)c1cccc(C(F)F)c1] | (6'R,8a'S)-6'-[8-amino-1-(4-{(1R)-1-[3-(difluoromethyl)phenyl]-1-hydroxyethyl}phenyl)imidazo[1,5-a]pyrazin-3-yl]tetrahydro-5'H-spiro[cyclopropane-1,1'-indolizin]-3'(2'H)-one | Calc'd 544.3, found 544.2 | 2.524(C) |

TABLE 3-continued

| Example number | Structure | IUPAC Name | Exact Mass [M + H]+ | LC-MS retention time (min, method) |
|---|---|---|---|---|
| 190 | 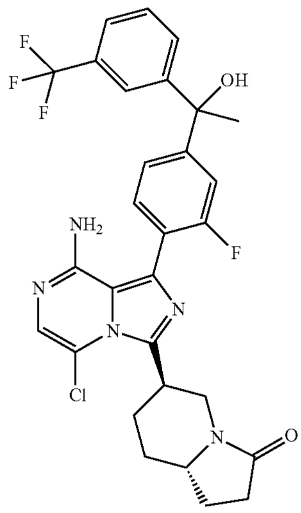 | (6R,8aS)-6-[8-amino-5-chloro-1-(2-fluoro-4-{1-hydroxy-1-[3-(trifluoromethyl)phenyl]ethyl}phenyl)imidazo[1,5-a]pyrazin-3-yl]hexahydroindolizin-3(2H)-one | Calc'd 588.2, found 588.1 | 2.353(C) |
| 191 | 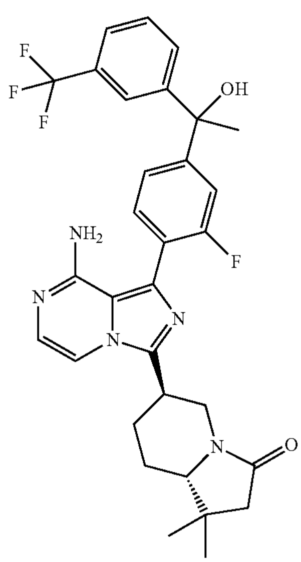 [SMILES: CC(O)(c1cccc(C(F)(F)F)c1)c1ccc(-c2nc([C@@H]3CC[C@@H]4N(C3)C(=O)CC4(C)C)n3ccnc(N)c23)c(F)c1] | (6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-1,1-dimethylhexahydroindolizin-3(2H)-one | Calc'd 582.2, found 582.2 | 2.375(C) |

TABLE 3-continued

| Example number | Structure | IUPAC Name | Exact Mass [M + H]+ | LC-MS retention time (min, method) |
|---|---|---|---|---|
| 192 | 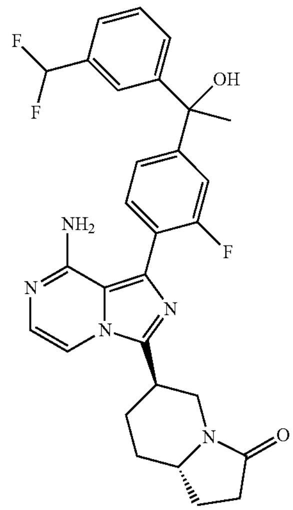 [SMILES: CC(O)(c1cccc(C(F)F)c1)c1ccc(-c2nc([C@@H]3CC[C@H]4CCC(=O)N4C3)n3ccnc(N)c23)c(F)c1] | (6R,8aS)-6-(8-amino-1-(4-{1-[3-(difluoromethyl)phenyl]-1-hydroxyethyl}-2-fluorophenyl)imidazo[1,5-a]pyrazin-3-yl]hexahydroindolizin-3(2H)-one | Calc'd 536.2, found 536.2 | 2.406(C) |
| 193 | 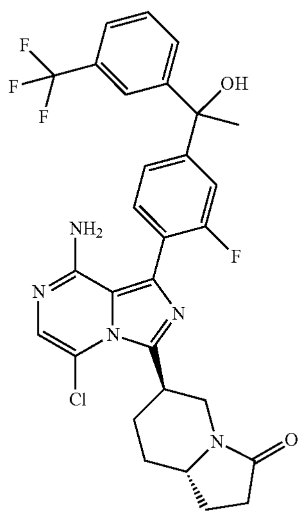 [SMILES: CC(O)(c1cccc(C(F)(F)F)c1)c1ccc(-c2nc([C@@H]3CC[C@H]4CCC(=O)N4C3)n3c(Cl)cnc(N)c23)c(F)c1] | (6R,8aS)-6-[8-amino-5-chloro-1-(2-fluoro-4-{1-hydroxy-1-[3-(trifluoromethyl)phenyl]ethyl}phenyl)imidazo[1,5-a]pyrazin-3-yl]hexahydroindolizin-3(2H)-one | Calc'd 588.2, found 588.2 | 2.343(C) |
| 194 | 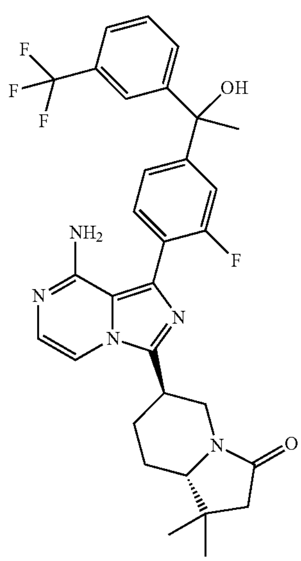 [SMILES: CC(O)(c1cccc(C(F)(F)F)c1)c1ccc(-c2nc([C@@H]3CC[C@@H]4N(C3)C(=O)CC4(C)C)n3ccnc(N)c23)c(F)c1] | (6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-1,1-dimethylhexahydroindolizin-3(2H)-one | Calc'd 582.2, found 582.2 | 2.380(C) |

TABLE 3-continued
| Example number | Structure | IUPAC Name | Exact Mass [M + H]+ | LC-MS retention time (min, method) |
|---|---|---|---|---|
| 195 | 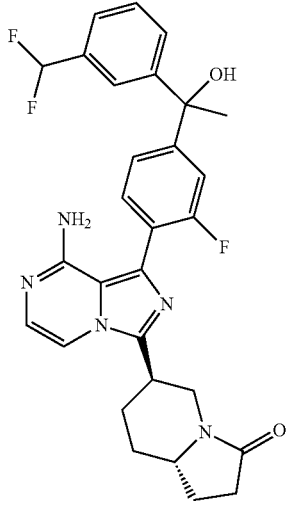 [SMILES: CC(O)(c1cccc(C(F)F)c1)c1ccc(-c2nc([C@@H]3CC[C@H]4CCC(=O)N4C3)n3ccnc(N)c23)c(F)c1] | (6R,8aS)-6-[8-amino-1-(4-{1-[3-(difluoromethyl)phenyl]-1-hydroxyethyl -2-fluorophenyl)imidazo[1,5-a]pyrazin-3-yl]hexahydroindolizin-3(2H)-one | Calc'd 536.2, found 536.2 | 2.414(C) |
| 196 | 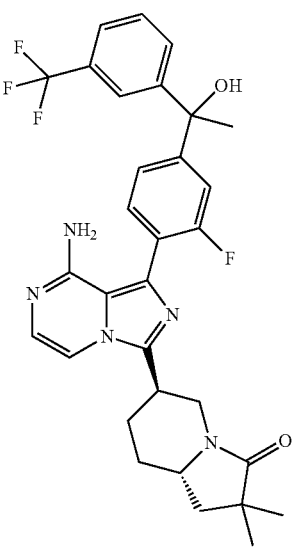 [SMILES: CC1(C)C[C@@H]2CC[C@@H](c3nc(-c4ccc(C(C)(O)c5cccc(C(F)(F)F)c5)cc4F)c4c(N)nccn34)CN2C1=O] | (6R,8aS)-6-[8-amino-1-(2-fluoro-4-{1-hydroxy-1-[3-(trifluoromethyl)pheyl]ethyl}phenyl)imidazo[1,5-a]pyrazin-3-yl]-2,2-dimethylhexahydroindolizin-3(2H)-one | Calc'd 582.2, found 582.2 | 2.263(C) |

TABLE 3-continued

| Example number | Structure | IUPAC Name | Exact Mass [M + H]+ | LC-MS retention time (min, method) |
|---|---|---|---|---|
| 197 | 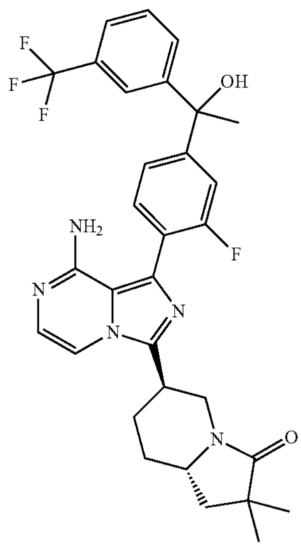 [SMILES: CC1(C)C[C@@H]2CC[C@@H](c3nc(-c4ccc(C(C)(O)c5cccc(C(F)(F)F)c5)cc4F)c4c(N)nccn34)CN2C1=O] | (6R,8aS)-6-[ 8-amino-1-(2-fluoro-4-{1-hydroxy-1-[3-(trifluoromethyl)phenyl]ethyl}phenyl)imidazo[1,5-a]pyrazin-3-yl]-2,2-dimethylhexahydroindolizin-3(2H)-one | Calc'd 582.2, found 582.2 | 2.316(C) |
| 198 | 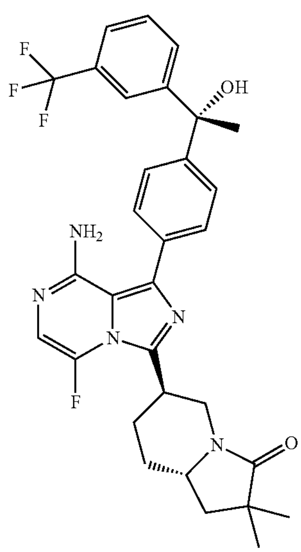 [SMILES: CC1(C)C[C@@H]2CC[C@@H](c3nc(-c4ccc([C@@](C)(O)c5cccc(C(F)(F)F)c5)cc4)c4c(N)ncc(F)n34)CN2C1=O] | (6R,8aS)-6-[8-amino-5-fluoro-1-(4-{(1R)-1-hydroxy-1-[3-(trifluoromethyl)phenyl]ethyl}phenyl)imidazo[1,5-a]pyrazin-3-yl]-2,2-dimethylhexahydroindolizin-3(2H)-one | Calc'd 582.2, found 582.2 | 2.953(C) |

TABLE 3-continued
| Example number | Structure | IUPAC Name | Exact Mass [M + H]+ | LC-MS retention time (min, method) |
|---|---|---|---|---|
| 199 | 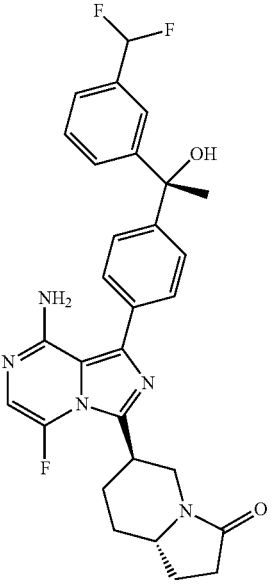 [SMILES: C[C@@](O)(c1ccc(-c2nc([C@@H]3CC[C@H]4CCC(=O)N4C3)n3c(F)cnc(N)c23)cc1)c1cccc(C(F)F)c1] | (6R,8aS)-6-(8-amino-1-(4-{(1R)-1-[3-(difluoromethyl)phenyl]-1-hydroxyethyl}phenyl)-5-fluoroimidazo[1,5-a]pyrazin-3-yl]hexahydroindolizin-3(2H)-one | Calc'd 536.2, found 536.2 | 2.429(C) |
| 200 | 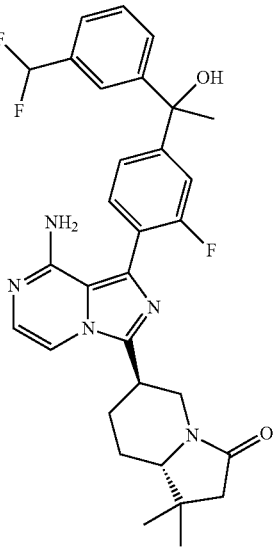 | (6R,8aS)-6-[8-amino-1-(4-{1-[3-(difluoromethyl)phenyl]-1-hydroxyethyl}-2-fluorophenyl)imidazo[1,5-a]pyrazin-3-yl]-1,1-dimethylhexahydroindolizin-3(2H)-one | Calc'd 564.3, found 564.2 | 2.246(C) |

TABLE 3-continued

| Example number | Structure | IUPAC Name | Exact Mass [M + H]+ | LC-MS retention time (min, method) |
|---|---|---|---|---|
| 201 | 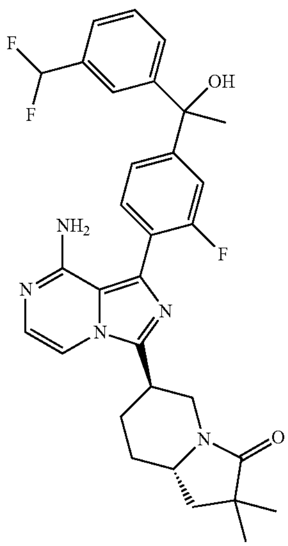 [SMILES: CC1(C)C[C@@H]2CC[C@@H](c3nc(-c4ccc(C(C)(O)c5cccc(C(F)F)c5)cc4F)c4c(N)nccn34)CN2C1=O] | (6R,8aS)-6-[8-amino-1-(4-{1-[3-(difluoromethyl)phenyl]-1-hydroxyethyl}-2-fluorophenyl)imidazo[1,5-a]pyrazin-3-yl]-2,2-dimethylhexahydroindolizin-3(2H)-one | Calc'd 564.3, found 564.2 | 2.223(C) |
| 202 | 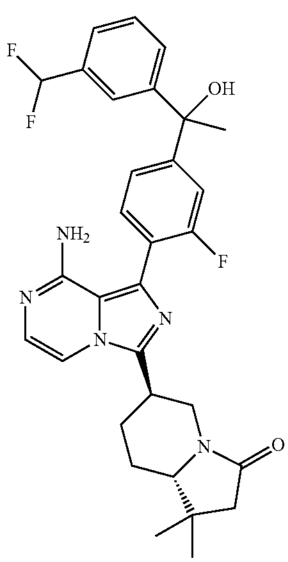 [SMILES: CC(O)(c1cccc(C(F)F)c1)c1ccc(-c2nc([C@@H]3CC[C@@H]4N(C3)C(=O)CC4(C)C)n3ccnc(N)c23)c(F)c1] | (6R,8aS)-6-(8-amino-1-(4-{1-[3-(difluoromethyl)phenyl]-1-hydroxyethyl}-2-fluorophenyl)imidazo[1,5-a]pyrazin-3-yl]-1,1-dimethylhexahydroindolizin-3(2H)-one | Calc'd 564.3, found 564.2 | 2.233(C) |

| Example number | Structure | IUPAC Name | Exact Mass [M + H]+ | LC-MS retention time (min, method) |
|---|---|---|---|---|
| 203 | 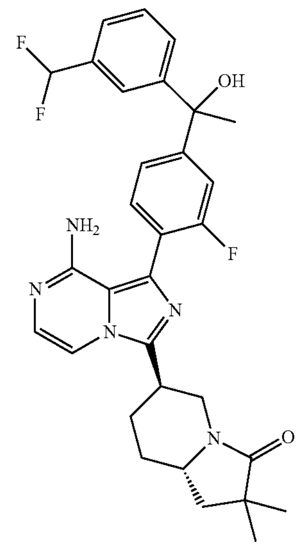 [SMILES: CC1(C)C[C@@H]2CC[C@@H](c3nc(-c4ccc(C(C)(O)c5cccc(C(F)F)c5)cc4F)c4c(N)nccn34)CN2C1=O] | (6R,8aS)-6-[8-amino-1-(4-{1-[3-(difluoromethyl)phenyl]-1-hydroxyethyl}-2-fluorophenyl)imidazo[1,5-a]pyrazin-3-yl]-2,2-dimethylhexahydroindolizin-3(2H)-one | Calc'd 564.3, found 564.2 | 2.224(C) |
| 204 | 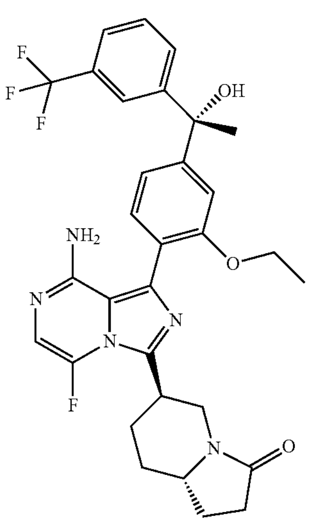 [SMILES: CCOc1cc([C@@](C)(O)c2cccc(C(F)(F)F)c2)ccc1-c1nc([C@@H]2CC[C@H]3CCC(=O)N3C2)n2c(F)cnc(N)c12] | (6R,8aS)-6-[8-amino-1-(2-ethoxy-4-{(1S)-1-hydroxy-1-[3-(trifluoromethyl)phenyl]ethyl}phenyl)-5-fluoroimidazo[1,5-a]pyrazin-3-yl]hexahydroindolizin-3(2H)-one | Calc'd 598.2, found 598.2 | 2.779(C) |

TABLE 3-continued

| Example number | Structure | IUPAC Name | Exact Mass [M + H]+ | LC-MS retention time (min, method) |
|---|---|---|---|---|
| 205 | 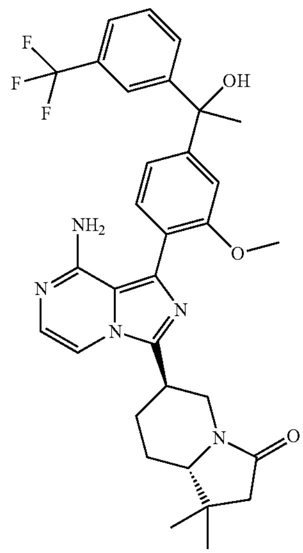 [SMILES: COc1cc(C(C)(O)c2cccc(C(F)(F)F)c2)ccc1-c1nc([C@@H]2CC[C@@H]3N(C2)C(=O)CC3(C)C)n2ccnc(N)c12] | (6R,8aS)-6-[8-amino-1-(4-{1-hydroxy-1-[3-(trifluoromethyl)phenyl]ethyl}-2-methoxyphenyl)imidazo[1,5-a]pyrazin-3-yl]-1,1-dimethylhexahydroindolizin-3(2H)-one | Calc'd 594.3, found 594.2 | 2.369(C) |
| 206 | 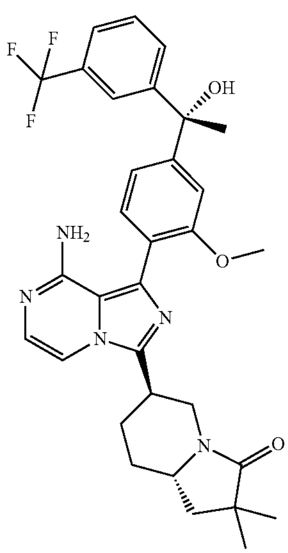 [SMILES: COc1cc([C@@](C)(O)c2cccc(C(F)(F)F)c2)ccc1-c1nc([C@@H]2CC[C@H]3CC(C)(C)C(=O)N3C2)n2ccnc(N)c12] | (6R,8aS)-6-[8-amino-1-(4-{(1S)-1-hydroxy-1-[3-(trifluoromethyl)phenyl]ethyl}-2-methoxyphenyl)imidazo[1,5-a]pyrazin-3-yl]-2,2-dimethylhexahydroindolizin-3(2H)-one | Calc'd 594.3, found 594.3 | 2.572(C) |

TABLE 3-continued

| Example number | Structure | IUPAC Name | Exact Mass [M + H]+ | LC-MS retention time (min, method) |
|---|---|---|---|---|
| 207 | 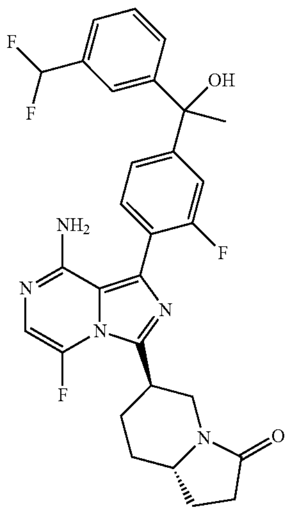 [SMILES: CC(O)(c1cccc(C(F)F)c1)c1ccc(-c2nc([C@@H]3CC[C@H]4CCC(=O)N4C3)n3c(F)cnc(N)c23)c(F)c1] | (6R,8aS)-6-[8-amino-1-(4-{1-[3-(difluoromethyl)phenyl]-1-hydroxyethyl}-2-fluorophenyl)-5-fluoroimidazo[1,5-a]pyrazin-3-yl]hexahydroindolizin-3(2H)-one | Calc'd 554.2, found 554.2 | 2.467(C) |
| 208 | 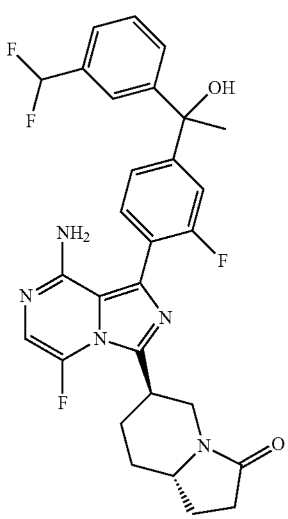 [SMILES: CC(O)(c1cccc(C(F)F)c1)c1ccc(-c2nc([C@@H]3CC[C@H]4CCC(=O)N4C3)n3c(F)cnc(N)c23)c(F)c1] | (6R,8aS)-6-(8-amino-1-(4-{1-[3-(difluoromethyl)phenyl]-1-hydroxyethyl}-2-fluorophenyl)-5-fluoroimidazo[1,5-a]pyrazin-3-yl)hexahydroindolizin-3(2H)-one | Calc'd 554.2, found 554.2 | 2.463(C) |

TABLE 3-continued

| Example number | Structure | IUPAC Name | Exact Mass [M + H]+ | LC-MS retention time (min, method) |
|---|---|---|---|---|
| 209 | 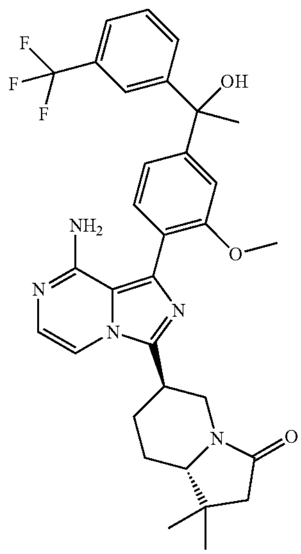 [SMILES: COc1cc(C(C)(O)c2cccc(C(F)(F)F)c2)ccc1-c1nc([C@@H]2CC[C@@H]3N(C2)C(=O)CC3(C)C)n2ccnc(N)c12] | (6R,8aS)-6-[8-amino-1-(4-{1-hydroxy-1-[3-(trifluoromethyl)phenyl]ethyl}-2-methoxyphenyl)imidazo[1,5-a]pyrazin-3-yl]-1,1-dimethylhexahydroindolizin-3(2H)-one | Calc'd 594.3, and 594.2 | 2.345(C) |
| 210 | 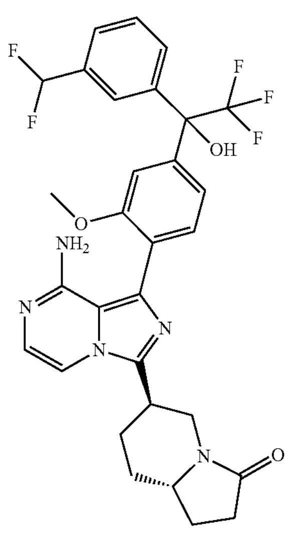 [SMILES: COc1cc(C(O)(c2cccc(C(F)F)c2)C(F)(F)F)ccc1-c1nc([C@@H]2CC[C@H]3CCC(=O)N3C2)n2ccnc(N)c12] | (6R,8aS)-6-[8-amino-1-(4-{1-[3-(difluoromethyl)phenyl]-2,2,2-trifluoro-1-hydroxyethyl}-2-methoxyphenyl)imidazo[1,5-a]pyrazin-3-yl]hexahydroindolizin-3(2H)-one | Calc'd 602.2, found 602.1 | 2.585(C) |

TABLE 3-continued

| Example number | Structure | IUPAC Name | Exact Mass [M + H]+ | LC-MS retention time (min, method) |
|---|---|---|---|---|
| 211 | 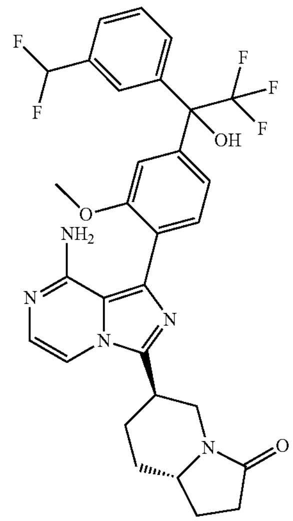 [SMILES: COc1cc(C(O)(c2cccc(C(F)F)c2)C(F)(F)F)ccc1-c1nc([C@@H]2CC[C@H]3CCC(=O)N3C2)n2ccnc(N)c12] | (6R,8aS)-6-[8-amino-1-(4-{1-[3-(difluoromethyl)phenyl]-2,2,2-trifluoro-1-hydroxyethyl}-2-methoxyphenyl)imidazo[1,5-a]pyrazin-3-yl]hexahydroindolizin-3(2H)-one | Calc'd 602.2, found 602.1 | 2.577(C) |
| 212 | 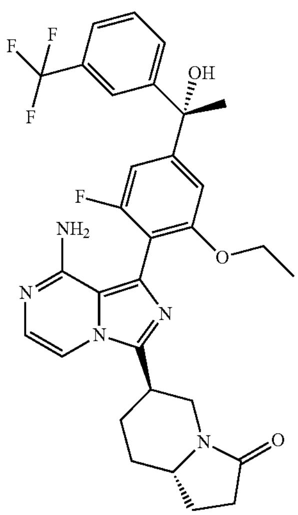 [SMILES: CCOc1cc([C@@](C)(O)c2cccc(C(F)(F)F)c2)cc(F)c1-c1nc([C@@H]2CC[C@H]3CCC(=O)N3C2)n2ccnc(N)c12] | (6R,8aS)-6-[8-amino-1-(2-ethoxy-6-fluoro-4-{(1S)-1-hydroxy-1-[3-(trifluoromethyl)phenyl]ethyl}phenyl)imidazo[1,5-a]pyrazin-3-yl]hexahydroindolizin-3(2H)-one | Calc'd 598.2, found | |
| 213 | 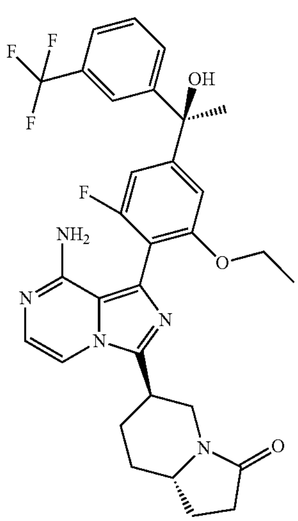 [SMILES: CCOc1cc([C@](C)(O)c2cccc(C(F)(F)F)c2)cc(F)c1-c1nc([C@@H]2CC[C@H]3CCC(=O)N3C2)n2ccnc(N)c12] | (6R,8aS)-6-[8-amino-1-(2-ethoxy-6-fluoro-4-{(1R)-1-hydroxy-1-[3-(trifluoromethyl)phenyl]ethyl}phenyl)imidazo[1,5-a]pyrazin-3-yl]hexahydroindolizin-3(2H)-one | Calc'd 598.2, found | |

TABLE 3-continued

| Example number | Structure | IUPAC Name | Exact Mass [M + H]+ | LC-MS retention time (min, method) |
|---|---|---|---|---|
| 214 | 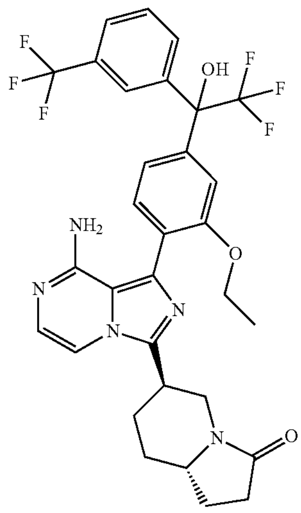 [SMILES: CCOc1cc(C(O)(c2cccc(C(F)(F)F)c2)C(F)(F)F)ccc1-c1nc([C@@H]2CC[C@H]3CCC(=O)N3C2)n2ccnc(N)c12] | (6R,8aS)-6-[8-amino-1-(2-ethoxy-4-{2,2,2-trifluoro-1-hydroxy-1-[3-(trifluoromethyl)phenyl]ethyl}phenyl)imidazo[1,5-a]pyrazin-3-yl]hexahydroindolizin-3(2H)-one | Calc'd 634.2, found 634.2 | 2.813(C) |
| 215 | 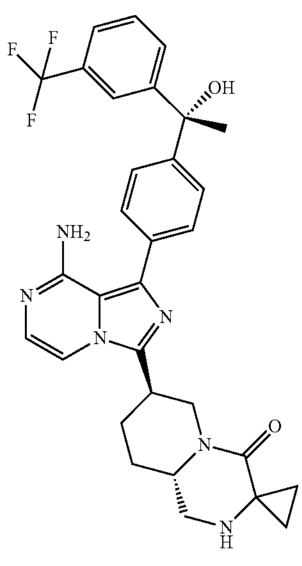 [SMILES: C[C@@](O)(c1ccc(-c2nc([C@@H]3CC[C@H]4CNC5(CC5)C(=O)N4C3)n3ccnc(N)c23)cc1)c1cccc(C(F)(F)F)c1] | (7'R,9a'S)-7'-[8-amino-1-(4-{(1R)-1-hydroxy-1-[3-(trifluoromethyl)phenyl]ethyl}phenyl)imidazo[1,5-a]pyrazin-3-yl]hexahydro-2'H-spiro[cyclopropane-1,3'-pyrido[1,2-a]pyrazin]-4'-one | Calc'd 577.3, found 577.2 | 1.84(C) |

TABLE 3-continued

| Example number | Structure | IUPAC Name | Exact Mass [M + H]+ | LC-MS retention time (min, method) |
| --- | --- | --- | --- | --- |
| 216 | 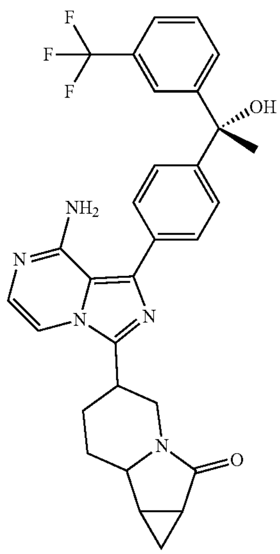 [SMILES: C[C@@](O)(c1ccc(-c2nc(C3CCC4C5CC5C(=O)N4C3)n3ccnc(N)c23)cc1)c1cccc(C(F)(F)F)c1] | 5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indoliin-2-one(D1) | Calc'd 548.2, found 548.3 | 2.75(C) |
| 217 | 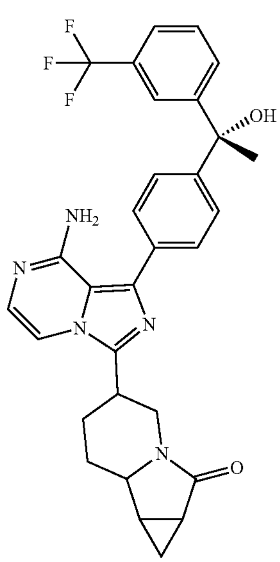 [SMILES: C[C@@](O)(c1ccc(-c2nc(C3CCC4C5CC5C(=O)N4C3)n3ccnc(N)c23)cc1)c1cccc(C(F)(F)F)c1] | 5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one (D2) | Calc'd 548.2, found 548.3 | 2.77(C) |

TABLE 3-continued

| Example number | Structure | IUPAC Name | Exact Mass [M + H]+ | LC-MS retention time (min, method) |
|---|---|---|---|---|
| 218 | 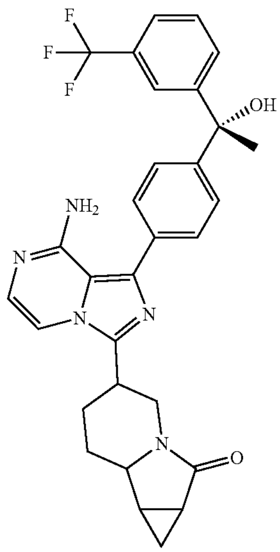 [SMILES: C[C@@](O)(c1ccc(-c2nc(C3CCC4C5CC5C(=O)N4C3)n3ccnc(N)c23)cc1)c1cccc(C(F)(F)F)c1] | 5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one (D3) | Calc'd 548.2, found 548.3 | 2.87 |
| 219 | 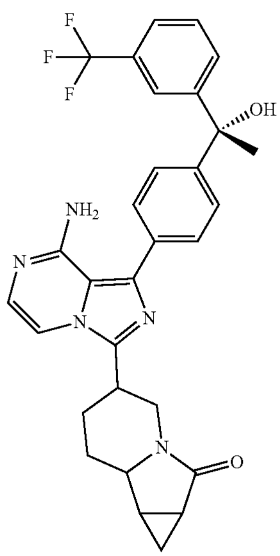 [SMILES: C[C@@](O)(c1ccc(-c2nc(C3CCC4C5CC5C(=O)N4C3)n3ccnc(N)c23)cc1)c1cccc(C(F)(F)F)c1] | 5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one (D4) | Calc'd 548.2, found 548.3 | 2.80 |

Biological Activity

The Btk inhibitor compounds of the invention having Formula I inhibit the Btk kinase activity. All compounds of the invention have an IC50 of 10 μM or lower. In another aspect the invention relates to compounds of Formula I which have an IC50 of less than 100 nM. In yet another aspect the invention relates to compounds of Formula I which have an IC50 of less than 10 nM.

The term IC50 means the concentration of the test compound that is required for 50% inhibition of its maximum effect in vitro.

Btk Enzyme Activity Assay Methods

BTK enzymatic activity was determined with the LANCE (Lanthanide Chelate Excite) TR-FRET (Time-resolved fluorescence resonance energy transfer) assay. In this assay, the potency (IC$_{50}$) of each compound was determined from an eleven point (1:3 serial dilution; final compound concentration range in assay from 1 μM to 0.017 nM) titration curve using the following outlined procedure. To each well of a black non-binding surface Corning 384-well microplate (Corning Catalog #3820), 5 nL of compound (2000 fold dilution in final assay volume of 10 μL) was dispensed, followed by the addition of 7.5 μL of 1× kinase buffer (50 mM Hepes 7.5, 10 mM MgCl$_2$, 0.01% Brij-35, 1 mM EGTA, 0.05% BSA & 1 mM DTT) containing 5.09 pg/μL (66.67 pM) of BTK enzyme (recombinant protein from baculovirus-transfected Sf9 cells: full-length BTK, 6HIS-tag cleaved). Following a 60 minute compound & enzyme incubation, each reaction was initiated by the addition of 2.5 μL 1× kinase buffer containing 8 μM biotinylated "A5" peptide (Biotin-EQEDEPEGDYFEWLE-NH2) (SEQ-.ID.NO.: 1), and 100 μM ATP. The final reaction in each well of 10 μL consists of 50 pM hBTK, 2 μM biotin-A5-peptide, and 25 μM ATP. Phosphorylation reactions were allowed to proceed for 120 minutes. Reactions were immediately quenched by the addition of 20 uL of 1× quench buffer (15 mM EDTA, 25 mM Hepes 7.3, and 0.1% Triton X-100) containing detection reagents (0.626 nM of LANCE-Eu-W1024-anti-phosphoTyrosine antibody, PerkinElmer and 86.8 nM of Streptavidin-conjugated Dylight 650, Dyomics/ThermoFisher Scientific). After 60 minutes incubation with detection reagents, reaction plates were read on a PerkinElmer EnVision plate reader using standard TR-FRET protocol. Briefly, excitation of donor molecules (Eu-chelate: anti-phospho-antibody) with a laser light source at 337 nm produces energy that can be transferred to Dylight-650 acceptor molecules if this donor:acceptor pair is within close proximity. Fluorescence intensity at both 665 nm (acceptor) and 615 nm (donor) are measured and a TR-FRET ratio calculated for each well (acceptor intensity/donor intensity). $IC_{50}$ values were determined by 4 parameter robust fit of TR-FRET ratio values vs. ($Log_{10}$) compound concentrations.

The following Table 4 provides specific IC50 values for all the examples. The IC50 values set forth below were determined according to Assay method described above.

TABLE 4

Data on compounds in the BTK binding potency assay

| Example number | BTK binding IC50 (nM) |
|---|---|
| Example 1 | 65.2 |
| Example 2 | 1.6 |
| Example 3 | 883.5 |
| Example 4 | 0.62 |
| Example 5 | 376.7 |
| Example 6 | 0.76 |
| Example 7 | 0.82 |
| Example 8 | 20.6 |
| Example 9 | 13.0 |
| Example 10 | 496 |
| Example 11 | 1.8 |
| Example 12 | 3.4 |
| Example 13 | 1.7 |
| Example 14 | 255.5 |
| Example 15 | 387.9 |
| Example 16 | 7.3 |
| Example 17 | 323.8 |
| Example 18 | 359.3 |
| Example 19 | 169.8 |
| Example 20 | 229.9 |
| Example 21 | 5.8 |
| Example 22 | 1.7 |
| Example 23 | 3.5 |
| Example 24 | 5.2 |
| Example 25 | 1.8 |
| Example 26 | 155.6 |
| Example 27 | 9.8 |
| Example 28 | 792.5 |
| Example 29 | 6.9 |
| Example 30 | 2.8 |
| Example 31 | 78.3 |
| Example 32 | 160.9 |
| Example 33 | 0.54 |
| Example 34 | 0.74 |
| Example 35 | 218.4 |
| Example 36 | 1000 |
| Example 37 | 254.7 |
| Example 38 | 0.07 |
| Example 39 | 9.6 |
| Example 40 | 0.27 |
| Example 41 | 116 |
| Example 42 | 1000 |
| Example 43 | 1000 |
| Example 44 | 81.4 |
| Example 45 | 1.1 |
| Example 46 | 0.23 |
| Example 47 | 183.1 |
| Example 48 | 2.5 |
| Example 49 | 45.2 |
| Example 50 | 243.2 |
| Example 51 | 5.9 |
| Example 52 | 0.47 |
| Example 53 | 6.5 |
| Example 54 | 1000 |
| Example 55 | 1000 |
| Example 56 | 582.6 |
| Example 57 | 0.88 |
| Example 58 | 63.1 |
| Example 59 | 0.93 |
| Example 60 | 36.7 |
| Example 61 | 72.0 |
| Example 62 | 19.7 |
| Example 63 | 1000 |
| Example 64 | 59.1 |
| Example 65 | 7.0 |
| Example 66 | 795.9 |
| Example 67 | 15.4 |
| Example 68 | 459.8 |
| Example 69 | 4.9 |
| Example 70 | 30.4 |
| Example 71 | 0.19 |
| Example 72 | 20.4 |
| Example 73 | 0.41 |
| Example 74 | 15 |
| Example 75 | 0.21 |
| Example 76 | 1000 |
| Example 77 | 24.2 |
| Example 78 | 0.17 |
| Example 79 | 204.5 |
| Example 80 | 808.4 |
| Example 81 | 1000 |
| Example 82 | 4.7 |
| Example 83 | 0.12 |
| Example 84 | 1000 |
| Example 85 | 23.4 |
| Example 86 | 1000 |
| Example 87 | 123.1 |
| Example 88 | 576.5 |
| Example 89 | 1000 |
| Example 90 | 1000 |
| Example 91 | |
| Example 92 | 0.48 |
| Example 93 | 0.15 |
| Example 94 | 201 |
| Example 95 | 1.8 |
| Example 96 | 576.1 |
| Example 97 | 893.7 |
| Example 98 | 0.28 |
| Example 99 | 10.1 |
| Example 100 | 17.4 |
| Example 101 | 773.7 |
| Example 102 | 1.6 |
| Example 103 | 1000 |
| Example 104 | 10.7 |
| Example 105 | 1000 |
| Example 106 | 152.9 |
| Example 107 | 938.6 |
| Example 108 | 677.7 |
| Example 109 | 44.9 |
| Example 110 | 0.95 |
| Example 111 | 1000 |
| Example 112 | 5.6 |
| Example 113 | 30.9 |
| Example 114 | 0.22 |
| Example 115 | 51.9 |
| Example 116 | 0.87 |
| Example 117 | 0.12 |
| Example 118 | 83.2 |
| Example 119 | 33.1 |
| Example 120 | 5.1 |
| Example 121 | 0.18 |
| Example 122 | 2.7 |

TABLE 4-continued

Data on compounds in the BTK binding potency assay

| Example number | BTK binding IC50 (nM) |
|---|---|
| Example 123 | 116.9 |
| Example 124 | 1.2 |
| Example 125 | 823.9 |
| Example 126 | 1000 |
| Example 127 | 459.4 |
| Example 128 | 12.4 |
| Example 129 | 12.2 |
| Example 130 | 12.7 |
| Example 131 | 64.4 |
| Example 132 | 0.30 |
| Example 133 | 118.1 |
| Example 134 | 0.14 |
| Example 135 | 1000 |
| Example 136 | 87.6 |
| Example 137 | 876.5 |
| Example 138 | 25.0 |
| Example 139 | 24.9 |
| Example 140 | 0.22 |
| Example 141 | 93.8 |
| Example 142 | 2.0 |
| Example 143 | 900 |
| Example 144 | 67.6 |
| Example 145 | 1000 |
| Example 146 | 752.4 |
| Example 147 | 26.2 |
| Example 148 | 0.20 |
| Example 149 | 888 |
| Example 150 | 1.6 |
| Example 151 | 12.1 |
| Example 152 | 39.1 |
| Example 153 | 1000 |
| Example 154 | 1000 |
| Example 155 | 857.5 |
| Example 156 | 72.3 |
| Example 157 | 1.9 |
| Example 158 | 4.7 |
| Example 159 | 0.10 |
| Example 160 | 0.07 |
| Example 161 | 0.27 |
| Example 162 | 0.63 |
| Example 163 | 169.1 |
| Example 164 | 48.0 |
| Example 165 | 28.9 |
| Example 166 | 2.0 |
| Example 167 | 20.6 |
| Example 168 | 60.3 |
| Example 169 | 7.2 |
| Example 170 | 556 |
| Example 171 | 89.0 |
| Example 172 | 257.6 |
| Example 173 | 22.2 |
| Example 174 | 85.7 |
| Example 175 | 1.5 |
| Example 176 | 7.5 |
| Example 177 | 0.10 |
| Example 178 | 1.3 |
| Example 179 | 3.5 |
| Example 180 | 4.2 |
| Example 181 | 0.20 |
| Example 182 | 0.43 |
| Example 183 | 323.8 |
| Example 184 | 1.4 |
| Example 185 | 5.0 |
| Example 186 | 1.3 |
| Example 187 | 2.8 |
| Example 188 | 1.2 |
| Example 189 | 0.17 |
| Example 190 | 310 |
| Example 191 | 36.9 |
| Example 192 | 109.5 |
| Example 193 | 1.2 |
| Example 194 | 1.1 |
| Example 195 | 0.33 |
| Example 196 | 499.5 |
| Example 197 | 2.5 |
| Example 198 | 7.1 |
| Example 199 | 0.66 |
| Example 200 | 53.8 |
| Example 201 | 42.2 |
| Example 202 | 0.16 |
| Example 203 | 0.43 |
| Example 204 | 2.2 |
| Example 205 | 2.0 |
| Example 206 | 3.8 |
| Example 207 | 459 |
| Example 208 | 1.6 |
| Example 209 | 26.0 |
| Example 210 | 67.0 |
| Example 211 | 0.60 |
| Example 212 | 329.3 |
| Example 213 | 0.63 |
| Example 214 | 4.1 |
| Example 215 | |
| Example 216 | |
| Example 217 | |
| Example 218 | |
| Example 219 | |
| Example 220 | |
| Example 221 | |
| Example 222 | |
| Example 223 | |
| Example 224 | |
| Example 225 | |
| Example 226 | |
| Example 227 | |
| Example 228 | |
| Example 229 | |
| Example 230 | |
| Example 231 | |
| Example 232 | |
| Example 233 | |
| Example 234 | |
| Example 235 | |
| Example 236 | |
| Example 237 | |
| Example 238 | |
| Example 239 | |
| Example 240 | |

Compounds are also screened in an adenosine uptake functional cellular assay using the protocol described below:

[$^3$H]Adenosine Uptake Assay Methods

Adenosine uptake activity was determined by monitoring the accumulation of tritiated adenosine into HeLa cells (ATCC catalog # CCL-2) using a PMT-based radiometric detection instrument. In this assay, the potency (IC$_{50}$) of each compound was determined from a ten point (1:3 serial dilution; final compound concentration range in assay from 10 □M to 0.032 nM) titration curve using the following outlined procedure. To each well of a 96-well CytoStar-T scintillating microplate (Perkin Elmer Catalog # RPNQ0163), 25 000 HeLa cells in 100 □□L of growth medium comprising: Minimum Essential Media (Life Technologies Catalog #11095-080)+10% (v/v) foetal bovine serum (FBS; Sigma Aldrich Catalog # F2442) was added. These cells were incubated overnight at 37° C. in a humidified atmosphere with 5% (v/v) CO$_2$. After this time the growth medium was removed and replaced with 40 μL assay medium comprising: Hanks balanced salts solution (HBSS; Thermo Fisher Catalog # SH30268.01)+5% (v/v) FBS. Compound stock solutions in DMSO were diluted in assay medium to 2.5× final compound concentration maintaining a constant DMSO concentration of 0.25% (v/v). 40 μL of compound in assay medium was dispensed into individual wells of the Cytostar-T plates and the plates were incubated for 30 minutes under ambient laboratory conditions. Following this incubation, 20 μL of 500 nM [$^3$H] adenosine (American Radiolabeled Chemicals Inc. Catalog # ART0287) in assay medium was added and incubated for a further 60 minutes under ambient laboratory conditions. The amount of radiolabel accumulation was then determined using a Perkin Elmer Topcount NXT microplate reader. In brief, HeLa cells adhere to the bottom of the Cytostar-T plate, uptake of [$^3$H]adenosine into these cells brings the radiolabel into sufficient proximity to excite the scintillant in the base of the plates. These events are captured by single PMT, time-resolved coincidence counting. $IC_{50}$ values were determined by 4 parameter robust fit of counts per second values vs. ($Log_{10}$) compound concentrations.

TABLE 5

Adenosine uptake inhibition potency assay

| Example number | ADU inhibition IC50 (nM) |
|---|---|
| Example 1 | 3335 |
| Example 2 | 6348 |
| Example 3 | 404.7 |
| Example 4 | 3482 |
| Example 5 | 553.2 |
| Example 6 | 1728 |
| Example 7 | 2790 |
| Example 8 | 5084 |
| Example 9 | 5540 |
| Example 10 | 2155 |
| Example 11 | 5343 |
| Example 12 | 1238 |
| Example 13 | 873.1 |
| Example 14 | 6949 |
| Example 15 | 1784 |
| Example 16 | 2435 |
| Example 17 | 5723 |
| Example 18 | 10000 |
| Example 19 | 2361 |
| Example 20 | 2573 |
| Example 21 | 7480 |
| Example 22 | 3822 |
| Example 23 | |
| Example 24 | 2486 |
| Example 25 | 3827 |
| Example 26 | 2614 |
| Example 27 | 1238 |
| Example 28 | |
| Example 29 | 1994 |
| Example 30 | 1309 |
| Example 31 | 4807 |
| Example 32 | |
| Example 33 | |
| Example 34 | |
| Example 35 | 2227 |
| Example 36 | 703.5 |
| Example 37 | 3469 |
| Example 38 | 1844 |
| Example 39 | 607.7 |
| Example 40 | 1759 |
| Example 41 | 587.6 |
| Example 42 | 3227 |
| Example 43 | 535.4 |
| Example 44 | 1781 |
| Example 45 | 2756 |
| Example 46 | 3206 |
| Example 47 | 2042 |
| Example 48 | 3305 |
| Example 49 | 2946 |
| Example 50 | 1220 |
| Example 51 | 568.6 |
| Example 52 | 3831 |
| Example 53 | 670.6 |
| Example 54 | 473.4 |
| Example 55 | 399.8 |
| Example 56 | 900.6 |
| Example 57 | 3323 |

TABLE 5-continued

Adenosine uptake inhibition potency assay

| Example number | ADU inhibition IC50 (nM) |
|---|---|
| Example 58 | 449.5 |
| Example 59 | 1250 |
| Example 60 | 3364 |
| Example 61 | 1707 |
| Example 62 | 2299 |
| Example 63 | 1470 |
| Example 64 | 936.1 |
| Example 65 | 10000 |
| Example 66 | 4188 |
| Example 67 | 8503 |
| Example 68 | 5554 |
| Example 69 | 6474 |
| Example 70 | 1014 |
| Example 71 | 5121 |
| Example 72 | 469 |
| Example 73 | 1348 |
| Example 74 | 462.7 |
| Example 75 | 2010 |
| Example 76 | 2102 |
| Example 77 | 1038 |
| Example 78 | 2849 |
| Example 79 | 1472 |
| Example 80 | 1733 |
| Example 81 | 684.5 |
| Example 82 | 746.2 |
| Example 83 | 1333 |
| Example 84 | 2379 |
| Example 85 | 3533 |
| Example 86 | 589.2 |
| Example 87 | 1583 |
| Example 88 | 1100 |
| Example 89 | 3492 |
| Example 90 | 968.9 |
| Example 91 | |
| Example 92 | 619 |
| Example 93 | 1381 |
| Example 94 | 800.4 |
| Example 95 | 1984 |
| Example 96 | 7145 |
| Example 97 | 10000 |
| Example 98 | 3167 |
| Example 99 | 1188 |
| Example 100 | 310.8 |
| Example 101 | 371.2 |
| Example 102 | 1685 |
| Example 103 | 486.6 |
| Example 104 | 1701 |
| Example 105 | 860.8 |
| Example 106 | 6966 |
| Example 107 | 529.9 |
| Example 108 | 467.1 |
| Example 109 | 892.4 |
| Example 110 | 1695 |
| Example 111 | 721.8 |
| Example 112 | 1874 |
| Example 113 | 2138 |
| Example 114 | 888.4 |
| Example 115 | 172.1 |
| Example 116 | 458.2 |
| Example 117 | 955.7 |
| Example 118 | 1491 |
| Example 119 | 2408 |
| Example 120 | 4669 |
| Example 121 | 1938 |
| Example 122 | 966.5 |
| Example 123 | 945 |
| Example 124 | 1451 |
| Example 125 | 1175 |
| Example 126 | 1070 |
| Example 127 | 2143 |
| Example 128 | 1472 |
| Example 129 | 1660 |
| Example 130 | 1444 |
| Example 131 | 436.2 |
| Example 132 | 2951 |
| Example 133 | 460.2 |

TABLE 5-continued

Adenosine uptake inhibition potency assay

| Example number | ADU inhibition IC50 (nM) |
| --- | --- |
| Example 134 | 2330 |
| Example 135 | 972.6 |
| Example 136 | 4617 |
| Example 137 | 865 |
| Example 138 | 4765 |
| Example 139 | 449.4 |
| Example 140 | 1196 |
| Example 141 | 1980 |
| Example 142 | 7164 |
| Example 143 | 839 |
| Example 144 | 984.8 |
| Example 145 | 1217 |
| Example 146 | 1491 |
| Example 147 | 3831 |
| Example 148 | 2992 |
| Example 149 | 700.8 |
| Example 150 | 2413 |
| Example 151 | 2042 |
| Example 152 | 2957 |
| Example 153 | 1957 |
| Example 154 | 464 |
| Example 155 | 2748 |
| Example 156 | 1470 |
| Example 157 | 2224 |
| Example 158 | 6300 |
| Example 159 | 1883 |
| Example 160 | 1838 |
| Example 161 | 2137 |
| Example 162 | 4213 |
| Example 163 | 1565 |
| Example 164 | 829.5 |
| Example 165 | 1091 |
| Example 166 | 10000 |
| Example 167 | 2408 |
| Example 168 | 3652 |
| Example 169 | 4534 |
| Example 170 | 7111 |
| Example 171 | 7963 |
| Example 172 | 5325 |
| Example 173 | 5111 |
| Example 174 | 1156 |
| Example 175 | 1381 |
| Example 176 | 4272 |
| Example 177 | 1833 |
| Example 178 | 4610 |
| Example 179 | 3299 |
| Example 180 | 2455 |
| Example 181 | 3624 |
| Example 182 | 2798 |
| Example 183 | 560.6 |
| Example 184 | 2655 |
| Example 185 | 2387 |
| Example 186 | 3079 |
| Example 187 | 2644 |

TABLE 5-continued

Adenosine uptake inhibition potency assay

| Example number | ADU inhibition IC50 (nM) |
| --- | --- |
| Example 188 | 2496 |
| Example 189 | 2076 |
| Example 190 | 315.9 |
| Example 191 | 431.1 |
| Example 192 | 521.5 |
| Example 193 | 1865 |
| Example 194 | 1300 |
| Example 195 | 3502 |
| Example 196 | 369 |
| Example 197 | 3486 |
| Example 198 | 6850 |
| Example 199 | 4499 |
| Example 200 | 230.3 |
| Example 201 | 417.7 |
| Example 202 | 1919 |
| Example 203 | 2265 |
| Example 204 | 5874 |
| Example 205 | 3500 |
| Example 206 | 5463 |
| Example 207 | 932.8 |
| Example 208 | 5409 |
| Example 209 | 1120 |
| Example 210 | 2703 |
| Example 211 | 7031 |
| Example 212 | 3516 |
| Example 213 | 6000 |
| Example 214 | 3112 |
| Example 215 | |
| Example 216 | |
| Example 217 | |
| Example 218 | |
| Example 219 | |
| Example 220 | |
| Example 221 | |
| Example 222 | |
| Example 223 | |
| Example 224 | |
| Example 225 | |
| Example 226 | |
| Example 227 | |
| Example 228 | |
| Example 229 | |
| Example 230 | |
| Example 231 | |
| Example 232 | |
| Example 233 | |
| Example 234 | |
| Example 235 | |
| Example 236 | |
| Example 237 | |
| Example 238 | |
| Example 239 | |
| Example 240 | |

What is claimed is:

1. A compound according to Formula I, or a pharmaceutically acceptable salt, thereof

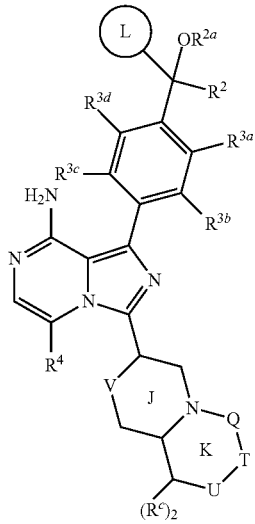

Formula I wherein:
L is selected from the group consisting of:

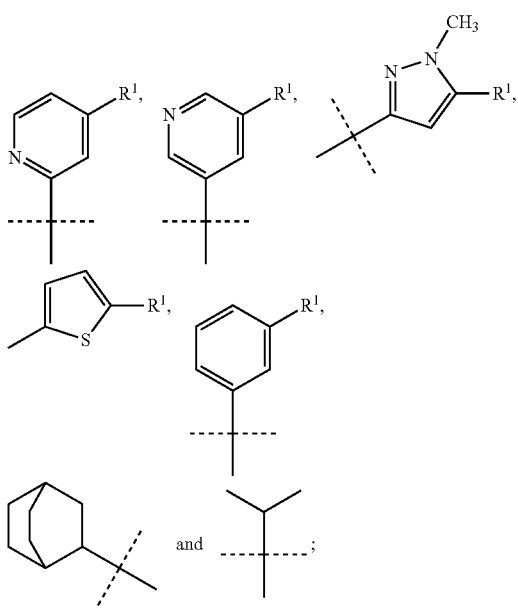

and ;

$R^1$ is H, cyano, halogen, (1-4C)alkyl, (3-6C)cycloalkyl, (1-3C)alkoxy, (3-6C)cycloalkoxy, morpholino, aryl or imidazolyl,
wherein (1-4C)alkyl or (1-3C)alkoxy may optionally be substituted with one, two or three halogens;
$R^2$ is selected from H, (1-3C)alkyl, (1-3C)alkoxy, cyclopropyl, aminocarbonyl,
wherein the (1-3C)alkyl or (1-3C)alkoxy may optionally be substituted with hydroxyl or one, two or three halogen;
$R^{2a}$ is hydrogen or methyl;
$R^{3a}$, $R^{3b}$, $R^{3c}$ and $R^{3d}$ are each independently selected from H, halogen, (1-3C)alkyl, (1-6C)alkoxy, and (3-6C)cycloalkyl, wherein (1-3C)alkyl may be substituted with hydroxyl or one, two or three halogen;
$R^4$ is independently selected from the group consisting of:
a) H,
b) halogen, and
c) haloalkyl;
wherein in ring system J-K:
Q is C=O or $CH_2$;
T is $C(R^e)_2$, O, $NR^e$, or a bond;
U is $C(R^d)_2$, O, or $NR^d$;
V is $CH_2$ or O;
$R^c$ is independently selected from H, fluoro, methyl or trifluoromethyl,
or two $R^c$ groups can join to form a spirofused cyclopropyl group with the carbon atom to which they are attached;
$R^d$ is independently selected from H, (1-3C)alkyl or trifluoromethyl;
$R^e$ is independently selected from H or (1-6C)alkyl,
or two $R^e$ groups can join to form a spirofused cyclopropyl group with the carbon atom to which they are attached;
when T is a bond, Q is C=O and U is $C(R^d)2$,
$R^c$ and $R^d$ can join to form a 3-6 membered ring with the carbons to which they are attached; and
with the proviso that:
when Q is $CH_2$, then T is $C(R^e)_2$.

2. The compound of claim 1, or a pharmaceutically acceptable salt thereof, wherein the ring system J-K is selected from the group consisting of

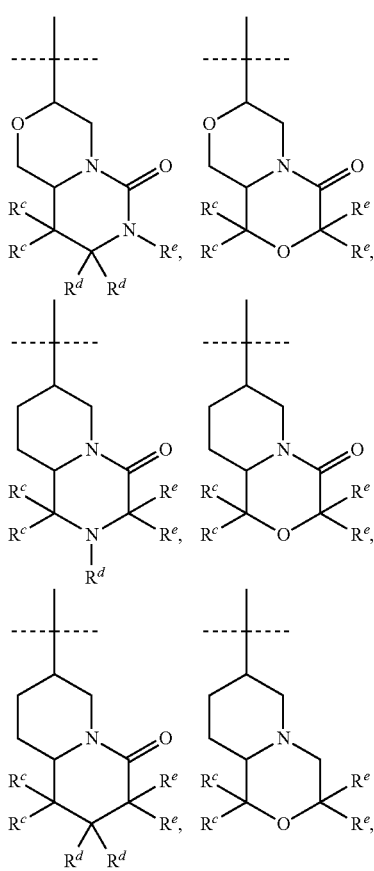

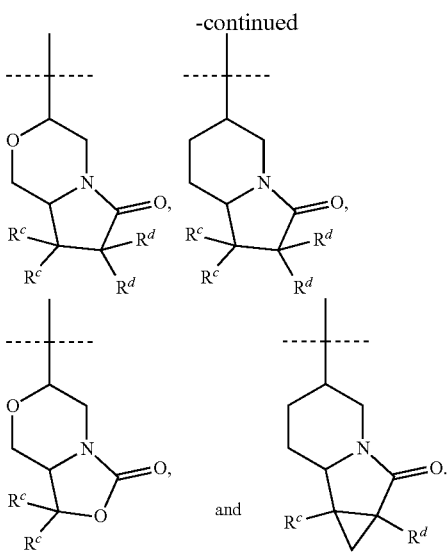

3. The compound of claim 1, or a pharmaceutically acceptable salt thereof, wherein L is

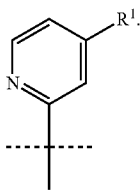

4. The compound of claim 1, or a pharmaceutically acceptable salt thereof, wherein $R^1$ is trifluoromethyl.

5. The compound of claim 1 having Formula Ia

Formula Ia

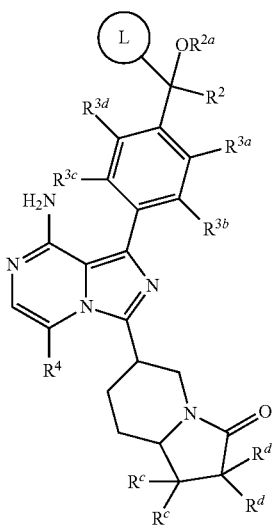

or a pharmaceutically acceptable salt thereof.

6. A compound selected from the group consisting of:
(6R,8aS)-6-(8-amino-1-{4-[(1S)-1-hydroxy-1-phenylethyl]phenyl}imidazo[1,5-a]pyrazin-3-yl)hexahydroindolizin-3 (2H)-one;
(6R,8aS)-6-(8-amino-1-{4-[(1R)-1-hydroxy-1-phenylethyl]phenyl}imidazo[1,5-a]pyrazin-3-yl)hexahydroindolizin-3 (2H)-one;
(6R,8aS)-6-[8-amino-1-(4-{(1R)-1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-[8-amino-1-(4-{(1S)-1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-[8-amino-5-chloro-1-(4-{(1S)-1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-[8-amino-5-chloro-1-(4-{(1R)-1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-[8-amino-1-(4-{(1R)-1-hydroxy-1-[3-(trifluoromethyl)phenyl]ethyl}phenyl)imidazo[1,5-a]pyrazin-3-yl]-2,2-dimethylhexahydroindolizin-3 (2H)-one;
(1S,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-methyltetrahydro-1H-[1,3]oxazolo[4,3-c][1,4]oxazin-3-one;
(1R,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-methyltetrahydro-1H-[1,3]oxazolo[4,3-c][1,4]oxazin-3-one;
(6R,8aS)-6-[8-amino-1-(2-methoxy-4-{2,2,2-trifluoro-1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-[8-amino-1-(2-methoxy-4-{2,2,2-trifluoro-1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-{8-amino-1-[4-(2,2,2-trifluoro-1-hydroxy-1-phenylethyl)phenyl]imidazo[1,5-a]pyrazin-3-yl}hexahydroindolizin-3 (2H)-one;
(6R,8aS)-6-[8-amino-1-(4-{1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-{8-amino-1-[4-(1-hydroxy-1,2-dimethylpropyl)phenyl]imidazo[1,5-a]pyrazin-3-yl}hexahydroindolizin-3 (2H)-one;
(6R,8aS)-6-[8-amino-1-(4-{1-hydroxy-1-[4-(trifluoromethyl)phenyl]ethyl}phenyl)imidazo[1,5-a]pyrazin-3-yl]hexahydroindolizin-3 (2H)-one;
(6R,8aS)-6-(8-amino-1-{4-[1-(3-fluorophenyl)-1-hydroxyethyl]phenyl}imidazo[1,5-a]pyrazin-3-yl)hexahydroindolizin-3 (2H)-one;
(6R,8aS)-6-{8-amino-1-[4-(1-hydroxy-1-pyridin-2-ylethyl)phenyl]imidazo[1,5-a]pyrazin-3-yl}hexahydroindolizin-3 (2H)-one;
(6R,8aS)-6-{8-amino-1-[4-(1-hydroxy-1-pyridin-3-ylethyl)phenyl]imidazo[1,5-a]pyrazin-3-yl}hexahydroindolizin-3 (2H)-one;
(6R,8aS)-6-(8-amino-1-{4-[1-(4-fluorophenyl)-1-hydroxyethyl]phenyl}imidazo[1,5-a]pyrazin-3-yl)hexahydroindolizin-3 (2H)-one;
(6R,8aS)-6-{8-amino-1-[2-(hydroxymethyl)-4-{(1S)-1-hydroxy-1-[3-(trifluoromethyl)phenyl]ethyl}phenyl]imidazo[1,5-a]pyrazin-3-yl}hexahydroindolizin-3 (2H)-one;
(6R,8aS)-6-{8-amino-1-[2-(hydroxymethyl)-4-{(1R)-1-hydroxy-1-[3-(trifluoromethyl)phenyl]ethyl}phenyl]imidazo[1,5-a]pyrazin-3-yl}hexahydroindolizin-3 (2H)-one;

(6R,8aS)-6-[8-amino-1-(2-ethoxy-6-fluoro-4-{1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-{8-amino-1-[4-(1-hydroxy-1-phenylethyl)phenyl]imidazo[1,5-a]pyrazin-3-yl}hexahydroindolizin-3 (2H)-one;
(6R,8aS)-6-{8-amino-1-[2-fluoro-4-(1-hydroxy-1-phenylethyl)phenyl]imidazo[1,5-a]pyrazin-3-yl}hexahydroindolizin-3 (2H)-one;
(6R,8aS)-6-(8-amino-1-{4-[(1R)-2,2,2-trifluoro-1-hydroxy-1-phenylethyl]phenyl}imidazo[1,5-a]pyrazin-3-yl)hexahydroindolizin-3 (2H)-one;
(6R,8aS)-6-(8-amino-1-{4-[(1S)-2,2,2-trifluoro-1-hydroxy-1-phenylethyl]phenyl}imidazo[1,5-a]pyrazin-3-yl)hexahydroindolizin-3 (2H)-one;
(6R,8aS)-6-[8-amino-1-(4-{2,2,2-trifluoro-1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-[8-amino-1-(4-{2,2,2-trifluoro-1-hydroxy-1-[4-(trifluoromethyl)phenyl]ethyl}phenyl)imidazo[1,5-a]pyrazin-3-yl]hexahydroindolizin-3 (2H)-one;
(6R,8aS)-6-(8-amino-1-{4-[2,2,2-trifluoro-1-(3-fluorophenyl)-1-hydroxyethyl]phenyl}imidazo[1,5-a]pyrazin-3-yl)hexahydroindolizin-3(2H)-one;
(6R,8aS)-6-{8-amino-1-[2-fluoro-4-(2,2,2-trifluoro-1-hydroxy-1-phenylethyl)phenyl]imidazo[1,5-a]pyrazin-3-yl}hexahydroindolizin-3 (2H)-one;
(6R,8aS)-6-[8-amino-1-(4-{1-hydroxy-1-[2-(trifluoromethyl)phenyl]ethyl}phenyl)imidazo[1,5-a]pyrazin-3-yl]hexahydroindolizin-3 (2H)-one;
(6R,8aS)-6-(8-amino-1-{4-[2,2,2-trifluoro-1-(4-fluorophenyl)-1-hydroxyethyl]phenyl}imidazo[1,5-a]pyrazin-3-yl)hexahydroindolizin-3(2H)-one;
(6R,8aS)-6-(8-amino-1-{2-methoxy-4-[(1S)-2,2,2-trifluoro-1-hydroxy-1-phenylethyl]phenyl}imidazo[1,5-a]pyrazin-3-yl)hexahydroindolizin-3 (2H)-one;
(6R,8aS)-6-(8-amino-1-{2-methoxy-4-[(1S)-2,2,2-trifluoro-1-hydroxy-1-phenylethyl]phenyl}imidazo[1,5-a]pyrazin-3-yl)hexahydroindolizin-3 (2H)-one;
(6R,8aS)-6-[8-amino-1-(4-{1-hydroxy-1-[1-methyl-5-(trifluoromethyl)-1H-pyrazol-3-yl]ethyl}phenyl)imidazo[1,5-a]pyrazin-3-yl]hexahydroindolizin-3 (2H)-one;
(6R,8aS)-6-[8-amino-1-(4-{(1S)-1-hydroxy-1-[4-(trifluoromethyl)pyridin-2-yl]ethyl}phenyl)imidazo[1,5-a]pyrazin-3-yl]hexahydroindolizin-3 (2H)-one;
(6R,8aS)-6-[8-amino-1-(4-{(1R)-1-hydroxy-1-[4-(trifluoromethyl)pyridin-2-yl]ethyl}phenyl)imidazo[1,5-a]pyrazin-3-yl]hexahydroindolizin-3 (2H)-one;
(6R,8aS)-6-(8-amino-1-{4-[(1R)-1-(3-cyclopropylphenyl)-1-hydroxyethyl]phenyl}imidazo[1,5-a]pyrazin-3-yl)hexahydroindolizin-3 (2H)-one;
(6R,8aS)-6-(8-amino-1-{4-[(1S)-1-(3-tert-butylphenyl)-1-hydroxyethyl]phenyl}imidazo[1,5-a]pyrazin-3-yl)hexahydroindolizin-3 (2H)-one;
(6R,8aS)-6-(8-amino-1-{4-[(1R)-1-(3-tert-butylphenyl)-1-hydroxyethyl]phenyl}imidazo[1,5-a]pyrazin-3-yl)hexahydroindolizin-3 (2H)-one;
(6R,8aS)-6-(8-amino-1-{4-[(1S)-1-(3-chlorophenyl)-1-hydroxyethyl]phenyl}imidazo[1,5-a]pyrazin-3-yl)hexahydroindolizin-3 (2H)-one;
(6R,8aS)-6-[8-amino-1-(4-{1-hydroxy-1-[3-(trifluoromethyl)phenyl]ethyl}-3-methylphenyl)imidazo[1,5-a]pyrazin-3-yl]hexahydroindolizin-3 (2H)-one;
(6R,8aS)-6-[8-amino-1-(4-{1-hydroxy-1-[3-(trifluoromethyl)phenyl]ethyl}-3-methylphenyl)imidazo[1,5-a]pyrazin-3-yl]hexahydroindolizin-3 (2H)-one;
(6R,8aS)-6-(8-amino-1-{4-[(1S)-1-hydroxy-1-(3-methoxyphenyl)ethyl]phenyl}imidazo[1,5-a]pyrazin-3-yl)hexahydroindolizin-3 (2H)-one;
(6R,8aS)-6-(8-amino-1-{4-[(1R)-1-hydroxy-1-(3-methoxyphenyl)ethyl]phenyl}imidazo[1,5-a]pyrazin-3-yl)hexahydroindolizin-3 (2H)-one;
(6R,8aS)-6-(8-amino-1-{4-[(1R)-1-hydroxy-1-(3-methylphenyl)ethyl]phenyl}imidazo[1,5-a]pyrazin-3-yl)hexahydroindolizin-3 (2H)-one;
(6R,8aS)-6-(8-amino-1-{4-[(1S)-1-hydroxy-1-(2-methylphenyl)ethyl]phenyl}imidazo[1,5-a]pyrazin-3-yl)hexahydroindolizin-3 (2H)-one;
(6R,8aS)-6-(8-amino-1-{4-[(1R)-1-hydroxy-1-(2-methylphenyl)ethyl]phenyl}imidazo[1,5-a]pyrazin-3-yl)hexahydroindolizin-3 (2H)-one;
(6R,8aS)-6-(8-amino-1-{4-[(1S)-1-hydroxy-1-(2-methoxyphenyl)ethyl]phenyl}imidazo[1,5-a]pyrazin-3-yl)hexahydroindolizin-3 (2H)-one;
(6R,8aS)-6-(8-amino-1-{4-[(1R)-1-hydroxy-1-(2-methoxyphenyl)ethyl]phenyl}imidazo[1,5-a]pyrazin-3-yl)hexahydroindolizin-3 (2H)-one;
(6R,8aS)-6-(8-amino-1-{4-[(1S)-1-(3-cyclopropylphenyl)-1-hydroxyethyl]phenyl}imidazo[1,5-a]pyrazin-3-yl)hexahydroindolizin-3 (2H)-one;
(6R,8aS)-6-(8-amino-1-{4-[(1R)-1-(3-chlorophenyl)-1-hydroxyethyl]phenyl}imidazo[1,5-a]pyrazin-3-yl)hexahydroindolizin-3 (2H)-one;
(6R,8aS)-6-(8-amino-1-{4-[(1S)-1-hydroxy-1-(3-methylphenyl)ethyl]phenyl}imidazo[1,5-a]pyrazin-3-yl)hexahydroindolizin-3 (2H)-one;
(6R,8aS)-6-[8-amino-1-(3-fluoro-4-{1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-(8-amino-1-(4-{1-hydroxy-1-[3-(trifluoromethyl)phenyl]propyl}phenyl)imidazo[1,5-a]pyrazin-3-yl]hexahydroindolizin-3 (2H)-one;
(6R,8aS)-6-[8-amino-1-(4-{(1S)-1-hydroxy-1-[3-(trifluoromethoxy)phenyl]ethyl}phenyl)imidazo[1,5-a]pyrazin-3-yl]hexahydroindolizin-3 (2H)-one;
(6R,8aS)-6-[8-amino-1-(4-{(1R)-1-hydroxy-1-[3-(trifluoromethoxy)phenyl]ethyl}phenyl)imidazo[1,5-a]pyrazin-3-yl]hexahydroindolizin-3 (2H)-one;
(6R,8aS)-6-(8-amino-1-{4-[(1S)-1-biphenyl-3-yl-1-hydroxyethyl]phenyl}imidazo[1,5-a]pyrazin-3-yl)hexahydroindolizin-3 (2H)-one;
(6R,8aS)-6-(8-amino-1-{4-[(1R)-1-biphenyl-3-yl-1-hydroxyethyl]phenyl}imidazo[1,5-a]pyrazin-3-yl)hexahydroindolizin-3 (2H)-one;
(6R,8aS)-6-[8-amino-1-(3-fluoro-4-{1-hydroxy-1-[3-(trifluoromethyl)phenyl]ethyl}phenyl)imidazo[1,5-a]pyrazin-3-yl]hexahydroindolizin-3 (2H)-one;
(6R,8aS)-6-[8-amino-1-(4-{1-hydroxy-1-[3-(trifluoromethyl)phenyl]propyl}phenyl)imidazo[1,5-a]pyrazin-3-yl]hexahydroindolizin-3 (2H)-one;
(1R)-1-(4-{8-amino-3-[(6R,8aS)-octahydroindolizin-6-yl]imidazo[1,5-a]pyrazin-1-yl}phenyl)-1-[3-(trifluoromethyl)phenyl]ethanol;
(1S)-1-(4-{8-amino-3-[(6R,8aS)-octahydroindolizin-6-yl]imidazo[1,5-a]pyrazin-1-yl}phenyl)-1-[3-(trifluoromethyl)phenyl]ethanol;
(6R,8aS)-6-[8-amino-1-(4-{1-hydroxy-1-[3-(trifluoromethyl)phenyl]ethyl}-3-methoxyphenyl)imidazo[1,5-a]pyrazin-3-yl]hexahydroindolizin-3 (2H)-one;

(6R,8aS)-6-[8-amino-1-(4-{1-hydroxy-1-[3-(trifluoromethyl)phenyl]ethyl}-3-methoxyphenyl)imidazo[1,5-a]pyrazin-3-yl]hexahydroindolizin-3 (2H)-one;

(6R,8aS)-6-(8-amino-1-{4-[(1R)-1-hydroxy-1-(3-morpholin-4-ylphenyl)ethyl]phenyl}imidazo[1,5-a]pyrazin-3-yl)hexahydroindolizin-3 (2H)-one;

(6R,8aS)-6-(8-amino-1-{4-[(1S)-1-hydroxy-1-(3-morpholin-4-ylphenyl)ethyl]phenyl}imidazo[1,5-a]pyrazin-3-yl)hexahydroindolizin-3 (2H)-one;

(6R,8aS)-6-(8-amino-1-{4-[(1S)-1-(2-fluorophenyl)-1-hydroxyethyl]phenyl}imidazo[1,5-a]pyrazin-3-yl)hexahydroindolizin-3 (2H)-one;

(6R,8aS)-6-(8-amino-1-{4-[(1R)-1-(2-fluorophenyl)-1-hydroxyethyl]phenyl}imidazo[1,5-a]pyrazin-3-yl)hexahydroindolizin-3 (2H)-one;

(6R,8aS)-6-[8-amino-1-(4-{(1S)-1-[3-(difluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1R)-1-[3-(difluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{hydroxy[3-(trifluoromethyl)phenyl]methyl}phenyl)imidazo[1,5-a]pyrazin-3-yl]hexahydroindolizin-3 (2H)-one;

(6R,8aS)-6-[8-amino-1-(4-{hydroxy[3-(trifluoromethyl)phenyl]methyl}phenyl)imidazo[1,5-a]pyrazin-3-yl]hexahydroindolizin-3 (2H)-one;

(6R,8aS)-6-[8-amino-1-(4-{((1S)-1-hydroxy-1-[3-(1-methylethyl)phenyl]ethyl}phenyl)imidazo[1,5-a]pyrazin-3-yl]hexahydroindolizin-3 (2H)-one;

(6R,8aS)-6-[8-amino-1-(4-{(1R)-1-hydroxy-1-[3-(1-methylethyl)phenyl]ethyl}phenyl)imidazo[1,5-a]pyrazin-3-yl]hexahydroindolizin-3 (2H)-one;

(6R,8aS)-6-[8-amino-1-(4-{1-hydroxy-2-methyl-1-[3-(trifluoromethyl)phenyl]propyl}phenyl)imidazo[1,5-a]pyrazin-3-yl]hexahydroindolizin-3 (2H)-one;

(6R,8aS)-6-[8-amino-1-(4-{(1S)-1-hydroxy-1-[3-(2,2,2-trifluoroethyl)phenyl]ethyl}phenyl)imidazo[1,5-a]pyrazin-3-yl]hexahydroindolizin-3 (2H)-one;

(6R,8aS)-6-[8-amino-1-(4-{(1R)-1-hydroxy-1-[3-(2,2,2-trifluoroethyl)phenyl]ethyl}phenyl)imidazo[1,5-a]pyrazin-3-yl]hexahydroindolizin-3 (2H)-one;

(6R,8aS)-6-[8-amino-1-(4-{1-hydroxy-2-methyl-1-[3-(trifluoromethyl)phenyl]propyl}phenyl)imidazo[1,5-a]pyrazin-3-yl]hexahydroindolizin-3 (2H)-one;

(6R,8aS)-6-{8-amino-1-[2-(difluoromethyl)-4-{(1S)-1-hydroxy-1-[3-(trifluoromethyl)phenyl]ethyl}phenyl]imidazo[1,5-a]pyrazin-3-yl}hexahydroindolizin-3 (2H)-one;

(6R,8aS)-6-{8-amino-1-[2-(difluoromethyl)-4-{(1R)-1-hydroxy-1-[3-(trifluoromethyl)phenyl]ethyl}phenyl]imidazo[1,5-a]pyrazin-3-yl}hexahydroindolizin-3 (2H)-one;

(6R,8aS)-6-(8-amino-1-{4-[(1S)-1-(3-cyclobutylphenyl)-1-hydroxyethyl]phenyl}imidazo[1,5-a]pyrazin-3-yl)hexahydroindolizin-3 (2H)-one;

(6R,8aS)-6-(8-amino-1-{4-[(1R)-1-(3-cyclobutylphenyl)-1-hydroxyethyl]phenyl}imidazo[1,5-a]pyrazin-3-yl)hexahydroindolizin-3 (2H)-one;

3-[(1S)-1-(4-{8-amino-3-[(6R,8aS)-3-oxooctahydroindolizin-6-yl]imidazo[1,5-a]pyrazin-1-yl}phenyl)-1-hydroxyethyl]benzonitrile;

3-[(1R)-1-(4-{8-amino-3-[(6R,8aS)-3-oxooctahydroindolizin-6-yl]imidazo[1,5-a]pyrazin-1-yl}phenyl)-1-hydroxyethyl]benzonitrile;

(6R,8aS)-6-[8-amino-1-(4-{cyclopropyl(hydroxy)[3-(trifluoromethyl)phenyl]methyl}phenyl)imidazo[1,5-a]pyrazin-3-yl]hexahydroindolizin-3 (2H)-one;

(6R,8aS)-6-[8-amino-1-(4-{cyclopropyl(hydroxy)[3-(trifluoromethyl)phenyl]methyl}phenyl)imidazo[1,5-a]pyrazin-3-yl]hexahydroindolizin-3 (2H)-one;

(6R,8aS)-6-[8-amino-1-(2-cyclopropyl-4-{1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{(1R)-1-methoxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{((1S)-1-methoxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{1-hydroxy-1-[3-(trifluoromethyl)phenyl]ethyl}-2-methoxyphenyl)imidazo[1,5-a]pyrazin-3-yl]hexahydroindolizin-3 (2H)-one;

(6R,8aS)-6-(8-amino-1-{4-[(1S)-1-(3-ethylphenyl)-1-hydroxyethyl]phenyl}imidazo[1,5-a]pyrazin-3-yl)hexahydroindolizin-3 (2H)-one;

(6R,8aS)-6-(8-amino-1-{4-[(1R)-1-(3-ethylphenyl)-1-hydroxyethyl]phenyl}imidazo[1,5-a]pyrazin-3-yl)hexahydroindolizin-3 (2H)-one;

(6R,8aS)-6-[8-amino-1-(4-{(1S)-1-[3-(cyclopropyloxy)phenyl]-1-hydroxyethyl}phenyl)imidazo[1,5-a]pyrazin-3-yl]hexahydroindolizin-3(2H)-one;

(6R,8aS)-6-[8-amino-1-(4-{(1R)-1-[3-(cyclopropyloxy)phenyl]-1-hydroxyethyl}phenyl)imidazo[1,5-a]pyrazin-3-yl]hexahydroindolizin-3(2H)-one;

2-(4-{8-amino-3-[(6R,8aS)-3-oxooctahydroindolizin-6-yl]imidazo[1,5-a]pyrazin-1-yl}phenyl)-2-hydroxy-2-[3-(trifluoromethyl)phenyl]acetamide;

2-(4-{8-amino-3-[(6R,8aS)-3-oxooctahydroindolizin-6-yl]imidazo[1,5-a]pyrazin-1-yl}phenyl)-2-hydroxy-2-[3-(trifluoromethyl)phenyl]acetamide;

(6R,8aS)-6-(8-amino-1-{4-[(1R)-1-(3-cyclopropylphenyl)-1-hydroxyethyl]-3-methoxyphenyl}imidazo[1,5-a]pyrazin-3-yl)hexahydroindolizin-3 (2H)-one;

(6R,8aS)-6-(8-amino-1-{4-[(1S)-1-(3-cyclopropylphenyl)-1-hydroxyethyl]-3-methoxyphenyl}imidazo[1,5-a]pyrazin-3-yl)hexahydroindolizin-3 (2H)-one;

(6R,8aS)-6-[8-amino-1-(2-chloro-4-{1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(2-fluoro-4-{(1S)-1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(2-fluoro-4-{(1R)-1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{(1R)-1-hydroxy-1-[3-(trifluoromethyl)phenyl]ethyl}-2-methylphenyl)imidazo[1,5-a]pyrazin-3(2H)-one;

(6R,8aS)-6-[8-amino-1-(4-{(1S)-1-hydroxy-1-[3-(trifluoromethyl)phenyl]ethyl}-2-methylphenyl)imidazo[1,5-a]pyrazin-3-yl]hexahydroindolizin-3 (2H)-one;

(6R,8aS)-6-{8-amino-1-[4-{1-hydroxy-1-[3-(trifluoromethyl)phenyl]ethyl}-2-(trifluoromethyl)phenyl]imidazo[1,5-a]pyrazin-3-yl}hexahydroindolizin-3 (2H)-one;

(6R,8aS)-6-[8-amino-1-(4-{(1S)-1,2-dihydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{(1R)-1,2-dihydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{2,2-difluoro-1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{((1S)-1-hydroxy-1-[3-(2,2,2-trifluoro-1,1-dimethylethyl)phenyl]ethyl}phenyl)imidazo[1,5-a]pyrazin-3-yl]hexahydroindolizin-3 (2H)-one;

(6R,8aS)-6-[8-amino-1-(4-{(1R)-1-hydroxy-1-[3-(2,2,2-trifluoro-1,1-dimethylethyl)phenyl]ethyl}phenyl)imidazo[1,5-a]pyrazin-3-yl]hexahydroindolizin-3 (2H)-one;

(6R,8aS)-6-[8-amino-1-(4-{(1S)-1-hydroxy-1-[5-(trifluoromethyl)thiophen-2-yl]ethyl}phenyl)imidazo[1,5-a]pyrazin-3-yl]hexahydroindolizin-3(2H)-one;

(6R,8aS)-6-[8-amino-1-(4-{2,2-difluoro-1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{(1S)-1-hydroxy-1-[5-(trifluoromethyl)thiophen-2-yl]ethyl}phenyl)imidazo[1,5-a]pyrazin-3-yl]hexahydroindolizin-3 (2H)-one;

(4aS,7R)-7-[8-amino-1-(4-{(1R)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one;

(4aS,7R)-7-[8-amino-1-(4-{(1S)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one;

(6R,8aS)-6-(8-amino-5-chloro-1-{4-[(1S)-1-(3-cyclopropylphenyl)-1-hydroxyethyl]phenyl}imidazo[1,5-a]pyrazin-3-yl)hexahydroindolizin-3(2H)-one;

(6R,8aS)-6-(8-amino-5-chloro-1-{4-[(1R)-1-(3-cyclopropylphenyl)-1-hydroxyethyl]phenyl}imidazo[1,5-a]pyrazin-3-yl)hexahydroindolizin-3(2H)-one;

(4aR,7S)-7-[8-amino-1-(4-{(1R)-1-hydroxy-1-[3-(trifluoromethyl)phenyl]ethyl}phenyl)imidazo[1,5-a]pyrazin-3-yl]-2-methyloctahydro-1H-pyrido[1,2-c]pyrimidin-1-one;

(7R,9aS)-7-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)octahydro-4H-pyrido[1,2-a]pyrazin-4-one;

(7S,9aR)-7-[8-amino-1-(4-{(1R)-1-hydroxy-1-[3-(trifluoromethyl)phenyl]ethyl}phenyl)imidazo[1,5-a]pyrazin-3-yl]-2-(1-methylethyl)octahydro-4H-pyrido[1,2-a]pyrazin-4-one;

(6R,8aS)-6-[8-amino-5-chloro-1-(4-{(1R)-1-hydroxy-1-[3-(2,2,2-trifluoroethyl)phenyl]ethyl}phenyl)imidazo[1,5-a]pyrazin-3-yl]hexahydroindolizin-3(2H)-one;

(6R,8aS)-6-[8-amino-5-chloro-1-(4-{(1S)-1-hydroxy-1-[3-(2,2,2-trifluoroethyl)phenyl]ethyl}phenyl)imidazo[1,5-a]pyrazin-3-yl]hexahydroindolizin-3 (2H)-one;

(6R,8aS)-6-[8-amino-5-chloro-1-(4-{(1S)-1-hydroxy-1-[3-(2,2,2-trifluoro-1,1-dimethylethyl)phenyl]ethyl}phenyl)imidazo[1,5-a]pyrazin-3-yl]hexahydroindolizin-3 (2H)-one;

(6R,8aS)-6-[8-amino-5-chloro-1-(4-{(1R)-1-hydroxy-1-[3-(2,2,2-trifluoro-1,1-dimethylethyl)phenyl]ethyl}phenyl)imidazo[1,5-a]pyrazin-3-yl]hexahydroindolizin-3 (2H)-one;

(6R,8aS)-6-[8-amino-1-(4-{[2-fluoro-5-(trifluoromethyl)phenyl](hydroxy)methyl}phenyl)imidazo[1,5-a]pyrazin-3-yl]hexahydroindolizin-3 (2H)-one;

(6R,8aS)-6-[8-amino-5-chloro-1-(4-{[2-fluoro-5-(trifluoromethyl)phenyl](hydroxy)methyl}phenyl)imidazo[1,5-a]pyrazin-3-yl]hexahydroindolizin-3 (2H)-one;

(6R,8aS)-6-[8-amino-1-(4-{hydroxy[2-methyl-5-(trifluoromethyl)phenyl]methyl}phenyl)imidazo[1,5-a]pyrazin-3-yl]hexahydroindolizin-3 (2H)-one;

(6R,8aS)-6-[8-amino-1-(4-{[2-fluoro-5-(trifluoromethyl)phenyl](hydroxy)methyl}phenyl)imidazo[1,5-a]pyrazin-3-yl]hexahydroindolizin-3 (2H)-one;

(6R,8aS)-6-[8-amino-5-chloro-1-(4-{[2-fluoro-5-(trifluoromethyl)phenyl](hydroxy)methyl}phenyl)imidazo[1,5-a]pyrazin-3-yl]hexahydroindolizin-3 (2H)-one;

(6R,8aS)-6-[8-amino-1-(4-{hydroxy[2-methyl-5-(trifluoromethyl)phenyl]methyl}phenyl)imidazo[[1,5-a]pyrazin-3-yl]hexahydroindolizin-3 (2H)-one;

(6R,8aS)-6-[8-amino-1-(4-{(1S)-1-[3-(1,1-difluoroethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1R)-1-[3-(1,1-difluoroethyl)phenyl]-1-hydroxyethyl}phenyl)imidazo[1,5-a]pyrazin-3-yl]hexahydroindolizin-3(2H)-one;

(6R,8aS)-6-[8-amino-5-chloro-1-(4-{(1S)-1-[3-(difluoromethyl)phenyl]-1-hydroxyethyl}phenyl)imidazo[1,5-a]pyrazin-3-yl]hexahydroindolizin-3(2H)-one;

(6R,8aS)-6-[8-amino-5-chloro-1-(4-{(1R)-1-[3-(difluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1S)-1-hydroxy-1-[5-(trifluoromethyl)pyridin-3-yl]ethyl}phenyl)imidazo[1,5-a]pyrazin-3-yl]hexahydroindolizin-3 (2H)-one;

(6R,8aS)-6-[8-amino-1-(4-{(1R)-1-hydroxy-1-[5-(trifluoromethyl)pyridin-3-yl]ethyl}phenyl)imidazo[1,5-a]pyrazin-3-yl]hexahydroindolizin-3(2H)-one;

(6R,8aS)-6-[8-amino-1-(4-{(1S)-1-hydroxy-1-[6-(trifluoromethyl)pyridin-2-yl]ethyl}phenyl)imidazo[1,5-a]pyrazin-3-yl]hexahydroindolizin-3 (2H)-one;

(6R,8aS)-6-[8-amino-1-(4-{(1R)-1-hydroxy-1-[6-(trifluoromethyl)pyridin-2-yl]ethyl}phenyl)imidazo[1,5-a]pyrazin-3-yl]hexahydroindolizin-3 (2H)-one;

(6R,8aS)-6-[8-amino-5-chloro-1-(4-{(1S)-1-[3-(1,1-difluoroethyl)phenyl]-1-hydroxyethyl}phenyl)imidazo[1,5-a]pyrazin-3-yl]hexahydroindolizin-3(2H)-one;

(6R,8aS)-6-[8-amino-5-chloro-1-(4-{(1R)-1-[3-(1,1-difluoroethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1S)-1-hydroxy-1-[3-(trifluoromethyl)phenyl]ethyl}-2-methoxyphenyl)imidazo[1,5-a]pyrazin-3-yl]hexahydroindolizin-3 (2H)-one;

(6R,8aS)-6-[8-amino-1-(4-{(1R)-1-hydroxy-1-[3-(trifluoromethyl)phenyl]ethyl}-2-methoxyphenyl)imidazo[1,5-a]pyrazin-3-yl]hexahydroindolizin-3 (2H)-one;

(6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3 (2H)-one;

(6R,8aS)-6-[8-amino-1-(4-{1-[3-(difluoromethoxy)phenyl]-1-hydroxyethyl}phenyl)imidazo[1,5-a]pyrazin-3-yl]hexahydroindolizin-3 (2H)-one;

(6R,8aS)-6-[8-amino-1-(4-{1-[2-fluoro-5-(trifluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{1-[3,5-bis(trifluoromethyl)phenyl]-1-hydroxyethyl}phenyl)imidazo[1,5-a]pyrazin-3-yl]hexahydroindolizin-3(2H)-one;

(6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3 (2H)-one;

(6R,8aS)-6-[8-amino-1-(4-{1-[3-(difluoromethoxy)phenyl]-1-hydroxyethyl}phenyl)imidazo[1,5-a]pyrazin-3-yl]hexahydroindolizin-3 (2H)-one;

(6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3 (2H)-one;

(6R,8aS)-6-{8-amino-1-[4-(1-bicyclo[2.2.2]oct-2-yl-1-hydroxyethyl)phenyl]imidazo[1,5-a]pyrazin-3-yl}hexahydroindolizin-3 (2H)-one;

(6R,8aS)-6-[8-amino-1-(4-{1-[2-fluoro-5-(trifluoromethyl)phenyl]-1-hydroxyethyl}phenyl)imidazo[1,5-a]pyrazin-3-yl]hexahydroindolizin-3(2H)-one;

(6R,8aS)-6-[8-amino-1-(4-{(1R)-1-hydroxy-1-[3-(1H-imidazol-1-yl)phenyl]ethyl}phenyl)imidazo[1,5-a]pyrazin-3-yl]hexahydroindolizin-3 (2H)-one;

(6R,8aS)-6-[8-amino-1-(4-{(1S)-1-hydroxy-1-[3-(1H-imidazol-1-yl)phenyl]ethyl}phenyl)imidazo[1,5-a]pyrazin-3-yl]hexahydroindolizin-3 (2H)-one;

(6R,8aS)-6-[8-amino-1-(4-{(1S)-1-hydroxy-1-[2-(trifluoromethyl)pyridin-4-yl]ethyl}phenyl)imidazo[1,5-a]pyrazin-3-yl]hexahydroindolizin-3 (2H)-one;

(6R,8aS)-6-[8-amino-1-(4-{(1R)-1-hydroxy-1-[2-(trifluoromethyl)pyridin-4-yl]ethyl}phenyl)imidazo[1,5-a]pyrazin-3-yl]hexahydroindolizin-3 (2H)-one;

(7S,9aR)-7-[8-amino-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one;

(7R,9aS)-7-[8-amino-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one;

(6R,8aS)-6-[8-amino-5-fluoro-1-(4-{(1R)-1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one;

(6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one;

(6S,8aR)-6-[8-amino-1-(4-{(1R)-1-hydroxy-1-[3-(trifluoromethyl)phenyl]ethyl}phenyl)imidazo[1,5-a]pyrazin-3-yl]-1,1-dimethylhexahydroindolizin-3 (2H)-one;

(6R,8aS)-6-[8-amino-1-(2-ethoxy-4-{1-hydroxy-1-[3-(trifluoromethyl)phenyl]ethyl}phenyl)imidazo[1,5-a]pyrazin-3-yl]hexahydroindolizin-3 (2H)-one;

(6S,8aR)-6-[8-amino-1-(4-{(1R)-1-hydroxy-1-[3-(trifluoromethyl)phenyl]ethyl}phenyl)imidazo[1,5-a]pyrazin-3-yl]-1,1-dimethylhexahydroindolizin-3 (2H)-one;

(6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one;

(6R,8aS)-6-[8-amino-1-(4-{1-[3-(2,2-difluorocyclopropyl)phenyl]-1-hydroxyethyl}phenyl)imidazo[1,5-a]pyrazin-3-yl]hexahydroindolizin-3(2H)-one;

(6R,8aS)-6-(8-amino-1-{2-ethoxy-4-[1-hydroxy-1-(3-methylphenyl)ethyl]phenyl}imidazo[1,5-a]pyrazin-3-yl)hexahydroindolizin-3 (2H)-one;

(6R,8aS)-6-[8-amino-1-(2-ethoxy-4-{1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-{8-amino-1-{2-ethoxy-4-[1-hydroxy-1-(3-methylphenyl)ethyl]phenyl}imidazo[1,5-a]pyrazin-3-yl)hexahydroindolizin-3 (2H)-one;

(3R,8aR)-3-[8-amino-1-(4-{(1R)-1-hydroxy-1-[3-(trifluoromethyl)phenyl]ethyl}phenyl)imidazo[1,5-a]pyrazin-3-yl]hexahydro-6H-pyrrolo[2,1-c][1,4]oxazin-6-one;

(7R,9aR)-7-[8-amino-1-(4-{(1R)-1-hydroxy-1-[3-(trifluoromethyl)phenyl]ethyl}phenyl)imidazo[1,5-a]pyrazin-3-yl]-1,1-difluorooctahydro-4H-quinolizin-4-one;

(7S,9aS)-7-[8-amino-1-(4-{(1R)-1-hydroxy-1-[3-(trifluoromethyl)phenyl]ethyl}phenyl)imidazo[1,5-a]pyrazin-3-yl]-1,1-difluorooctahydro-4H-quinolizin-4-one;

(1S,6R,8aR)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3 (2H)-one;

(6R,8aS)-6-[8-amino-1-(4-{(R)-1-hydroxy-1-[3-(trifluoromethyl)phenyl]ethyl}phenyl)-5-(trifluoromethyl)imidazo[1,5-a]pyrazin-3-yl]hexahydroindolizin-3 (2H)-one;

(7S,9aS)-7-[8-amino-5-chloro-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one;

(7R,9aS)-7-[8-amino-5-chloro-1-(4-{(1R)-1-hydroxy-1-[3-(trifluoromethyl)phenyl]ethyl}phenyl)imidazo[1,5-a]pyrazin-3-yl]hexahydropyrido[2,1-c][1,4]oxazin-4(3H)-one;

(7R,9aR)-7-[8-amino-1-(4-{(1R)-1-hydroxy-1-[3-(trifluoromethyl)phenyl]ethyl}phenyl)imidazo[1,5-a]pyrazin-3-yl]tetrahydro-1H-[1,4]oxazino[3,4-c][1,4]oxazin-4(3H)-one;

(6R,8aS)-6-[8-amino-1-(4-{(1R)-1-[3-(difluoromethyl)phenyl]-1-hydroxyethyl}phenyl)imidazo[[1,5-a]pyrazin-3-yl]-1,1-dimethylhexahydroindolizin-3(2H)-one;

(6R,8aS)-6-[8-amino-1-(4-{(1R)-1-[3-(difluoromethyl)phenyl]-1-hydroxyethyl}phenyl)-5-fluoroimidazo[1,5-a]pyrazin-3-yl]-2,2-dimethylhexahydroindolizin-3 (2H)-one;

(1R,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3 (2H)-one;

(1R,6R,8aS)-6-[8-amino-1-(4-{(1R)-1-hydroxy-1-[3-(trifluoromethyl)phenyl]ethyl}phenyl)imidazo[1,5-a]pyrazin-3-yl]-1-(trifluoromethyl)hexahydroindolizin-3 (2H)-one;

(6R,8aS)-6-[8-amino-1-(4-{(1R)-1-[3-(difluoromethyl)phenyl]-1-hydroxyethyl}phenyl)imidazo[1,5-a]pyrazin-3-yl]-2,2-dimethylhexahydroindolizin-3(2H)-one;

(1R,6R,8aS)-6-[8-amino-1-(4-{(1R)-1-[3-(difluoromethyl)phenyl]-1-hydroxyethyl}phenyl)imidazo[[1,5-a]pyrazin-3-yl]-1-(trifluoromethyl)hexahydroindolizin-3 (2H)-one;

(6R,8aS)-6-[8-amino-5-fluoro-1-(2-fluoro-4-{1-hydroxy-1-[3-(trifluoromethyl)phenyl]ethyl}phenyl)imidazo[1,5-a]pyrazin-3-yl]hexahydroindolizin-3 (2H)-one;

(1R,6R,8aS)-6-[8-amino-1-(4-{(1R)-1-[3-(difluoromethyl)phenyl]-1-hydroxyethyl}phenyl)imidazo[1,5-a]pyrazin-3-yl]-1-(trifluoromethyl)hexahydroindolizin-3 (2H)-one;

(6R,8aS)-6-[8-amino-5-fluoro-1-(2-fluoro-4-{1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(2-ethoxy-4-{(1S)-1-hydroxy-1-[3-(trifluoromethyl)phenyl]ethyl}phenyl)imidazo[1,5-a]pyrazin-3-yl]-1,1-dimethylhexahydroindolizin-3(2H)-one;

(6R,8aS)-6-[8-amino-1-(4-{(1R)-1-[3-(difluoromethyl)phenyl]-1-hydroxyethyl}phenyl)imidazo[1,5-a]pyrazin-3-yl]-1,1-dimethyltetrahydro-1H-[1,3]oxazolo[4,3-c][1,4]oxazin-3-one;

(6'R,8a'S)-6'-[8-amino-1-(4-{(1R)-1-hydroxy-1-[3-(trifluoromethyl)phenyl]ethyl}phenyl)imidazo[1,5-a]pyrazin-3-yl]tetrahydro-5'H-spiro[cyclopropane-1,1'-indolizin]-3'(2'H)-one;

(6'R,8a'S)-6'-[8-amino-1-(4-{(1R)-1-[3-(difluoromethyl)phenyl]-1-hydroxyethyl}phenyl)imidazo[[1,5-a]pyrazin-3-yl]tetrahydro-5'H-spiro[cyclopropane-1,1'-indolizin]-3'(2'H)-one;

(6R,8aS)-6-[8-amino-5-chloro-1-(2-fluoro-4-{1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-1,1-dimethylhexahydroindolizin-3 (2H)-one;

(6R,8aS)-6-[8-amino-1l-(4-{1-[3-(difluoromethyl)phenyl]-1-hydroxyethyl}-2-fluorophenyl)imidazo[1,5-a]pyrazin-3-yl]hexahydroindolizin-3 (2H)-one;

(6R,8aS)-6-[8-amino-5-chloro-1-(2-fluoro-4-{1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-1,1-dimethylhexahydroindolizin-3 (2H)-one;

(6R,8aS)-6-[8-amino-1l-(4-{1-[3-(difluoromethyl)phenyl]-1-hydroxyethyl}-2-fluorophenyl)imidazo[1,5-a]pyrazin-3-yl]hexahydroindolizin-3 (2H)-one;

(6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-2,2-dimethylhexahydroindolizin-3 (2H)-one;

(6R,8aS)-6-[8-amino-1-(2-fluoro-4-{1-hydroxy-1-[3-(trifluoromethyl)phenyl]ethyl}phenyl)imidazo[1,5-a]pyrazin-3-yl]-2,2-dimethylhexahydroindolizin-3 (2H)-one;

(6R,8aS)-6-[8-amino-5-fluoro-1-(4-{(1R)-1-hydroxy-1-[3-(trifluoromethyl)phenyl]ethyl}phenyl)imidazo[1,5-a]pyrazin-3-yl]-2,2-dimethylhexahydroindolizin-3 (2H)-one;

(6R,8aS)-6-[8-amino-1-(4-{(1R)-1-[3-(difluoromethyl)phenyl]-1-hydroxyethyl}phenyl)-5-fluoroimidazo[1,5-a]pyrazin-3-yl]hexahydroindolizin-3 (2H)-one;

(6R,8aS)-6-[8-amino-1-(4-{1-[3-(difluoromethyl)phenyl]-1-hydroxyethyl}-2-fluorophenyl)imidazo[[1,5-a]pyrazin-3-yl]-1,1-dimethylhexahydroindolizin-3 (2H)-one;

(6R,8aS)-6-[8-amino-1l-(4-{1-[3-(difluoromethyl)phenyl]-1-hydroxyethyl}-2-fluorophenyl)imidazo[1,5-a]pyrazin-3-yl]-2,2-dimethylhexahydroindolizin-3 (2H)-one;

(6R,8aS)-6-[8-amino-1-(4-{1-[3-(difluoromethyl)phenyl]-1-hydroxyethyl}-2-fluorophenyl)imidazo[[1,5-a]pyrazin-3-yl]-1,1-dimethylhexahydroindolizin-3 (2H)-one;

(6R,8aS)-6-[8-amino-1l-(4-{1-[3-(difluoromethyl)phenyl]-1-hydroxyethyl}-2-fluorophenyl)imidazo[1,5-a]pyrazin-3-yl]-2,2-dimethylhexahydroindolizin-3 (2H)-one;

(6R,8aS)-6-[8-amino-1-(2-ethoxy-4-{(1S)-1-hydroxy-1-[3-(trifluoromethyl)phenyl]ethyl}phenyl)-5-fluoroimidazo[1,5-a]pyrazin-3-yl]hexahydroindolizin-3 (2H)-one;

(6R,8aS)-6-[8-amino-1-(4-{1-hydroxy-1-[3-(trifluoromethyl)phenyl]ethyl}-2-methoxyphenyl)imidazo[1,5-a]pyrazin-3-yl]-1,1-dimethylhexahydroindolizin-3(2H)-one;

(6R,8aS)-6-[8-amino-1-(4-{(1S)-1-hydroxy-1-[3-(trifluoromethyl)phenyl]ethyl}-2-methoxyphenyl)imidazo[1,5-a]pyrazin-3-yl]-2,2-dimethylhexahydroindolizin-3 (2H)-one;

(6R,8aS)-6-[8-amino-1-(4-{1-[3-(difluoromethyl)phenyl]-1-hydroxyethyl}-2-fluorophenyl)-5-fluoroimidazo[1,5-a]pyrazin-3-yl]hexahydroindolizin-3 (2H)-one;

(6R,8aS)-6-[8-amino-1-(4-{1-[3-(difluoromethyl)phenyl]-1-hydroxyethyl}-2-fluorophenyl)-5-fluoroimidazo[1,5-a]pyrazin-3-yl]hexahydroindolizin-3 (2H)-one;

(6R,8aS)-6-[8-amino-1-(4-{1-hydroxy-1-[3-(trifluoromethyl)phenyl]ethyl}-2-methoxyphenyl)imidazo[1,5-a]pyrazin-3-yl]-1,1-dimethylhexahydroindolizin-3(2H)-one;

(6R,8aS)-6-[8-amino-1-(4-{1-[3-(difluoromethyl)phenyl]-2,2,2-trifluoro-1-hydroxyethyl}-2-methoxyphenyl)imidazo[1,5-a]pyrazin-3-yl]hexahydroindolizin-3 (2H)-one;

(6R,8aS)-6-[8-amino-1-(4-{1-[3-(difluoromethyl)phenyl]-2,2,2-trifluoro-1-hydroxyethyl}-2-methoxyphenyl)imidazo[1,5-a]pyrazin-3-yl]hexahydroindolizin-3 (2H)-one;

(6R,8aS)-6-[8-amino-1-(2-ethoxy-6-fluoro-4-{(1S)-1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(2-ethoxy-6-fluoro-4-{(1R)-1-hydroxy-1-[3-(trifluoromethyl)phenyl]ethyl}phenyl)imidazo[1,5-a]pyrazin-3-yl]hexahydroindolizin-3 (2H)-one;

(6R,8aS)-6-[8-amino-1-(2-ethoxy-4-{2,2,2-trifluoro-1-hydroxy-1-[3-(trifluoromethyl)phenyl]ethyl}phenyl)imidazo[1,5-a]pyrazin-3-yl]hexahydroindolizin-3 (2H)-one;

(7'R,9a'S)-7'-[8-amino-1-(4-{(1R)-1-hydroxy-1-[3-(trifluoromethyl)phenyl]ethyl}phenyl)imidazo[1,5-a]pyrazin-3-yl]hexahydro-2'H-spiro[cyclopropane-1,3'-pyrido[1,2-a]pyrazin]-4'-one;

5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one(D1);

5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one(D2);

5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one(D3); and 5-[8-amino-1-(4-{(1R)-1-hydroxy-1-[3-(trifluoromethyl)phenyl]ethyl}phenyl)imidazo[1,5-a]pyrazin-3-yl]octahydro-2H-cyclopropa[a]indolizin-2-one(D4);

or a pharmaceutically acceptable salt thereof.

7. A pharmaceutical composition which comprises the compound of claim 1 or a pharmaceutically acceptable salt thereof and one or more pharmaceutically acceptable carriers.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Glu Gln Glu Asp Glu Pro Glu Gly Asp Tyr Phe Glu Trp Leu Glu
1               5                   10                  15